(12) United States Patent
Dale et al.

(10) Patent No.: US 8,916,529 B2
(45) Date of Patent: Dec. 23, 2014

(54) OLIGONUCLEOTIDE-CONTAINING PHARMACOLOGICAL COMPOSITIONS AND THEIR USE

(75) Inventors: Roderic M. K. Dale, Wilsonville, OR (US); Amy Arrow, Bethel, ME (US); Terry Thompson, Wilsonville, OR (US)

(73) Assignee: Lakewood-Amedex, Inc., Sarasota, FL (US)

( * ) Notice: Subject to any disclaimer, the term of this patent is extended or adjusted under 35 U.S.C. 154(b) by 842 days.

(21) Appl. No.: 11/673,486

(22) Filed: Feb. 9, 2007

(65) Prior Publication Data

US 2008/0161257 A1 Jul. 3, 2008

Related U.S. Application Data

(63) Continuation of application No. 10/191,997, filed on Jul. 10, 2002, now abandoned.

(60) Provisional application No. 60/303,820, filed on Jul. 10, 2001.

(51) Int. Cl.
*C12N 15/113* (2010.01)
*A61K 38/00* (2006.01)

(52) U.S. Cl.
CPC .............. *C12N 15/113* (2013.01); *A61K 38/00* (2013.01); *C12Y 301/01003* (2013.01); *C12Y 114/99001* (2013.01); *C12Y 304/15001* (2013.01); *C12Y 101/01088* (2013.01); *C12Y 306/0301* (2013.01); *C12Y 203/01085* (2013.01); *C12Y 113/11012* (2013.01); *C12Y 203/01026* (2013.01); *C12Y 301/03048* (2013.01); *C12Y 304/24011* (2013.01); *C12N 15/1138* (2013.01); *C12Y 111/01006* (2013.01); *C12N 15/1136* (2013.01); *C12N 2310/321* (2013.01); *C12N 15/1137* (2013.01); *C12Y 604/01002* (2013.01); *C12Y 304/1401* (2013.01); *C12Y 103/99005* (2013.01)
USPC ........................................ 514/44 A; 536/24.5

(58) Field of Classification Search
None
See application file for complete search history.

(56) References Cited

U.S. PATENT DOCUMENTS

| | | | |
|---|---|---|---|
| 4,897,355 A | 1/1990 | Eppstein et al. | |
| 5,217,866 A | 6/1993 | Summerton et al. | |
| 5,256,649 A | 10/1993 | Le Fur et al. | |
| 5,474,796 A | 12/1995 | Brennan | |
| 5,514,788 A | 5/1996 | Bennett et al. | |
| 5,576,208 A | 11/1996 | Monia et al. | |
| 5,591,840 A | 1/1997 | Narayanan et al. | |
| 5,603,915 A | 2/1997 | Nelson et al. | |
| 5,652,131 A | 7/1997 | Beavo et al. | |
| 5,734,039 A * | 3/1998 | Calabretta et al. | 536/24.5 |
| 5,776,905 A | 7/1998 | Gibbons et al. | |
| 5,801,154 A * | 9/1998 | Baracchini et al. | 514/44 A |
| 5,821,234 A * | 10/1998 | Dzau | 514/44 A |
| 5,830,140 A | 11/1998 | Dillinger et al. | |
| 5,834,443 A | 11/1998 | Masiello | |
| 5,849,902 A | 12/1998 | Arrow et al. | |
| 5,948,768 A | 9/1999 | McMichael et al. | |
| 5,951,455 A | 9/1999 | Cowsert | |
| 5,989,912 A | 11/1999 | Arrow et al. | |
| 5,998,203 A | 12/1999 | Matulic-Adamic et al. | |
| 6,008,048 A | 12/1999 | Monia et al. | |
| 6,015,886 A | 1/2000 | Dale et al. | |
| 6,037,346 A | 3/2000 | Doherty, Jr. et al. | |
| 6,087,112 A | 7/2000 | Dale | |
| 6,211,162 B1 | 4/2001 | Dale et al. | |
| 6,211,349 B1 | 4/2001 | Dale et al. | |
| 6,344,323 B1 * | 2/2002 | Seifert | 435/6 |
| 6,395,736 B1 | 5/2002 | Parks et al. | |
| 6,403,597 B1 | 6/2002 | Wilson et al. | |
| 6,440,723 B1 | 8/2002 | Dale | |
| 6,562,569 B1 | 5/2003 | Dale | |
| 6,582,908 B2 | 6/2003 | Fodor et al. | |
| 6,627,215 B1 | 9/2003 | Dale et al. | |
| 6,656,717 B1 | 12/2003 | Xin et al. | |
| 6,844,151 B1 | 1/2005 | Dale | |
| 2002/0032164 A1 | 3/2002 | Dale et al. | |
| 2002/0142980 A1 * | 10/2002 | Thompson et al. | 514/44 |
| 2003/0045490 A1 | 3/2003 | Dale et al. | |
| 2003/0083477 A1 | 5/2003 | Arrow et al. | |
| 2003/0180789 A1 | 9/2003 | Dale | |
| 2003/0207834 A1 | 11/2003 | Dale et al. | |
| 2004/0121352 A1 | 6/2004 | Dale | |
| 2005/0025815 A1 | 2/2005 | Dale et al. | |
| 2005/0107344 A1 | 5/2005 | Dale et al. | |
| 2005/0118618 A1 | 6/2005 | Dale | |
| 2008/0161257 A1 | 7/2008 | Dale et al. | |
| 2008/0167257 A1 | 7/2008 | Dale et al. | |
| 2008/0234214 A1 | 9/2008 | Dale et al. | |

FOREIGN PATENT DOCUMENTS

| | | |
|---|---|---|
| WO | WO 90/14074 A1 | 11/1990 |
| WO | WO 91/16024 A1 | 10/1991 |
| WO | WO 91/17424 A1 | 11/1991 |
| WO | WO 92/03568 | 3/1992 |
| WO | WO-9415619 A1 | 7/1994 |

(Continued)

OTHER PUBLICATIONS

Nemoz et al. FEBS Letters 1996, vol. 384, pp. 97-102.*

(Continued)

*Primary Examiner* — Tracy Vivlemore

(74) *Attorney, Agent, or Firm* — Mintz Levin Cohn Ferris Glovsky and Popeo, P.C.; Ingrid A. Beattie, Esq.

(57) ABSTRACT

The present invention relates to methods and compositions containing oligonucleotides suitable for administration to humans and other mammals.

6 Claims, No Drawings

(56) References Cited

FOREIGN PATENT DOCUMENTS

| | | |
|---|---|---|
| WO | WO 94/28144 A1 | 12/1994 |
| WO | WO 95/10938 | 4/1995 |
| WO | WO 95/15761 A1 | 6/1995 |
| WO | WO 9747325 A1 * | 12/1997 |
| WO | WO 98/03533 A1 | 1/1998 |
| WO | WO 98/13526 A1 | 4/1998 |
| WO | WO 98/49348 A1 | 11/1998 |
| WO | WO 99/14346 | 3/1999 |
| WO | WO-9953101 A1 | 10/1999 |
| WO | WO 00/40525 A2 | 7/2000 |
| WO | WO 00/40591 A1 | 7/2000 |
| WO | WO 00/40592 A1 | 7/2000 |
| WO | WO 00/40714 A2 | 7/2000 |
| WO | WO 00/57890 A1 | 10/2000 |
| WO | WO 00/70093 A1 | 11/2000 |
| WO | WO 01/23620 A2 | 4/2001 |
| WO | WO 02/000854 A1 | 11/2002 |
| WO | WO 02/089581 A1 | 11/2002 |
| WO | WO 03/006478 A1 | 11/2003 |

OTHER PUBLICATIONS

Doherty Current Opinion in Chemical Biology 1999, vol. 3, pp. 466-473.*
Taylor et al. Drug Discovery Today 1999 vol. 4, pp. 562-567.*
Bost et al., "The jun kinase 2 isoform is preferentially required for epidermal growth factor-induced transformation of human A549 lung carcinoma cells", *Mol. Cell. Biol*, 19(3):1938-1949 (1999).
Lisziewicz et al., "Specific inhibition of human immunodeficiency virus type 1 replication by antisense oligonucleotides: an in vitro model for treatment", *Proc. Natl. Acad. Sci. USA*, 89:11209-11213 (1992).
Normanno et al., "Growth inhibition of human colon carcinoma cellsby combinations of anti-epidermal growth factor-related growth factor antisense oligonucleotides", *Clin. Cancer Res.*, 2:601-609 (1996).
Agrawal et al., "Absorption, Tissue Distribution and In Vivo Stability in Rats of a Hybrid Antisense Oligonucleotide Following Oral Administration", Biochemical Pharmacology, v50 n4, pp. 571-576 (1995).
Agrawal et al., "Modified Oligonucleotides as Therapeutic and Diagnostic Agents", Current Opinion in Biotechnology, v 6 n1, pp. 12-19 (1995).
Agrawal et al., "Antisense Therapeutics: Is it as Simple as Simple as Complementary Base Recognition", Molecular Medicine Today, v 6 n2, pp. 72-81 (2000).
Altschul et al., "Issues in Searching Molecular Sequence Databases", Nature Genetics, v6, pp. 119-129 (1994).
Altschul et al., "Gapped BLAST and PSI-BLAST: A New Generation of Protein Database Search Programs", Nucleic Acid Research, v25 n17, pp. 3389-3402 (1997).
Belikova et al., Synthesis of Rebonucleosides and Diribonucleoside Phosphates Containing 2-Chloro-Ethylamine and Nitrogen Mustard Residues, Tetrahedron Letters, v37, pp. 3557-3562 (1967).
Bennett et al., "Parmacology of Antisense Therapeutic Agents", Methods in Molecular Medicine: Antisense Therapeutics, pp. 13-46 (1996).
Branch., "A Good Antisense Molecule Is Hard to Find", Trends in Biochemical Sciences, v23, pp. 45-50 (1998).
Chen et al., "In Vivo Expression of Single-Stranded DNA in Mammalian Cells With DNA Enzyme Sequences Targeted to C-raf", Antisense & Nucleic Acid Drug Development, v10. pp. 415-422 (2000).
Cohen et al., "Phosphorothioate Oligodeoxynucleotide Analogues", CRC Press:Boca Raton, FL, pp. 82-92, 97-117 (1989).
Dagle et al., "Oligonucleotide-Based Strategies to Reduce Gene Expression", Differentiation v69, pp. 75-82 (2001).
Egholm et al., "Peptide Nucleic Acids (PNA) Oligonucleotide Analogues With an Achiral Peptide Backbone", Journal American Chemical Society, v114, pp. 1895-1897 (1992).

Flanagan et al., "Cellular Penetration and Antisense Activity by a Phenoxazine-Substituted Heptanucleotide", Nature Biotechnology, v17 n1, pp. 48-52 (1999).
Froehler et al., "Phosporamidate Analogues of DNA: Synthesis and Thermal Stability of Heteroduplexes", Nucleic Acids Research, v16 n11, pp. 4831-4839 (1988).
Ghosh et al., "Evaluation of Some Properties of a Phosphorodithioate Oligodeoxyribonucleotide for Antisense Application", Nucleic Acids Research, v21 n24, pp. 5761-5765 (1993).
Green et al., "Antisense Oligonucleotides: An Evolving Technology for the Modulation of Gene Expression in Human Disease", Journal American College of Surgeons, v191 n1, pp. 93-105 (2000).
Henikoff et al., "Amino Acid Substitution Matrices From Protein Blocks", Proceedings of the National Academy of Sciences USA, v89, pp. 10915-10919 (1992).
Huang et al., "Acyclic Nucleic Acid Analogues: Synthesis and Oligomerization of Gamma, 4-Diamino-2oxo-1(2H)-pyrimidinepentanoic Acid and Delta, 4-Diamino-2-oxo-1(2H)-pyrimidinehexanoic Acid", Journal Organic Chemistry, v56, pp. 6007-6017 (1991).
Jen et al., "Suppression of Gene Expression by Targeted Disruption of Messenger RNA: Available Options and Current Strategies", Stem Cells, v18 n5, pp. 307-319 (2000).
Karlin et al., "Methods for Assessing the Statistical Significance of Molecular Sequence Features by Using General Scoring Schemes", Proceedings of the National Academy of Sciences USA, v 87:2264-2268 (1990).
Kushner et al., "Antisense Cancer Therapy: The State of the Science", Current Oncology Reports, v2, pp. 23-30 (2000).
Lesnick et al., "Ologiodeoxynucleotides Containing 2'-O-Modified Adeosine: Synthesis and Effects on Stability of DNA:RNA Duplexes", Biochemistry, v32 n30, pp. 7832-7838 (1993).
Ma et al., "Synthetic Oligonucleotides As Therapeutics: The Coming of Age", Biotechnology Annual Review, v5, pp. 155-196 (2000).
Marcus-Sekura et al., "Comparative Inhibition of Chloramphenicol Acetyltransferase Gene Expression by Antisense Oligonucleotide Analogus Having Alkyl Phospotriester, Methylphosphonate and Phosphothioate Linkages", Nucleic Acids Research, v15 n14, pp. 5749-5763 (1987).
Matthews et al., "Expanded Sequence Dependence of Thermodynamic Parameters Improves Prediction of RNA Secondary Structure", Journal Molecular Biology, v288, pp. 911-940 (1999).
Matthews et al., "Predicting Oligonucleotide Affinity to Nucleic Acid Targets", RNA, v5, pp. 1458-1469 (1999).
Micklefield., "Backbone Modification of Nucleic Acids: Synthesis, Structure and Therapeutic Applications", Current Medicinal Chemistry, v8 n10, pp. 1157-1179 (2001).
Milligan et al., "Current concepts in Antisense Drug Design", Journal of Medicinal Chemistry, v36 n14, pp. 1923-1937 (1993).
Miraglia et al., "Variations in mRNA Contect Have No Effect on the Potency of Antisense Oligonucleotides", Antisense & Nucleic Acid Drug Development, v10, pp. 453-461 (2000).
Neurath et al., "Cytokine Gene Transcription by NF-Kappa B Family Members in Patients With Inflammatory Bowel Disease", Annals of the New York Academy of Sciences, v859, pp. 149-159 (1998).
Neurath et al., "Local Administration of Antisense Phosphorothioate Oligonucleotides to the p65 Subunit of NF-Kappa B Abrogates Established Experimental Colitis in Mice", Nature Medicine, v2 n9, pp. 998-1004 (1996).
Rudin et al., "Phase I Trial of ISIS 5132, An Antisense Oligonucleotide Inhibitor of c-raf-1, Administered by 24-Hour Weekly Infusion to Patients With Advance Cancer", Clinical Cancer Research, v7, pp. 1214-1220 (2001).
Sambrook et al., "Molecular Cloning: A Laboratory Manual", Cold Spring Harbor Laboratory Press (1989).
Shibahara et al., "Inhibition of Human Immunodeficiency Virus (HIV-1) Replication by Synthetic Oligo-RNA Derivatives", Nucleic Acids Research, v17 n1, pp. 239-252 (1989).
Summerton., "Intracellular Inactivation of Specific Nucleotide Sequences: A General Approach to the Treatment of Viral Diseases and Virally-Mediated Cancers", Journal of Theoretical Biology, v78, pp. 77-99 (1979).

(56) References Cited

OTHER PUBLICATIONS

Summerton et al., "Sequence-specific Crosslinking Agents for Nucleic Acids", Journal of Molecular Biology, v122, pp. 145-162 (1978).
Vlassov et al., "Penetration of Oligonucleotides Into Mouse Organism Through Mucosa and Skin", Federation of European Biochemical Societies, v327 n3, pp. 271-274 (1993).
Weller et al., "Molecular Modeling of Acyclic Polyamide Oligonucleotide Analogues", Journal Organic Chemistry, v56 n21, pp. 6000-6006 (1991).
Zamecnik et al., "Inhibition of Rous Sarcoma Virus Replication and Cell Transformation by a Specific Oligodeoxynucleotide", Proceedings of the National Academy of Science USA, v75 n1, pp. 280-284 (1978).
Zhu et al., "Inhibition of the expression of Phosphodiesterase 5 by Antisense Inhibits the Growth of Human colon Carcinoma (HT-29) Cells in Culture", Journal for the Federation of American Societies for Experimental Biology, v15 n5, p. A924 (2001).
Zhu et al., "Stable Expression of Phospodiesterase (PDE) 5 Antisense in Human Colon Turmor HT29 Cell Is Associated With Delayed G2/M Cell Cycle Progression", Proceedings of the American Association for Cancer Research Annual Meeting, v43, p. 64 (2002).
Calculated melting temperature of sequence CCC CCA CCA CTT CCC CTC CT from the Oligonucleotide Properties Calculator at www.basic.northwestern.edu1biotoolsloiigocalc.html.
Galym, et al., "Complex Host Cell Responses to Antisense Suppression of ACHE Gene Expression", Antisese & Nucleic Acid Drug Development, 11:51-57 (2001).
National Center for Homeopathy Home Page. www.homeopathic.org.
Rubenstein, et al., "A Review of Various Antisense Oligonucleotide Therapeutic Approaches for Prostate Cancer" Prostate Journal, 2(4):179-188 (2000).
Shohami, et al., "Antisense Prevention of Neuronal Damages Following a Head Injury in Mice" J. Mol. Med., 78:228-236 (2000).
Dobashi et al. "Simultaneous Suppression of cdc2 and cdk2 Activities Induces Neuronal Differentiation of PC12 Cells." J. Biol. Chem. 275.17(Apr. 2000):12572-12580.
Miyake et al. "Inhibition of Progression to Androgen-Independence by Combined Adjuvant Treatment with Antisense BCL-XL and Antisense BCL-2 Oligonucleotides plus Taxol After Castration in the Shionogi Tumor Model." Int. J. Cancer. 86.6(Jun. 2000):855-862.
Francischi, et al., "Anti-inflammatory and analgesic effects of the phosphodiesterase 4 inhibitor rolipram in a rat model of arthritis", Eur J. Pharmacol., 2000, vol. 399, No. 2-3, pp. 243-249.
Higashi, et al., "Enhanced Expression of Cyclooxygenase (COX)-2 in Human Skin Epidermal Cancer Cells: Evidence for Growth Suppression by Inhibiting COX-2 Expression", Int. J. Cancer, vol. 86, pp. 667-671, 2000, ISSN: 0020-7136.
Khan, et al., "In Vivo Inhibition of Cyclooxygenase-2 by a Selective Phosphorothioated Oligonucleotide", Antisense & Nucleic Acid Drug Development, vol. 11, pp. 199-207, 2001, ISSN: 1087-2906.
Lazzeri, et al., "Effects of Prostaglandin $E_2$ and cAMP Elevating Drugs on GM-CSF Release by Cultured Human Airway Smooth Muscle Cells", Am. J. Respir. Cell Mol. Biol., vol. 24, pp. 44-48 2001, XP001180092ISSN: 1044-1549.
Mardini, et al., "Selective Inhibitors of Cyclooxygenase-2: A Growing Class of Anti-Inflammatory Drugs," Mol. Interv., 2001, vol. 1, No. 1, pp. 30-38.
Seibert, et al., "Pharmacological and biochemical demonstration of the role of cyclooxygenase 2 in inflammation and pain", Proc. Natl. Acad. Sci. USA, vol. 91, pp. 12013-12017, 1994, ISSN: 0027-8424.
Sumitani, et al., "Specific inhibition of cyclooxygenase-2 results in inhibition of proliferation of oral cancer cell lines via suppression of prostaglandin $E_2$ production", J. Oral Pathol. Med., vol. 30, pp. 41-47, 2001, ISSN: 0904-2512.
Yamada, et al., "Selective Inhibition of Cyclooxygenase-2 with Antisense Oligodeoxynucleotide Restricts Induction of Rat Adjuvant-Induced Arthritis", Biochemical and Biophysical Research Communications, vol. 269, pp. 415-421, 2000, ISSN: 0006-291X.
Agrawal et al. "Antisense Therapeutics." Curr. Opin. Chem. Biol. 2.4(1998):519-528.
Hughes et al. "The Cellular Delivery of Antisense Oligonucleotides and Ribozymes." Drug Disc. Today. 6.6(2001):303-315.
Okamoto et al. "Attempt for Liver-Targeted Delivery of Antisense Oligonucleotides by Cholesterol Modification and Oral Administration." Heptaol. Res. 13.3(1999):252-258.
Tortora et al. "Oral Antisense That Targets Protein Kinase A Cooperates With Taxol and Inhibits Tumor Growth, Antiogenesis and Growth Factor Production." Clin. Cancer Res. 6.1(2000):2506-2512.
Wang. "Antitumor Activity and Pharmacokineticc of a Mixed-Backbone Antisense Oligonucleotide Targeted to the RIα Subunit of Protein Kinase A After Oral Administration." PNAS. 96.24(1999):13989-13994.
Sano. "Genetic Therapy for Chronic Rheumatoid Arthritis." J. Clin. Exp. Med. (Igaku No Ayumi). 195.7(2000):463-468. (Japanese Original and English Translation).

* cited by examiner

OLIGONUCLEOTIDE-CONTAINING PHARMACOLOGICAL COMPOSITIONS AND THEIR USE

This application is a Continuation of U.S. patent application Ser. No. 10/191,997, "Oligonucleotide-Containing Pharmacological Compositions and Their Use", Roderic M. K. Dale, first author, filed Jul. 10, 2002, now abandoned and claims the benefit of U.S. Provisional Application No. 60/303,820, filed on Jul. 10, 2001.

FIELD OF THE INVENTION

The present invention relates to compositions containing oligonucleotides, and particularly to oligonucleotide-containing compositions suitable for administration to humans and other mammals.

BACKGROUND OF THE INVENTION

Oligonucleotides, oligonucleotide analogs and other sequence-specific binding polymers designed to block translation of selected messenger RNA (the sense strand) are commonly called antisense oligonucleotides. Development of such oligonucleotides, for therapeutic applications entails selecting a target genetic sequence unique and critical to the pathogen or pathogenic state one wishes to treat. One then assembles an oligomer of genetic bases (adenine, cytosine, guanine, and thymine or uracil) complementary to that selected sequence. When such an antisense oligonucleotide binds to its targeted disease-causing sequence, it can inactivate that target and thereby alleviate the disease.

Antisense oligonucleotides offer the prospect of safe and effective therapeutics for a broad range of intractable diseases. Nonetheless, developing therapeutics that function by a true antisense mechanism presents a number of forbidding challenges. The oligonucleotides should achieve adequate efficacy at a concentration attainable within the cells of the patient. They should inhibit their selected target sequences without concomitant attack on any other sequences in the patient's pool of approximately 200 million bases of unique-sequence RNA. They should be stable in extracellular compartments and within cells. They must be deliverable into the cellular compartments containing their targeted sequences. They should be adequately soluble in aqueous solution. Finally, they should exhibit little or no toxicity at therapeutic concentrations.

First-generation antisense oligonucleotides comprised natural genetic material (Belikova et al. (1967) Tetrahedron Lett. 37, 3557-3562; Zamecnik et al. (1978) Proc. Natl. Acad. Sci. USA 75, 280-284; Summerton (1979) J. Theor. Biol. 78, 77-99) and often contained crosslinking agents for binding their targets irreversibly (Summerton et al. (1978) J. Mol. Biol. 122, 145-162). As the design challenges became more fully appreciated, a number of non-natural antisense structural types were developed in an effort to improve efficacy, stability and delivery. Of particular note are the early non-ionic DNA analogs including phosphotriester-linked DNA and methylphosphonate-linked DNA (Cohen (1989) Oligodeoxynucleotides: Antisense Inhibitors of Gene Expression, CRC Press, pp. 82-92). Other nucleic acid analogs of note include carbamate-linked DNA (Cohen (1989) Oligodeoxynucleotides Antisense Inhibitors of Gene Expression, CRC Press, pp. 97-117), phosphoroamidate-linked DNA (Froehler et al. (1988) Nucleic Acids Res. 16, 4831-4839) and 2'-O-methyl RNA (Shibahara et al. (1989) Nucleic Acids Res. 17, 239-252). These second generation oligonucleotides include oligonucleotides containing acyclic backbone moieties, including nylon (Weller et al. (1991) J. Org. Chem. 56, 6000-6006; Huang et al. (1991) J. Org. Chem. 56, 6007-6018), the exceptionally high-affinity peptide nucleic acids (PNA) (Egholm et al. (1992) J. Am. Chem. Soc. 114, 1895-1897) and related types (U.S. Pat. No. 5,217,866).

One approach to improving the potency of antisense oligonucleotides is to enhance the affinity or the efficiency with which the antisense oligonucleotides interact with their targets and induce RNase degradation of their target gene transcripts. The doses at which effects have been observed generally range from 10 to 30 mg/kg i.v. (Miraglia et al. (2000) Antisense Nuc. Acid Drug Devel. 10, 453-461). Some clinical studies, however, have not demonstrated antisense activity at doses up to 30 mg/kg i.v. (Rudin et al. (2001) Clin. Cancer Res. 7, 1214-1220; Kushner et al. (2000) Curr. Oncol. Reports 2, 23-30), indicating that results vary based on the structure of the oligonucleotide administered. Typical dose-response curves for antisense oligonucleotides both in vivo and in vitro, often reveal that less than a factor of ten often separates the concentration producing antisense activity from the concentration producing no activity (Branch (1998) Trends Biochem. Sci. 23, 45-50). Since the ratio of antisense to non-antisense effects drops sharply outside a restricted concentration range, it remains challenging to identify common structural features for any antisense oligonucleotide that will enhance affinity and efficiency of the oligonucleotide for its target. Furthermore, no studies to date have identified common structural features of antisense oligonucleotides that would make them suitable for oral administration, thus necessitating intravenous administration (Chen et al. (2000) Antisense Nuc. Acid. Drug Develop. 10, 415-422). Identification of common structural modifications of antisense oligonucleotides that facilitate oral or topical administration would therefore also be advantageous.

Although each of these newer structural types provides one or more significant advantages over the first-generation oligonucleotides, none yet appear to provide the full combination of properties needed in antisense therapeutics for successful therapeutic applications.

SUMMARY OF THE INVENTION

The invention encompasses a composition suitable for administration in a mammal comprising a modified oligonucleotide of about seven to seventy-five nucleotides containing seven or more contiguous ribose groups linked by achiral 5' to 3' internucleoside phosphate linkages, wherein the modified oligonucleotide is complementary to a region of a gene associated with a pathological disorder. In some embodiments, the mammal is a human and the oligonucleotide is a ribonucleotide or deoxyribonucleotide. The modified oligonucleotide can be complementary to a region of the gene selected from the group consisting of the 5' UTR region, translational start site, the 3' UTR, and translational termination site.

In some embodiments, the gene is a gene selected from Table 1 and the pathological disorder is selected from the group consisting of abnormal appetite, hypertension, hypercholesteroremia, hyperlipidemia, erectile dysfunction, eczema, depression, anxiety, stress, inflammatory bowel syndrome, ulcerative colitis, Crohn's disease, renal stones, gall stones, constipation, migraine headache, seizure, multiple sclerosis, polymyositis, fibromyalgia, Parkinson's disease, ALS, chronic pain, pre-menstrual syndrome, sinusitis, colds, trauma, carpal tunnel syndrome, chronic fatigue syndrome, rosacea, arthritis, psoriasis, prostatitis, inflammation, heartburn, infection, poison ivy, colon cancer, malignant melanoma and malignant nasal polyps. In preferred embodiments, the modified oligonucleotide is selected from the group consisting of SEQ ID NO: 1-81

In some embodiments, the modified oligonucleotide is present in the composition at a concentration effective to reduce the expression of the gene when administered. When the composition is administered, the modified oligonucleotide is administered at a dose of less than 100 µg/kg, preferably less than 50 µg/kg, more preferably less than 5.0 µg/kg, even more preferably less than 0.50 µg/kg, yet even more preferably less than 0.050 µg/kg, and most preferably less than 0.0050 µg/kg. Furthermore, the modified oligonucleotide present in the composition may be suitable for oral administration.

The modified oligonucleotides present in the compositions of the invention preferably have a Tm of about 75-115° C. at a concentration of 1 mM and a length of 10 to 26 bases, or a Tm of 40° C. to 85° C. at a concentration of 1 pM and a length of 10 to 26 bases. In one embodiment, the ribose group has a modified 2' substituent selected from the group consisting of hydrogen, methoxy, propoxy, methoxy-ethoxy, flourine, chlorine, bromine and iodine. In another embodiment, the modified oligonucleotide is 3' or 5' end-blocked.

The compositions of the invention may be formulated as pharmaceutical compositions, nutritional or dietary supplement compositions, or as cosmetic compositions. In some embodiments, the compositions of the invention comprise two or more different modified oligonucleotides, while in other embodiments, three or more different modified oligonucleotides.

The invention also encompasses a method of treating a patient with a pathological disorder comprising administering one or more of the aforementioned modified oligonucleotides of the invention, wherein the modified oligonucleotides are about seven to seventy-five nucleotides, contain seven or more contiguous ribose groups linked by achiral 5' to 3' internucleoside phosphate linkages. Preferably, the modified oligonucleotide is complementary to a region of a gene associated with the pathological disorder. More preferably, the gene is selected from Table 1 and the aforementioned pathological disorders are selected from the group consisting of abnormal appetite, hypertension, hypercholesteroremia, hyperlipidemia, erectile dysfunction, eczema, depression, anxiety, stress, inflammatory bowel syndrome, ulcerative colitis, Crohn's disease, renal stones, gall stones, constipation, migraine headache, seizure, multiple sclerosis, polymyositis, fibromyalgia, Parkinson's disease, ALS, chronic pain, pre-menstrual syndrome, sinusitis, colds, trauma, carpal tunnel syndrome, chronic fatigue syndrome, rosacea, arthritis, psoriasis, prostatitis, inflammation, heart burn, infection, poison ivy, colon cancer, malignant melanoma and malignant nasal polyps.

As mentioned above, the invention includes a nutritional supplement comprising a modified oligonucleotide of about seven to seventy-file nucleotides containing seven or more contiguous ribose groups linked by achiral 5' to 3' internucleoside phosphate linkages. The invention also includes a method of supplementing the diet of an individual comprising administering this nutritional supplement, wherein administration of the nutritional supplement improves the health of the individual.

The invention further includes a cosmetic composition comprising a modified oligonucleotide of about seven to seventy-file nucleotides containing seven or more contiguous ribose groups linked by achiral 5' to 3' internucleoside phosphate linkages, wherein the modified oligonucleotide is complementary to a region of a gene associated with a skin disorder. The invention also includes a method of improving the appearance of the skin in an individual with a skin disorder comprising administering this cosmetic composition.

DETAILED DESCRIPTION

The present invention relates to compositions that comprise oligonucleotide molecules, and the use of such compositions to treat the symptoms of diseases/conditions such as acroparaesthsia, allergic (psoric) conditions, allergic reactions, alopecia, amnesia, anaphrodisia, angina, arthritis, asthenopia, biliary sycosis, burns, cancerous conditions, such as colon cancer, malignant melanoma and malignant nasal polyps, carpal tunnel syndrome, colds, conjunctivitis, Crohn's disease, depression, depressive psychosis, dysthyroidism, epilepsy, erectile dysfunction, excessive appetite (i.e., appetite control and suppression, promotion of healthy weight loss while naturally satisfying the appetite), gingivitis, heart burn (i.e., relief of occasional heartburn or occasional acid indigestion), hemorrhage, hypertension (i.e. helps maintain cardiovascular function, and a healthy heart and circulatory system), high cholesterol (i.e., helps to maintain cholesterol levels that are already within the normal range), hyperthyroidism, infections, inflammatory disease, lack of willpower, laryngitis, leucopenia, liver disorders, mental disorders (i.e., reduces stress, frustration, muscle tension, anxiety, and occasional simple nervous tension; enhances resistance to stress), myopia, neurosis, neurological disorders such as multiple sclerosis and ALS, obesity, pain (i.e., relief of minor or temporary aches and pains), pancreatic disorders, poison ivy, premature senescence, pre-menstrual syndrome (i.e., treatment of common symptoms associated with the menstrual cycle such as edema, breast tenderness, headaches, skin problems, cramps and mild mood changes), prostatitis, psoriasis, rosacea, seborrhea, sinusitis, and trauma.

The Oligonucleotide

Generally

A double-stranded DNA molecule encoding a gene has both a sense and an antisense strand. The transcription of RNA uses the antisense strand to make an exact sequence copy of the sense strand (with the minor changes of employing uridine for thymidine, and an RNA backbone in lieu of a DNA backbone). Thus, the RNA formed in transcription has the same nucleotide sequence as the sense strand of the gene. The RNA transcript is processed in the cell to become mRNA, which may subsequently be used as a template to make protein.

The term "oligonucleotides" as used herein, refers to a molecule comprised of nucleotides (i.e., ribonucleotides, deoxyribonucleotides, or both). The term includes monomers and polymers of ribonucleotides and deoxyribonucleotides, or mixtures thereof, with the nucleotides being connected together via, for example 5' to 3' linkages, 5' to 2' linkages, etc. The nucleotides used in the oligonucleotides may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, etc.

The oligonucleotides of the present invention are at least five contiguous nucleotides in length. For example, the oligonucleotide can be five to seventy-five nucleotides in length.

The oligonucleotide can also be at least ten sequential nucleotides and alternatively, at least fifteen sequential nucleotides in length. In one embodiment, the oligonucleotide is twelve to twenty-six nucleotides in length. The oligonucleotide sequence can be derived from any of the genes listed in Table 1 (SEQ ID NO: 82-132). Examples of suitable antisense oligonucleotide sequences for the compositions of the present invention are described in Table 1 below.

TABLE 1

Representative antisense oligonucleotides

| Oligo Name(s) | Gene Target (Accession #) | Nucleic Acid Sequence | SEQ ID |
|---|---|---|---|
| Asm | PDE-4 phosphodiesterase 4 (U50158) (SEQ ID NO: 82) | CGTGTCAGGAGAAC | 1 |
| Ace1, Ace12 | angiotensin I converting enzyme (J04144.1) (SEQ ID NO: 83) | CATGACGCGGTGCG | 2 |
| Acid-2 | ATP4A H+/K+ ATPase alpha (NM_000704) (SEQ ID NO: 84) | GGCAGTCGTCCCTCTA | 3 |
| Acid B2 | ATP4B H+/K+ ATPase beta (NM_000705) (SEQ ID NO: 85) | AACGTTTCACTTCTCA | 4 |
| cd18-1 | Cd-18 (M15395) (SEQ ID NO: 86) | TTGCTACCAGTCT | 5 |
| COX2 CX2 | cyclooxygenase 2 (M90100) (SEQ ID NO: 87) | TCTACAGTTCAGTCGA | 6 |
| Mg44 | HMGCoA reductase 3-hydroxy-3-methylglutaryl-coenzyme A reductase (NM_000859) (SEQ ID NO: 88) | TGACAACATTGTAGCTAC, AGCTACAGAATCCTTGGA, GTCGGGCTATTCAGGC | 7 8 9 |
| P65-2M 65 | NfkappaB p65 (NM_021975) (SEQ ID NO: 89) | GAACAGTTCGTCCATG | 10 |
| IL-501 | IL-5 (NM_000879) (SEQ ID NO: 90) | CCTCATGGCTCTGAA | 11 |
| LO5 | lipoxygenase 5 (J03571) (SEQ ID NO: 91) | GGAGGGCATGGCGCGG | 12 |
| MPB-19 | SRD5A2 steroid 5-alpha-reductase-2 (M74047) (SEQ ID NO: 92) | CCTGCATCGCGCCGTG | 13 |
| NEP-1 CALLA | neutral endopeptidase (NM_000902) (SEQ ID NO: 93) | GACTTGCCCATCACCT | 14 |
| NPY-1 | Neuropeptide Y (K01911) (SEQ ID NO: 94) | ACCTAGCATGGTGGCT | 15 |
| D5 PDE5.1 | phosphodiesterase 5 (SEG_AB001615) (SEQ ID NO: 95) | CGCTCCATGGTTGGC | 16 |

TABLE 1-continued

Representative antisense oligonucleotides

| Oligo Name(s) | Gene Target (Accession #) | Nucleic Acid Sequence | SEQ ID |
|---|---|---|---|
| D7 | phosphodiesterase 7A (L12052) (SEQ ID NO: 96) | CTTCCATTGAATACGC | 17 |
| Per | Perilipin (AB005293) (SEQ ID NO: 97) | ACTGCCATCCTCGCTC | 18 |
| TTP TTPII | tripeptidyl peptidase II (M73047) (SEQ ID NO: 98) | CGGTGGCCATGGACGC, AAGTTCATGGTTTCGGA | 19 20 |
| MTP | Microsomal triglyceride protein (X59657) (SEQ ID NO: 99) | GAATCATATTTGACCAGCA | 21 |
| HisR1 | Histamine receptor 1 (D14436) (SEQ ID NO: 100) | GGCTCATTGGCGCAAG, AGAGCCTCCCTTAGGA | 22 23 |
| CRP | C-reactive protein (M11880) (SEQ ID NO: 101) | CATGGTCACGTCCTGC | 24 |
| CETP | Cholesteryl ester transfer protein (XM_008050) (SEQ ID NO: 102) | ATGGTTATCAGGCAGTGG, CATGGTTATCAGGCAGTGG, CTGAAGAATTGACCAC | 25 26 27 |
| ICAM | ICAM-1 (J03132) (SEQ ID NO: 103) | CATAGCGAGGCTGAGG | 28 |
| TNF-α | Tumor necrosis factor-alpha (X02910) (SEQ ID NO: 104) | GTGCTCATGGTGTCC | 29 |
| BMP-4 | Bone morphogenic protein-4 (U43842) (SEQ ID NO: 105) | CGACCATCAGCATTC | 30 |
| BAR-1, BB1 | beta adrenergic receptor-1 (NM_000684) (SEQ ID NO: 106) | GCCCATGCCGAGCTGC | 31 |
| IL-6 | Interleukin-6 (X04430) (SEQ ID NO: 107) | AGGAGTTCATAGCTGG | 32 |
| FAAH, FA$_2$H | fatty acid amid hydrolase (U82535) (SEQ ID NO: 108) | GCACCATGATCCCTTC | 33 |
| ACAT-1 | sterol-O-acyl-transferase (XM_031119) (SEQ ID NO: 109) | CTTCACCCACCATTGT | 34 |
| IBAT | ileal sodium dependent bile acid transporter (NM_000452) (SEQ ID NO: 110) | CATTCATTGCTGGGTCTG | 35 |
| HMGIC | Highly mobility group phosphor-protein isoform C (U28749) (SEQ ID NO: 111) | CGTGCGCTCATCCTG, AACGTTGCGCCCCCTA | 36 37 |
| Ghre | Ghrelin (NM_016362) (SEQ ID NO: 112) | TGCAGACAGGTGGGCC, GCATGGCCTCAGCTGGG, TGGGCGATACACTTGTC | 38 39 40 |

TABLE 1-continued

Representative antisense oligonucleotides

| Oligo Name(s) | Gene Target (Accession #) | Nucleic Acid Sequence | SEQ ID |
|---|---|---|---|
| AAT1R | angiotensin II receptor (S77410) (SEQ ID NO: 113) | CATTTTGATCACCTGGGT, CGAACATGTCACTCAA | 41 42 |
| VEGF | vascular endothelial growth factor (XM_166457) (SEQ ID NO: 114) | AAGTTCATGGTTTCGGA, TCACCGCCTCGGCTTGT | 43 44 |
| FAS | fatty acid synthase (U29344) (SEQ ID NO: 115) | CCTCCTCCATGGCTG, GCCTAGCCCTCCCGC | 45 46 |
| AmP | amyloid P (NM_001639) (SEQ ID NO: 116) | GCAGCGGCTTGTTCAT, GAGTCAAGACCTCAG | 47 48 |
| PanLip | pancreatic lipase (NM_000936) (SEQ ID NO: 117) | GTGGCAGCATCGTGGC, CCTAACACGGTGTGAG | 49 50 |
| ACC2 | Acetyl-CoA carboxylase (U89344) (SEQ ID NO: 118) | GAAGCAAGACCATTCAG, TCAGGTGGAGGCCGGGC | 51 52 |
| PKARIIbeta | cAMP dependent protein kinase subunit RII-beta (M31158) (SEQ ID NO: 119) | TGCTCATCCTGCCTCC, GCTTCATGCAGTGGGT | 53 54 |
| VR1R | vanilloid receptor subtype 1 (XM_008512) (SEQ ID NO: 120) | TCTTCATCCTTGCTGG, CTCACTTCTCCCCGGA | 55 56 |
| ADAMTS | disintegrin-like and metalloprotease with thrombospodin type 1 motif 4 (NM_005099) (SEQ ID NO: 121) | GGGACATGGCACTGGT, TTATTTCCTGCCCGCC | 57 58 |
| NPY-Y5R | neuropeptide Y5 receptor (U94320) (SEQ ID NO: 122) | TGTGGCAGGTCAGTTG, ATCCATATTATAGTCT, TATTACATATGAAGAC | 59 60 61 |
| GNTV | mannosyl (alpha-1,6)glycoprotein beta-1,6-N-acetyl glucosaminyl transferase (NM_002410) (SEQ ID NO: 123) | AGCCATTGCTCTCTGG, TGCTATAGGCAGTCTT | 62 63 |
| FCRG3 | FC-gamma receptor III-1 (X16863) (SEQ ID NO: 124) | TGCCACATGATGCCAC, GTTGAGCTTCAAATGT | 64 65 |
| CD40L | tumor necrosis factor (ligand) superfamily, member 5 (XM_042961) (SEQ ID NO: 125) | TCGATCATGCTGTGTT, AGGTGACACTGTTCAG | 66 67 |
| ETS-1 | erythorblastosis virus oncogene homolog 1 (J04101) (SEQ ID NO: 126) | ACGGCCGCCTTCATGG, GCCATCACTCGTCGGC | 68 69 |
| ADAMTS-5 | disintegrin-like metalloprotease with throbospondin type 1, motif 5 (XM_047802) (SEQ ID NO: 127) | CCGAGCAGCATAGTGC, TCATAACCACAGGCTA | 70 71 |

TABLE 1-continued

Representative antisense oligonucleotides

| Oligo Name(s) | Gene Target (Accession #) | Nucleic Acid Sequence | SEQ ID |
|---|---|---|---|
| PTP-1B | protein tyrosine phosphatase, non-receptor type 1 (NM_002827) (SEQ ID NO: 128) | CATGACGGGCCAGGGC, GGGTCAGGCTATGTGT | 72 73 |
| MMP-1 | matrix metalloprotrinase 1 (NM_002421) (SEQ ID NO: 129) | GCATACTGGCCTTTGTC, TCAATTTTTCCTGCAGT | 74 75 |
| Cat | catalase (NM_001752) (SEQ ID NO: 130) | GCCATAGCGTGCGGTT, CCCGGCCTCACAGATT | 76 77 |
| MMP-17 | matrix metalloproteinase 17 (NM_016155) (SEQ ID NO: 131) | CATGGCGCTCACATGGG, TGTCATAGCGTCAGGGC | 78 79 |
| OPG | osteoprotegerin (U94332) (SEQ ID NO: 132) | TCATTGTGGTCCCCGG, TCCAGTTATAAGCAGC | 80 81 |
| Nu-3 | | 3'5'-dibutyl-diphospho-thymidine | |

In one embodiment, the oligonucleotide composition of the present invention comprises at least about two oligonucleotides of differing sequence. In another embodiment, the oligonucleotide composition of the present invention comprises at least about three, four, five, six, seven, eight, nine, or ten oligonucleotides of differing sequences. Although Table 1 depicts the sequences as oligonucleotides containing only deoxyribonucleotide residues, it is to be understood that the present invention also includes the embodiments wherein the oligonucleotides are composed of ribonucleotide residues (e.g., by substituting uridine for thymidine, and ribosyl substituents for deoxyribosyl substituents). Moreover, it is to be understood that the present invention also includes the embodiments in which the oligonucleotides are composed of only deoxyribonucleotide residues, of only ribonucleotide residues, or of mixtures of deoxyribonucleotide and ribonucleotide residues.

The oligonucleotides in the present invention display greater than or equal to 80 percent sequence identity to a nucleotide sequence selected from the group of SEQ ID NO: 1-81 (see Table 1). Also preferred, the oligonucleotides display greater than or equal to 85 percent sequence identity to a nucleotide sequence selected from the group of SEQ ID NO: 1-81. Still preferred, the oligonucleotides display 90 percent sequence identity and still more preferred, the oligonucleotides display 95 percent sequence identity. Most preferably, the oligonucleotides of the present invention are selected such that their nucleotide sequence is complementary to the sense strand of a gene.

The degree of similarity between two sequences can be determined using methods well known to the art (e.g., computer programs including Fasta (Oxford Molecular Group Inc.) and BLAST (www.ncbi.nlm.nih.gov) (Altschul et al. (1997) Nucleic Acid Res. 25, 3389-3402). These methods can be employed to take into account gaps in the sequences due to deletions or insertions. Homology or sequence identity at the nucleotide or amino acid sequence level determined by BLAST (Basic Local Alignment Search Tool) analysis uses the algorithm employed by the programs blastp, blastn, blastx, tblastn and tblastx (Altschul et al. (1997) Nucleic Acids Res. 25, 3389-3402 and Karlin et al. (1990) Proc. Natl. Acad. Sci. USA 87, 2264-2268, both fully incorporated by reference) which are tailored for sequence similarity searching. The approach used by the BLAST program is to first consider similar segments, with gaps (non-contiguous) and without gaps (contiguous), between a query sequence and a database sequence, then to evaluate the statistical significance of all matches that are identified and finally to summarize only those matches which satisfy a preselected threshold of significance.

For a discussion of basic issues in similarity searching of sequence databases, see Altschul et al. (1994) Nature Genetics 6, 119-129 which is fully incorporated by reference. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al. (1992) Proc. Natl. Acad. Sci. USA 89, 10915-10919, fully incorporated by reference), recommended for query sequences over 85 nucleotides or amino acids in length.

For blastn, the scoring matrix is set by the ratios of M (i.e., the reward score for a pair of matching residues) to N (i.e., the penalty score for mismatching residues), wherein the default values for M and N are +5 and −4, respectively. Four blastn parameters were adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In a related vein, the oligonucleotides described herein have a Guanine:Cytosine (GC content) greater than 35 percent. The GC content is preferably greater than 40 percent and most preferably, greater than 45 percent.

The Modified Oligonucleotide

The oligonucleotides that may be employed in accordance with the present invention may be modified. An oligonucleotide that comprises at least one modification has one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. For example, oligonucleotides can be end-blocked, protonated, exhibit substantial acid resistance, substantial nuclease resistance, and contain achiral internucleoside phosphate linkages and modified ribose or deoxyribose substituents.

The term "end-blocked" as used herein refers to a nucleic acid with a chemical modification at the molecular level that prevents the degradation of selected nucleotides, e.g., by exonuclease action. This chemical modification is positioned such that it protects the integral portion of the nucleic acid, for example the portion of an RNA or DNA that is chemically similar to the gene involved in the physiological condition. An end block may be a 3' end block, a 5' end block, or both. For example, a 3' end block may be at the 3'-most position of the molecule, or it may be internal to the 3' ends, provided it is 3' of the integral sequences of the nucleic acid.

The term "protonated compound" refers to a molecule of the invention that, when dissolved in water having a pH of 7 causes the pH of the solution to fall. Generally, compounds are protonated by adding protons to the reactive sites on the molecule, although other modifications of the molecule are possible, and are intended to be encompassed by this term. Such protonation can be accomplished, for example by incubating the compound in the presence of a strong acid, most preferably one with a volatile conjugate base. The term "protonation" and "acidification" as used interchangeably herein refers to the process by which protons (or positively charged hydrogen ions) are added to proton acceptor sites on a compound of the invention. The proton acceptor sites include the substituted or unsubstituted phosphates of the central group, as well as any additional proton acceptor sites on either the central group or the end blocking groups. As the pH of the solution is decreased, the number of these acceptor sites which are protonated increases, resulting in a more highly protonated compound.

Many nucleic acid backbones are not stable at low pH (e.g., pH 1-3) and experience depurination, although a number of backbones are relatively stable at pH 4-5. One aspect of the present invention reflects the recognition that certain modifications, including 2'-halide, 2'-O-alkyl, 3'-O-alkyl, and 2'-O-alkyl-n(O-alkyl) nucleic acid molecules are stable at the desired pH of 2 to 1. These modifications enhance the ability of the oligonucleotides of the pharmacological compositions of the present invention to affect a condition in vivo. Thus, the composition of the present invention may include nucleic acid molecules that are substantially acid resistant. The compositions of the present invention may also include nucleic acid molecules that are nuclease resistant. This includes nucleic acid molecules completely derivatized by 2'-O-methylphosphodiesters, 2'-O-alkyl, 2'-O-alkyl-n(O-alkyl), 2'-fluoro, 2'-deoxy-erythropentofuranosyl, chimeric linkages, and any other backbone modifications, as well as other modifications, which render the nucleic acid molecules substantially resistant to endogenous nuclease activity. Additional suitable methods of rendering nucleic acid molecules nuclease resistant include, but are not limited to, covalently modifying the purine or pyrimidine bases that comprise the nucleic acid. For example, bases may be methylated, hydroxymethylated, or otherwise substituted (e.g., glycosylated) such that the nucleic acid molecules comprising the modified bases are rendered substantially nuclease resistant. Nuclease resistance also aids the oligonucleotides of the compositions of the present invention in retaining their effect in vivo.

Preferably, the oligonucleotides of the of the present invention remain relatively unchanged chemically upon administration to a subject and retain their activity in acidic conditions (pH less than 6.0) or in the presence of an endonuclease or exonuclease (e.g., in an in vivo setting).

The term "substantially acid resistant" as used herein refers to nucleic acid molecules that are resistant to acid degradation as compared to unmodified nucleic acid molecules. Typically, the relative acid resistance of a nucleic acid will be measured by comparing the percent degradation of a resistant nucleic acid with the percent degradation of its unmodified counterpart (i.e., a corresponding nucleic acid of the same length and sequence having a "normal" backbone and bases). A nucleic acid that is acid resistant is preferably at least one and a half times more resistant to acid degradation, more preferably at least two times more resistant, even more preferably at least five times more resistant, and most preferably at least ten times more resistant than their unmodified counterpart.

Although certain acid resistant nucleic acid molecules exhibit marked acid stability and endonuclease resistance, they are sensitive to 3' exonucleases. In order to enhance the exonuclease resistance of 2'-O-alkyl substituted nucleic acid molecules, the 3' or 5' and 3' ends of the nucleic acid are preferably attached to a chemical moiety that provides an exonuclease blocking function. For example, one or more phosphorothioate nucleotides can be placed at either end of the RNA or DNA. Additionally, one or more inverted bases can be placed on either end of the RNA or DNA, or one or more alkyl or alcohol (e.g., butanol-substituted) nucleotides or chemical groups can be placed on one or both ends. Accordingly, a preferred embodiment of the present invention is a nucleic acid comprising a nucleic acid having the following structure: A-B-C, wherein "B" is a 2'-O-alkyl or 2'-O-alkyl-n(O-alkyl) substituted RNA between about 1 and about 98 bases in length, and "A" and "C" are respective 5' and 3' end blocking groups (e.g., one or more phosphorothioate nucleotides (but typically fewer than six), inverted base linkages, or alkyl, alkenyl, alkynyl, O-alkyl, and O-alkyl-n (O-alkyl) groups or substituted nucleotides). A partial list of blocking groups includes inverted bases, dideoxynucleotides, methylphosphates, alkyl groups, aryl groups, cordycepin, cytosine arabanoside, 2'-methoxy, ethoxy nucleotides, phosphoramidates, a peptide linkage, dinitrophenyl group, 2'- or 3'-O-methyl bases with phosphorothioate linkages, 3'-O-methyl bases, fluorescein, cholesterol, biotin, acridine, rhodamine, psoralen, glyceryl, methyl phosphonates, butanol, butyl, hexanol, and 3'-O-alkyls. An enzyme-resistant butanol preferably has the structure OH—$CH_2CH_2CH_2CH_2$ (4-hydroxybutyl), which is also referred to as a C4 spacer.

The term "substantially nuclease resistant" refers to nucleic acid molecules that are resistant to nuclease degradation, as compared to naturally occurring or unmodified nucleic acid molecules. Modified oligonucleotides of the invention are at least 1.25 times more resistant to nuclease degradation than an unmodified nucleic acid having the same sequence and number of nucleotides, more preferably at least 2 times more resistant, even more preferably at least 5 times more resistant, and most preferably at least 10 times more resistant than their unmodified counterpart. Such substantially nuclease resistant nucleic acid molecules include, but are not limited to, nucleic acid molecules with modified backbones such as ethylphosphotriesters, 2'-O-methylphosphorothioates, 2'-O-methyl-p-ethoxy ribonucleotides, 2'-O-alkyls, 2'-O-alkyl-n(O-alkyl), 2'-fluoros, 2'-deoxy-erythropentofuranosyls, 2'-O-methyl ribonucleosides, 3'-O-methylribonucleotides, inverted bases (e.g., inverted T's), or chimeric versions of these backbones.

The modified oligonucleotide includes RNA or DNA comprising modifications to the sugar moieties such as 2'-substituted or 3'-substituted ribonucleotides, or deoxyribonucleotide monomers, any of which are connected together via internucleoside linkages. Modified RNA or DNA may also be comprised of PNA or morpholino modified backbones where specificity of the sequence is maintained.

The ribose groups and the internucleoside linkages link the bases in a nucleic acid and are referred to as the nucleic acid backbone. A modified backbone includes modifications to the chemical linkage between nucleotides, as well as other modifications that may be used to enhance stability and affinity, such as modifications to the sugar structure. For example, an L-anomer of deoxyribose may be used, where the base is inverted with respect to the natural D-anomer. In one embodiment, the 2'-OH of the sugar group may be altered to 2'-halogen, 2'-O-alkyl or 2'-O-alkyl-n(O-alkyl), which provides resistance to degradation without compromising affinity. Other suitable modified backbones include the following types of internucleotide linkages: 2'-O-methyl-phosphodiesters, 2'-O-alkyl, 2'-O-ethyl, 2'-O-propyl, 2'-O-butyl, 2'-O-alkyl-n(O-alkyl), 2'-methoxyethoxy, 2'-fluoro, 2'-deoxy-erythropentofuranosyl, 3'-O-methyl, p-isopropyl oligonucleotides, 2'-O(CH$_2$CH$_2$O)$_x$CH$_3$, and/or butyne linkages. An oligonucleotide may have combinations of such modified backbones, may be completely modified, or may comprise all or some linkages being phosphodiester linkages.

Preferred internucleoside linkages on the modified oligonucleotide are achiral. The term "achiral" as used herein, refers to a molecule that is superimposable with its mirror image, whereas the term "chiral" refers to a molecule that is not superimposable with its mirror image. Oligonucleotides containing achiral 5' to 3' internucleoside phosphate linkages have internucleotide linkages which are achiral (i.e., no stereochemistry). The achiral oligonucleotides preferably contain at least about three to eight contiguous achiral internucleoside linkages, more preferably, nine to ten contiguous achiral internucleoside linkages, even more preferably, eleven to twelve contiguous achiral internucleoside linkages, and most preferably, is completely comprised of achiral internucleoside linkages through the entire contiguous sequence. In another embodiment, the achiral internucleoside linkages are interspersed with chiral internucleoside linkages (e.g., two contiguous achiral linkages followed by one chiral linkage followed by two contiguous achiral linkages; three contiguous achiral linkages followed by one chiral linkage; four contiguous achiral linkages followed by two achiral linkages, etc.). Examples of achiral internucleoside linkages include, but are not limited to, phosphodiester and diphosphorothioate linkages. Achiral RNA and DNA linkages in the backbone are routinely generated during automated synthesis of oligonucleotides if the final structure is a symmetrical molecule (i.e., a phosphate with the same atom attached to both sides).

The internucleoside phosphate linkages can be phosphodiester, or 3' to 3', 5' to 2' or 5' to 5' linkages, and combinations of such similar linkages (to produce mixed backbone modified RNA or DNA). The modifications can be internal (single or repeated) or at the end(s) of the RNA or DNA molecule. These modifications can include additions to the nucleic acid molecule, such as cholesteryl, diamine compounds with varying numbers of carbon residues between amino groups and terminal ribose, and deoxyribose or phosphate modifications which cleave or cross-link to the opposite chains or to associated enzymes or other proteins. Electrophilic groups such as ribose-dialdehyde could covalently link with an epsilon amino group of the lysyl-residue of such a protein. A nucleophilic group such as n-ethylmaleimide tethered to an RNA or DNA could covalently attach to the 5' end of an mRNA or to another electrophilic site.

Suitable oligonucleotides for the present invention can be determined by evaluating the Delta G or Gibbs Free energy of oligonucleotide binding to the complementary RNA strand at 37° C. and the Tm. The Gibbs Free energy and Tm are measured from the part of the target gene that corresponds to the RNA oligonucleotide that is added. These values can be calculated using the program found on ftp://rna.chem.rochester.edu and are described in Matthews et al. (1999) J. Mol. Biol. 288, 911-940 and Matthews et al. (1999) RNA 5, 1458-1469.

Accordingly, a composition comprising an oligonucleotide, (i) wherein said oligonucleotide is at least 10 nucleotides in length, (ii) the Gibbs Free energy of the binding of said oligonucleotide/RNA target duplex at 37° C. is −15 kCal, (iii) said oligonucleotide is complementary to a region within the target gene selected from the group consisting of 5' UTR, translational start site and translational termination site and (iv) wherein said target gene is a gene as listed in Table 1. The Gibbs free energy is measured between that part of the target gene that corresponds to the oligonucleotide, that part typically being the 5'UTR, translational start site or the translational termination site.

In a preferred embodiment, the Gibbs Free energy of the binding of said oligonucleotide/RNA target duplex at 37° C. is ≤−20 kCal. Also preferred, the Gibbs Free energy is ≤−25 kCal. For 12-14 mer oligonucleotides, the Gibbs Free energy is preferably ≤−15 kCal, for 15-17 mer oligonucleotides, the Gibbs Free energy is preferably ≤−20 kCal, for 18-20 mer oligonucleotides, the Gibbs Free energy is preferably ≤−25 kCal, for 21-23 mer oligonucleotides, the Gibbs Free energy is ≤−30 kCal, and for 24-26 mer oligonucleotides, the Gibbs Free energy is ≤35 kCal.

Further described in the present invention is a composition comprising an oligonucleotide, (i) wherein said oligonucleotide is at least 10 nucleotides in length, (ii) the Tm of said oligonucleotide to a target gene is about 65-90° C., (iii) said oligonucleotide is complementary to a region within the target gene selected from the group consisting of 5' UTR, translational start site an termination site, and (iv) wherein said target gene is selected from a gene as listed in Table 1. Preferably, the oligonucleotide has a Tm of about 75-90° C. Still preferred, the oligonucleotide has a Tm of about 85-90° C. Still preferred, the Tm of said oligonucleotide to a target gene at 1M monovalent cation concentration is about 65-90° C. The Gibbs free energy is measured between that part of the target gene that corresponds to the oligonucleotide, that part typically being the 5' UTR, translational start site or the translational termination site.

Nutritional Supplements

As used herein, the term "nutritional supplement" refers to a composition that is intended to supplement the diet. A nutritional supplement includes any dietary substance used in mammals to supplement the diet by increasing total dietary intake; or a concentrate, metabolite, constituent, extract, etc. Nutritional supplement includes any product that is intended for ingestion in tablet, capsule, powder, soft-gel, gel-cap, or liquid form. As used herein, the term "nutritional supplement" is used synomously with the term "dietary supplement" and "nutraceutical" throughout the specification.

The present invention provides a composition which is useful as a nutritional supplement to maintain or improve the an individual's health. Preferred indications for dietary supplements include, hut are not limited to, maintenance of cardiovascular function and a healthy circulatory system, maintenance of cholesterol levels that are already within the normal range, reduction of stress and frustration, relief of occasional simple nervous tension, relief of nervousness due to common everyday overwork and fatigue, alleviation of restlessness, reduction in nervous irritability, relief from anxiety, relief of muscle tension, enhancement of resistance to stress, promotion of emotional balance and a positive outlook, relief of sour stomach or upset stomach, relief of occasional heartburn or occasional acid indigestion, appetite suppression, promotion of healthy weight loss while naturally satisfying the appetite, appetite control, relief of minor or temporary aches and pains, treatment of common symptoms associated with the menstrual cycle, treatment of mild mood changes, cramps, and edema associated with the menstrual cycle, maintenance of a normal, healthy attitude during premenstrual syndrome, diminish the normal symptoms of premenstrual syndrome and maintenance of hormonal balance and alleviation of minor pre-menstrual syndrome symptoms such as cramping, breast tenderness, minor mood changes, headaches, bloating and skin problems.

The nutritional supplement composition of the present invention include compositions with a single oligonucleotide and/or a combination of about two or more oligonucleotides. The use of the nutritional supplement compositions of the present invention can be used to treat any of the aforementioned indications. These agents may be combined in an oral dosage with other well known nutritional supplements and/or non-flavonoid antioxidants (e.g., selenium, vitamin E (tocopherol, particularly alpha-tocopherol), vitamin C (ascorbic acid) and coenzyme Q10). Dietary fiber supplements may also be used in the composition.

Other additives may be incorporated in the nutritional supplement of the present invention. Such additives include minerals, (e.g., boron, etc. and trace metals such as zinc, magnesium, manganese, chromium, molybdenum, copper, iron, calcium, and potassium; and other micronutrients such as thiamine, riboflavin, niacin, pantothenic acid, pyridoxine, choline, biotin, inositol, para-aminobenzoic acid, vitamin D, vitamin K, vitamin A). In another embodiment of the invention a dietary fiber supplement such as oat bran or other natural fiber source may also be added to the composition.

Typically the nutritional supplement will further include a pharmaceutically acceptable carrier such as lactose, glucose, sucrose, corn starch, potato starch, cellulose acetate, ethyl cellulose, etc. Diluents and other additives such as one or more pharmaceutically acceptable binding agents, fillers, supports, thickening agents, taste-improving agents, coloring agents, preservatives, stabilizers, regulators, emulsifiers or mixtures thereof may be used depending on the form of the composition employed.

In addition to providing the aforementioned compositions, the invention also includes a method for orally administering the nutritional supplement composition in dosages effective to aid in the maintenance and improvement of an individual's health. The supplement is preferably administered orally. Suitable forms for the nutritional supplement composition for oral administration include tablets, capsules, lozenges, syrups, granules, solutions and suspensions which contain unit doses of the supplement for administration once or several times a day. The nutritional supplement composition of the invention will typically be administered orally as a liquid, tablet or a capsule. Tablets, gel tabs, capsules, liquid and sustained release formulations can be formulated and prepared according to manufacturing techniques well known in the pharmaceutical industry and in a variety of dosage forms.

In one embodiment, the nutritional supplement is a sports drink comprising one or more modified antisense oligonucleotides capable of hybridizing to one or more of the genes listed in Table 1. In a preferred embodiment, the sport drink comprises the modified oligonucleotides Asm (SEQ ID NO: 1), Pde5 (SEQ ID NO: 16), FAAH (SEQ ID NO: 23), CX2 (SEQ ID NO: 6), CRP (SEQ ID NO: 24), LO5 (SEQ ID NO: 12), P65 (SEQ ID NO: 10), CD18 (SEQ ID NO: 5).

Therapeutic Oligonucleotide Compositions

In a related vein, the present invention includes a pharmaceutical composition comprising at least about one oligonucleotide, wherein said oligonucleotide comprises (i) at least about ten contiguous nucleotides in length, (ii) at least about three to eight contiguous achiral internucleoside linkages, (iii) further comprising a pharmaceutically suitable excipient. In alternative embodiments, other oligonucleotides, described herein, are used in the inventive compositions. In some embodiments, the therapeutic composition can be a pharmaceutical or homeopathic composition.

As used herein, the term "pharmaceutical composition" refers to a therapeutic composition that is used to treat a particular disease or pathological disorder that is suitable for parenteral, oral or topical administration in humans.

The compositions containing the modified oligonucleotides of the invention in an admixture with a pharmaceutically acceptable carrier can be prepared according to known techniques. The carrier may take a wide variety of forms depending on the form of preparation desired for administration, e.g., intravenous, oral, topical, aerosol (for topical or inhalation therapy), suppository, parenteral, or spinal injection. The excipient may contain any number of carriers. In the case of homeopathic pharmaceuticals the carriers would preferably be homeopathic carriers, e.g. homeopathic agents that may increase the efficacy of the homeopathic composition or help to alleviate symptoms associated with a physiological condition. In addition, the composition may contain stabilizers, preservatives, and other ingredients, preferably in amounts from about 0.5 to 2.0 percent by weight, provided they do not adversely affect the ability of the pharmacological composition to treat the physiological condition. It is well within the skill of one in the art to determine an appropriate mode of administration and to select an appropriate delivery system.

Administration of the composition will introduce the modified oligonucleotides to the individual in a diluted amount. Exemplary ranges of dosage for oral or topical administration are between about 0.001 mg and 10 mg per day, and preferably between about 0.010 mg and 1.0 mg per day of oligonucleotide in the composition. When orally administered, it is preferred that one dosage unit be administered one to four times per day until relief is achieved or until the symptoms disappear or are satisfactorily attenuated. Normally, a patient is instructed to orally take two to three dosage units per day. The dosage unit may be placed under the tongue of the patient or simply swallowed for such oral administration.

The pharmaceutical compositions of the present invention may be formulated for administration to humans and animals in liquid form, or in tablets, pills, granules, powders, or in ointments, creams, injectables, or suppositories. Ointments and creams are impregnated with a low liquid potency or, sometimes, mother tinctures and are generally prescribed as specific remedies. Liquid compositions may be supplied in amber glass dropper bottles to protect them from light.

In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs, and solutions); or carriers such as starches, sugars, diluents, granulating agents, lubricants, binders, disintegrating agents and the like in the case of oral solid preparations (such as, for example, powders, capsules and tablets). For homeopathic preparations for example, RNA can be dissolved in a liquid 1 part by weight to produce a ten volumes of liquid attenuation labeled 1×. To produce lower dilutions 1 ml of the 1× attenuation is used (mixed thoroughly) with 9 ml of diluent to produce 2×. This process is repeated until the desired attenuation is achieved.

For administration by injection, preparations may comprise an aqueous solution of a water soluble, or solubilized, and pharmacologically acceptable form of the nucleic acid in an appropriate liquid, e.g., water or saline solution. Injectable suspensions may also be prepared using appropriate liquid carriers, suspending agents, agents for adjusting the isotonicity, preserving agents, and the like. Actual methods for preparing administrable pharmacological compositions and adjustments necessary for administration to subjects will be known or apparent to those skilled in the art.

For topical administration, the carrier may take a wide variety of forms depending on the preparation, which may be a cream, dressing, gel, lotion, ointment, or liquid. A surfactant can be included in the composition to provide deeper penetration of the ingredients. Although natural surfactants are preferred, others such as isopropyl myristate can be used. In one embodiment, the composition is a cosmetic composition for topical administration to the skin. As used herein, the term "cosmetic composition" refers to a composition that is applied topically to the skin to improve the appearance of the skin.

Aerosols are prepared by dissolving or suspending the nucleic acid in a propellant such as ethyl alcohol or in propellant and solvent phases. The pharmaceutical compositions for topical or aerosol form will generally contain from about 0.001 percent by weight (of the nucleic acid) to about 40 percent by weight, preferably about 0.02 percent to about 10 percent by weight, and more preferably about 0.05 percent to about 5 percent by weight depending on the particular form employed. Suppositories are prepared by mixing the nucleic acid with a lipid vehicle such as theobroma oil, cacao butter, glycerin, gelatin, or polyoxyethylene glycols.

The compositions of the invention may also include plant or herbal extracts. For example, topical compositions may include Paraguay tea, Kola and Guarana which provide a source of methylxanthines, saponius, tannins and glycosides which have been shown to reduce swelling and redness. The extract of Paraguay tea is known as "Mate extract" and is described in the International Cosmetic Ingredient Dictionary, 5th Edition. Mate extract is commercially available in combination with extracts of Kola and Guarana that is sold by Cosmetic Ingredient Resources (Stamford, Conn.) under the "QUENCHT" trademark. Suitable herbs which can be used also include *Symphytum officinale, Moschus moscheferous, Pripalia geniculata, Plantago asiatica, Causticum, Helianthemum canadense, Ornithogalum umbellatum, Clematis crispa, Impatiens pallida, Prunus cerasus, arnica*, etc.

The nucleic acid molecule(s) may be combined with a lipid, cationic lipid, or anionic lipid and the active agent delivered via a nucleic acid/lipid emulsion, or a liposomal suspension. The use of cationic, anionic, and/or neutral lipid compositions or liposomes is generally described in International Publications WO90/14074, WO91/16024, WO91/17424, and U.S. Pat. No. 4,897,355, all herein incorporated by reference. By assembling nucleic acid molecules into lipid-associated structures, the nucleic acid molecules may exhibit an increased half-life in vivo. Examples of suitable anionic lipids for use with RNA or DNA include, but are not limited to, cardiolipin, dimyristoyl, dipalmitoyl, or dioleoyl phosphatidyl choline or phosphatidyl glycerol, palmitoyloleoyl phosphatidyl choline or phosphatidyl glycerol, phosphatidic acid, lysophosphatidic acid, phosphatidyl serine, phosphatidyl inositol, and anionic forms of cholesterol.

Making an Oligonucleotide Composition

The invention includes a method for making an oligonucleotide composition comprising (i) selecting an oligonucleotide that is adjacent to or overlaps a target region of a gene, (ii) determining the Gibbs Free energy value associated with said oligonucleotide in reference to said target gene, (iii) assessing Tm in reference to said target gene, and (iv) performing a sequence database search to determine if said oligonucleotide overlaps the 5' UTR, the translational start sequence, or the translational termination site of an mRNA of a gene different from the target gene.

The oligonucleotide of the present invention can be directed to a translational start site, a 5' UTR or a termination site. Preferably, the oligonucleotide is adjacent to or overlaps the translational start site of the gene by at least about one base. Still preferred, the oligonucleotide overlaps the translational start site by at least about two bases. Still more preferred, the oligonucleotide overlaps the translational start site by at least about three bases.

It is generally preferable to design an RNA or DNA that has the same or similar base sequence as the portion of the complement of a gene that encodes the 5' end of an RNA. However, a nucleic acid may also have, for example, a same or similar base sequence as other regions of the gene, such as the region encoding a translation start site or the 3' untranslated region. In another example, a nucleic acid may be designed to reflect the region around a splice donor or splice acceptor site, either with or without the intervening intron. Of particular interest are nucleic acid molecules whose sequences comprise all or a fragment of the sequence of the complement of a gene that is over-expressed in individuals exhibiting the disease or condition. The identification of overexpression of a gene can be through molecular means, e.g., detection of expression in affected tissue using conventional molecular techniques (e.g., Sambrook et al. (1989) Molecular Cloning: A Laboratory Manual, Cold Spring Harbor Laboratory Press). Overexpression of a gene may also be detected using array technology, or inferred from the results of protein assays, such as ELISA.

Making a Homeopathic Oligonucleotide Composition

A method of making a homeopathic composition comprising (i) triturating solid RNA in a 1/9 ratio with lactose to produce a 1× solid and (ii) repeating the process until the desired attenuation is achieved, is described in the present invention. In a related vein, a method of making a homeopathic composition comprising (i) dissolving 1 part RNA by weight in liquid to produce ten volumes of liquid attenuation labeled 1× and optionally (ii) mixing 1 ml of the 1× attenuation with 9 ml of diluent to produce a lower concentration, is also addressed.

In another embodiment, the invention includes homeopathic compositions containing modified oligonucleotides. In one embodiment, tablets for homeopathic use are preferably produced as placebo tablets that are then medicated by dripping or spraying liquid potencies onto the tablets in such a manner as to ensure a coefficient of impregnation of almost 100 percent. The placebo tablets are preferably formed by compression. Pills or granules are preferably spherical in shape, of about 4 millimeters diameter and 3 to 5 centigrams in weight. They are preferably prepared (form pure lactose) and medicated in the same manner as tablets. For example, solid RNA can be triturated (i.e., ground up) in a 1/9 ratio with lactose (1 gram of RNA+9 grams of lactose) to produce a 1× solid. The process is repeated (1 gram of that material plus 9 grams of lactose) until the desired attenuation is achieved.

For homeopathic compositions, the excipient may contain any number of carriers, and preferably homeopathic carriers, e.g., homeopathic agents that may increase the efficacy of the homeopathic composition or help to alleviate symptoms associated with a physiological condition. For example, RNA can be dissolved in a liquid 1 part by weight to produce a ten volumes of liquid attenuation labeled 1×. To produce lower dilutions 1 ml of the 1× attenuation is used (mixed thoroughly) with 9 ml of diluent to produce 2×. This process is repeated until the desired attenuation is achieved. A homeopathic carrier solution such as that described in U.S. Pat. No. 5,603,915 may be used for increasing the efficacy of the homeopathic agent. This carrier solution is sequentially subjected to an alternating current electrical treatment and a direct current electrical treatment, after which additional ingredients such as seawater, brain hormones, and biologically active enzymes are added. The electrical treatment of the carrier, along with the addition of homeopathically active substances, can be used to increase the efficacy of the homeopathic composition. Alternatively, an electromagnetic carrier, such as described in U.S. Pat. No. 5,830,140 may be employed.

Methods of Treatment

The invention includes a method of treating a disorder comprising administering an oligonucleotide to a patient in a therapeutically effective amount. As used herein, the term "therapeutically effective" amount is meant to refer to an amount of a pharmacological composition that is non-toxic and is the lowest amount necessary to provide a desired physiological effect. Preferably, the oligonucletide compositions of the present invention are administered at concentrations at or below 100 μg per kg of body weight. Also preferred, the concentration is at or below 10 μg per kg of body weight, still preferred, the concentration is at or below 1 μg per kg of body weight, and still more preferred, the concentration is at or below 0.1 μg per kg of body weight. Furthermore, for homeopathic use, the oligonucleotide compositions of the present invention can be combined with any homeopathic drug and still elicit a therapeutic effect.

Preferably, the oligonucleotide comprises at least one modification according to the present invention. A preferred modification is the incorporation of at least about three to eight contiguous achiral internucleoside phosphate linkages into the oligonucleotide backbone. More preferably the oligonucleotide incorporates at least nine to ten continuous achiral internucleoside phosphate linkages, even more preferably, eleven to fifteen achiral internucleoside phosphate linkages, and most preferably, the entire oligonucleotide contains achiral internucleoside phosphate linkages. Also preferred, the oligonucleotide is 3' end-blocked, comprises at least 10 contiguous nucleotides greater than or equal to 80 percent identical to a nucleotide sequence selected from SEQ ID NO: 1-81. Also preferred, the oligonucleotide is at least 85 percent identical to a nucleotide sequence selected from the group of SEQ ID NO: 1-81. Still preferred, the oligonucleotide is at least 90 percent identical and more preferred, at least 95 percent identical. Most preferably, the oligonucleotide comprises a sequence from SEQ ID NO: 1-81.

The methods of the present invention can be used to treat disorders including, but not limited to, acroparaesthsia, allergic (psoric) conditions, allergic reactions, alopecia, amnesia, anaphrodisia, angina, arthritis, asthenopia, biliary sycosis, burns, cancerous conditions, such as colon cancer, malignant melanoma and malignant nasal polyps, carpal tunnel syndrome, colds, conjunctivitis, Crohn's disease, depression, depressive psychosis, dysthyroidism, epilepsy, erectile dysfunction, excessive appetite (i.e., appetite control and suppression, promotion of healthy weight loss while naturally satisfying the appetite), gingivitis, heart burn (i.e., relief of occasional heartburn or occasional acid indigestion), hemorrhage, hypertension (i.e., helps maintain cardiovascular function, and a healthy heart and circulatory system), high cholesterol (i.e., helps to maintain cholesterol levels that are already within the normal range), hyperthyroidism, infections, inflammatory disease, lack of willpower, laryngitis, leucopenia, liver disorders, mental disorders (i.e., reduces stress, frustration, muscle tension, anxiety, and occasional simple nervous tension; enhances resistance to stress), myopia, neurosis, neurological disorders such as multiple sclerosis and ALS, obesity, pain (i.e., relief of minor or temporary aches and pains), pancreatic disorders, poison ivy, premature senescence, pre-menstrual syndrome (i.e., treatment of common symptoms associated with the menstrual cycle such as edema, breast tenderness, headaches, skin problems, cramps and mild mood changes), prostatitis, psoriasis, rosacea, seborrhea, sinusitis, and trauma.

Table 2 lists the oligonucleotides, or combinations of oligonucleotides that are preferably employed in remedies for the treatment of various symptoms and conditions. In Table 2, the use of a combination of oligonucleotides is denoted by a "/" (for example, "A/B/C" denotes the combined use of oligonucleotides A, B and C); where two or more different combinations are preferred, each such combination is presented on a separate line. The oligonucleotides are usually used in a 1:1:1 ratio, but this can vary. For example, a combination of 4×, 5×, and 6× solutions may be used, which deviates from 1:1:1.

TABLE 2

| Indication or Condition | Oligonucleotide Combination |
| --- | --- |
| Arthritis | Asm/X2/P65-2M |
|  | Asm/X2/P65-2M/LO5-38 |
| Carpal Tunnel Syndrome | Asm |
|  | Asm/X2/P65-2M |
| Chronic Fatigue/Fibromyalgia | Asm/D5/X2 |
| Colds | Asm |
| Crohn's Disease | X2/P65-2M |
| Depression | Asm/D5 |
| Erectile Dysfunction (ED) | Asm/D5 |
| Heartburn | Acid-2/B2 |
| High Cholesterol Hyperlipidemia | Mg44 |
|  | Mg44/Asm/D5 |
| Hypertension | Ace1 |
|  | Ace1/Nep-1 |
| Inflammation | Asm/X2 |
|  | Asm/X2/P65-2M |
|  | Asm/X2/P65-2M/LO5-38 |
| Pain | Asm/X2 |
|  | Asm/X2/P65-2M |
| Pre-Menstrual Syndrome (PMS) | Asm/D5/X2 |
| Psoriasis | Asm/D5/P65-2M |
| Rosacea | Asm |
|  | Asm/D5 |
| Prostatitis | MBP |

TABLE 2-continued

| Indication or Condition | Oligonucleotide Combination |
|---|---|
| Stress | Asm/D5 |
| Trauma | Asm |
|  | Asm/X2/P65-2M |
| Ulcerative colitis | X2/P65-2M/LO5-38 |
| Weight Management | TTP |

The compositions of the present invention are formulated to contain a "nutritionally effective" or "allopathically effective" or "homeopathically effective" amount of one or more nucleic acid molecules. As used herein, the term "nutritionally effective" amount is meant to refer to an amount of a oligonucleotide composition that is non-toxic and greater than the minimum amount necessary to maintain a desired physiological effect. As used herein, the term "allopathically effective" amount is meant to refer to an amount of a oligonucleotide composition that is non-toxic and greater than the minimum amount necessary to produce a desired physiological effect.

As used herein, the term "homeopathically effective" amount is meant to refer to an amount of a oligonucleotide composition that is non-toxic and is the lowest amount necessary to provide a desired physiological effect. A homeopathic effect, in accordance with the present invention, is achieved by a dose of modified nucleic acid that will be effective in treating (i.e., relieving, ameliorating, or preventing) symptoms of a particular condition or disease. Such treatment may be prophylactic in nature (i.e., completely or partially preventing the future occurrence of a symptom) and/or it may be therapeutic in nature (i.e., providing a partial or complete cessation or amelioration of a symptom). The method of treating of the present invention covers any treatment of symptoms of a disorder in a mammal, particularly a human, and includes:

(a) preventing symptoms of a disorder from occurring in a subject that may be predisposed to a condition but has not yet been diagnosed as having it;

(b) inhibiting symptoms of a disorder (i.e., arresting its development); or (c) relieving symptoms of a disorder (i.e., ameliorating and/or causing regression of the condition); and/or (d) maintaining homeostasis (i.e., the normal balance of RNA or DNA in a subject).

One of ordinary skill will appreciate that, from a medical practitioner's or patient's perspective, virtually any alleviation or prevention of an undesirable symptom would be desirable. Homeopathic compositions typically employ substantially less nucleic acid than is employed in allopathic compositions. Exemplary dosages to be employed in accordance with the present invention, are described in Table 3 below.

| Homeopathic RNA/DNA Concentration | |
|---|---|
| Dilution/Potency | µg/kg |
| 2× | 50 |
| 3× | 5 |
| 4× | 0.5 |
| 5× | 0.05 |
| 6× | 0.005 |

When used in the therapeutic treatment of disease, an appropriate dosage of one or more therapeutic compositions of the invention may be determined by any of several well-established methodologies. Additionally, dosages may also be altered depending upon factors such as the severity of infection, and the size or species of the host.

Preferably, animals are treated using compositions of the present invention having agents with compositions containing nucleic acid molecules having a sequence appropriate for the particular animal. Targeted species include, but are not limited to birds, fish, and mammals (especially pigs, goats, sheep, cows, dogs, horses, cats, and most preferably, humans).

Having now generally described the invention, the same will be more readily understood through reference to the following examples, which are provided by way of illustration, and are not intended to be limiting of the present invention, unless specified. The effectiveness of the RNA oligonucleotide compositions according to the preferred embodiments of the present invention is demonstrated in the Examples below.

Example 1

Individuals with cancers were typically administered a composition containing oligonucleotides complementary to cyclo-oxygenase 2 and NFκB p65 at concentrations of 3 to 30 $A_{260}$/RNA/ml (1.0-10 µg/kg). Some individuals were additionally administered oligonucleotides complementary to lipoxygenase 5. After approximately one to two months of therapy, the effect of the composition was then evaluated on individuals who completed the study (see Table 4). Treatment efficacy was evaluated by each patient and confirmed by the treating physician. A scaled score of 1 to 10 was used to evaluate treatment efficacy over a period of one to two months where a score=10 represented no improvement and a score=1 represented total alleviation of symptoms.

Example 2

Individuals with excessive appetite were orally administered an oligonucleotide composition containing RNA oligonucleotides complementary to the tripeptidyl gene. RNA oligonucleotide concentrations were typically 0.3 to 3.0 $A_{260}$/RNA/ml and given in dosages (0.1-1.0 µg/kg of 0.5 ml twice daily). The effect of the composition was then evaluated after approximately one to two months of therapy (see Table 5). Treatment efficacy was evaluated by each patient and confirmed by the treating physician. A scaled score of 1 to 10 was used to evaluate treatment efficacy where a score=10 represented a voracious appetite and a score=1 represented the absence of hunger and the ability to lose weight.

Example 3

Individuals diagnosed with arthritis were orally administered oligonucleotide compositions with RNA oligonucleotides complementary to phosphodiesterase 4 and NFκB p65. Some people were additionally given compositions further containing RNA oligonucleotides complementary to other genes. RNA oligonucleotide concentrations were typically between the range of 0.3 to 300 $A_{260}$/RNA/ml and given in dosages (0.1-100 µg/kg) of 0.5 ml twice daily. The effect of the composition was then evaluated after approximately one to two months of therapy (see Table 6). Treatment efficacy was evaluated by each patient and confirmed by the treating physician. A scaled score of 1 to 10 was used to evaluate treatment efficacy where a score=10 represented severe arthritis characterized by inability to freely move affected joints, restricted movement, pain and inflammation and a score=1 represented reduced inflammation, restoration of movement and the absence of pain.

Example 4

Individuals with elevated blood pressure were orally administered oligonucleotide compositions with RNA oligonucleotides complementary to CE and/or neutral endopeptidase genes. Some individuals were additionally given compositions with RNA oligonucleotides complementary to other genes. Concentrations were typically 3.0 to 30 $A_{260}$/RNA/ml and given in dosages (1.0-10 µg/kg) of 0.5 ml twice daily. The effect of the composition was evaluated after approximately one to two months of therapy (see Table 7). Treatment efficacy was determined by measuring changes in blood pressure where a decrease in blood pressure below 160/89 was assessed as a successful treatment because blood pressure above this level has been associated with stroke, heart disease and kidney failure.

Example 5

Individuals with elevated cholesterol were orally administered oligonucleotide compositions containing RNA oligonucleotides complementary to the 3-hydroxy-3-methylglutaryl-coenzyme A reductase gene. Some individuals were also given oligonucleotide compositions further containing RNA oligonucleotides complementary to other genes such as phosphodiesterase 4 and phosphodiesterase 5. RNA oligonucleotide concentrations were typically 3.0 to 30 $A_{260}$/RNA/ml and given in dosages (1.0-10 µg/kg) of 0.5 ml twice daily. The effect of the composition on serum cholesterol was evaluated after approximately one to two months of therapy (see Table 8). Treatment efficacy was determined by measuring changes in serum cholesterol where a one-point drop corresponded to a two percent reduction in the probability of heart disease and a twenty-five-point drop corresponded to a fifty percent reduction in the probability of heart disease.

In addition, the effect of compositions containing RNA oligonucleotide with eight or more contiguous achiral internucleoside phosphate linkages on cholesterol levels was also assessed. In a representative individual, oligonucleotide compositions containing achiral RNA oligonucleotides complementary to 3-hydroxy-3-methylglutaryl-coenzyme A reductase, phosphodiesterase 4 and phosphodiesterase 5 were given orally in combination at a concentration of 3.0 $A_{260}$/RNA/ml at dosages of 0.5 ml, twice daily. The achiral RNA oligonucleotides produced a decrease of 46 mg/dL in serum cholesterol. The achiral 2'methoxy-RNA supplements resulted in a 31 mg/dL decrease in serum cholesterol levels. Chiral RNA or DNA did not effect cholesterol levels.

Example 6

Individuals with emotional distress were orally administered an oligonucleotide composition containing RNA oligonucleotides complementary to the phosphodiesterase 4 and phosphodiesterase 5 genes. RNA oligonucleotide concentrations were typically 0.3 to 3.0 $A_{260}$/RNA/ml and were given in dosages (0.1-1.0 µg/kg) of 0.5 ml two to six times per day. The effect of the composition was evaluated after approximately one to two months of therapy (see Table 9). A scaled score of 1 to 10 was used to evaluate treatment efficacy where a score=10 represented a severely depressed patient with suicidal tendencies and a score=1 represented a emotionally stable patient.

Example 7

Individuals with various gastrointestinal disorders were orally administered oligonucleotide compositions with RNA oligonucleotides complementary to the phosphodiesterase 4 and/or cyclooxygenase 2 genes. Some individuals were given compositions additionally containing RNA oligonucleotides complementary to other genes such as phosphodiesterase 5 and NFκB p65. Oligonucleotide concentrations were typically 0.3 to 3.0 $A_{260}$/RNA/ml and given in 0.5 ml dosages (0.1-1.0 µg/kg) twice per day. The effect of the composition was evaluated after approximately one to two months of therapy (see Table 10). A scaled score of 1 to 10 was used to evaluate treatment efficacy where a score=10 represented a patient with above normal bowel movement frequency and the presence of blood in the feces and a score=1 represented a patient with normal frequency of bowel movements and the absence of blood in the feces.

Example 8

Individuals with various types of inflammation were orally or topically (as indicated) administered oligonucleotide compositions containing oligonucleotides complementary to the phosphodiesterase 4 or interleukin 5 genes. Some individuals were given compositions additionally containing RNA oligonucleotides complementary to other genes such as cyclooxygenase 2 and NFκB p65. RNA oligonucleotide concentrations were typically 0.03 to 300 A260/RNA/ml given in doses (0.01-100 µg/kg) of 0.5 ml twice per day. The effect of the composition was then evaluated (see Table 11). A scaled score of 1 to 10 was used to evaluate treatment efficacy after approximately one to two months of therapy, where a score=10 represented presence of debilitating inflammation with severe pain and a score=1 represented the absence of inflammation and pain.

Example 9

Individuals suffering from migraine headaches were orally administered oligonucleotide compositions containing RNA oligonucleotides complementary to the phosphodiesterase 4, phosphodiesterase 5 cyclooxygenase 2 and 3-hydroxy-3-methylglutaryl-coenzyme A reductase genes. Oligonucleotide concentrations were typically 3.0 to 30 $A_{260}$/RNA/ml taken in dosages (1.0-10 µg/kg) of 0.5 ml two to four times per day. The effect of the composition was evaluated after approximately one to two months of therapy (see Table 12). A scaled score of 1 to 10 was used to evaluate treatment efficacy where a score=10 represented severe debilitating headache pain including facial pain accompanied by nausea and sensitivity to light and a score=1 represented the absence of these conditions.

Example 10

Individuals with various neurological disorders were orally administered oligonucleotide compositions containing RNA oligonucleotides complementary to the phosphodiesterase 4, cyclooxygenase 2 and p65 genes. Some individuals were given compositions containing additional RNA oligonucleotides complementary to other genes such as lipoxygenase 5. Oligonucleotide concentrations were typically 3.0 to 30 $A_{260}$/RNA/ml taken in dosages (1-10 µg/kg) of 0.5 ml two to four times per day. The effect of the compositions was evaluated after approximately one to two months of therapy (see Table 13). A scaled score of 1 to 10 was used to evaluate treatment efficacy where a score=10 represented a patient with a debilitating form of the indicated neurological disorder (i.e., amyotrophic lateral sclerosis, multiple sclerosis, alzheimer's disease, parkinson's disease) and a score=1 represented a patient with no symptoms or mild symptoms associated with the indicated neurological disorder.

Example 11

Individuals suffering from various types of pain were orally administered oligonucleotide compositions containing RNA oligonucleotides complementary to phosphodiesterase 4 and/or cyclooxygenase 2. Some individuals were given compositions containing additional RNA oligonucleotides complementary to other genes such as phosphodiesterase 5 and p65. Oligonucleotide concentrations were typically 0.3 to 3.0 A260/RNA/ml and taken in dosages (0.1-10 µg/kg) of 0.5 ml two to four times a day. The effect of the composition was evaluated after approximately one to two months of therapy (see Table 14). A scaled score of 1 to 10 was used to evaluate treatment efficacy where a score=10 represented a patient with severe pain requiring treatment with a subscription analgesic and a score=1 represented a patient with the absence of pain.

Example 12

Female individuals diagnosed with pre-menstrual syndrome were orally administered oligonucleotide compositions containing RNA oligonucleotides complementary to the phosphodiesterase 4 gene. Some individuals were given compositions containing additional RNA oligonucleotides complementary to other genes such as phosphodiesterase 5 and cyclooxygenase 2. RNA oligonucleotide concentrations were typically 0.03 to 3.0 $A_{260}$/RNA/ml taken in doses (0.01-1.0 µg/kg) of 0.5 ml two to four times per day. The effect of the composition was evaluated after approximately one to two months of therapy (see Table 15). A scaled score of 1 to 10 was used to evaluate treatment efficacy where a score=10 represented a patient with cramps, bloating, irritability, nausea and vomiting and a score=1 represented a patient with the absence of these conditions.

Example 13

Male individuals diagnosed with prostatitis were orally administered oligonucleotide compositions containing RNA oligonucleotides complementary to the steroid 5-alpha-reductase-2 gene. Some individuals were given compositions containing additional RNA oligonucleotides complementary to other genes such as phosphodiesterase 4 and p65 (Super 8+composition=Asm, X2, D5, P65, cd-18, IL-5, LOS and ICAM). Oligonucleotide concentrations were typically 3.0 $A_{260}$/RNA/ml taken in doses (1.0 µg/kg) of 0.5 ml two to four times per day. The effect of the composition was evaluated after approximately one to two months of therapy (see Table 16). A scaled score of 1 to 10 was used to evaluate treatment efficacy where a score=10 represented a patient with urgent need to urinate three to five times per night and a score=1 represented a patient who slept through the night without urinating.

Example 14

Individuals suffering from cold and sinusitis symptoms were administered (intranasal) oligonucleotide compositions containing RNA oligonucleotides complementary to phosphodiesterase 4 and a DNA monomer, Nu 3. Some individuals were given compositions containing additional RNA oligonucleotides complementary to other gene targets such as cylooxygenase 2 and NFκB p65. RNA and DNA concentrations were typically 0.3 to 30 A26/RNA/ml (0.1-10 µg/kg). Treatment efficacy was evaluated after approximately one to two months of therapy (see Table 17). A scaled score of 1 to 10 was used to evaluate treatment efficacy where a score=10 represented a patient with sneezing, stuffy nose and watery eyes and a score=1 represented a patient with the absence of these conditions.

Example 15

Individuals with various types of trauma were orally or topically (as indicated) administered oligonucleotide compositions containing RNA oligonucleotides complementary to phosphodiesterase 4. Some individuals were given compositions containing additional RNA oligonucleotides complementary to other genes such as cyclooxygenase 2 and NFκB p65. Oligonucleotide concentrations ranged from 0.3 to 3.0 $A_{260}$/RNA/ml and taken in 0.5 ml doses (0.1-1.0 µg/kg) two to four times per day. The effect of the composition was evaluated after approximately one to two months of therapy (see Table 18). A scaled score of 1 to 10 was used to evaluate treatment efficacy where a score=10 represented a patient with severe inflammation and pain associated with the indicated trauma and a score=1 represented a patient with no inflammation or pain.

Example 16

Individuals diagnosed with carpal tunnel syndrome were orally administered oligonucleotide compositions containing RNA oligonucleotides complementary to the phosphodiesterase 4 gene. Some individuals were given compositions containing additional RNA oligonucleotides complementary to other genes such as cyclooxygenase 2, NFκB p65 and other gene targets. Oligonucleotide concentrations were typically 0.03 to 300 A260/RNA/ml taken in doses (0.01-100 µg/kg) of 0.5 ml two to four times per day. The effect of the composition was evaluated after approximately one to two months of therapy (see Table 19). A scaled score of 1 to 10 was used to evaluate treatment efficacy where a score=10 represented a patient with pain, tingling and numbness in the wrist area necessitating the use of a wrist brace and a score=1 represented a patient with the absence of these conditions and who did not require the assistance of a wrist brace.

Example 17

Individuals diagnosed with chronic fatigue syndrome or fibromyalgia were orally administered oligonucleotide compositions containing RNA oligonucleotides complementary to the phosphodiesterase 4 gene. Some individuals were given compositions containing additional RNA oligonucleotides complementary to other genes such as cyclooxygenase 2 and p65. Oligonucleotide concentrations were typically 3.0 to 30 $A_{260}$/RNA/ml taken in doses (1.0-10 µg/kg) of 0.5 ml two to four times per day. The effect of the composition was evaluated after approximately one to two months of therapy (see Table 20). A scaled score of 1 to 10 was used to evaluate treatment efficacy where a score=10 represented a patient who complained of being chronically exhaustion accompanied by minor aches and pain and a score=1 represented a patient who did not complain of any such symptom.

Example 18

Individuals suffering from eczema and atopic dermatitis were orally or topically (as indicated) administered oligonucleotide compositions containing RNA oligonucleotides complementary to the phosphodiesterase 4 gene. Some individuals were given compositions containing additional RNA oligonucleotides complementary to other genes such as cyclooxygenase 2 and p65 and other gene targets. Oligonucleotide concentrations were typically 0.3 to 3.0 $A_{260}$/RNA/ml taken in doses (0.1-1.0 g/kg) of 0.5 ml two to four times per day. The effect of the composition was evaluated after approximately one to two months of therapy (see Table 21). A scaled score of 1 to 10 was used to evaluate treatment efficacy where a score=10 represented patient with itching, inflamed skin and minor bleeding, and a score=1 represented a patient with normal skin.

Example 19

Male individuals suffering from erectile dysfunction were orally administered compositions containing RNA oligonucleotides complementary to the phosphodiesterase 4 gene. Some individuals were given compositions containing additional RNA oligonucleotides complementary to other genes such as phosphodiesterase-5. Oligonucleotide concentrations were typically 3.0 to 3.0 $A_{260}$/RNA/ml taken in doses (1.0-10 μg/kg) of 0.5 ml two to four times per day. The effect of the composition was evaluated after approximately one to two months of therapy (see Table 22). A scaled score of 1 to 10 was used to evaluate treatment efficacy where a score=10 represented a patient who could not obtain or maintain an erection and a score=1 represented a patient who was able to obtain and maintain an erection.

Example 20

Individuals suffering from acid reflux were orally administered compositions containing RNA oligonucleotides complementary to the ATP4A gene. Some individuals were given compositions containing additional RNA oligonucleotides complementary to other genes such as ATP4B. Oligonucleotide concentrations were typically 3.0 to 30 A260/RNA/ml taken in doses (1.0-10 μg/kg) of 0.5 ml two to four times per day. The effect of the composition was evaluated after approximately one to two months of therapy (see Table 23). A scaled score of 1 to 10 was used to evaluate treatment efficacy where a score=10 represented a patient with heartburn requiring treatment with excessive amounts of antacid medication and a score=1 represented a patient with no heartburn.

Example 21

Individuals suffering from poison ivy were orally or topically (as indicated) administered compositions containing RNA oligonucleotides complementary to the phosphodiesterase 4 gene. Oligonucleotide concentrations were typically 0.3 to 300 $A_{260}$/RNA/ml taken in doses 0.1-100 μg/kg) of 0.5 ml two to four times per day. The effect of the composition was evaluated after approximately one to two months of therapy (see Table 24). A scaled score of 1 to 10 was used to evaluate treatment efficacy where a score=10 represented a patient with poison ivy covering up to ninety-five percent of the entire body with dermal discharge and secondary inflammation restricting eye openings and a score=1 represented a patient without these symptoms.

Example 22

Individuals with psoriasis were orally or topically administered compositions containing RNA oligonucleotides complementary to the phosphodiesterase 4 gene. Some individuals were given compositions containing additional RNA oligonucleotides complementary to other genes such as phosphodiesterase-5 and p65. Oligonucleotide concentrations were typically 0.3 to 300 $A_{260}$/RNA/ml taken in doses of 0.5 ml (0.1-100 μg/kg) two to four times per day. The effect of the composition was evaluated after approximately one to two months of therapy (see Table 25). A scaled score of 1 to 10 was used to evaluate treatment efficacy where a score=10 represented a patient with thick silvery-colored scaly patches of skin with dermal discharge and bleeding and a score=1 represented a patient with normal skin.

Example 23

Ten individuals with rosacea were orally or topically administered compositions containing RNA oligonucleotides complementary to the phosphodiesterase 4 gene. Some individuals were given compositions containing additional RNA oligonucleotides complementary to other genes such as cyclooxygenase 2 and p65. Oligonucleotide concentrations were typically 0.3 to 300 $A_{260}$/RNA/ml taken in doses (0.1-100 μg/kg) of 0.5 ml two to four times per day. The effect of the composition was evaluated after approximately one to two months of therapy (see Table 26). A scaled score of 1 to 10 was used to evaluate treatment efficacy where a score=10 represented a patient with red, inflamed facial skin with pimples (e.g., acne) and a score represented a patient normal skin.

TABLE 4

Cancer Therapy

|   | sex | age | condition | oligonucleotides | Severity before | Severity after |
|---|-----|-----|-----------|------------------|--------|-------|
| 1 | m | 38 | Skin cancer | X2/65 | 7-8 | 1-2 |
| 2 | m | 72 | Skin cancer | X2/65/LO5-38 | 7-8 | stable |
| 3 | f | 52 | Malignant nasal polyps | X2/65/LO5-38/Mg44 | 10 | 1 |
| 4 | f | 47 | Malignant melanoma | X2/65/LO5-38/Mg44 | 10 | stable |
| 5 | f | 56 | Breast cancer | X2/65/LO5-38 | 10 | stable |

TABLE 5

Appetite Control

|   | sex | age | condition | oligonucleotide | Efficacy |
|---|-----|-----|-----------|-----------------|----------|
| 1 | f | 37 | appetite control | Ttp | 7 |
| 2 | f | 52 | appetite control | Ttp | 10 |
| 3 | f | 65 | appetite control | Ttp | 5 |
| 4 | f | 46 | appetite control | Ttp | 8 |
| 5 | f | 44 | appetite control | Ttp | 7 |
| 6 | f | 63 | appetite control | Ttp | 8 |
| 7 | f | 48 | appetite control | Ttp | 6 |
| 8 | f | 59 | appetite control | Ttp | 7 |
| 9 | m | 40 | appetite control | Ttp | 7 |
| 10 | f | 40 | appetite control | Ttp | 8 |
| 11 | f | 54 | appetite control | Ttp | 8 |
| 12 | f | 52 | appetite control | Ttp | 7 |

TABLE 5-continued

Appetite Control

|    | sex | age | condition       | oligonucleotide | Efficacy |
|----|-----|-----|-----------------|-----------------|----------|
| 13 | f   | 58  | appetite control | Ttp            | 7        |
| 14 | f   | 41  | Appetite control | Ttp            | 8        |
| 15 | f   | 39  | Appetite control | Ttp            | 8        |
| 16 | f   | 54  | Appetite control | Ttp            | 7        |

TABLE 6

Arthritis Treatment

|    | sex | age | condition              | oligonucleotide         | Severity before | Severity after |
|----|-----|-----|------------------------|-------------------------|-----------------|----------------|
| 1  | m   | 50  | Arthritis (back)       | Asm/X2/65               | 5               | 1              |
| 2  | f   | 60  | Arthritis (general)    | Asm/X2/65               | 6               | 1              |
| 3  | f   | 63  | Rheumatoid Arthritis   | Asm/X2/65/LO5-38/CRP    | 10              | 5              |
| 4  | f   | 66  | Arthritis (general)    | Asm/X2/65/D5            | 7               | 1              |
| 5  | m   | 50  | Arthritis (hands)      | Asm/65                  | 10              | 2              |
| 6  | f   | 28  | Arthritis (knee)       | Asm/X2/65               | 7               | 1-2            |
| 7  | f   | 74  | Arthritis (knee)       | Asm/X2/65               | 8               | 2-3            |
| 8  | f   | 82  | Arthritis (general)    | Asm/X2/65/LO5-38        | 8               | 2              |
| 9  | m   | 65  | Arthritis (back/hand)  | Asm/X2/65               | 6               | 2              |
| 10 | f   | 63  | Arthritis (knee)       | Asm/X2/65/LO5-38/CRP    | 10              | 3-4            |
| 11 | f   | 55  | Arthritis (back/hands) | Asm/X2/65               | 7               | 1              |
| 12 | m   | 48  | Arthritis (general)    | Asm/X2/65               | 6               | 1              |
| 13 | m   | 46  | Arthritis (general)    | Asm/X2/65               | 5               | 1              |
| 14 | f   | 90  | Arthritis (hand)       | Asm/X2/65               | 9-10            | 1              |
| 15 | m   | 53  | Arthritis (fingers)    | Asm/X2/65               | 8               | 1              |
| 16 | f   | 28  | Arthritis (neck)       | Asm/X2/65               | 7-8             | 1              |
| 17 | f   | 49  | Arthritis (hands)      | 65                      | 5-6             | 1              |
| 18 | f   | 51  | Arthritis (shoulder)   | Asm/X2/65               | 5               | 1              |
| 19 | m   | 77  | Arthritis (knee)       | Asm/X2/65/LO5-38/CRP/D5 | 10              | 3-4            |
| 20 | m   | 52  | Arthritis (knee)       | Asm/X2/65/LO5-38/D7/CRP | 7               | 3-4            |
| 21 | f   | 53  | Arthritis (back)       | Asm/X2/65/LO5-38/CRP    | 7               | 4              |
| 22 | f   | 64  | Arthritis (thumbs)     | Asm/X2/65/LO5-38/CRP    | 7               | 3              |
| 23 | f   | 47  | Arthritis (general)    | Asm/X2/65               | 8-9             | 2              |
| 24 | f   | 74  | Arthritis (general)    | Asm/X2/65/LO5-38/Mg44   | 10              | 1              |
| 25 | m   | 65  | Arthritis (back)       | Asm/X2/65               | 9               | 2-3            |
| 26 | f   | 61  | Arthritis (knees)      | Asm/X2/65               | 8-9             | 2              |

TABLE 7

Blood Pressure

|   | sex | age | Condition | oligonucleotides | Blood Pressure before | Blood Pressure after |
|---|-----|-----|-----------|------------------|----------------------|---------------------|
| 1 | f | 74 | Untreated hypertension | CE/NEP-1/Asm/D5 | 190/100 | 165/75 |
| 2 | f | 56 | Untreated hypertension | CE/NEP-1/Asm/D5 | 190/100 | 160/80 |
| 3 | f | 62 | Hypertension despite treatment with Zestril. Atenolol & Furosemide | CE/NEP-1/Asm/D5 | 200/90 | 170/75 |
| 4 | f | 63 | Hypertension despite treatment with Atenolol & Prinivil | CE/NEP-1/Asm/D5 | 170/70 | 150/70 |
| 5 | m | 65 | Hypertension despite treatment with Atenolol | CE/NEP-1/Asm/D5 | 190/98 | 150/80 |
| 6 | f | 55 | Untreated Hypertension | CE | 190/100 | 160/100 |
| 7 | m | 76 | Hypertension | NEP-1 | 170/69 | 158/74 |
| 8 | m | 36 | Untreated Hypertension | NEP-1 | 214/144 | 160/80 |

TABLE 8

Elevated Cholesterol

|    | sex | age | Condition | oligonucleotides | Cholesterol Level before | Cholesterol Level after |
|----|-----|-----|-----------|------------------|--------------------------|-------------------------|
| 1  | f   |     | Hyperlipidemia | Mg44/Asm/D5   | 244 | 125 |
| 2  | f   |     | Hyperlipidemia | Mg44/Asm/D5   | 220 | <150 |
| 3  | m   |     | Hyperlipidemia | Mg44          | 265 | 177 |
| 4  | f   |     | Hyperlipidemia | Mg44          | 212 | 205 |
| 5  | m   |     | Hyperlipidemia | Mg44/Asm/D5   | 207 | 168 |
| 6  | f   |     | Hyperlipidemia | Mg44/Asm/D5   | 229 | 163 |
| 7  | f   |     | Hyperlipidemia | Mg44/Asm/D5   | 300 | 184 |
| 8  | m   |     | Hyperlipidemia | Mg44/Asm/D5/MTP (shifted from Zocor) | 213 | <150 |
| 9  | m   |     | Hyperlipidemia | Mg44/Asm/D5 (shifted from Zocor) | <150 | <150 |
| 10 | m   |     | Hyperlipidemia | Mg44/Asm/D5   | 201 | 164 |

TABLE 9

Emotional Distress

|    | sex | age | condition | oligonucleotides | Severity before | Severity after |
|----|-----|-----|-----------|------------------|-----------------|----------------|
| 1  | f | 39 | Stress            | Asm/D5 | 9    | 1-2 |
| 2  | f | 46 | Stress            | Asm/D5 | 8    | 2   |
| 3  | f | 52 | Depression        | Asm/D5 | 10   | 1-2 |
| 4  | f | 29 | Stress/depression | Asm/D5 | 10   | 3   |
| 5  | m | 56 | Severe depression | Asm/D5 | 10   | 2   |
| 6  | f | 47 | Spousal abuse     | Asm/D5 | 8-9  | 1-2 |
| 7  | f | 57 | stress            | Asm/D5 | 10   | 1-2 |
| 8  | f | 40 | stress            | Asm/D5 | 9    | 3   |
| 9  | f | 52 | Severe depression | Asm/D5 | 10   | 1   |
| 10 | f | 26 | stress            | Asm/D5 | 8-9  | 1   |
| 11 | f | 36 | stress            | Asm/D5 | 4-5  | 1   |
| 12 | f | 62 | Severe depression | Asm/D5 | 10   | 1   |
| 13 | m | 31 | stress            | Asm/D5 | 8-9  | 1   |
| 14 | f | 52 | Stress/anxiety    | Asm/D5 | 9-10 | 2-3 |
| 15 | f | 56 | Mild stress       | Asm/D5 | 6    | 1   |
| 16 | f | 51 | mood swings       | Asm/D5 | 7    | 1   |
| 17 | m | 47 | High stress       | Asm/D5 | 10   | 2-3 |
| 18 | f | 56 | Spousal abuse     | Asm/D5 | 10   | 5   |
| 19 | m | 56 | Stress            | Asm/D5 | 7    | 2   |
| 20 | f | 63 | Depression        | Asm/D5 | 10   | 1-2 |
| 21 | m | 51 | SAD               | Asm/D5 | 10   | 1-2 |
| 22 | f | 35 | Suicidal          | Asm/D5 | 10   | 1-2 |
| 23 | f | 38 | Severe depression | Asm/D5 | 10   | 1-3 |
| 24 | f | 63 | Severe depression | Asm/D5 | 10   | 1-2 |
| 25 | f | 45 | Depression        | Asm/D5 | 8-9  | 1-2 |
| 26 | f | 31 | depression        | Asm/D5 | 8    | 1-2 |
| 27 | f | 34 | stress            | Asm/D5 | 9    | 2   |
| 28 | m | 63 | anxiety           | Asm/D5 | 9    | 1   |

TABLE 9-continued

Emotional Distress

| | sex | age | condition | oligonucleotides | Severity before | Severity after |
|---|---|---|---|---|---|---|
| 29 | m | 32 | Stress/anxiety | Asm/D5 | 10 | 1 |
| 30 | f | 60 | Severe depression | Asm/D5 | 10 | 1-2 |
| 31 | f | 25 | OCD/stress | Asm/D5 | 10 | 3 |
| 32 | m | 41 | agoraphobic | Asm/D5 | 10 | 3-4 |
| 33 | f | 42 | Severe anxiety | Asm/D5 | 10 | 1 |
| 34 | f | 36 | depression | Asm/D5 | 9-10 | 1-2 |
| 35 | m | 59 | Spousal abuse | Asm/D5 | 10 | 2 |
| 36 | f | 52 | Depression | Asm/D5 | 8 | 2 |
| 37 | f | 31 | stress | Asm/D5 | 9 | 1 |
| 38 | f | 63 | stress | Asm/D5 | 8 | 1 |
| 39 | m | 55 | Anxiety/stress | Asm/D5 | 7 | 4 |
| 40 | m | 45 | stress | Asm/D5 | 4 | 1 |
| 41 | f | 42 | stress | Asm/D5 | 10 | 1 |
| 42 | f | 38 | Severe depression | Asm/D5 | 10 | 1-2 |
| 43 | m | 50 | Mild stress | Asm/D5 | 4 | 1 |
| 44 | f | 33 | Mild stress | Asm/D5 | 5 | 1 |
| 45 | f | 42 | depression | Asm/D5 | 8 | 1 |
| 46 | f | 65 | depression | Asm/D5 | 9 | 2-3 |
| 47 | f | 63 | Stress/anxiety | Asm/D5 | 10 | 2-3 |
| 48 | f | 44 | Stress/anxiety | Asm/D5 | 9-10 | 1-2 |
| 49 | f | 34 | stress | Asm/D5 | 9 | 2 |
| 50 | f | 50 | Mild stress | Asm/D5 | 7 | 1 |
| 51 | m | 65 | depression | Asm/D5 | 9-10 | 1-2 |
| 52 | f | 38 | stress | Asm/D5 | 8 | 1 |
| 53 | f | 32 | Stress/anxiety | Asm/D5 | 9 | 2-3 |
| 54 | f | 40 | stress | Asm/D5 | 8-9 | 1-2 |
| 55 | f | 54 | stress | Asm/D5 | 7-8 | 1 |
| 56 | f | 33 | anxiety | Asm/D5 | 8 | 1 |
| 57 | f | 54 | Stress/depression | Asm/D5 | 9 | 2-3 |
| 58 | f | 41 | stress | Asm/D5 | 10 | 1-2 |
| 59 | m | 15 | Panic attacks | Asm/D5 | 10 | 1 |
| 60 | f | 44 | stress | Asm/D5 | 6 | 1 |
| 61 | f | 41 | stress | Asm/D5 | 9 | 1 |
| 62 | m | 40 | stress | Asm/D5 | 7-8 | 1-2 |
| 63 | f | 13 | Mood swings | Asm/D5 | 8-9 | 1-2 |
| 64 | f | 15 | Mood swings | Asm/D5 | 7-8 | 1 |
| 65 | f | 22 | stress | Asm/D5 | 10 | 1 |
| 66 | f | 51 | anxiety | Asm/D5 | 9 | 1 |
| 67 | m | 54 | Depression | Asm/D5 | 8 | 2 |
| 68 | f | 54 | depression | Asm/D5 | 8-9 | 3 |
| 69 | f | 51 | depression | Asm/D5 | 10 | 1-2 |
| 70 | f | 51 | stress | Asm/D5 | 5 | 1 |
| 71 | f | 56 | stress | Asm/D5 | 10 | 1-2 |
| 72 | f | 58 | depression | Asm/D5 | 8 | 2 |
| 73 | f | 39 | Mild stress | Asm/D5 | 5 | 1 |
| 74 | m | 24 | anxiety | Asm/D5 | 6 | 1 |
| 75 | m | 29 | stress | Asm/D5 | 8 | 4 |
| 76 | f | 43 | anxiety | Asm/D5 | 5 | 1 |
| 77 | m | 21 | Panic attacks | Asm/D5 | 10 | 1 |
| 78 | m | 66 | stress | Asm/D5 | 7-8 | 1-2 |
| 79 | f | 45 | Stress/anxiety | Asm/D5 | 7 | 1 |
| 80 | f | 74 | stress | Asm/D5 | 8-9 | 2 |
| 81 | f | 50 | Mild anxiety | Asm/D5 | 4 | 1 |
| 82 | f | 18 | Severe depression | Asm/D5 | 10 | 1 |
| 83 | f | 53 | stress | Asm/D5 | 9 | 3 |
| 84 | f | 32 | stress | Asm/D5 | 7 | 3 |
| 85 | f | 25 | stress | Asm/D5 | 8 | 1-2 |
| 86 | m | 47 | Severe depression | Asm/D5 | 9 | 1-2 |
| 87 | f | 38 | stress | Asm/D5 | 7 | 2 |
| 88 | m | 52 | stress | Asm/D5 | 5 | 1 |
| 89 | f | 14 | Panic attacks | Asm/D5 | 10 | 1-2 |
| 90 | m | 65 | anxiety | Asm/D5 | 8 | 1 |
| 91 | m | 39 | stress | Asm/D5 | 9 | 2 |
| 92 | m | 11 | stress | Asm/D5 | 7 | 1-2 |
| 93 | f | 31 | Severe depression | Asm/D5 | 10 | 3 |
| 94 | m | 67 | depression | Asm/D5 | 7 | 3 |
| 95 | f | 58 | stress | Asm/D5 | 7 | 2 |
| 96 | m | 67 | stress | Asm/D5 | 9 | 2 |
| 97 | m | 12 | ADD | Asm/D5 | 8 | 1 |
| 98 | f | 58 | stress | Asm/D5 | 9-10 | 2-3 |
| 99 | f | 30 | stress | Asm/D5 | 7 | 1 |
| 100 | m | 45 | stress | Asm/D5 | 6 | 1 |
| 101 | m | 13 | ADD | Asm/D5 | 9-10 | 2-3 |

TABLE 10

Gastrointestinal Disorders

| | sex | age | condition | oligonucleotides | Elimination/day b/f | Elimination/day after | Severity b/f | Severity after |
|---|---|---|---|---|---|---|---|---|
| 1 | f | 46 | IBS | Asm/X2/65 | 11 | 2 | 10 | 3 |
| 2 | m | 40 | Ulcerative colitis | Asm/X2/65 | 5 | 2 | 7 | 1 |
| 3 | f | 40 | IBS | Asm/X2/65 | 20 | 1-2 | 10 | 1 |
| 4 | f | 38 | Ulcerative colitis | Asm/X2/65 | 10-20 | 1 | 10 | 3 |
| 5 | f | 31 | Crohn's | X2/65 | 22 | 1 | 10 | 1 |
| 6 | f | 34 | Crohn's | X2/65 | 8-10 | 1-2 | 7 | 2 |
| 7 | f | 33 | IBS | Asm/X2/65 | 20 | 1-2 | 8 | 1 |
| 8 | m | 50 | IBS | Asm/X2/65 | 5 | 1-2 | 5 | 1 |
| 9 | f | 22 | Chronic constipation | Asm/X2/65 | 0 | 1-2 | 10 | 2 |
| 10 | f | 26 | Crohn's | X2/65 | 19-20 | 1 | 10 | 1 |
| 11 | f | 57 | Ulcerative colitis | Asm/X2/65 | 5-6 | 1 | 6 | 2 |
| 12 | f | 42 | IBS | Asm/X2/65 | 12 | 1 | 9 | 1 |
| 14 | f | 8 | IBS | Asm/65 (testing + X2) | 8 | 3-4 | 10 | 3 |
| 16 | f | 47 | IBS | Asm/X2/65 | 8 | 1-2 | 9 | 1 |
| 17 | f | 55 | IBS | Asm/X2/65 | 10 | 1 | 10 | 1 |
| 18 | m | 67 | IBS | Asm/X2/65 | 6-7 | 1-2 | 6 | 1 |
| 19 | f | 36 | IBS | Asm/X2/65 | 4 | 1 | 7-8 | 1 |
| 20 | m | 31 | Gall bladder | Asm/D5/Mg44 | nd | nd | 10 | 1 |
| 21 | m | 56 | Kidney stones | Mg44 | nd | nd | 10 | 1 |
| 22 | f | 37 | Gall bladder attack | Asm/X2/65/Mg44 | nd | nd | 4 | 1 |
| 23 | f | 57 | Gall bladder attack | Asm/D5/Mg44 | nd | nd | 7-8 | 1 |
| 25 | f | 54 | IBS | Super 8 | 5 | 1-2 | 5 | 1 |
| 26 | f | 7 | IBS | Super 8 | nd | nd | 8 | 2 |
| 27 | f | 38 | Ulcerative colitis | Super 8 | 3 | 1-2 | 4-5 | 1 |

TABLE 11

Inflammation

| | sex | age | condition | oligonucleotides | Severity before | Severity after |
|---|---|---|---|---|---|---|
| 1 | f | 39 | Post surgical | Asm/X2/65/cd18-1 | 10 | 4 |
| 2 | f | 64 | Post surgical | Asm | 10 | 2 |
| 3 | m | 55 | Asthma/emphysema | Asm/X2/65 | 9 | 7 |
| 4 | f | 33 | asthma | Asm/X2/65 | 10 | 1-2 |
| 5 | f | 40 | asthma | Asm | 10 | 1 |
| 6 | f | 40 | Bee sting | Asm | 10 | 1 |
| 7 | m | 5 | Bee sting | Asm/topical | 10 | 1 |
| 8 | f | 44 | Black fly bite | IL-501 | 10 | 1 |
| 9 | f | 8 | Black fly bite | IL-501 | 10 | 1 |
| 10 | f | 6 | Black fly bite | IL-501 | 10 | 1 |
| 11 | f | 63 | Hair implants | Asm | 10 | 1 |
| 12 | m | 66 | gout | Asm | 8 | 2 |
| 13 | m | 51 | gout | Asm | 10 | 1 |
| 14 | m | 45 | gout | Asm | 10 | 1 |
| 15 | f | 56 | Polymyalgia rheumatica | Asm/X2/65/D7/CRP | 10 | 3 |
| 16 | f | 31 | Multiple sclerosis | Asm/X2/65 | 9-10 | 2 |
| 17 | f | 67 | polymyositis | Asm/X2/65/D7/CRP | 8-9 | 3-4 |
| 18 | m | 32 | Swollen joints | Asm | 9 | 1-2 |
| 19 | m | 65 | Inner ear inflammation | Asm | 7 | 1 |
| 20 | m | 26 | hemorrhoids | Asm | 10 | 5 |

TABLE 11-continued

Inflammation

| | sex | age | condition | oligonucleotides | Severity before | Severity after |
|---|---|---|---|---|---|---|
| 21 | f | 41 | hemorrhoids | Asm | 10 | 1 |
| 22 | m | 75 | shingles | Asm/D7 | 10 | 3 |
| 23 | m | 48 | Sore muscles | Asm | 7 | 1 |
| 24 | f | 36 | Varicose veins | Asm | 7 | 7 |
| 25 | f | 74 | Swollen ankle | Asm/X2/65 | 10 | 2 |
| 26 | f | 41 | Swollen ankle | Asm | 10 | 1 |
| 27 | f | 63 | Swollen knee | Asm/X2/65/cd18-1 | 10 | 2 |
| 28 | f | 45 | Ganglion cyst | Asm/X2/65 | 7 | 1 |
| 29 | f | 73 | sciatica | Asm | 10 | 1 |
| 30 | m | 25 | sciatica | Asm | 10 | 1 |
| 31 | m | 54 | sciatica | Asm/X2/65 | 10 | 6 |
| 32 | m | 47 | sciatica | Asm/X2/65 | 10 | 1 |
| 33 | f | 44 | sciatica | Asm | 10 | 1 |
| 34 | f | 46 | Itchy ears | Asm | 6 | 1 |
| 35 | m | 59 | cellulitis | Asm/Nu-3 | 10 | 3-4 |
| 36 | f | 22 | Stomach inflammation | Asm/X2/65 | 9 | 2 |
| 37 | f | 44 | Pinched nerve | Asm/X2/65 | 10 | 1 |
| 38 | f | 44 | Pinched nerve | Asm/X2/65 | 10 | 1 |
| 39 | m | 46 | Hockey/tennis elbow | Asm/X2/65 | 9 | 1 |
| 40 | m | 40 | Hockey/tennis elbow | Asm/X2/65 | 10 | 1 |
| 41 | m | 16 | Pitcher's arm | Asm | 10 | 1 |
| 42 | f | 58 | Heel spur | Asm | 7 | 1 |
| 43 | f | 46 | Multiple sclerosis | Asm/X2/65 | 8 | 2 |
| 44 | f | 63 | hemorrhoids | Asm/Nu-3 | 10 | 3 |
| 45 | m | 64 | bursitis | Asm/X2/65/LO5-38 | 9 | 1-2 |
| 46 | f | 25 | Interstitial cystitis | Asm/X2/65/LO5-38 | 10 | 2 |
| 47 | m | 67 | Inflamed hands | Asm/D5/X2/65/IL-501 | 10 | 5 |
| 48 | f | 30 | Morning sickness | Asm/D5 | 10 | 7 |
| 49 | f | 12 | Inflamed tonsils | Asm | 10 | 1-2 |
| 50 | f | 33 | Inflamed cat scratch | Asm/topical | 6 | 1 |
| 51 | f | 38 | Allergies | Asm | 10 | 3 |
| 52 | f | 42 | Insect bite | IL-501/topical | 9 | 1 |
| 53 | f | 10 | Severe wasp bites | Asm/topical | 10 | 1 |
| 54 | f | 45 | Black fly bites | IL-501/topical | 9 | 1 |
| 55 | f | 62 | Wasp bite | Asm | 8 | 1 |
| 56 | f | 7 | Ear piercing | Asm | 8 | 1 |
| 57 | f | 9 | Ear piercing | Asm | 8 | 1 |
| 58 | m | 37 | Pinched nerve | Asm/X2/65 | 9-10 | 1 |
| 59 | f | 7 | "goose egg" on forehead | Asm/topical | 8 | 1 |
| 60 | m | 12 | Knee injury | Asm/topical | 6 | 1 |
| 61 | f | 43 | sciatica | Asm/topical | 9-10 | 1 |
| 62 | f | 45 | Pulled muscle (knee) | Asm/topical | 6 | 1 |
| 63 | m | 43 | Degenerative hip | Asm/topical | 5 | 1-2 |
| 64 | m | 65 | Chronic cough | D7 | 10 | 4 |
| 65 | m | 38 | Extreme autoimmune graft rejection/sinusitis/Erosive Peptic Esophagitis | Asm/X2/65/D7/LO5-38/ICAM/cd-18-1/IL6/HisR1 | 10 | 3 |
| 66 | f | 10 | Seasonal allergies | Asm | 7-8 | 1 |
| 67 | f | 42 | Interstitial cystitis | Asm/X2/65 | 9 | 1 |
| 68 | f | 34 | Chronic allergies | Asm/X2/65/D5 | 8 | 2 |
| 69 | f | 44 | Seasonal allergies/cough | IL-501 | 6 | 1 |
| 70 | f | 61 | Seasonal allergies/cough | IL-501 | 6 | 1 |

TABLE 12

Migraines

| | sex | age | Condition | oligonucleotides | Severity before | Severity after |
|---|---|---|---|---|---|---|
| 1 | f | 42 | migraine | Asm/D5/X2/Mg44 | 10 | 1 |
| 2 | f | 51 | migraine | Asm/D5/X2/Mg44 | 9 | 1-2 |
| 3 | f | 28 | migraine | Asm/D5/X2/Mg44 | 10 | 1 |
| 4 | f | 36 | migraine | Asm/D5/X2/Mg44 | 10 | 2 |
| 5 | f | 46 | migraine | Asm/D5/X2/Mg44 | 10 | 1 |
| 6 | f | 51 | migraine | Asm/D5/X2/Mg44 | 9 | 1 |
| 7 | f | 39 | migraine | Asm/D5/X2/Mg44 | 8 | 1 |
| 8 | f | 30 | migraine | Asm/D5/X2/Mg44 | 9 | 1 |
| 9 | f | 58 | Migraine | Asm/D5/X2/Mg44 | 9 | 1 |
| 10 | f | 57 | Migraine | Asm/D5/X2/Mg44 | 10 | 1 |
| 11 | f | 21 | migraine | Asm/D5/X2/Mg44 | 9 | 2-3 |

TABLE 13

Neurological Disorders

| | sex | age | Condition | oligonucleotides | Severity before | Severity after |
|---|---|---|---|---|---|---|
| 1 | f | 56 | polymyalgia | Asm/X2/65/D7/CRP | 10 | 3 |
| 2 | f | 31 | multiple sclerosis | Asm/X2/65 | 9-10 | 2 |
| 3 | f | 67 | polymyositis | Asm/X2/65/D7/CRP | 8-9 | 3-4 |
| 4 | f | 46 | multiple sclerosis | Asm/X2/65 | 8 | 2 |

TABLE 14

Pain

| | sex | age | Condition | oligonucleotides | Severity before | Severity after |
|---|---|---|---|---|---|---|
| 1 | f | 74 | Back | Asm/X2/65/LO5-38/Mg44 | 10 | 5 |
| 2 | m | 54 | back | Asm/X2/65 | 9 | 2 |
| 3 | f | 37 | shoulder | Asm/X2 | 6-7 | 1 |
| 4 | f | 41 | ankle | X2 | 5 | 1 |
| 5 | f | 61 | knee | X2 | 8 | 3 |
| 6 | f | 41 | ovarian | Asm/X2 | 8-9 | 3 |
| 7 | f | 61 | headache | Asm/X2 | 8 | 1 |
| 8 | f | 54 | headache | Asm/X2/65 | 8 | 5 |
| 9 | m | 26 | headache | Asm/X2 | 9 | 1 |
| 10 | f | 65 | headache | Asm/X2/65 | 8 | 1 |
| 11 | f | 36 | headache | Asm/X2 | 7 | 1 |
| 12 | f | 39 | headache | Asm/X2/D5 | 6 | 1 |
| 13 | f | 62 | headache | Asm/X2/D5 | 10 | 1-2 |
| 14 | f | 46 | knee | Asm/X2/65 | 6 | 2 |
| 15 | f | 31 | knee | Asm/X2/65 | 7 | 1 |
| 16 | f | 62 | knee | Asm/X2/65 | 7 | 2 |
| 17 | f | 61 | knee | Asm/X2 | 8 | 3 |
| 18 | f | 37 | knee | Asm/X2 | 9 | 1-2 |
| 19 | f | 39 | Surgical pain | Asm/X2/65 | 10 | 4 |
| 20 | m | 56 | Cancer pain | X2 | 10 | 6 |
| 21 | m | 30 | stitches | Asm/X2 | 10 | 1-2 |
| 22 | f | 20 | Tooth extraction | Asm/X2 | 10 | 1 |
| 23 | f | 53 | Tooth extraction | Asm/X2 | 9 | 1-2 |
| 24 | f | 30 | Tooth extraction | Asm/X2 | 10 | 1 |
| 25 | f | 45 | Tooth extraction | Asm/X2 | 8 | 1-2 |
| 26 | f | 74 | Rib soreness | Asm/X2/LO5-38/Mg44 | 10 | 1 |
| 27 | f | 48 | shoulder | Asm/X2/65 | 8 | 1 |
| 28 | f | 43 | headache | X2 | 8-9 | 1-2 |
| 29 | m | 38 | headache | X2 | 7 | 1-2 |
| 30 | f | 76 | Tooth extraction | Asm/X2/65 | 8 | 1-2 |
| 31 | m | 23 | Wisdom tooth pain | Asm/X2/65 | 9 | 2-3 |
| 32 | f | 42 | headaches | Asm/D5/X2 | 7 | 1 |
| 33 | f | 47 | Neck pain | Super 8 | 7 | 1 |
| 34 | f | 31 | Headaches | Asm/D5/X2 | 10 | 3 |

TABLE 14-continued

Pain

| | sex | age | Condition | oligonucleotides | Severity before | Severity after |
|---|---|---|---|---|---|---|
| 35 | f | 59 | Teeth pain | Super 8 | 6 | 1 |
| 36 | f | 31 | Knee pain | Super 8 | 6 | 1 |
| 37 | m | 10 | Ankle pain | Asm/65 | 5 | 1 |
| 38 | f | 13 | Tooth extraction | Asm/X2/65 | 7 | 1 |
| 39 | m | 65 | thyroidectomy | Super 8 | 10 | 1 |
| 40 | f | 46 | Surgical pain | Super 8 | 9 | 1 |

TABLE 15

Premenstrual Syndrome

| | sex | age | Condition | oligonucleotides | Severity before | Severity after |
|---|---|---|---|---|---|---|
| 1 | f | 41 | PMS | Asm/D5/X2 | 10 | 1-2 |
| 2 | f | 34 | PMS | Asm/D5/X2 | 10 | 1 |
| 3 | f | 37 | PMS | Asm/D5/X2 | 10 | 1 |
| 4 | f | 53 | PMS | Asm | 10 | 1 |
| 5 | f | 13 | PMS | Asm/D5/X2 | 10 | 1 |
| 6 | f | 15 | PMS | Asm/D5/X2 | 10 | 1 |
| 7 | f | 47 | PMS | Asm/D5/X2 | 10 | 9 |
| 8 | f | 44 | PMS | Asm | 10 | 1 |
| 9 | f | 20 | PMS | Asm/D5/X2 | 10 | 1 |

TABLE 16

Prostatitis

| | sex | age | Condition | oligonucleotides | Severity before | Severity after |
|---|---|---|---|---|---|---|
| 1 | m | 63 | BPH | MPB/Asm/X2/65 | 10 | 1 |
| 2 | m | 77 | BPH | Asm/D5/X2 | 3 | 1 |
| 3 | m | 45 | Inflamed prostate | Asm/D5/X2 | 4 | 1 |
| 4 | m | 69 | BPH | MPB/Asm/X2/65 | 7 | 1-2 |

TABLE 17

Sinus

| | sex | age | Condition | oligonucleotides | Severity before | Severity after |
|---|---|---|---|---|---|---|
| 1 | m | 8 | Sinus/cold | Asm/Nu-3 nasal | 5 | 1-2 |
| 2 | f | 60 | Sinus/cold | Asm/Nu-3 nasal | 7 | 2 |
| 3 | f | 42 | Sinus/cold | Asm/Nu-3 nasal | 8 | 1 |
| 4 | f | 41 | Sinus/cold | Asm/Nu-3 nasal | 6 | 4 |
| 5 | m | 55 | Sinus/cold | Asm/Nu-3 nasal | 6 | 1 |
| 6 | f | 47 | Sinus/cold | Asm/Nu-3 nasal | 7 | 1-2 |
| 7 | f | 40 | Sinus/cold | Asm/Nu-3 nasal | 5 | 1-2 |
| 8 | f | 35 | Sinus/cold | Asm/Nu-3 nasal | 7 | 1 |
| 9 | f | 12 | Sinus/cold | Asm/Nu-3 nasal | 5 | 1 |
| 10 | f | 34 | Sinus/cold | Asm/Nu-3 nasal | 9 | 1 |
| 11 | m | 17 | Sinus/cold | Asm/Nu-3 nasal | 7 | 2 |
| 12 | m | 15 | Sinus/cold | Asm/Nu-3 nasal | 6 | 2 |
| 13 | m | 70 | Sinus/cold | Asm/Nu-3 nasal | 5 | 1 |
| 14 | f | 53 | Sinus/cold | Asm/Nu-3/CRP | 7 | 3 |
| 15 | m | 77 | Sinus/cold | Asm/Nu-3 nasal | 8 | 3 |
| 16 | f | 37 | Sinus/cold | Asm/Nu-3 nasal | 8 | 2 |
| 17 | f | 55 | Sinus/cold | Asm/Nu-3 nasal | 9 | 2 |
| 18 | m | 17 | Sinus/cold | Asm/Nu-3 nasal | 7 | 1 |
| 19 | f | 62 | Sinus/cold | Asm/Nu-3 nasal | 7 | 1 |
| 20 | m | 43 | Sinus/cold | Asm/Nu-3 nasal | 9 | 1 |
| 21 | f | 41 | Sinus/cold | Asm/Nu-3 nasal | 6 | 1 |

TABLE 17-continued

Sinus

| | sex | age | Condition | oligonucleotides | Severity before | Severity after |
|---|---|---|---|---|---|---|
| 22 | f | 58 | Sinus/cold | Asm/Nu-3 nasal | 6 | 1 |
| 23 | f | 34 | Sinus/cold | Asm/Nu-3 nasal | 8 | 1 |
| 24 | f | 61 | Sinus/cold | Asm/Nu-3 nasal | 6 | 2 |
| 25 | f | 19 | Sinus/cold | Asm/Nu-3 nasal | 8 | 1 |
| 26 | f | 50 | Sinus/cold | Asm/Nu-3 nasal | 6 | 1 |
| 27 | m | 36 | Sinus/cold | Asm/Nu-3 nasal | 7 | 6 |
| 28 | f | 48 | Sinus/cold | Asm/Nu-3 nasal | 8 | 2 |
| 29 | f | 60 | Sinus/cold | Asm/Nu-3 nasal | 7 | 1 |
| 30 | m | 40 | Sinus/cold | Asm/Nu-3 nasal | 8 | 1 |
| 31 | f | 45 | Sinus/cold | Asm/Nu-3 nasal | 8 | 1 |
| 32 | f | 32 | Sinus/cold | Asm/Nu-3 nasal | 6 | 1 |
| 33 | f | 48 | Sinus/cold | Asm/Nu-3 nasal | 9 | 2-3 |
| 34 | f | 37 | Sinus/cold | Asm/Nu-3 nasal | 7 | 2 |
| 35 | f | 49 | Sinus/cold | Asm/Nu-3 nasal | 7 | 1-2 |
| 36 | m | 30 | Sinus/cold | Asm/Nu-3 nasal | 8-9 | 1 |
| 37 | m | 52 | Sinus/cold | Asm/Nu-3 nasal | 7 | 3 |
| 38 | f | 67 | Sinus/cold | Asm/Nu-3 nasal | 8 | 1 |
| 39 | m | 53 | Sinus/cold | Asm/Nu-3 nasal | 7 | 1 |
| 40 | f | 12 | Sinus/cold | Asm/Nu-3 nasal | 9 | 2-3 |
| 41 | f | 8 | Sinus/cold | Asm/Nu-3 nasal | 5 | 1 |
| 42 | f | 25 | Sinus/cold | Asm/Nu-3 nasal | 7 | 1 |
| 43 | f | 42 | Sinus/cold | Asm/Nu-3 nasal | 9 | 1-2 |
| 44 | f | 54 | Sinus/cold | Asm/Nu-3 nasal | 9 | 2-3 |
| 45 | f | 42 | Sinus/cold | Asm/Nu-3 nasal | 7 | 2 |
| 46 | f | 45 | Sinus/cold | Asm/Nu-3 nasal | 6 | 1 |
| 47 | m | 47 | Sinus/cold | Asm/Nu-3 nasal | 7 | 1 |
| 48 | f | 60 | Sinus/cold | Asm/Nu-3 nasal | 8 | 1 |
| 49 | f | 34 | Sinus/cold | Asm/Nu-3 nasal | 9 | 2 |
| 50 | f | 37 | Sinus/cold | Asm/Nu-3 nasal | 9 | 2-3 |
| 51 | f | 49 | Sinus/cold | Asm/Nu-3 nasal | 7 | 1 |
| 52 | f | 39 | Sinus/cold | Asm/Nu-3 nasal | 9 | 1 |
| 53 | f | 51 | Sinus/cold | Asm/Nu-3 nasal | 10 | 1-2 |

TABLE 18

Trauma

| | sex | age | Condition | oligonucleotides | Severity before | Severity after |
|---|---|---|---|---|---|---|
| 1 | f | 41 | Broke femur | Asm | 10 | 1 |
| 2 | f | 54 | Torn ligament | Asm | 7 | 1 |
| 3 | m | 57 | Compound fracture/leg | Asm/X2/65 | 10 | 4 |
| 4 | f | 72 | Sprained ankle | Asm/X2/65 | 6 | 1 |
| 5 | f | 47 | Root canal | Asm/X2/65 | 7 | 2 |
| 6 | f | 28 | Neck surgery | Asm/X2/65 | 9 | 1 |
| 7 | f | 47 | Torn rotator cup | Asm/X2/65/LO5-38 | 7 | 2-3 |
| 8 | f | 28 | Fractured ankle | Asm/X2/65 | 10 | 1 |
| 9 | m | 48 | Hyperextended elbow | Asm/X2/65/D7 | 7 | 2 |
| 10 | m | 19 | Motorcycle back injury | Asm/X2/65 | 9 | 2 |
| 11 | f | 64 | Fractured tibia | Asm/X2/65/LO5-38 | 10 | 3 |
| 12 | f | 41 | Cellulitis from impaled object | Asm/X2/65/D7 | 10 | 3-4 |
| 13 | f | 74 | Broken ribs | Asm/X2/65/LO5-38/Mg44 | 10 | 1 |
| 14 | f | 36 | Lumpectomy pain | Asm/topical | 10 | 1 |
| 15 | f | 37 | Torn miniscus | Asm/topical | 10 | 1 |
| 16 | m | 43 | Two broken arms | Asm | 10 | 2-3 |
| 17 | m | 1 | Finger slammed in door | Asm | 9 | 1 |
| 18 | f | 48 | Hysterectomy scar | Asm/topical | 7 | 1 |
| 19 | f | 45 | Broken toe | Asm/topical | 10 | 1-2 |
| 20 | f | 37 | Shoulder injury | Asm/X2 | 6 | 1 |
| 21 | m | 59 | Fluid on knee | Super 8 | 7 | 1 |
| 22 | f | 33 | Broken collarbone | Super 8 | 9 | 2 |

TABLE 18-continued

Trauma

| | sex | age | Condition | oligonucleotides | Severity before | after |
|---|---|---|---|---|---|---|
| 23 | m | 12 | Sprained finger | Asm/65 | 8 | 1 |
| 24 | f | 43 | Broken foot | Super 8/Mg44 | 9 | 1 |

TABLE 19

Carpal tunnel

| | sex | age | Condition | oligonucleotides | Severity before | after |
|---|---|---|---|---|---|---|
| 1 | m | 36 | Carpal tunnel | Asm | 9 | 1 |
| 2 | f | 42 | Carpal tunnel | Asm | 10 | 1 |
| 3 | f | 56 | Carpal tunnel | Asm | 9 | 1 |
| 4 | m | 75 | Carpal tunnel | Asm | 8 | 1-2 |
| 5 | m | 55 | Carpal tunnel | Asm/X2/65 | 8 | 1 |
| 6 | m | 21 | Carpal tunnel | Asm | 9 | 2 |
| 7 | m | 56 | Carpal tunnel | Asm/X2/65 | 10 | 1-2 |
| 8 | f | 63 | Carpal tunnel | Asm | 10 | 2-3 |
| 9 | f | 45 | Carpal tunnel | Super 8 | 7 | 2 |

TABLE 20

Chronic Fatigue/Fibromyalgia

| | sex | age | Condition | oligonucleotides | Severity before | after |
|---|---|---|---|---|---|---|
| 1 | f | 62 | CFS | Asm/D5/X2 | 9 | 1 |
| 2 | f | 60 | Fibromyalgia | Asm/D5/X2 | 10 | 1 |
| 3 | f | 56 | CFS | Asm/D5/X2 | 9 | 1 |
| 4 | m | 36 | CFS | Asm/D5/X2 | 8 | 1-2 |
| 5 | m | 69 | CFS | Asm/D5/X2 | 8 | 1 |
| 6 | m | 51 | CFS | Asm/D5/X2 | 9 | 2 |
| 7 | m | 38 | CFS | Asm/D5/X2 | 10 | 1-2 |
| 8 | f | 40 | Fibromyalgia | Asm/D5/X2 | 10 | 2-3 |

TABLE 21

Eczema/Atopic Dermatitis

| | sex | age | Condition | oligonucleotides | Severity before | after |
|---|---|---|---|---|---|---|
| 1 | f | 63 | Foot rash | Asm | 8 | 1 |
| 2 | f | 49 | hives | Asm/X2/65/D7 | 10 | 1-2 |
| 3 | f | 13 | Severe leg rashes | Asm | 10 | 3-4 |
| 4 | m | 36 | eczema | Asm/X2/65 | 7-8 | 3-4 |
| 5 | f | 41 | Non-specific rash | Asm | 8 | 1 |
| 6 | m | 11 | eczema | Asm | 10 | 1-2 |
| 7 | f | 51 | rash | Asm/X2 | 5 | 1 |
| 8 | m | 48 | rash | Asm | 6-7 | 1-2 |
| 9 | f | 30 | Atopic dermatitis | Asm | 9 | 1 |
| 10 | f | 26 | Face rash | Asm | 7 | 1 |
| 11 | m | 42 | Severe rash | Asm/X2/65/D7 | 10 | 1 |
| 12 | f | 8 | Rash | Asm | 4 | 1 |
| 13 | f | 12 | eczema | Asm | 6 | 1 |
| 14 | m | 67 | Severely inflamed fingers | Asm/X2/65/IL-501 | 10 | 3-4 |
| 15 | f | 52 | rash | Asm | 6 | 1 |
| 16 | f | 42 | Severe hives | Asm/X2/65 | 10 | 1 |
| 17 | f | 14 | Chronic eczema | Asm | 7 | 1 |
| 18 | m | 64 | eczema | Asm/X2/65 | 8 | 1 |

TABLE 21-continued

Eczema/Atopic Dermatitis

| | sex | age | Condition | oligonucleotides | Severity before | after |
|---|---|---|---|---|---|---|
| 19 | f | 63 | Non-specific itching | Asm | 7-8 | 1 |
| 20 | f | 58 | Contact dermatitis | Asm/topical | 8 | 1 |
| 21 | m | 47 | Itchy scar | Asm/topical | 5 | 1 |
| 22 | f | 37 | Severe contact dermatitis | Asm/topical | 7 | 2 |
| 23 | m | 36 | Severe atopic dermatitis | Asm | 10 | 1 |
| 24 | m | 1 | Severe diaper rash | Asm/topical | 10 | 1 |
| 25 | f | 40 | Eczema | Asm | 6 | 1-2 |
| 26 | f | 35 | Itchy/scaly patches on feet | Asm | 7-8 | 1 |
| 27 | m | 17 | Atopic dermatitis | Asm | 7 | 1 |
| 28 | f | 19 | Severe razor burn | Asm/topical | 10 | 1 |
| 29 | m | 24 | Severe razor burn | Asm/topical | 10 | 1 |
| 30 | f | 40 | Inflamed hands | Asm/topical | 7 | 1 |
| 31 | m | 19 | split, cracked cuticles | cd18-1 | 7 | 1 |
| 32 | f | 51 | Split lips | cd18-1 | 5 | 1 |
| 33 | f | 30 | Dry, cracked skin on hands | cd18-1/topical | 8 | 1 |
| 34 | f | 60 | rash | Super 8 | 9 | 1 |
| 35 | f | 38 | Spider bite | Super 8 | 10 | 2-3 |
| 36 | f | 15 | rash | Super 8 | 5 | 1 |

TABLE 22

Erectile Dysfunction

| | sex | age | Condition | oligonucleotides | Severity before | after |
|---|---|---|---|---|---|---|
| 1 | m | 65 | ED/blood pressure med. | D5 | 10 | 1 |
| 2 | m | 69 | ED/blood pressure med. | Asm/D5 | 9 | 2-3 |
| 3 | m | 52 | ED | Asm/D5 | 10 | 1 |

TABLE 23

Heartburn/Acid Reflux

| | sex | age | Condition | oligonucleotides | Severity before | after |
|---|---|---|---|---|---|---|
| 1 | f | 63 | heartburn | Acid-2/Acid B2 | 10 | 1 |
| 2 | f | 49 | heartburn | Acid-2/Acid B2 | 10 | 1 |
| 3 | f | 22 | Heartburn | Acid-2/Acid B2 | 10 | 1 |
| 4 | f | 42 | Heartburn | Acid-2 | 7-8 | 1 |
| 5 | f | 41 | Heartburn | Acid-2/Acid B2 | 9-10 | 1 |
| 6 | f | 70 | Heartburn | Acid-2/Acid B2 | 5 | 1 |
| 7 | f | 47 | heartburn | Acid-2/Acid B2 | 8 | 1 |
| 8 | f | 41 | heartburn | Acid-2/Acid B2 | 10 | 1 |
| 9 | f | 19 | heartburn | Acid-2/Acid B2 | 7 | 1 |
| 10 | m | 77 | heartburn | Acid-2/Acid B2 | 10 | 1 |
| 11 | f | 52 | heartburn | Acid-2/Acid B2 | 10 | 1 |
| 12 | f | 21 | Heartburn | Acid-2/Acid B2 | 10 | 1 |
| 13 | f | 41 | heartburn | Acid-2/Acid B2 | 10 | 1 |
| 14 | f | 46 | heartburn | Acid-2/Acid B2 | 10 | 1 |
| 15 | f | 63 | heartburn | Acid-2/Acid B2 | 10 | 1 |
| 16 | f | 62 | heartburn | Acid-2/Acid B2 | 10 | 1 |

TABLE 24

Poison Ivy

| | sex | age | Condition | oligonucleotides | Severity before | Severity after |
|---|---|---|---|---|---|---|
| 1 | m | 10 | Poison ivy | Asm | 7 | 1 |
| 2 | f | 43 | Poison ivy | Asm | 7 | 1 |
| 3 | f | 63 | Poison ivy | Asm | 10 | 1 |
| 4 | f | 42 | Poison ivy | Asm | 6 | 1 |
| 5 | m | 3 | Poison ivy | Asm | 6 | 1 |
| 6 | m | 47 | Poison ivy | Asm | 10 | 1 |
| 7 | f | 53 | Poison ivy | Asm | 10 | 1 |
| 8 | m | 21 | Poison ivy | Asm/topical | 8-9 | 1 |
| 9 | f | 12 | Poison ivy | Asm/topical | 10 | 1 |
| 10 | f | 56 | Poison ivy | Asm/topical | 9 | 1 |
| 11 | f | 40 | Poison ivy | Asm/topical | 7-8 | 1 |
| 12 | f | 49 | Poison ivy | Asm | 10 | 1 |
| 13 | m | 17 | Poison ivy | Asm | 7 | 1 |
| 14 | f | 65 | Poison ivy | Asm | 5-6 | 1 |

TABLE 25

Psoriasis

| | sex | age | Condition | oligonucleotides | Severity before | Severity after |
|---|---|---|---|---|---|---|
| 1 | m | 59 | stress induced psoriasis | Asm/D5/X2 | 10 | 3 |
| 2 | f | 77 | psoriasis | Asm/D5/65 | 5 | 1 |
| 3 | f | 34 | psoriasis | Asm/D5/65 | 9-10 | 1 |
| 4 | m | 27 | psoriasis | Asm/D5/65 | 7 | 1 |
| 5 | f | 41 | psoriasis | Asm/D5/65 | 7 | 2-3 |
| 6 | f | 19 | psoriasis | Asm/D5/65 | 9 | 1 |
| 7 | f | 6 | psoriasis | Asm | 6 | 1 |
| 8 | f | 75 | psoriasis | Asm | 4 | 1 |
| 9 | m | 47 | Severe psoriasis | Asm | 10 | 2-3 |
| 10 | m | 36 | psoriasis | Asm/D5/65 | 5 | 1 |
| 11 | f | 24 | psoriasis | Asm/D5/65 | 9 | 1 |

TABLE 26

Rosacea

| | sex | age | Condition | oligonucleotides | Severity before | Severity after |
|---|---|---|---|---|---|---|
| 1 | f | 40 | Rosacea | Asm | 6 | 1-2 |
| 2 | f | 38 | Rosacea | Asm | 4 | 1 |
| 3 | f | 58 | Rosacea | Asm | 7 | 1 |
| 4 | f | 40 | Rosacea | Asm | 8 | 1 |
| 5 | f | 40 | Rosacea | Asm | 8-9 | 1 |
| 6 | f | 36 | Rosacea | Asm | 6 | 3 |
| 7 | f | 48 | Rosacea | Asm/X2/65 | 6-7 | 1 |
| 8 | f | 32 | Rosacea | Asm | 6 | 1 |

TABLE 27

Average of Results

| Condition | # cases | pre-treatment average | post-treatment average |
|---|---|---|---|
| elevated cholesterol | 10 | 230 | 166 |
| hypertension | 8 | 190/96 | 159/79 |
| inflammatory bowel | 12 | 10 toilet trips | 1-2 toilet trips |
| crohn's disease | 3 | 17 toilet trips | 1-2 toilet trips |
| ulcerative colitis | 5 | 8 toilet trips | 1-2 toilet trips |
| acid reflux/heartburn | 16 | 9.2 | 1.0 |
| emotional distress | 127 | 8.2 | 1.4 |
| PMS | 9 | 10.0 | 1.0 |
| inflammation | 70 | 9.0 | 1.7 |
| pain | 40 | 8.8 | 2.0 |
| infection | 78 | 7.1 | 1.6 |
| migraine | 14 | 9.4 | 1.3 |
| neurological disorders | 9 | 9.0 | 3.0 |
| poison ivy | 14 | 8.0 | 1.0 |
| prostatitis | 5 | 6.6 | 1.2 |
| psoriasis | 14 | 7.1 | 1.5 |
| rocacea | 10 | 6.3 | 1.1 |
| trauma | 25 | 8.7 | 1.7 |
| sinus/cold | 53 | 7.3 | 1.6 |
| erectile dysfunction | 5 | 9.0 | 1.5 |
| eczema/rash | 36 | 8.5 | 1.4 |
| fibromyalgia | 7 | 10.0 | 1.8 |
| chronic fatigue | 9 | 9.5 | 1.2 |
| carpal tunnel syndrome | 9 | 8.9 | 1.3 |
| arthritis | 30 | 7.6 | 2.0 |
| appetite | 16 | 9.5 | 2.3 |

Example 24

For animal studies, animals with different indications were provided with oligonucleotide compositions containing RNA oligonucleotides complementary to the phosphodiesterase 4, phosphodiesterase 5 genes or as indicated in Figure 24. Some animals were additionally given compositions containing additional RNA oligonucleotides complementary to other genes such as cyclooxygenase 2 and p65. Oligonucleotide concentrations were typically 0.3 to 300 $A_{260}$/RNA/ml taken in doses (0.1-100 μg/kg) of 0.5 ml two to four times per day. The effect of the composition was then evaluated (see Table 27). Treatment efficacy was evaluated by an attending veterinarian.

TABLE 27

Animal studies

| animal | Condition | oligonucleotides | Severity before | Severity after |
|---|---|---|---|---|
| dog | skin allergy | Asm | 8 | 2 |
| dog | inflammatory bowel disease | Asm, CX2, P65 | 7 | 2 |
| horse | nervous and agitated | Asm, D5 | 8 | 2 |

Example 24

The following is the method for selecting nucleic acid sequences from a known gene sequence for the design of oligonucleotides. Preferred choices are sequences that either are adjacent to, or overlap the start site, followed by sequences that are in the 5' un-translated region, followed by sequences immediately adjacent to or overlapping the termination signal. This method is very effective and when combined with, achiral RNA, it produces oligonucleotides that display therapeutic efficacy consistently.

For example, achiral RNA oligonucleotides (10-30 bases in length), or achiral 2'-methoxy oligonucleotides (10-30 bases in length), or achiral 2'-methoxy oligonucleotides (10-30 bases in length) with (a) 3' or 3' & 5' acid stable end-blocks located in the 5' UTR, or
(b) immediately adjacent to or more preferably overlapping at least one of the three bases of the start site and extending either 5' or 3' of the start site, or
(c) immediately adjacent to or overlapping one of the three bases of the termination signal and extending 3' or 5' of the termination site that are ten to thirty contiguous bases in length and complementary to a RNA or DNA and that have the following binding characteristics:
(d) ΔG of the oligonucleotide binding the complementary RNA strand at 37° C.
  (i) $(G_{37}°) \leq -15$ KCal or less (more negative=more stable) for 10 to 14 mer,
  (ii) $(G_{37}°) \leq -20$ KCal or less (more negative more stable) for 15 to 17 mer,
  (iii) $(G_{37}°) \leq -25$ KCal or less (more negative=more stable) for 18 to 20 mer,
  (iv) $(G_{37}°) \leq -30$ KCal or less (more negative=more stable) for 21 to 23 mer,
  (v) $(G_{37}°) \leq -35$ KCal or less (more negative=more stable) for 24 to 30 mer,
(e) the ΔG of any hairpin structure the oligonucleotide could assume is ≥−3.0,
(f) the Tm any hairpin that could form is at least 10° C. lower than the Tm of the oligonucleotide binding to the target RNA or DNA,
(g) a melting temperature for the oligonucleotide binding to the target RNA is 45° C. by the percent GC method at 1.0 M salt For composition parameters, the percent G+C of the oligonucleotide to be used is >35 percent and are administered so that each specific RNA is at a concentration (1.0 g/100 ml), or lower in doses not to exceed 100 μg/kg per RNA, or more preferably 10 μg/kg, or more preferably 1 μg/kg, or still more preferably <1 μg/kg. Sequences are then screened to be sure they do not overlap the same regions in other known genes by conducting BLAST searches against the entire GenBank list of human sequences.

Factors contributing to the selective inhibition of gene expression in vivo by the modified oligonucleotides of the invention include the influence of chirality on melting temperature. 2'-O-methyl modified RNA oligonucleotides with achiral linkages resemble backbone linkages that very closely resemble normal unmodified nucleic acids. Typically, oligonucleotides synthesized using phosphoramidite based synthesis of phosphorothioates produces mixed isomers present at each modified phosphorothioate linkage. A measurable result of the presence of these mixed isomers is a decrease in melting temperature of the phosphorothioate oligonucleotide in a primer target duplex as compared to an unmodified oligonucleotide in the same duplex. The melting temperature of a 2'-O-methyl RNA oligonucleotide, however, is not substantially lowered relative to an unmodified oligonucleotide. Thus, the melting temperatures for 2'-O-methyl RNA oligonucleotides closely resemble those for unmodified RNA because the presence of the 2'-O-methyl group does not result in the generation of isomers.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents and patent applications referred to in this application are herein incorporated by reference in their entirety.

We claim:

1. A composition suitable for administration in a mammal suffering from a pathological disorder or disease comprising two or more modified oligonucleotides, wherein
    a.) a first and a second modified oligonucleotide each comprise about seven to seventy-five nucleotides containing seven or more contiguous ribose groups linked by achiral 5' to 3' internucleotide phosphate linkages, wherein said ribose groups of said modified oligonucleotides have a 2' modification, and wherein said 5' and 3' ends of said modified oligonucleotides are blocked;
    b.) said first modified oligonucleotide is complementary to a region of a first gene associated with said pathological disorder or disease and said second modified oligonucleotide is complementary to a region of a second gene associated with said pathological disorder or disease, wherein the sequence of each of said modified oligonucleotides is selected from the group consisting of SEQ ID NO: 1, SEQ ID NO: 6, SEQ ID NO: 10, SEQ ID NO: 12 and SEQ ID NO: 24; and
    c.) wherein said first and second modified oligonucleotides are present in a total amount of less than about 7 mg.

2. The composition of claim 1, wherein said composition comprises more than two modified oligonucleotides each comprising about seven to seventy-five nucleotides containing seven or more contiguous ribose groups linked by achiral 5' to 3' internucleotide phosphate linkages; wherein each of said more than two modified oligonucleotides is complementary to a region of a gene associated with said pathological disorder or disease, wherein the sequence of each of said modified oligonucleotides is selected from the group consisting of SEQ ID NO: 1, SEQ ID NO: 6, SEQ ID NO: 10, SEQ ID NO: 12 and SEQ ID NO: 24; and wherein said more than two modified oligonucleotides are present in a total amount of less than 7 mg.

3. A composition suitable for administration in a mammal suffering from a pathological disorder or disease comprising two or more modified oligonucleotides, wherein
    a.) a first and a second modified oligonucleotide each comprise about seven to seventy-five nucleotides containing seven or more contiguous ribose groups linked by achiral 5' to 3' internucleotide phosphate linkages, wherein said ribose groups of said modified oligonucleotides have a 2' modification, and wherein said 5' and 3' ends of said modified oligonucleotides are blocked;
    b.) said first modified oligonucleotide is complementary to a region of a first gene associated with said pathological disorder or disease and said second modified oligonucleotide is complementary to a region of a second gene associated with said pathological disorder or disease, wherein said first modified oligonucleotide is modified CGTGTCAGGAGAAC (SEQ ID NO: 1); and said second modified oligonucleotide is modified TCTACAGTTCAGTCGA (SEQ ID NO: 6); and c.) wherein said first and second modified oligonucleotides are present in a total amount of less than about 7 mg.

4. The composition of claim 3, wherein said composition comprises more than two modified oligonucleotides each comprising about seven to seventy-five nucleotides containing seven or more contiguous ribose groups linked by achiral 5' to 3' internucleotide phosphate linkages; wherein each of said more than two modified oligonucleotides is complementary to a region of a gene associated with said pathological disorder or disease; wherein said more than two modified oligonucleotides are present in a total amount of less than 7 mg; and wherein a third modified oligonucleotide is modified GAACAGTTCGTCCATG (SEQ ID NO: 10).

5. The composition of claim 4, wherein a fourth modified oligonucleotide is modified GGAGGGCATGGCGCGG (SEQ ID NO: 12).

6. The composition of claim 5, wherein a fifth modified oligonucleotide is modified CATGGTCACGTCCTGC (SEQ ID NO: 24).

* * * * *

SEQUENCE LISTING

```
<160> NUMBER OF SEQ ID NOS: 132

<210> SEQ ID NO 1
<211> LENGTH: 14
<212> TYPE: DNA
<213> ORGANISM: Artificial sequence
<220> FEATURE:
<223> OTHER INFORMATION: ASM oligonucleotide

<400> SEQUENCE: 1
cgtgtcagga gaac                                                     14

<210> SEQ ID NO 2
<211> LENGTH: 14
<212> TYPE: DNA
<213> ORGANISM: Artificial sequence
<220> FEATURE:
<223> OTHER INFORMATION: Ace1 oligonucleotide

<400> SEQUENCE: 2
catgacgcgg tgcg                                                     14

<210> SEQ ID NO 3
<211> LENGTH: 16
<212> TYPE: DNA
<213> ORGANISM: Artificial sequence
<220> FEATURE:
<223> OTHER INFORMATION: Acid-2 oligonucleotide
```

```
<400> SEQUENCE: 3
ggcagtcgtc cctcta                                                     16

<210> SEQ ID NO 4
<211> LENGTH: 16
<212> TYPE: DNA
<213> ORGANISM: Artificial sequence
<220> FEATURE:
<223> OTHER INFORMATION: Acid B2 oligonucleotide

<400> SEQUENCE: 4
aacgtttcac ttctca                                                     16

<210> SEQ ID NO 5
<211> LENGTH: 13
<212> TYPE: DNA
<213> ORGANISM: Artificial sequence
<220> FEATURE:
<223> OTHER INFORMATION: cd18-1 oligonucleotide

<400> SEQUENCE: 5
ttgctaccag tct                                                        13

<210> SEQ ID NO 6
<211> LENGTH: 16
<212> TYPE: DNA
<213> ORGANISM: Artificial sequence
<220> FEATURE:
<223> OTHER INFORMATION: CX2 (X2) oligonucleotide

<400> SEQUENCE: 6
tctacagttc agtcga                                                     16

<210> SEQ ID NO 7
<211> LENGTH: 18
<212> TYPE: DNA
<213> ORGANISM: Artificial sequence
<220> FEATURE:
<223> OTHER INFORMATION: Mg44 oligonucleotide

<400> SEQUENCE: 7
tgacaacatt gtagctac                                                   18

<210> SEQ ID NO 8
<211> LENGTH: 18
<212> TYPE: DNA
<213> ORGANISM: Artificial sequence
<220> FEATURE:
<223> OTHER INFORMATION: Mg44 oligonucleotide

<400> SEQUENCE: 8
agctacagaa tccttgga                                                   18

<210> SEQ ID NO 9
<211> LENGTH: 16
<212> TYPE: DNA
<213> ORGANISM: Artificial sequence
<220> FEATURE:
<223> OTHER INFORMATION: Mg44 oligonucleotide

<400> SEQUENCE: 9
gtcgggctat tcaggc                                                     16

<210> SEQ ID NO 10
<211> LENGTH: 16
```

```
<212> TYPE: DNA
<213> ORGANISM: Artificial sequence
<220> FEATURE:
<223> OTHER INFORMATION: P65-2M (65) oligonucleotide

<400> SEQUENCE: 10
gaacagttcg tccatg                                                   16

<210> SEQ ID NO 11
<211> LENGTH: 15
<212> TYPE: DNA
<213> ORGANISM: Artificial sequence
<220> FEATURE:
<223> OTHER INFORMATION: IL-501 oligonucleotide

<400> SEQUENCE: 11
cctcatggct ctgaa                                                    15

<210> SEQ ID NO 12
<211> LENGTH: 16
<212> TYPE: DNA
<213> ORGANISM: Artificial sequence
<220> FEATURE:
<223> OTHER INFORMATION: LO5-38 oligonucleotide

<400> SEQUENCE: 12
ggagggcatg gcgcgg                                                   16

<210> SEQ ID NO 13
<211> LENGTH: 16
<212> TYPE: DNA
<213> ORGANISM: Artificial sequence
<220> FEATURE:
<223> OTHER INFORMATION: MPB-19 oligonucleotide

<400> SEQUENCE: 13
cctgcatcgc gccgtg                                                   16

<210> SEQ ID NO 14
<211> LENGTH: 16
<212> TYPE: DNA
<213> ORGANISM: Artificial sequence
<220> FEATURE:
<223> OTHER INFORMATION: NEP-1 (CALLA) oligonucleotide

<400> SEQUENCE: 14
gacttgccca tcacct                                                   16

<210> SEQ ID NO 15
<211> LENGTH: 16
<212> TYPE: DNA
<213> ORGANISM: Artificial sequence
<220> FEATURE:
<223> OTHER INFORMATION: NPY-1 oligonucleotide

<400> SEQUENCE: 15
acctagcatg gtggct                                                   16

<210> SEQ ID NO 16
<211> LENGTH: 15
<212> TYPE: DNA
<213> ORGANISM: Artificial sequence
<220> FEATURE:
<223> OTHER INFORMATION: D5 (PDE5.1) oligonucleotide

<400> SEQUENCE: 16
```
cgctccatgg ttggc                                                    15

<210> SEQ ID NO 17
<211> LENGTH: 16
<212> TYPE: DNA
<213> ORGANISM: Artificial sequence
<220> FEATURE:
<223> OTHER INFORMATION: D7 oligonucleotide

<400> SEQUENCE: 17
cttccattga atacgc                                                   16

<210> SEQ ID NO 18
<211> LENGTH: 16
<212> TYPE: DNA
<213> ORGANISM: Artificial sequence
<220> FEATURE:
<223> OTHER INFORMATION: Per oligonucleotide

<400> SEQUENCE: 18
actgccatcc tcgctc                                                   16

<210> SEQ ID NO 19
<211> LENGTH: 16
<212> TYPE: DNA
<213> ORGANISM: Artificial sequence
<220> FEATURE:
<223> OTHER INFORMATION: TTP (TTPII) oligonucleotide

<400> SEQUENCE: 19
cggtggccat ggacgc                                                   16

<210> SEQ ID NO 20
<211> LENGTH: 17
<212> TYPE: DNA
<213> ORGANISM: Artificial sequence
<220> FEATURE:
<223> OTHER INFORMATION: TTPII oligonucleotide

<400> SEQUENCE: 20
aagttcatgg tttcgga                                                  17

<210> SEQ ID NO 21
<211> LENGTH: 19
<212> TYPE: DNA
<213> ORGANISM: Artificial sequence
<220> FEATURE:
<223> OTHER INFORMATION: MTP oligonucleotide

<400> SEQUENCE: 21
gaatcatatt tgaccagca                                                19

<210> SEQ ID NO 22
<211> LENGTH: 16
<212> TYPE: DNA
<213> ORGANISM: Artificial sequence
<220> FEATURE:
<223> OTHER INFORMATION: HisR1 oligonucleotide

<400> SEQUENCE: 22
ggctcattgg cgcaag                                                   16

<210> SEQ ID NO 23
<211> LENGTH: 16
<212> TYPE: DNA
<213> ORGANISM: Artificial sequence

```
<220> FEATURE:
<223> OTHER INFORMATION: HisR1 oligonucleotide

<400> SEQUENCE: 23
agagcctccc ttagga                                                    16

<210> SEQ ID NO 24
<211> LENGTH: 16
<212> TYPE: DNA
<213> ORGANISM: Artificial sequence
<220> FEATURE:
<223> OTHER INFORMATION: CRP oligonucleotide

<400> SEQUENCE: 24
catggtcacg tcctgc                                                    16

<210> SEQ ID NO 25
<211> LENGTH: 18
<212> TYPE: DNA
<213> ORGANISM: Artificial sequence
<220> FEATURE:
<223> OTHER INFORMATION: CETP oligonucleotide

<400> SEQUENCE: 25
atggttatca ggcagtgg                                                  18

<210> SEQ ID NO 26
<211> LENGTH: 19
<212> TYPE: DNA
<213> ORGANISM: Artificial sequence
<220> FEATURE:
<223> OTHER INFORMATION: CETP oligonucleotide

<400> SEQUENCE: 26
catggttatc aggcagtgg                                                 19

<210> SEQ ID NO 27
<211> LENGTH: 16
<212> TYPE: DNA
<213> ORGANISM: Artificial sequence
<220> FEATURE:
<223> OTHER INFORMATION: CETP oligonucleotide

<400> SEQUENCE: 27
ctgaagaatt gaccac                                                    16

<210> SEQ ID NO 28
<211> LENGTH: 16
<212> TYPE: DNA
<213> ORGANISM: Artificial sequence
<220> FEATURE:
<223> OTHER INFORMATION: ICAM oligonucleotide

<400> SEQUENCE: 28
catagcgagg ctgagg                                                    16

<210> SEQ ID NO 29
<211> LENGTH: 15
<212> TYPE: DNA
<213> ORGANISM: Artificial sequence
<220> FEATURE:
<223> OTHER INFORMATION: TNF-alpha oligonucleotide

<400> SEQUENCE: 29
gtgctcatgg tgtcc                                                     15
```

```
<210> SEQ ID NO 30
<211> LENGTH: 15
<212> TYPE: DNA
<213> ORGANISM: Artificial sequence
<220> FEATURE:
<223> OTHER INFORMATION: Bone morphgenic protein-4 oligonucleotide

<400> SEQUENCE: 30
cgaccatcag cattc                                                      15

<210> SEQ ID NO 31
<211> LENGTH: 16
<212> TYPE: DNA
<213> ORGANISM: Artificial sequence
<220> FEATURE:
<223> OTHER INFORMATION: Beta adrenergic receptor-1 oligonucleotide

<400> SEQUENCE: 31
gcccatgccg agctgc                                                     16

<210> SEQ ID NO 32
<211> LENGTH: 16
<212> TYPE: DNA
<213> ORGANISM: Artificial sequence
<220> FEATURE:
<223> OTHER INFORMATION: IL-6 oligonucleotide

<400> SEQUENCE: 32
aggagttcat agctgg                                                     16

<210> SEQ ID NO 33
<211> LENGTH: 16
<212> TYPE: DNA
<213> ORGANISM: Artificial sequence
<220> FEATURE:
<223> OTHER INFORMATION: FAAH oligonucleotide

<400> SEQUENCE: 33
gcaccatgat cccttc                                                     16

<210> SEQ ID NO 34
<211> LENGTH: 16
<212> TYPE: DNA
<213> ORGANISM: Artificial sequence
<220> FEATURE:
<223> OTHER INFORMATION: ACAT oligonucleotide

<400> SEQUENCE: 34
cttcacccac cattgt                                                     16

<210> SEQ ID NO 35
<211> LENGTH: 18
<212> TYPE: DNA
<213> ORGANISM: Artificial sequence
<220> FEATURE:
<223> OTHER INFORMATION: IBAT oligonucleotide

<400> SEQUENCE: 35
cattcattgc tgggtctg                                                   18

<210> SEQ ID NO 36
<211> LENGTH: 15
<212> TYPE: DNA
<213> ORGANISM: Artificial sequence
<220> FEATURE:
<223> OTHER INFORMATION: HMGIC oligonucleotide
```

-continued

```
<400> SEQUENCE: 36
cgtgcgctca tcctg                                                    15

<210> SEQ ID NO 37
<211> LENGTH: 16
<212> TYPE: DNA
<213> ORGANISM: Artificial sequence
<220> FEATURE:
<223> OTHER INFORMATION: HMGIC oligonucleotide

<400> SEQUENCE: 37
aacgttgcgc ccccta                                                   16

<210> SEQ ID NO 38
<211> LENGTH: 16
<212> TYPE: DNA
<213> ORGANISM: Artificial sequence
<220> FEATURE:
<223> OTHER INFORMATION: Ghre oligonucleotide

<400> SEQUENCE: 38
tgcagacagg tgggcc                                                   16

<210> SEQ ID NO 39
<211> LENGTH: 17
<212> TYPE: DNA
<213> ORGANISM: Artificial sequence
<220> FEATURE:
<223> OTHER INFORMATION: Ghre oligonucleotide

<400> SEQUENCE: 39
gcatggcctc agctggg                                                  17

<210> SEQ ID NO 40
<211> LENGTH: 16
<212> TYPE: DNA
<213> ORGANISM: Artificial sequence
<220> FEATURE:
<223> OTHER INFORMATION: Ghre oligonucleotide

<400> SEQUENCE: 40
tgggcgatca cttgtc                                                   16

<210> SEQ ID NO 41
<211> LENGTH: 18
<212> TYPE: DNA
<213> ORGANISM: Artificial sequence
<220> FEATURE:
<223> OTHER INFORMATION: AAT1R oligonucleotide

<400> SEQUENCE: 41
cattttgatc acctgggt                                                 18

<210> SEQ ID NO 42
<211> LENGTH: 16
<212> TYPE: DNA
<213> ORGANISM: Artificial sequence
<220> FEATURE:
<223> OTHER INFORMATION: AAT1R oligonucleotide

<400> SEQUENCE: 42
cgaacatgtc actcaa                                                   16

<210> SEQ ID NO 43
```

```
<211> LENGTH: 17
<212> TYPE: DNA
<213> ORGANISM: Artificial sequence
<220> FEATURE:
<223> OTHER INFORMATION: VEGF oligonucleotide

<400> SEQUENCE: 43
aagttcatgg tttcgga                                                        17

<210> SEQ ID NO 44
<211> LENGTH: 17
<212> TYPE: DNA
<213> ORGANISM: Artificial sequence
<220> FEATURE:
<223> OTHER INFORMATION: VEGF oligonucleotide

<400> SEQUENCE: 44
tcaccgcctc ggcttgt                                                        17

<210> SEQ ID NO 45
<211> LENGTH: 15
<212> TYPE: DNA
<213> ORGANISM: Artificial sequence
<220> FEATURE:
<223> OTHER INFORMATION: FAS oligonucleotide

<400> SEQUENCE: 45
cctcctccat ggctg                                                          15

<210> SEQ ID NO 46
<211> LENGTH: 15
<212> TYPE: DNA
<213> ORGANISM: Artificial sequence
<220> FEATURE:
<223> OTHER INFORMATION: FAS oligonucleotide

<400> SEQUENCE: 46
gcctagccct cccgc                                                          15

<210> SEQ ID NO 47
<211> LENGTH: 16
<212> TYPE: DNA
<213> ORGANISM: Artificial sequence
<220> FEATURE:
<223> OTHER INFORMATION: AmP oligonucleotide

<400> SEQUENCE: 47
gcagcggctt gttcat                                                         16

<210> SEQ ID NO 48
<211> LENGTH: 15
<212> TYPE: DNA
<213> ORGANISM: Artificial sequence
<220> FEATURE:
<223> OTHER INFORMATION: AmP oligonucleotide

<400> SEQUENCE: 48
gagtcaagac ctcag                                                          15

<210> SEQ ID NO 49
<211> LENGTH: 16
<212> TYPE: DNA
<213> ORGANISM: Artificial sequence
<220> FEATURE:
<223> OTHER INFORMATION: PanLip oligonucleotide

<400> SEQUENCE: 49
```

```
gtggcagcat cgtggc                                                   16

<210> SEQ ID NO 50
<211> LENGTH: 16
<212> TYPE: DNA
<213> ORGANISM: Artificial sequence
<220> FEATURE:
<223> OTHER INFORMATION: PanLip oligonucleotide

<400> SEQUENCE: 50
cctaacacgg tgtgag                                                   16

<210> SEQ ID NO 51
<211> LENGTH: 17
<212> TYPE: DNA
<213> ORGANISM: Artificial sequence
<220> FEATURE:
<223> OTHER INFORMATION: ACC2 oligonucleotide

<400> SEQUENCE: 51
gaagcaagac cattcag                                                  17

<210> SEQ ID NO 52
<211> LENGTH: 17
<212> TYPE: DNA
<213> ORGANISM: Artificial sequence
<220> FEATURE:
<223> OTHER INFORMATION: ACC2 oligonucleotide

<400> SEQUENCE: 52
tcaggtggag gccgggc                                                  17

<210> SEQ ID NO 53
<211> LENGTH: 16
<212> TYPE: DNA
<213> ORGANISM: Artificial sequence
<220> FEATURE:
<223> OTHER INFORMATION: PKARIIbeta oligonucleotide

<400> SEQUENCE: 53
tgctcatcct gcctcc                                                   16

<210> SEQ ID NO 54
<211> LENGTH: 16
<212> TYPE: DNA
<213> ORGANISM: Artificial sequence
<220> FEATURE:
<223> OTHER INFORMATION: PKARIIbeta oligonucleotide

<400> SEQUENCE: 54
gcttcatgca gtgggt                                                   16

<210> SEQ ID NO 55
<211> LENGTH: 16
<212> TYPE: DNA
<213> ORGANISM: Artificial sequence
<220> FEATURE:
<223> OTHER INFORMATION: VR1R oligonucleotide

<400> SEQUENCE: 55
tcttcatcct tgctgg                                                   16

<210> SEQ ID NO 56
<211> LENGTH: 16
<212> TYPE: DNA
```

```
<213> ORGANISM: Artificial sequence
<220> FEATURE:
<223> OTHER INFORMATION: VR1R oligonucleotide

<400> SEQUENCE: 56
ctcacttctc cccgga                                                 16

<210> SEQ ID NO 57
<211> LENGTH: 16
<212> TYPE: DNA
<213> ORGANISM: Artificial sequence
<220> FEATURE:
<223> OTHER INFORMATION: ADAMTS oligonucleotide

<400> SEQUENCE: 57
gggacatggc actggt                                                 16

<210> SEQ ID NO 58
<211> LENGTH: 16
<212> TYPE: DNA
<213> ORGANISM: Artificial sequence
<220> FEATURE:
<223> OTHER INFORMATION: ADAMTS oligonucleotide

<400> SEQUENCE: 58
ttatttcctg cccgcc                                                 16

<210> SEQ ID NO 59
<211> LENGTH: 16
<212> TYPE: DNA
<213> ORGANISM: Artificial sequence
<220> FEATURE:
<223> OTHER INFORMATION: NPY-Y5R oligonucleotide

<400> SEQUENCE: 59
tgtggcaggt cagttg                                                 16

<210> SEQ ID NO 60
<211> LENGTH: 16
<212> TYPE: DNA
<213> ORGANISM: Artificial sequence
<220> FEATURE:
<223> OTHER INFORMATION: NPY-Y5R oligonucleotide

<400> SEQUENCE: 60
atccatatta tagtct                                                 16

<210> SEQ ID NO 61
<211> LENGTH: 16
<212> TYPE: DNA
<213> ORGANISM: Artificial sequence
<220> FEATURE:
<223> OTHER INFORMATION: NPY-Y5R oligonucleotide

<400> SEQUENCE: 61
tattacatat gaagac                                                 16

<210> SEQ ID NO 62
<211> LENGTH: 16
<212> TYPE: DNA
<213> ORGANISM: Artificial sequence
<220> FEATURE:
<223> OTHER INFORMATION: GNTV oligonucleotide

<400> SEQUENCE: 62
agccattgct ctctgg                                                 16
```

```
<210> SEQ ID NO 63
<211> LENGTH: 16
<212> TYPE: DNA
<213> ORGANISM: Artificial sequence
<220> FEATURE:
<223> OTHER INFORMATION: GNTV oligonucleotide

<400> SEQUENCE: 63
tgctataggc agtctt                                                    16

<210> SEQ ID NO 64
<211> LENGTH: 16
<212> TYPE: DNA
<213> ORGANISM: Artificial sequence
<220> FEATURE:
<223> OTHER INFORMATION: FCRG3 oligonucleotide

<400> SEQUENCE: 64
tgccacatga tgccac                                                    16

<210> SEQ ID NO 65
<211> LENGTH: 16
<212> TYPE: DNA
<213> ORGANISM: Artificial sequence
<220> FEATURE:
<223> OTHER INFORMATION: FCRG3 oligonucleotide

<400> SEQUENCE: 65
gttgagcttc aaatgt                                                    16

<210> SEQ ID NO 66
<211> LENGTH: 16
<212> TYPE: DNA
<213> ORGANISM: Artificial sequence
<220> FEATURE:
<223> OTHER INFORMATION: CD40L oligonucleotide

<400> SEQUENCE: 66
tcgatcatgc tgtgtt                                                    16

<210> SEQ ID NO 67
<211> LENGTH: 16
<212> TYPE: DNA
<213> ORGANISM: Artificial sequence
<220> FEATURE:
<223> OTHER INFORMATION: CD40L oligonucleotide

<400> SEQUENCE: 67
aggtgacact gttcag                                                    16

<210> SEQ ID NO 68
<211> LENGTH: 16
<212> TYPE: DNA
<213> ORGANISM: Artificial sequence
<220> FEATURE:
<223> OTHER INFORMATION: ETS-1 oligonucleotide

<400> SEQUENCE: 68
acggccgcct tcatgg                                                    16

<210> SEQ ID NO 69
<211> LENGTH: 16
<212> TYPE: DNA
<213> ORGANISM: Artificial sequence
<220> FEATURE:
```

<223> OTHER INFORMATION: ETS-1 oligonucleotide

<400> SEQUENCE: 69
gccatcactc gtcggc                                                   16

<210> SEQ ID NO 70
<211> LENGTH: 16
<212> TYPE: DNA
<213> ORGANISM: Artificial sequence
<220> FEATURE:
<223> OTHER INFORMATION: ADAMTS-5 oligonucleotide

<400> SEQUENCE: 70
ccgagcagca tagtgc                                                   16

<210> SEQ ID NO 71
<211> LENGTH: 16
<212> TYPE: DNA
<213> ORGANISM: Artificial sequence
<220> FEATURE:
<223> OTHER INFORMATION: ADAMTS-5 oligonucleotide

<400> SEQUENCE: 71
tcataaccac aggcta                                                   16

<210> SEQ ID NO 72
<211> LENGTH: 16
<212> TYPE: DNA
<213> ORGANISM: Artificial sequence
<220> FEATURE:
<223> OTHER INFORMATION: PTP-1B oligonucleotide

<400> SEQUENCE: 72
catgacgggc cagggc                                                   16

<210> SEQ ID NO 73
<211> LENGTH: 16
<212> TYPE: DNA
<213> ORGANISM: Artificial sequence
<220> FEATURE:
<223> OTHER INFORMATION: PTP-1B oligonucleotide

<400> SEQUENCE: 73
gggtcaggct atgtgt                                                   16

<210> SEQ ID NO 74
<211> LENGTH: 17
<212> TYPE: DNA
<213> ORGANISM: Artificial sequence
<220> FEATURE:
<223> OTHER INFORMATION: MMP-1 oligonucleotide

<400> SEQUENCE: 74
gcatactggc ctttgtc                                                  17

<210> SEQ ID NO 75
<211> LENGTH: 17
<212> TYPE: DNA
<213> ORGANISM: Artificial sequence
<220> FEATURE:
<223> OTHER INFORMATION: MMP-1 oligonucleotide

<400> SEQUENCE: 75
tcaatttttc ctgcagt                                                  17

```
<210> SEQ ID NO 76
<211> LENGTH: 16
<212> TYPE: DNA
<213> ORGANISM: Artificial sequence
<220> FEATURE:
<223> OTHER INFORMATION: Cat oligonucleotide

<400> SEQUENCE: 76
gccatagcgt gcggtt                                              16

<210> SEQ ID NO 77
<211> LENGTH: 16
<212> TYPE: DNA
<213> ORGANISM: Artificial sequence
<220> FEATURE:
<223> OTHER INFORMATION: Cat oligonucleotide

<400> SEQUENCE: 77
cccggcctca cagatt                                              16

<210> SEQ ID NO 78
<211> LENGTH: 17
<212> TYPE: DNA
<213> ORGANISM: Artificial sequence
<220> FEATURE:
<223> OTHER INFORMATION: MMP-17 oligonucleotide

<400> SEQUENCE: 78
catggcgctc acatggg                                             17

<210> SEQ ID NO 79
<211> LENGTH: 17
<212> TYPE: DNA
<213> ORGANISM: Artificial sequence
<220> FEATURE:
<223> OTHER INFORMATION: MMP-17 oligonucleotide

<400> SEQUENCE: 79
tgtcatagcg tcagggc                                             17

<210> SEQ ID NO 80
<211> LENGTH: 16
<212> TYPE: DNA
<213> ORGANISM: Artificial sequence
<220> FEATURE:
<223> OTHER INFORMATION: OPG oligonucleotide

<400> SEQUENCE: 80
tcattgtggt ccccgg                                              16

<210> SEQ ID NO 81
<211> LENGTH: 16
<212> TYPE: DNA
<213> ORGANISM: Artificial sequence
<220> FEATURE:
<223> OTHER INFORMATION: OPG oligonucleotide

<400> SEQUENCE: 81
tccagttata agcagc                                              16

<210> SEQ ID NO 82
<211> LENGTH: 1684
<212> TYPE: DNA
<213> ORGANISM: Homo sapiens
<220> FEATURE:
<221> NAME/KEY: misc_feature
<223> OTHER INFORMATION: Pde4:  Acc. No. U50158
```

<400> SEQUENCE: 82

```
aatatgaagg agcagccctc atgtgccggc accgggcatc cgagcatggc gggaggaggc    60
ctaccagaaa ctggccagcg agaccctgga ggagctggac tggtgtctgg accagctaga   120
gaccctacag accaggcact ccgtcagtga gatggcctcc aacaagttta aaaggatgct   180
taatcgggag ctcacccatc tctctgaaat gagtcggtct ggaaatcaag tgtcagagtt   240
tatatcaaac acattcttag ataagcaaca tgaagtggaa attccttctc caactcagaa   300
ggaaaaggag aaaaagaaaa gaccaatgtc tcagatcagt ggagtcaaga aattgatgca   360
cagctctagt ctgactaatt caagtatccc aaggtttgga gttaaaactg aacaagaaga   420
tgtccttgcc aaggaactag aagatgtgaa caaatggggt cttcatgttt tcagaatagc   480
agagttgtct ggtaaccggc ccttgactgt tatcatgcac accatttttc aggaacggga   540
tttattaaaa acatttaaaa ttccagtaga tactttaatt acatatctta tgactctcga   600
agaccattac catgctgatg tggcctatca caacaatatc catgctgcag atgttgtcca   660
gtctactcat gtgctattat ctacacctgc tttggaggct gtgtttacag atttggagat   720
tcttgcagca ttttttgcca gtgcaataca tgatgtagat catcctggtg tgtccaatca   780
atttctgatc aatacaaact ctgaacttgc cttgatgtac aatgattcct cagtcttaga   840
gaaccatcat ttggctgtgg gctttaaatt gcttcaggaa gaaaactgtg acattttcca   900
gaatttgacc aaaaaacaaa gacaatcttt aaggaaaatg gtcattgaca tcgtacttgc   960
aacagatatg tcaaaacaca tgaatctact ggctgatttg aagactatgg ttgaaactaa  1020
gaaagtgaca agctctggag ttcttcttct tgataattat tccgatagga ttcaggttct  1080
tcagaatatg gtgcactgtg cagatctgag caacccaaca aagcctctcc agctgtaccg  1140
ccagtggacg gaccggataa tggaggagtt cttccgccaa ggagaccgag agagggaacg  1200
tggcatggag ataagcccca tgtgtgacaa gcacaatgct tccgtggaaa atcacaggt   1260
gggcttcata gactatattg ttcatcccct ctgggagaca tgggcagacc tcgtccaccc  1320
tgacgcccag gatattttgg acactttgga ggacaatcgt gaatggtacc agagcacaat  1380
ccctcagagc ccctctcctg cacctgatga cccagaggag ggccggcagg gtcaaactga  1440
gaaattccag tttgaactaa ctttagagga agatggtgag tcagacacgg aaaaggacag  1500
tggcagtcaa gtgaagaag acactagctg cagtgactcc aagactcttc gtactcaaga  1560
ctcagagtct actgaaattc cccttgatga acaggttgaa gaggaggcag taggggaaga  1620
agaggaaagc caacctgaag cctgtgtcat agatgatcgt tctcctgaca cgtaacagtg  1680
caaa                                                                1684
```

<210> SEQ ID NO 83
<211> LENGTH: 4020
<212> TYPE: DNA
<213> ORGANISM: Homo sapiens
<220> FEATURE:
<221> NAME/KEY: misc_feature
<223> OTHER INFORMATION: ACE-1: Acc. No. J04144.1

<400> SEQUENCE: 83

```
gccgagcacc gcgcaccgcg tcatgggggc cgcctcgggc cgccggggc cggggctgct    60
gctgccgctg ccgctgctgt tgctgctgcc gccgcagccc gcctggcgt tggaccccgg   120
gctgcagccc ggcaactttt ctgctgacga ggccggggcg cagctcttcg cgcagagcta   180
caactccagc gccgaacagg tgctgttcca gagcgtggcc gccagctggg cgcacgacac   240
```

```
caacatcacc gcggagaatg caaggcgcca ggaggaagca gccctgctca gccaggagtt    300
tgcggaggcc tggggccaga aggccaagga gctgtatgaa ccgatctggc agaacttcac    360
ggacccgcag ctgcgcagga tcatcggagc tgtgcgaacc ctgggctctg ccaacctgcc    420
cctggctaag cggcagcagt acaacgccct gctaagcaac atgagcagga tctactccac    480
cgccaaggtc tgcctcccca caagactgc cacctgctgg tccctggacc cagatctcac    540
caacatcctg gcttcctcgc gaagctacgc catgctcctg tttgcctggg agggctggca    600
caacgctgcg ggcatcccgc tgaaaccgct gtacgaggat tcactgccc tcagcaatga    660 agcctacaag caggacggct tcacagacac gggggcctac tggcgctcct ggtacaactc    720
ccccaccttc gaggacgatc tggaacacct ctaccaacag ctagagcccc tctacctgaa    780
cctccatgcc ttcgtccgcc gcgcactgca tcgccgatac ggagacagat acatcaacct    840
caggggaccc atccctgctc atctgctggg agacatgtgg gcccagagct gggaaaacat    900
ctacgacatg gtggtgcctt cccagacaa gcccaacctc gatgtcacca gtactatgct    960
gcagcagggc tggaacgcca cgcacatgtt ccgggtggca gaggagttct tcacctccct   1020
ggagctctcc cccatgcctc ccgagttctg gaagggtcg atgctggaga gccggccga   1080 cgggcgggaa gtggtgtgcc acgcctcggc ttgggacttc tacaacagga aagacttcag   1140
gatcaagcag tgcacacggg tcacgatgga ccagctctcc acagtgcacc atgagatggg   1200
ccatatacag tactacctgc agtacaagga tctgcccgtc tccctgcgtc gggggggccaa   1260 ccccggcttc catgaggcca ttggggacgt gctggcgctc tcggtctcca ctcctgaaca   1320
tctgcacaaa atcggcctgc tggaccgtgt caccaatgac acggaaagtg acatcaatta   1380
cttgctaaaa atggcactgg aaaaaattgc cttcctgccc tttggctact ggtggacca   1440 gtggcgctgg ggggtctta gtgggcgtac cccccttcc cgctacaact cgactggtg   1500 gtatcttcga accaagtatc aggggatctg tcctcctgtt acccgaaacg aaacccactt   1560
tgatgctgga gctaagtttc atgttccaaa tgtgacacca tacatcaggt actttgtgag   1620
ttttgtcctg cagttccagt tccatgaagc cctgtgcaag gaggcaggct atgagggccc   1680
actgcaccag tgtgacatct accggtccac caaggcaggg gccaagctcc ggaaggtgct   1740
gcaggctggc tcctccaggc cctggcagga ggtgctgaag gacatggtcg cttagatgc   1800 cctggatgcc cagccgctgc tcaagtactt ccagccagtc acccagtggc tgcaggagca   1860
gaaccagcag aacggcgagg tcctgggctg gcccgagtac cagtggcacc gccgttgcc   1920 tgacaactac ccggagggca tagacctggt gactgatgag gctgaggcca gcaagtttgt   1980
ggaggaatat gaccggacat cccaggtggt gtggaacgag tatgccgagg ccaactggaa   2040
ctacaacacc aacatcacca cagagaccag caagattctg ctgcagaaga acatgcaaat   2100
agccaaccac accctgaagt acggcaccca ggccaggaag tttgatgtga accagttgca   2160
gaacaccact atcaagcgga tcataaagaa ggttcaggac ctagaacggg cagcgctgcc   2220
tgcccaggag ctggaggagt acaacaagat cctgttggat atggaaacca cctacagcgt   2280
ggccactgtg tgccacccga atggcagctg cctgcagctc gagccagatc tgacgaatgt   2340
gatggccaca tcccggaaat atgaagacct gttatgggca tgggagggct ggcgagacaa   2400
ggcggggaga gccatcctcc agttttaccc gaaatacgtg gaactcatca accaggctgc   2460
ccggctcaat ggctatgtag atgcagggga ctcgtgagg tctatgtacg agacaccatc   2520
cctggagcaa gacctggagc ggctcttcca ggagctgcag ccactctacc tcaacctgca   2580
```

| | |
|---|---:|
| tgcctacgtg cgccgggccc tgcaccgtca ctacggggcc cagcacatca acctggaggg | 2640 |
| gcccattcct gctcacctgc tggggaacat gtgggcgcag acctggtcca acatctatga | 2700 |
| cttggtggtg cccttccctt cagcccccctc gatggacacc acagaggcta tgctaaagca | 2760 |
| gggctggacg cccaggagga tgtttaagga ggctgatgat ttcttcacct ccctgggggct | 2820 |
| gctgcccgtg cctcctgagt tctggaacaa gtcgatgctg gagaagccaa ccgacgggcg | 2880 |
| ggaggtggtc tgccacgcct cggcctggga cttctacaac ggcaaggact tccggatcaa | 2940 |
| gcagtgcacc accgtgaact tggaggacct ggtggtggcc caccacgaaa tgggccacat | 3000 |
| ccagtatttc atgcagtaca aagacttacc tgtggccttg agggagggtg ccaaccccgg | 3060 |
| cttccatgag gccattgggg acgtgctagc cctctcagtg tctacgccca agcacctgca | 3120 |
| cagtctcaac ctgctgagca gtgagggtgg cagcgacgag catgacatca actttctgat | 3180 |
| gaagatggcc cttgacaaga tcgcctttat ccccttcagc tacctcgtcg atcagtggcg | 3240 |
| ctggagggta tttgatggaa gcatcaccaa ggagaactat aaccaggagt ggtggagcct | 3300 |
| caggctgaag taccagggcc tctgcccccc agtgcccagg actcaaggtg actttgaccc | 3360 |
| aggggccaag ttccacattc cttctagcgt gccttacatc aggtactttg tcagcttcat | 3420 |
| catccagttc cagttccacg aggcactgtg ccaggcagct ggccacacgg ccccctgca | 3480 |
| caagtgtgac atctaccagt ccaaggaggc cgggcagcgc ctggcgaccg ccatgaagct | 3540 |
| gggcttcagt aggccgtggc cggaagccat gcagctgatc acgggccagc caacatgag | 3600 |
| cgcctcggcc atgttgagct acttcaagcc gctgctggac tggctccgca cggagaacga | 3660 |
| gctgcatggg gagaagctgg gctggccgca gtacaactgg acgccgaact ccgctcgctc | 3720 |
| agaagggccc ctcccagaca gcggccgcgt cagcttcctg ggcctggacc tggatgcgca | 3780 |
| gcaggcccgc gtgggccagt ggctgctgct cttcctgggc atcgccctgc tggtagccac | 3840 |
| cctgggcctc agccagcggc tcttcagcat ccgccaccgc agcctccacc ggcactccca | 3900 |
| cgggccccag ttcggctccg aggtggagct gagacactcc tgaggtgacc cggctgggtc | 3960 |
| ggccctgccc aagggcctcc caccagagac tgggatggga acactggtgg gcagctgagg | 4020 |

<210> SEQ ID NO 84
<211> LENGTH: 3556
<212> TYPE: DNA
<213> ORGANISM: Homo sapiens
<220> FEATURE:
<221> NAME/KEY: misc_feature
<223> OTHER INFORMATION: Acid2: Acc. No. NM_000704

<400> SEQUENCE: 84

| | |
|---|---:|
| tgttgggtgg gagcacaggc accgggcacc atggggaagg ccgagaacta tgagctctac | 60 |
| tcggtggagc tgggtcctgg ccctggcggg gacatggctg ccaagatgag caagaagaag | 120 |
| aaggcgggtg gcggggggtgg caagaggaag gagaagctgg agaacatgaa gaaggagatg | 180 |
| gagattaacg accaccagct gtcagtggcg gagctggaac agaaatacca gaccagtgcc | 240 |
| accaagggcc tctctgcgag cctggctgct gagctgctgc tgcgggatgg gcccaacgca | 300 |
| ctgcggccac cacggggcac cccagagtac gtcaagttcg cgaggcagct ggccgggggc | 360 |
| ctgcagtgcc tcatgtgggt tgccgccgcc atctgcctca tcgcctttgc catccaggct | 420 |
| agtgaggggg acctcaccac cgacgacaat ctgtacctgg caatcgctct cattgctgtg | 480 |
| gttgtcgtca ccgctgcttt tggctactac caggaattca agagcaccaa catcatcgcc | 540 |
| agctttaaga accttgtgcc acagcaagcc actgtcatcc gcgatggaga caaattccag | 600 |

```
atcaacgctg accaactggt ggtgggcgac ctggtggaga tgaaaggtgg ggacagagtg    660
cccgccgaca tccgcatcct ggcggcccag ggctgcaagg tggacaactc ctcgctgaca    720
ggggagtctg agccacaaac ccgctcaccc gagtgcacgc acgagagccc tctggagacc    780
cgcaacatcg ccttcttctc caccatgtgc cttgagggca ccgcgcaggg cctggtggtg    840
aacacgggcg accgcaccat cattgggcgc atcgcatcgc tggcgtcggg ggtggaaaac    900
gagaagacac ccatcgctat cgagatcgag cattttgtgg acatcatcgc gggcctggcc    960
attctcttcg gtgccacatt ttttattgtg gccatgtgca ttggctacac cttcctgcgg   1020
gccatggtct tcttcatggc catcgtggtg gcctatgtgc ctgaggggct gctggccact   1080
gtcacagtct gcctgtccct gacagccaag cgcctggcca gtaagaactg cgtggtcaag   1140
aacctggagg cggtggagac attgggctcc acttcggtga tctgctcgga caagacaggg   1200
actctcactc agaaccgcat gactgtgtcc catctgtggt tgacaaccca catccacaca   1260
gctgacacca cggaagacca gtcagggcag acgtttgacc agtcctcgga gacgtggcgg   1320
gcgctgtgcc gggtgctcac cctgtgcaac cgcgccgcct tcaagtccgg ccaggatgca   1380
gtgcctgtgc caagcgcat cgtgattgga gacgcatcgg agacggcgct gctcaagttc   1440
tcggagctga cgctgggcaa cgccatgggc taccgggacc gcttcccaaa agtctgcgag   1500
atacccttca actccaccaa caagttccag ctgtccatcc atacgctgga ggacccgcgg   1560
gacccgcgac acttgctggt gatgaagggc gcccccgagc gcgtgctgga gcgctgcagc   1620
tccatcctta tcaagggcca ggagctgccg ctggacgagc agtggcgcga ggccttccag   1680
accgcctacc tcagcctggg aggcctgggc gaacgcgtgc tcggcttctg ccagctctac   1740
ctgaatgaga aggactaccc gcctggctat gccttcgacg tagaggccat gaactttcca   1800
tctagcggcc tctgctttgc gggacttgta tccatgattg acccaccccg ggccaccgtc   1860
cctgatgctg tgctcaagtg tcgcaccgca ggcatccggg tgatcatggt aacgggtgac   1920
cacccccatca ccgccaaggc cattgcagcc agtgtgggca tcatctcgga aggcagcgag   1980
acagtggagg acatcgctgc ccgcctccgt gtgcccgtag accaggttaa tcgcaaggat   2040
gcccgtgcct gtgtgatcaa tggcatgcag ctgaaggaca tggacccatc ggaactggtc   2100
gaggccctgc gcacccaccc cgagatggtg tttgcgcgca ccagcccca gcagaagctg   2160
gtgatcgtgg agagctgcca gcggctgggt gcgattgtgg ccgtcacggg ggatggtgtg   2220
aatgactccc cagctctgaa gaaggcagac atcggagtag ccatgggcat cgctggctca   2280
gatgctgcca aaaatgcagc tgacatgatc ctgctggatg acaactttgc ctccattgtg   2340
acaggcgtgg agcagggtcg actgatcttc gacaacctga agaagtctat tgcctacaca   2400
ttgaccaaga acatcccaga gctgacaccc tacctcatct acatcaccgt cagcgtgccc   2460
ctgcccctcg ggtgcatcac catcctcttc atcgaactct gcactgacat tttcccatct   2520
gtgtccctgg catatgaaaa ggccgagagt gacatcatgc acctgcgtcc acgcaaccca   2580
aagcgtgaca gattggtcaa cgagcccctg gctgcctact cctacttcca gattggtgcc   2640
attcagtcct ttgctggctt cactgactac ttcacggcaa tggcccagga gggctggttc   2700
ccactgctgt gcgtggggct gcgggcgcag tgggaggacc accacctaca agatctgcag   2760
gacagctacg gccaggagtg gacattcggg cagcgcctgt accagcagta cacctgctac   2820
accgtgttct tcatcagcat tgaggtgtgc cagatcgccg atgtcctcat ccgcaagacg   2880
cgccgtctct ctgccttcca gcaaggcttc ttcaggaata gatcctggt gatcgccatc   2940
gtgttccagg tctgcatcgg ctgcttcctg tgctactgcc ccggcatgcc caacatcttc   3000
```

```
aacttcatgc ccattcggtt ccagtggtgg ctggtccccc tgccctacgg catcctcatc     3060
ttcgtctatg atgagatccg gaagcttgga gttcgctgtt gcccagggag ctggtgggac     3120
caggaactct actattagag ggacgactgc cttcaagcat ccctgcaact gccacagcag     3180 gtggggggcag ggcacgtggg accctctgga cagccaccaa gatatctgag caaccaagag    3240
tcccagcccc accagtatct gcttctgtag cccacggcac ccaaacttg gagggacctg      3300 cccactcccc tcccccattc ccaaggttcg cacctcctgg agcagcagcg cctgggcagt     3360
cctctgggct ggcctcggga aagccgccac ctgtggtggc ggtgggggctc tgacagggag    3420 tacagctgac cgcttctgga gggtgtttct gttcttagga ctccagtcca ggctggacgg    3480
ctgcctgagg gcccttcgtt aaagacacgc ttgtgtcctg ggcgatggta ataaaaccag    3540
ctcatgctga ctgtgc                                                    3556

<210> SEQ ID NO 85
<211> LENGTH: 1444
<212> TYPE: DNA
<213> ORGANISM: Homo sapiens
<220> FEATURE:
<221> NAME/KEY: misc_feature
<223> OTHER INFORMATION: AcidB2:  Acc. No. NM_000705

<400> SEQUENCE: 85
agtctgggcg tagagggtgc agggagcaga cgggaggatc tcaggccagg gacgatggcg      60
gctctgcagg agaagaagac gtgtggccag cgcatggagg agttccagcg ttactgctgg     120
aacccggaca cggggcagat gctgggccgc accctgtccc ggtgggtgtg gatcagcctg     180
tactacgtgg ccttctacgt ggtgatgact gggctcttcg ccctgtgcct ctatgtgctg     240
atgcagacag tggacccgta caccggac taccaagacc agctacggtc accagggta       300 accttaaggc cggatgttta cggggagaaa ggcctggaaa ttgtctacaa cgtctctgat     360
aacagaacct gggcagacct cacacagact ctccacgcct tcctagcagg ctactctcca     420
gcagcccagg aggacagcat caactgcacc tccgagcagt acttcttcca ggagagtttc     480
cgcgctccca accacaccaa gttctcctgc aagttcacgg cagatatgct gcagaactgc     540
tcaggcctgg cggatcccaa cttcggcttt gaagaaggaa agccatgttt tattattaaa     600
atgaacagga tcgtcaagtt cctccccagc aacggctcgg ccccagagt ggactgcgcc     660 ttcctggacc agccccgcga gctcggccag ccgctgcagg tcaagtacta ccctcccaac     720
ggcaccttca gtctgcacta cttcccttat tacgggaaga agcccagcc ccactacagc     780 aaccccctgg tggcagcgaa gctcctcaac atccccagga acgctgaggt cgccatcgtg     840
tgcaaggtca tggcagagca cgtgaccttc aacaatcccc acgacccgta tgaagggaaa     900
gtggagttca aactcaagat tgagaagtga aacgtttgcg caggggtcct gggcacgcct     960
gcggggtcgc tcaaggacac cctcctggtt gggcttacct tgcccgtcag ttccctgcca    1020
aatcatcccc aaagtggttt ggagcaacgg tgttgtcagt gtgcgaactc cagagaagcg    1080
cccacatctg aaggacctgc tcgcgagtat cagttcttcc ttgttgaatt cttacagttt    1140
ttagatggaa tttgctgcta taagaatgtc cagctaccat gggaacgcaa ggcagcaact    1200
ctctaattaa ccaggtcata aaaacgattc gtcttctatg tagacatcac tttcttacta    1260
taatttattt ttctacactt caatatgaac tgcccccccc acattaatat aaaaactact    1320
aatgcactga tatgaaacac ggcttacact aatgacattc tgaattcttg cttttaaaat    1380
tgcaattcct aagttgtaaa cataaaatat attaaagtta ctcttattgt atgtaaaaaa    1440
``` aaaa                                                            1444

<210> SEQ ID NO 86
<211> LENGTH: 2776
<212> TYPE: DNA
<213> ORGANISM: Homo sapiens
<220> FEATURE:
<221> NAME/KEY: misc_feature
<223> OTHER INFORMATION: Cd-18:  Acc. No. M15395

<400> SEQUENCE: 86
cagggcagac tggtagcaaa gcccccacgc ccagccagga gcaccgccgc ggactccagc      60
acaccgaggg acatgctggg cctgcgcccc ccactgctcg ccctggtggg gctgctctcc     120
ctcgggtgcg tcctctctca ggagtgcacg aagttcaagg tcagcagctg ccgggaatgc    180
atcgagtcgg ggcccggctg cacctggtgc cagaagctga acttcacagg gccgggggat    240
cctgactcca ttcgctgcga cacccggcca cagctgctca tgaggggctg tgcggctgac    300
gacatcatgg accccacaag cctcgctgaa acccaggaag accacaatgg gggccagaag    360
cagctgtccc cacaaaaagt gacgctttac ctgcgaccag gccaggcagc agcgttcaac    420
gtgaccttcc ggcgggccaa gggctacccc atcgacctgt actatctgat ggacctctcc    480
tactccatgc ttgatgacct caggaatgtc aagaagctag gtggcgacct gctccgggcc    540
ctcaacgaga tcaccgagtc cggccgcatt ggcttcgggt ccttcgtgga caagaccgtg    600
ctgccgttcg tgaacacgca ccctgataag ctgcgaaacc catgccccaa caaggagaaa    660
gagtgccagc cccgtttgc cttcaggcac gtgctgaagc tgaccaacaa ctccaaccag    720
tttcagaccg aggtcgggaa gcagctgatt ccggaaaacc tggatgcacc cgagggtggg    780
ctggacgcca tgatgcaggt cgccgcctgc ccggaggaaa tcggctggcg caacgtcacg    840
cggctgctgg tgtttgccac tgatgacggc ttccatttcg cgggcgacgg aaagctgggc    900
gccatcctga cccccaacga cggccgctgt cacctggagg acaacttgta caagaggagc    960
aacgaattcg actacccatc ggtgggccag ctggcgcaca gctggctga aaacaacatc    1020 cagcccatct tcgcggtgac cagtaggatg gtgaagacct acgagaaact caccgagatc    1080
atccccaagt cagccgtggg ggagctgtct gaggactcca gcaatgtggt ccatctcatt    1140
aagaatgctt acaataaact ctcctccagg gtcttcctgg atcacaacgc cctccccgac    1200
accctgaaag tcacctacga ctccttctgc agcaatggag tgacgcacag gaaccagccc    1260
agaggtgact gtgatggcgt gcagatcaat gtcccgatca ccttccaggt gaaggtcacg    1320
gccacagagt gcatccagga gcagtcgttt gtcatccggg cgctgggctt cacggacata    1380
gtgaccgtgc aggttcttcc ccagtgtgag tgccggtgcc gggaccagag cagagaccgc    1440
agcctctgcc atggcaaggg cttcttggag tgcggcatct gcaggtgtga cactggctac    1500
attgggaaaa actgtgagtg ccagacacag ggccggagca gccaggagct ggaaggaagc    1560
tgccggaagg acaacaactc catcatctgc tcagggctgg gggactgtgt ctgcgggcag    1620
tgcctgtgcc acaccagcga cgtccccggc aagctgatat acgggcagta ctgcgagtgt    1680
gacaccatca actgtgagcg ctacaacggc caggtctgcg gcggcccggg aggggggctc    1740
tgcttctgcg ggaagtgccg ctgccaccc ggctttgagg ctcagcgtg ccagtgcgag    1800 aggaccactg agggctgcct gaacccgcgg cgtgttgagt gtagtggtcg tggccggtgc    1860
cgctgcaacg tatgcgagtg ccattcaggc taccagctgc ctctgtgcca ggagtgcccc    1920
ggctgcccct caccctgtgg caagtacatc tcctgcgccg agtgcctgaa gttcgaaaag    1980

| | | | | |
|---|---|---|---|---|
| ggcccctttg | ggaagaactg | cagcgcggcg | tgtccgggcc | tgcagctgtc gaacaacccc 2040 |
| gtgaagggca | ggacctgcaa | ggagagggac | tcagagggct | gctgggtggc ctacacgctg 2100 |
| gagcagcagg | acgggatgga | ccgctacctc | atctatgtgg | atgagagccg agagtgtgtg 2160 |
| gcaggcccca | acatcgccgc | catcgtcggg | ggcaccgtgg | caggcatcgt gctgatcggc 2220 |
| attctcctgc | tggtcatctg | gaaggctctg | atccacctga | gcgacctccg ggagtacagg 2280 |
| cgctttgaga | aggagaagct | caagtcccag | tggaacaatg | ataatcccct tttcaagagc 2340 |
| gccaccacga | cggtcatgaa | ccccaagttt | gctgagagtt | aggagcactt ggtgaagaca 2400 |
| aggccgtcag | gacccaccat | gtctgcccca | tcacgcggcc | gagacatggc ttggccacag 2460 |
| ctcttgagga | tgtcaccaat | taaccagaaa | tccagttatt | tccgccctc aaaatgacag 2520 |
| ccatggccgg | ccggtgcttc | tgggggctcg | tcgggggggac | agctccactc tgactggcac 2580 |
| agtctttgca | tggagacttg | aggagggctt | gaggttggtg | aggttaggtg cgtgtttcct 2640 |
| gtgcaagtca | ggacatcagt | ctgattaaag | gtggtgccaa | tttatttaca tttaaacttg 2700 |
| tcagggtata | aaatgacatc | ccattaatta | tattgttaat | caatcacgtg tatagaaaaa 2760 |
| aaaataaaac | ttcaat | | | 2776 |

<210> SEQ ID NO 87
<211> LENGTH: 3387
<212> TYPE: DNA
<213> ORGANISM: Homo sapiens
<220> FEATURE:
<221> NAME/KEY: misc_feature
<223> OTHER INFORMATION: Cox2: Acc. No. M90100

<400> SEQUENCE: 87

| | | | | |
|---|---|---|---|---|
| gtccaggaac | tcctcagcag | cgcctccttc | agctccacag | ccagacgccc tcagacagca 60 |
| aagcctaccc | ccgcgccgcg | ccctgcccgc | cgctgcgatg | ctcgcccgcg ccctgctgct 120 |
| gtgcgcggtc | ctggcgctca | gccatacagc | aaatccttgc | tgttcccacc catgtcaaaa 180 |
| ccgaggtgta | tgtatgagtg | tgggatttga | ccagtataag | tgcgattgta cccggacagg 240 |
| attctatgga | gaaaactgct | caacaccgga | attttttgaca | agaataaaat tatttctgaa 300 |
| acccactcca | aacacagtgc | actacatact | tacccacttc | aagggatttt ggaacgttgt 360 |
| gaataacatt | cccttccttc | gaaatgcaat | tatgagttat | gtgttgacat ccagatcaca 420 |
| tttgattgac | agtccaccaa | cttacaatgc | tgactatggc | tacaaaagct gggaagcctt 480 |
| ctctaacctc | tcctattata | ctagagccct | tcctcctgtg | cctgatgatt gcccgactcc 540 |
| cttgggtgtc | aaaggtaaaa | agcagcttcc | tgattcaaat | gagattgtgg aaaattgct 600 |
| tctaagaaga | aagttcatcc | ctgatcccca | gggctcaaac | atgatgtttg cattctttgc 660 |
| ccagcacttc | acgcatcagt | ttttcaagac | agatcataag | cgagggccag ctttcaccaa 720 |
| cgggctgggc | catggggtgg | acttaaatca | tatttacggt | gaaactctgg ctagacagcg 780 |
| taaactgcgc | cttttcaagg | atggaaaaat | gaaatatcag | ataattgatg agagatgta 840 |
| tcctcccaca | gtcaaagata | tcaggcagga | tgatctac | cctcctcaag tccctgagca 900 |
| tctacggttt | gctgtgggc | aggaggtctt | tggtctggtg | cctggtctga tgatgtatgc 960 |
| cacaatctgg | ctgagggaac | acaacagagt | atgcgatgtg | cttaaacagg agcatcctga 1020 |
| atggggtgat | gagcagttgt | tccagacaag | caggctaata | ctgataggag agactattaa 1080 |
| gattgtgatt | gaagattatg | tgcaacactt | gagtggctat | cacttcaaac tgaaatttga 1140 |
| cccagaacta | cttttcaaca | aacaattcca | gtaccaaaat | cgtattgctg ctgaatttaa 1200 |

```
caccctctat cactggcatc cccttctgcc tgacaccttt caaattcatg accagaaata  1260
caactatcaa cagtttatct acaacaactc tatattgctg gaacatggaa ttacccagtt  1320
tgttgaatca ttcaccaggc aaattgctgg cagggttgct ggtggtagga atgttccacc  1380
cgcagtacag aaagtatcac aggcttccat tgaccagagc aggcagatga ataccagtc  1440 tttaatgag taccgcaaac gctttatgct gaagccctat gaatcatttg aagaacttac  1500
aggagaaaag gaaatgtctg cagagttgga agcactctat ggtgacatcg atgctgtgga  1560
gctgtatcct gcccttctgg tagaaaagcc tcggccagat gccatctttg gtgaaaccat  1620
ggtagaagtt ggagcaccat tctccttgaa aggacttatg ggtaatgtta tatgttctcc  1680
tgcctactgg aagccaagca cttttggtgg agaagtgggt tttcaaatca tcaacactgc  1740
ctcaattcag tctctcatct gcaataacgt gaagggctgt cccttttactt cattcagtgt  1800 tccagatcca gagctcatta aaacagtcac catcaatgca agttcttccc gctccggact  1860
agatgatatc aatcccacag tactactaaa agaacgttcg actgaactgt agaagtctaa  1920
tgatcatatt tatttattta tatgaaccat gtctattaat ttaattattt aataatattt  1980
atattaaact ccttatgtta cttaacatct tctgtaacag aagtcagtac tcctgttgcg  2040
gagaaaggag tcatacttgt gaagactttt atgtcactac tctaaagatt ttgctgttgc  2100
tgttaagttt ggaaaacagt tttattctg tttataaac cagagagaaa tgagttttga  2160 cgtctttta cttgaatttc aacttatatt ataaggacga agtaaagat gtttgaatac  2220 ttaaacacta tcacaagatg ccaaaatgct gaaagttttt acactgtcga tgtttccaat  2280
gcatcttcca tgatgcatta gaagtaacta atgtttgaaa tttttaaagta cttttgggta  2340 tttttctgtc atcaaacaaa acaggtatca gtgcattatt aaatgaatat ttaaattaga  2400
cattaccagt aatttcatgt ctactttta aaatcagcaa tgaaacaata atttgaaatt  2460
tctaaattca tagggtagaa tcacctgtaa aagcttgttt gatttcttaa agttattaaa  2520
cttgtacata taccaaaaag aagctgtctt ggatttaaat ctgtaaaatc agatgaaatt  2580
ttactacaat tgcttgttaa atatttttat aagtgatgtt cctttttcac caagagtata  2640 aacctttta gtgtgactgt taaaacttcc ttttaaatca aaatgccaaa tttattaagg  2700
tggtggagcc actgcagtgt tatctcaaaa taagaatatc ctgttgagat attccagaat  2760
ctgtttatat ggctggtaac atgtaaaaac cccataaccc cgccaaaagg ggtcctaccc  2820
ttgaacataa agcaataacc aaaggagaaa agcccaaatt attggttcca aatttagggt  2880 ttaaacttttt gaagcaaaac ttttttttag ccttgtgcac tgcagacctg gtactcgat  2940 tttgctatga ggttaatgaa gtaccaagct gtgcttgaat aacgatatgt tttctcagat  3000
tttctgttgt acagtttaat ttagcagtcc atatcacatt gcaaaagtag caatgacctc  3060
ataaaatacc tcttcaaaat gcttaaattc atttcacaca ttaattttat ctcagtcttg  3120
aagccaattc agtaggtgca ttggaatcaa gcctggctac ctgcatgctg ttccttttct  3180
tttcttcttt tagccatttt gctaagagac acagtcttct caaacacttc gtttctccta  3240
ttttgtttta ctagttttaa gatcagagtt cactttcttt ggactctgcc tatatttct  3300 tacctgaact tttgcaagtt ttcaggtaaa cctcagctca ggactgctat ttagctcctc  3360
ttaagaagat taaaaaaaaa aaaaaag                                      3387
```

<210> SEQ ID NO 88
<211> LENGTH: 4471
<212> TYPE: DNA

<213> ORGANISM: Homo sapiens
<220> FEATURE:
<221> NAME/KEY: misc_feature
<223> OTHER INFORMATION: HMG Co-A: Acc. No. NM_000859

<400> SEQUENCE: 88

| | | | | | |
|---|---|---|---|---|---|
| ttcggtggcc | tctagtgaga | tctggaggat | ccaaggattc | tgtagctaca | atgttgtcaa | 60 |
| gactttttcg | aatgcatggc | ctctttgtgg | cctcccatcc | ctgggaagtc | atagtgggga | 120 |
| cagtgacact | gaccatctgc | atgatgtcca | tgaacatgtt | tactggtaac | aataagatct | 180 |
| gtggttggaa | ttatgaatgt | ccaaagtttg | aagaggatgt | tttgagcagt | gacattataa | 240 |
| ttctgacaat | aacacgatgc | atagccatcc | tgtatattta | cttccagttc | cagaatttac | 300 |
| gtcaacttgg | atcaaaatat | attttgggta | ttgctggcct | tttcacaatt | ttctcaagtt | 360 |
| ttgtattcag | tacagttgtc | attcacttct | tagacaaaga | attgacaggc | ttgaatgaag | 420 |
| ctttgccctt | tttcctactt | tgattgacc | tttccagagc | aagcacatta | gcaaagtttg | 480 |
| ccctcagttc | caactcacag | gatgaagtaa | gggaaaatat | tgctcgtgga | atggcaattt | 540 |
| taggtcctac | gtttacccte | gatgctcttg | ttgaatgtct | tgtgattgga | gttggtacca | 600 |
| tgtcaggggt | acgtcagctt | gaaattatgt | gctgctttgg | ctgcatgtca | gttcttgcca | 660 |
| actacttcgt | gttcatgact | ttcttcccag | cttgtgtgtc | cttggtatta | gagctttctc | 720 |
| gggaaagccg | cgagggtcgt | ccaatttggc | agctcagcca | ttttgcccga | gttttagaag | 780 |
| aagaagaaaa | taagccgaat | cctgtaactc | agagggtcaa | gatgattatg | tctctaggct | 840 |
| tggttcttgt | tcatgctcac | agtcgctgga | tagctgatcc | ttctcctcaa | aacagtacag | 900 |
| cagatacttc | taaggtttca | ttaggactgg | atgaaaatgt | gtccaagaga | attgaaccaa | 960 |
| gtgtttccct | ctggcagttt | tatctctcta | aaatgatcag | catggatatt | gaacaagtta | 1020 |
| ttaccctaag | tttagctctc | cttctggctg | tcaagtacat | cttctttgaa | caaacagaga | 1080 |
| cagaatctac | actctcatta | aaaaaccecta | tcacatctcc | tgtagtgaca | caaaagaaag | 1140 |
| tcccagacaa | ttgttgtaga | cgtgaaccta | tgctggtcag | aaataaccag | aaatgtgatt | 1200 |
| cagtagagga | agagacaggg | ataaaccgag | aaagaaaagt | tgaggttata | aaaccccttag | 1260 |
| tggctgaaac | agatacccca | aacagagcta | catttgtggt | tggtaactcc | tccttactcg | 1320 |
| atacttcatc | agtactggtg | acacaggaac | ctgaaattga | acttcccagg | gaacctcggc | 1380 |
| ctaatgaaga | atgtctacag | atacttggga | atgcagagaa | aggtgcaaaa | ttccttagtg | 1440 |
| atgctgagat | catccagtta | gtcaatgcta | agcatatccc | agcctacaag | ttggaaactc | 1500 |
| tgatggaaac | tcatgagcgt | ggtgtatcta | ttcgccgaca | gttactttcc | aagaagcttt | 1560 |
| cagaaccttc | ttctctccag | tacctacctt | acagggatta | taattactcc | ttggtgatgg | 1620 |
| gagcttgttg | tgagaatgtt | attggatata | tgcccatccc | tgttggagtg | gcaggacccc | 1680 |
| tttgcttaga | tgaaaaagaa | tttcaggttc | caatggcaac | aacagaaggt | tgtcttgtgg | 1740 |
| ccagcaccaa | tagaggctgc | agagcaatag | gtcttggtgg | aggtgccagc | agccgagtcc | 1800 |
| ttgcagatgg | gatgactcgt | ggcccagttg | tgcgtcttcc | acgtgcttgt | gactctgcag | 1860 |
| aagtgaaagc | ctggctcgaa | acatctgaag | ggttcgcagt | gataaaggag | gcatttgaca | 1920 |
| gcactagcag | atttgcacgt | ctacagaaac | ttcatacaag | tatagctgga | cgcaaccttt | 1980 |
| atatccgttt | ccagtccagg | tcaggggatg | ccatggggat | gaacatgatt | tcaaagggta | 2040 |
| cagagaaagc | actttcaaaa | cttcacgagt | atttccctga | aatgcagatt | ctagccgtta | 2100 |
| gtggtaacta | ttgtactgac | aagaaacctg | ctgctataaa | ttggatagag | ggaagaggaa | 2160 |

```
aatctgttgt ttgtgaagct gtcattccag ccaaggttgt cagagaagta ttaaagacta    2220
ccacagaggc tatgattgag gtcaacatta acaagaattt agtgggctct gccatggctg    2280
ggagcatagg aggctacaac gcccatgcag caaacattgt caccgccatc tacattgcct    2340
gtggacagga tgcagcacag aatgttggta gttcaaactg tattacttta atggaagcaa    2400
gtggtcccac aaatgaagat ttatatatca gctgcaccat gccatctata gagataggaa    2460
cggtgggtgg tgggaccaac ctactacctc agcaagcctg tttgcagatg ctaggtgttc    2520
aaggagcatg caaagataat cctggggaaa atgcccggca gcttgcccga attgtgtgtg    2580
ggaccgtaat ggctggggaa ttgtcactta tggcagcatt ggcagcagga catcttgtca    2640
aaagtcacat gattcacaac aggtcgaaga tcaatttaca agacctccaa ggagcttgca    2700
ccaagaagac agcctgaata gcccgacagt tctgaactgg aacatgggca ttgggttcta    2760
aaggactaac ataaaatctg tgaattaaaa aagctcaatg cattgtcttg tggaggatga    2820
ataaatgtga tcactgagac agccacttgg ttttggctc tttcagagag gtctcaggtt    2880
cttttccatgc agactcctca gatctgaaca cagtttagtg ctttacatgc tgtgctcttt    2940
gaagagattt caacaagaat attgtatgtt aaagcatcag agatggtaat ctacagctca    3000
cctctgaaag caaatataag ctgggaaaaa gttttgatg aaattcttga agttcatggt    3060
gatcagtgca attgaccttc tccctcactc ctgccagttg aaaatggatt tttaaattat    3120
actgtagctg atgaaactcc tgattttgta gttaatttat taagtctggg atgtagaact    3180
tcaagaagta agagctaagt tctaagttca tgtttgtaaa ttaatacttc atttggtgct    3240
ggtctatttt gattttgggg ggtaatcagc attattcttc agaaggggac ctgttttctt    3300
caagggaaga aacactctta ttcccaaact acagaataat gtgttaaaca tgctaaatag    3360
ttctatcagg aaaacaaatc actgtattta tctccgcagg ctatttgttc agagaggcct    3420
tttgtttaaa tataaatgtt taaatataaa tgtttgtctg gattggctat aacatgtctt    3480
tcagcattag gcttttaaga aacacagggt tttgtattct ttactaaaga tatcagagct    3540
cttaatgttg cttagatgag ggtgactgtc aagtacaagc aagactggga ccttagaaat    3600
cattgtagaa acacagtttt gaaagatttt taccatgtct ctaagccaac tttaattgct    3660
taaaagacat ttttatttag ttgaaaaatc tagtttttt tgtaaactgt accaaatctg    3720
tatatgttgt aataaaactt atgctagttt attggaagtg ttcaagaaat aaaaatcaac    3780
ttgtgtactg ataaaatact ctagcctggg ccagagaaga taatgttctt taatgttgtc    3840
aggaaaccct ggcttgcttg ccgagcctaa tgaaagggaa agtcagcttt cagagccagt    3900
gaaggagcca cgtgaatggc cctagaactg tgcctagttc ctgtggccag gaggttggtg    3960
actgaaacat tcacacaggg ctcttggatg gacccacgaa cgctcttagc tttctcaggg    4020
ggtcagcaga gttattgaat cttaattttt tttaatgtac aagttttgta taaataataa    4080
agaactcctt attttgtatt acatctaatg cttaagtgtt gctcttggaa agctgatgat    4140
gtctcttgta gagatgactc tgaaaaacat tccaggaaac catggcagca tggagagcct    4200
cttagtgatt gtgtctgcat tgttattgtg gaagatttac ctttttctgtt gtacgtaaag    4260
cttaaattac ttttgttgtg acttttagc cagtgacttt ttctgagctt ttcatggaag    4320
tggcagtgaa aaatatgttg agtgttcaaa aaagtgactg taattaatat cttgctggat    4380
taatgttttg tacaattact aaattgtata cattttgtta tagaatactt ttttctagtt    4440
tcagtaaata atgaaaagga agttaatacc a                                    4471
```

<210> SEQ ID NO 89
<211> LENGTH: 2444
<212> TYPE: DNA
<213> ORGANISM: Homo sapiens
<220> FEATURE:
<221> NAME/KEY: misc_feature
<223> OTHER INFORMATION: NM_021975

<400> SEQUENCE: 89

| | | | | | |
|---|---|---|---|---|---|
| ggcacgaggc | ggggccgggt | cgcagctggg | cccgcggcat | ggacgaactg | ttccccctca | 60 |
| tcttcccggc | agagcagccc | aagcagcggg | gcatgcgctt | ccgctacaag | tgcgaggggc | 120 |
| gctccgcggg | cagcatccca | ggcgagagga | gcacagatac | caccaagacc | cacccccacca | 180 |
| tcaagatcaa | tggctacaca | ggaccaggga | cagtgcgcat | ctccctggtc | accaaggacc | 240 |
| ctcctcaccg | gcctcacccc | cacgagcttg | taggaaagga | ctgccgggat | ggcttctatg | 300 |
| aggctgagct | ctgcccggac | cgctgcatcc | acagtttcca | gaacctggga | atccagtgtg | 360 |
| tgaagaagcg | ggacctggag | caggctatca | gtcagcgcat | ccagaccaac | aacaacccct | 420 |
| tccaagttcc | tatagaagag | cagcgtgggg | actacgacct | gaatgctgtg | cggctctgct | 480 |
| tccaggtgac | agtgcgggac | ccatcaggca | ggcccctccg | cctgccgcct | gtcctttctc | 540 |
| atcccatctt | tgacaatcgt | gcccccaaca | ctgccgagct | caagatctgc | cgagtgaacc | 600 |
| gaaactctgg | cagctgcctc | ggtggggatg | agatcttcct | actgtgtgac | aaggtgcaga | 660 |
| agaggacat | tgaggtgtat | ttcacggac | caggctggga | ggcccgaggc | tccttttcgc | 720 |
| aagctgatgt | gcaccgacaa | gtggccattg | tgttccggac | ccctccctac | gcagaccccca | 780 |
| gcctgcaggc | tcctgtgcgt | gtctccatgc | agctgcggcg | gccttccgac | cgggagctca | 840 |
| gtgagcccat | ggaattccag | tacctgccag | atacagacga | tcgtcaccgg | attgaggaga | 900 |
| aacgtaaaag | gacatatgag | accttcaaga | gcatcatgaa | gaagagtcct | ttcagcggac | 960 |
| ccaccgaccc | ccggcctcca | cctcgacgca | ttgctgtgcc | ttcccgcagc | tcagcttctg | 1020 |
| tccccaagcc | agcaccccag | ccctatccct | tacgtcatc | cctgagcacc | atcaactatg | 1080 |
| atgagtttcc | caccatggtg | tttccttctg | ggcagatcag | ccaggcctcg | gccttggccc | 1140 |
| cggcccctcc | ccaagtcctg | ccccaggctc | cagccctgc | ccctgctcca | gccatggtat | 1200 |
| cagctctggc | ccaggcccca | gccctgtcc | cagtcctagc | cccaggccct | cctcaggctg | 1260 |
| tggccccacc | tgcccccaag | cccacccagg | ctggggaagg | aacgctgtca | gaggccctgc | 1320 |
| tgcagctgca | gtttgatgat | gaagacctgg | gggccttgct | tggcaacagc | acagacccag | 1380 |
| ctgtgttcac | agacctggca | tccgtcgaca | actccgagtt | tcagcagctg | ctgaaccagg | 1440 |
| gcatacctgt | ggccccccac | acaactgagc | ccatgctgat | ggagtaccct | gaggctataa | 1500 |
| ctcgcctagt | gacagcccag | aggcccccg | acccagctcc | tgctccactg | ggggcccgg | 1560 |
| ggctccccaa | tggcctcctt | tcaggagatg | aagacttctc | ctccattgcg | gacatggact | 1620 |
| tctcagccct | gctgagtcag | atcagctcct | aaggggtga | cgcctgccct | ccccagagca | 1680 |
| ctggttgcag | gggattgaag | ccctccaaaa | gcacttacgg | attctggtgg | ggtgtgttcc | 1740 |
| aactgccccc | aactttgtgg | atgtcttcct | tggaggggg | agccatattt | tattcttta | 1800 |
| ttgtcagtat | ctgtatctct | ctctcttttt | ggaggtgctt | aagcagaagc | attaacttct | 1860 |
| ctggaaaggg | gggagctggg | gaaactcaaa | cttttcccct | gtcctgatgg | tcagctccct | 1920 |
| tctctgtagg | gaactgtggg | gtccccatc | cccatcctcc | agcttctggt | actctcctag | 1980 |
| agacagaagc | aggctggagg | taaggccttt | gagcccacaa | agcctatca | agtgtcttcc | 2040 |
| atcatggatt | cattacagct | taatcaaaat | aacgcccag | ataccagccc | ctgtatggca | 2100 |

```
ctggcattgt ccctgtgcct aacaccagcg tttgaggggc tgccttcctg ccctacagag    2160
gtctctgccg gctctttcct tgctcaacca tggctgaagg aaacagtgca acagcactgg    2220
ctctctccag gatccagaag gggtttggtc tggacttcct tgctctcccc tcttctcaag    2280
tgccttaata gtagggtaag ttgttaagag tgggggagag caggctggca gctctccagt    2340
caggaggcat agttttttagt gaacaatcaa agcacttgga ctcttgctct ttctactctg    2400
aactaataaa gctgttgcca agctggacgg cacgagctcg tgcc                     2444
```

<210> SEQ ID NO 90
<211> LENGTH: 816
<212> TYPE: DNA
<213> ORGANISM: Homo sapiens

<400> SEQUENCE: 90

```
atgcactttc tttgccaaag gcaaacgcag aacgtttcag agccatgagg atgcttctgc     60
atttgagttt gctagctctt ggagctgcct acgtgtatgc catccccaca gaaattccca    120
caagtgcatt ggtgaaagag accttggcac tgctttctac tcatcgaact ctgctgatag    180
ccaatgagac tctgaggatt cctgttcctg tacataaaaa tcaccaactg tgcactgaag    240
aaatctttca gggaataggc acactggaga gtcaaactgt gcaggggggt actgtggaaa    300
gactattcaa aaacttgtcc ttaataaaga aatacattga cggccaaaaa aaaaagtgtg    360
gagaagaaag acggagagta aaccaattcc tagactacct gcaagagttt cttggtgtaa    420
tgaacaccga gtggataata gaaagttgag actaaactgg tttgttgcag ccaaagattt    480
tggaggagaa ggacatttta ctgcagtgag aatgagggcc aagaaagagt caggccttaa    540
ttttcaatat aatttaactt cagagggaaa gtaaatattt caggcatact gacactttgc    600
cagaaagcat aaaattctta aaatatattt cagatatcag aatcattgaa gtattttcct    660
ccaggcaaaa ttgatatact tttttcttat ttaacttaac attctgtaaa atgtctgtta    720
acttaatagt atttatgaaa tggttaagaa tttggtaaat tagtatttat ttaatgttat    780
gttgtgttct aataaaacaa aaatagacaa ctgttc                               816
```

<210> SEQ ID NO 91
<211> LENGTH: 2484
<212> TYPE: DNA
<213> ORGANISM: Homo sapiens
<220> FEATURE:
<221> NAME/KEY: misc_feature
<223> OTHER INFORMATION: LO5:  Acc. No. J03571

<400> SEQUENCE: 91

```
gggcccggcg ctcgctgctc ccgcggcccg cgccatgccc tcctacacgg tcaccgtggc     60
cactggcagc cagtggttcg ccggcactga cgactacatc tacctcagcc tcgtgggctc    120
ggcgggctgc agcgagaagc acctgctgga caagcccttc tacaacgact cgagcgtgg    180 cgcggtggat tcatacgacg tgactgtgga cgaggaactg ggcgagatcc agctggtcag    240
aatcgagaag cgcaagtact ggctgaatga cgactggtac ctgaagtaca tcacgctgaa    300
gacgccccac ggggactaca tcgagttccc ctgctaccgc tggatcaccg gcgatgtcga    360
ggttgtcctg agggatggac gcgcaaagtt ggcccgagat gaccaaattc acattctcaa    420
gcaacaccga cgtaaagaac tggaaacacg gcaaaaacaa tatcgatgga tggagtggaa    480
ccctggcttc cccttgagca tcgatgccaa atgcacaag gatttacccc gtgatatcca    540
gtttgatagt gaaaaaggag tggactttgt tctgaattac tccaaagcga tggagaacct    600
```

```
gttcatcaac cgcttcatgc acatgttcca gtcttcttgg aatgacttcg ccgactttga    660
gaaaatcttt gtcaagatca gcaacactat ttctgagcgg gtcatgaatc actggcagga    720
agacctgatg tttggctacc agttcctgaa tggctgcaac cctgtgttga tccggcgctg    780
cacagagctg cccgagaagc tcccggtgac cacggagatg gtagagtgca gcctggagcg    840
gcagctcagc ttggagcagg aggtccagca agggaacatt ttcatcgtgg actttgagct    900
gctggatggc atcgatgcca acaaaacaga cccctgcaca ctccagttcc tggccgctcc    960
catctgcttg ctgtataaga acctggccaa caagattgtc cccattgcca tccagctcaa   1020
ccaaatcccg ggagatgaga accctatttt cctcccttcg gatgcaaaat acgactggct   1080
tttggccaaa atctgggtgc gttccagtga cttccacgtc caccagacca tcacccacct   1140
tctgcgaaca catctggtgt ctgaggtttt tggcattgca atgtaccgcc agctgcctgc   1200
tgtgcacccc attttcaagc tgctggtggc acacgtgaga ttcaccattg caatcaacac   1260
caaggcccgt gagcagctca tctgcgagtg tggcctctct gacaaggcca acgccacagg   1320
gggcggtggg cacgtgcaga tggtgcagag ggccatgaag gacctgacct atgcctccct   1380
gtgctttccc gaggccatca aggcccgggg catgggagag aaagaagaca tccctacta   1440 cttctaccgg gacgacgggc tcctggtgtg ggaagccatc aggacgttca cggccgaggt   1500
ggtagacatc tactacgagg cgaccaggt ggtggaggag gacccggagc tgcaggactt   1560
cgtgaacgat gtctacgtgt acggcatgcg gggccgcaag tcctcaggct tccccaagtc   1620
ggtcaagagc cgggagcagc tgtcggagta cctgaccgtg gtgatcttca ccgcctccgc   1680
ccagcacgcc gcggtcaact tcggccagta cgactggtgc tcctggatcc ccaatgcgcc   1740
cccaaccatg cgagcccgc caccgactgc caagggcgtg gtgaccattg agcagatcgt   1800
ggacacgctg cccgaccgcg gccgctcctg ctggcatctg ggtgcagtgt gggcgctgag   1860
ccagttccag gaaaacgagc tgttcctggg catgtaccca gaagagcatt ttatcgagaa   1920
gcctgtgaag gaagccatgg cccgattccg caagaacctc gaggccattg tcagcgtgat   1980
tgctgagcgc aacaagaaga agcagctgcc atattactac ttgtcccag accggattcc   2040 gaacagtgtg gccatctgag cacactgcca gtctcactgt gggaaggcca gctgcccag   2100 ccagatggac tccagcctgc ctggcaggtg tctggccagg cctcttggca gtcacatctc   2160
ttcctccgag gccagtacct ttccatttat tctttgatct tcagggaact gcatagattg   2220
atcaaagtgt aaacaccata gggacccatt ctacacagag caggactgca cagcgtcctg   2280
tccacaccca gctcagcatt tccacaccaa gcagcaacag caaatcacga ccactgatag   2340
atgtctattc ttgttggaga catgggatga ttattttctg ttctatttgt gcttagtcca   2400
attccttgca catagtaggt acccaattca attactattg aatgaattaa gaattggttg   2460
ccataaaaat aaatcagttc attt                                          2484
```

<210> SEQ ID NO 92
<211> LENGTH: 2437
<212> TYPE: DNA
<213> ORGANISM: Homo sapiens
<220> FEATURE:
<221> NAME/KEY: misc_feature
<223> OTHER INFORMATION: MPB:  Acc. No.: M74047

<400> SEQUENCE: 92

```
gcggccaccg cgcaggaaca cggcgcgatg caggttcagt gccagcagag cccagtgctg     60
gcaggcagcg ccactttggt cgcccttggg gcactggcct tgtacgtcgc gaagccctcc    120
```

```
ggctacggga agcacacgga gagcctgaag ccggcggcta cccgcctgcc agcccgcgcc    180
gcctggttcc tgcaggagct gccttccttc gcggtgcccg cggggatcct cgcccggcag    240
cccctctccc tcttcgggcc acctgggacg gtacttctgg gcctcttctg cgtacattac    300
ttccacagga catttgtgta ctcactgctc aatcgaggga ggccttatcc agctatactc    360
attctcagag gcactgcctt ctgcactgga aatggagtcc ttcaaggcta ctatctgatt    420
tactgtgctg aataccctga tgggtggtac acagacatac ggtttagctt gggtgtcttc    480
ttatttattt tgggaatggg aataaacatt catagtgact atatattgcg ccagctcagg    540
aagcctggag aaatcagcta caggattcca caaggtggct gtttacgta tgtttctgga     600 gccaatttcc tcggtgagat cattgaatgg atcggctatg ccctggccac ttggtccctc    660
ccagcacttg catttgcatt tttctcactt tgtttccttg ggctgcgagc ttttcaccac    720
cataggttct acctcaagat gtttgaggac taccccaaat ctcggaaagc ccttattcca    780
ttcatctttt aaaggaacca aattaaaaag gagcagagct cccacaatgc tgatgaaaac    840
tgtcaagctg ctgaaactgt aattttcatg atataatagt catatatata tatatatata    900
tatatatata tatatatgt atatatgta atagtaggtc tcctggcgtt ctgccagctg     960
gcctggggat tctgagtggt gtctgcttag agtttactcc tacccttcca gggacccta    1020 tcctgatccc caactgaagc ttcaaaaagc cacttttcca aatggcgaca gttgcttctt    1080
agctattgct ctgagaaagt acaaacttct cctatgtctt tcaccgggca atccaagtac    1140
atgtggcttc atacccactc cctgtcaatg caggacaact ctgtaatcaa gaatttttg    1200 acttgaaggc agtacttata gaccttatta aaggtatgca ttttatacat gtaacagagt    1260
agcagaaatt taaactctga agccacaaag acccagagca aacccactcc caaatgaaaa    1320
ccccagtcat ggcttccttt ttcttggtta attaggaaag atgagaaatt attaggtaga    1380
ccttgaatac aggagccctc tcctcatagt gctgaaaaga tactgatgca ttgacctcat    1440
ttcaaatttg tgcagtgtct tagttgatga gtgcctctgt tttccagaag atttcacaat    1500
ccccggaaaa ctggtatggc tattcttgaa ggccaggttt taataaccac aaacaaaaag    1560
gcatgaacct gggtggctta tgagagagta gagaacaaca tgaccctgga tggctactaa    1620
gaggatagag aacagtttta caatagacat tgcaaactct catgtttttg gaaactggtg    1680
gcaatatcca aataatgagt agtgtaaaac aaagagaatt aatgatgagg ttacatgctg    1740
cttgcctcca ccagatgtcc acaacaatat gaagtacagc agaagcccca agcaactttc    1800 cttttcctgga gcttcttcct tgtagttctc aggacctgtt caagaaggtg tctcctaggg   1860
gcagcctgaa tgcctccctc aaaggacctg caggcagaga ctgaaaattg cagacagagg    1920
ggcacgtctg ggcagaaaac ctgttttgtt tggctcagac atatagtttt tttttttta    1980 caaagtttca aaacttaaa aatcaggaga ttccttcata aaactctagc attctagttt    2040
catttaaaaa gttggaggat ctgaacatac agagcccaca tttccacacc agaactggaa    2100
ctacgtagct agtaagcatt tgagtttgca aactcttgtg aagggggtcac cccagcatga   2160 gtgctgagat atggactctc taaggaaggg gccgaacgct tgtaattgga atacatggaa    2220
atatttgtct tctcaggcct atgtttgcgg aatgcattgt caatatttag caaactgttt    2280
tgacaaatga gcaccagtgg tactaagcac agaaactcac tatataagtc acataggaaa    2340
cttgaaaggt ctgaggatga tgtagattac tgaaaaatac aaattgcaat catataaata    2400
agtgtttttg ttgttcatta aatacccttta aatcatg                            2437
```

<210> SEQ ID NO 93
<211> LENGTH: 5595
<212> TYPE: DNA
<213> ORGANISM: Homo sapiens
<220> FEATURE:
<221> NAME/KEY: misc_feature
<223> OTHER INFORMATION: NEP=CALLA:  Acc. No. NM_000902

<400> SEQUENCE: 93

| | | | | | |
|---|---|---|---|---|---|
| gcggagatgt | gcaagtggcg | aagcttgacc | gagagcaggc | tggagcagcc | gcccaactcc | 60 |
| tggcgcggga | tctgctgagg | ggtcacggat | tttaggtgat | gggcaagtca | gaaagtcaga | 120 |
| tggatataac | tgatatcaac | actccaaagc | caaagaagaa | acagcgatgg | actcgactgg | 180 |
| agatcagcct | ctcggtcctt | gtcctgctcc | tcaccatcat | agctgtgaga | atgatcgcac | 240 |
| tctatgcaac | ctacgatgat | ggtatttgca | agtcatcaga | ctgcataaaa | tcagctgctc | 300 |
| gactgatcca | aaacatggat | gccaccactg | agccttgtag | agacttttc | aaatatgctt | 360 |
| gcggaggctg | gttgaaacgt | aatgtcattc | ccgagaccag | ctcccgttac | ggcaactttg | 420 |
| acatttaag | agatgaacta | gaagtcgttt | tgaaagatgt | ccttcaagaa | cccaaaactg | 480 |
| aagatatagt | agcagtgcag | aaagcaaaag | cattgtacag | gtcttgtata | atgaatctg | 540 |
| ctattgatag | cagaggtgga | gaacctctac | tcaaactgtt | accagacata | tatgggtggc | 600 |
| cagtagcaac | agaaaactgg | gagcaaaaat | atggtgcttc | ttggacagct | gaaaaagcta | 660 |
| ttgcacaact | gaattctaaa | tatgggaaaa | aagtccttat | taatttgttt | gttggcactg | 720 |
| atgataagaa | ttctgtgaat | catgtaattc | atattgacca | acctcgactt | ggcctccctt | 780 |
| ctagagatta | ctatgaatgc | actggaatct | ataaagaggc | ttgtacagca | tatgtggatt | 840 |
| ttatgatttc | tgtggccaga | ttgattcgtc | aggaagaaag | attgcccatc | gatgaaaacc | 900 |
| agcttgcttt | ggaaatgaat | aaagtatgg | aattggaaaa | agaaattgcc | aatgctacgg | 960 |
| ctaaacctga | agatcgaaat | gatccaatgc | ttctgtataa | caagatgaga | ttggcccaga | 1020 |
| tccaaaataa | cttttcacta | gagatcaatg | ggaagccatt | cagctggttg | aatttcacaa | 1080 |
| atgaaatcat | gtcaactgtg | aatattagta | ttacaaatga | ggaagatgtg | gttgtttatg | 1140 |
| ctccagaata | tttaaccaaa | cttaagccca | ttcttaccaa | atattctgcc | agagatcttc | 1200 |
| aaaatttaat | gtcctggaga | ttcataatgg | atcttgtaag | cagcctcagc | cgaacctaca | 1260 |
| aggagtccag | aaatgctttc | cgcaaggccc | tttatggtac | aacctcagaa | acagcaactt | 1320 |
| ggagacgttg | tgcaaactat | gtcaatggga | atatggaaaa | tgctgtgggg | aggctttatg | 1380 |
| tggaagcagc | atttgctgga | gagagtaaac | atgtggtcga | ggatttgatt | gcacagatcc | 1440 |
| gagaagttt | tattcagact | ttagatgacc | tcacttggat | ggatgccgag | acaaaaaaga | 1500 |
| gagctgaaga | aaaggccta | gcaattaaga | aaggatcgg | ctatcctgat | gacattgttt | 1560 |
| caaatgataa | caaactgaat | aatgagtacc | tcgagttgaa | ctacaaagaa | gatgaatact | 1620 |
| tcgagaacat | aattcaaaat | ttgaaattca | gccaaagtaa | acaactgaag | aagctccgag | 1680 |
| aaaaggtgga | caaagatgag | tggataagtg | gagcagctgt | agtcaatgca | tttactctt | 1740 |
| caggaagaaa | tcagatagtc | ttcccagccg | gcattctgca | gccccccttc | tttagtgccc | 1800 |
| agcagtccaa | ctcattgaac | tatggggca | tcggcatggt | cataggacac | gaaatcaccc | 1860 |
| atggcttcga | tgacaatggc | agaaacttta | acaaagatgg | agacctcgtt | gactggtgga | 1920 |
| ctcaacagtc | tgcaagtaac | tttaaggagc | aatcccagtg | catggtgtat | cagtatggaa | 1980 |
| acttttcctg | ggacctggca | ggtggacagc | accttaatgg | aattaataca | ctgggagaaa | 2040 |

```
acattgctga taatggaggt cttggtcaag catacagagc ctatcagaat tatattaaaa      2100
agaatggcga agaaaaatta cttcctggac ttgacctaaa tcacaaacaa ctattttttct    2160
tgaactttgc acaggtgtgg tgtggaacct ataggccaga gtatgcggtt aactccatta    2220
aaacagatgt gcacagtcca ggcaatttca ggattattgg actttgcag aactctgcag    2280
agttttcaga agcctttcac tgccgcaaga attcatacat gaatccagaa agaagtgcc    2340
gggtttggtg atcttcaaaa gaagcattgc agcccttggc tagacttgcc aacaccacag    2400
aaatggggaa ttctctaatc gaaagaaaat gggccctagg ggtcactgta ctgacttgag    2460
ggtgattaac agagagggca ccatcacaat acagataaca ttaggttgtc ctagaaaggg    2520
tgtggaggga ggaagggggt ctaaggtcta tcaagtcaat catttctcac tgtgtacata    2580
atgcttaatt tctaaagata atatattactgt ttatttctgt ttctcatatg gtctaccagt    2640
ttgctgatgt ccctagaaaa caatgcaaaa cctttgaggt agaccaggat ttctaatcaa    2700
aagggaaaag aagatgttga agaatagagt taggcaccag aagaagagta ggtgacacta    2760
tagtttaaaa cacattgcct aactactagt ttttactttt atttgcaaca tttacagtcc    2820
ttcaaaatcc ttccaaagaa ttcttataca cattggggcc ttggagctta catagtttta    2880
aactcatttt tgccatacat cagttattca ttctgtgatc atttatttta agcactctta    2940
aagcaaaaaa tgaatgtcta aaattgtttt ttgttgtacc tgctttgact gatgctgaga    3000
ttcttcaggc ttcctgcaat tttctaagca atttcttgct ctatctctca aaacttggta    3060
tttttcagag atttatataa atgtaaaaat aataatttttt atatttaatt attaactaca    3120
tttatgagta actattatta taggtaatca atgaatattg aagtttcagc ttaaaataaa    3180
cagttgtgaa ccaagatcta taaagcgata tacagatgaa aatttgagac tatttaaact    3240
tataaatcat attgatgaaa agatttaagc acaaacttta gggtaaaaat tgcgattgga    3300
cagttgtcta gagatatata tacttgtggt tttcaaattg gactttcaaa attaaatctg    3360
tccctgagag tgtctctgat aaagggcaa atctgcacct atgtagctct gcatctcctg    3420
tcttttcagg tttgtcatca gatggaaata ttttgataat aaattgaaat tgtgaactca    3480
ttgctcccta agactgtgac aactgtctaa ctttagaagt gcattctgaa atagaaatgg    3540
gaggcctctg atggaccttc tagaattata agtcacaaag agttctggaa aagaactgtt    3600
tactgcttga taggaattca tcttttgagg cttctgttcc tctcttttcc tgttgtattg    3660
actattttcg ttcattactt gattaagatt ttacaaaaga ggagcacttc caaaattctt    3720
attttttccta acaaaagatg aaagcaggga atttctatct aaatgatgag tattagttcc    3780
ctgtctcttg aaaaatgccc atttgccttt aaaaaaaaaa gttacagaaa tactataaca    3840
tatgtacata aattgcataa agcataagta tacagttcaa taaacttaac tttaactgaa    3900
caatggccct gtagccagca cctgtaagaa acagagcagt accagcgctc taaaagcacc    3960
tccttgtcac tttattactc ccagaacaac aactatcctg acttctaata tcattcacta    4020
gctttgcctg gttttgtctt ttatgcagat agaatcaatc agtatgtatt cttttgtgcc    4080
tggcttcttt ctctcagcct tacatttgtg agattcctct gtattgtgct gattgtggat    4140
cttttcattc tcattgcaga ataatgttct attgtgggac ttattacaat tgttcatcc    4200
tattgttgat gggcacttga gaactttcca ttttggcgct attacaaata gtgcaactat    4260
gaatgtactg catgttacca tcttacttga gcctttaatg gacttatttc ttcaaatcct    4320
tccaaaaatt attataagca ttgaaattat agtttcaagc caactgtgga tacccttacc    4380
ctttcctcct ttatcacaac caccgttaca agtatactta tatttcccta aaatacattt    4440
```

| | |
|---|---|
| aaaacttacc taagtgacat ttgtagttgg agtaatagga gcttccagct ctaataaaac | 4500 |
| agctgtctct aacttatttt atttccatca tgtcagagca ggtgaagagc cagaagtgaa | 4560 |
| gagtgactag tacaaattat aaaaagccac tagactcttc actgttagct ttttaaaaca | 4620 |
| ttaggctccc atcccatatgg aggaacaact ctccagtgcc tggatcccct ctgtctacaa | 4680 |
| atataagatt ttctgggcct aaaggataga tcaaagtcaa aaatagcaat gcctccctat | 4740 |
| ccctcacaca tccagacatc atgaatttta catggtactc ttgttgagtt ctatagagcc | 4800 |
| ttctgatgtc tctaaagcac taccgattct ttggagttgt cacatcagat aagacatatc | 4860 |
| tctaattcca tccataaatc cagttctact atggctgagt tctggtcaaa gaagaaagt | 4920 |
| ttagaagctg agacacaaag ggttgggagc tgatgaaact cacaaatgat ggtaggaaga | 4980 |
| agctctcgac aatacccgtt ggcaaggagt ctgcctccat gctgcagtgt tcgagtggat | 5040 |
| tgtaggtgca agatggaaag gattgtaggt gcaagctgtc cagagaaaag agtccttgtt | 5100 |
| ccagccctat tctgccactc ctgacagggt gaccttgggt atttgcaata ttcctttggg | 5160 |
| cctctgcttc tctcacctaa aaaaagagaa ttagattata ttggtggttc tcagcaagag | 5220 |
| aaggagtatg tgtccaatgc tgccttccca tgaatctgtc tcccagttat gaatcagtgg | 5280 |
| gcaggataaa ctgaaaactc ccatttaagt gtctgaatcg agtgagacaa aattttagtc | 5340 |
| caaataacaa gtaccaaagt tttatcaagt ttgggtctgt gctgctgtta ctgttaacca | 5400 |
| tttaagtggg gcaaaacctt gctaattttc tcaaaagcat ttatcattct tgttgccaca | 5460 |
| gctggagctc tcaaactaaa agacatttgt tatttggaa agaagaaaga ctctattctc | 5520 |
| aaagtttcct aatcagaaat ttttatcagt ttccagtctc aaaaatacaa aataaaaaca | 5580 |
| aacgttttta atact | 5595 |

<210> SEQ ID NO 94
<211> LENGTH: 551
<212> TYPE: DNA
<213> ORGANISM: Homo sapiens
<220> FEATURE:
<221> NAME/KEY: misc_feature
<223> OTHER INFORMATION: NPY: Acc. No. K01911

<400> SEQUENCE: 94

| | |
|---|---|
| accccatccg ctggctctca cccctcggag acgctcgccc gacagcatag tacttgccgc | 60 |
| ccagccacgc ccgcgcgcca gccaccatgc taggtaacaa gcgactgggg ctgtccggac | 120 |
| tgacccctcgc cctgtccctg ctcgtgtgcc tgggtgcgct ggccgaggcg taccctcca | 180 |
| agccggacaa cccgggcgag gacgcaccag cggaggacat ggccagatac tactcggcgc | 240 |
| tgcgacacta catcaacctc atcaccaggc agagatatgg aaaacgatcc agcccagaga | 300 |
| cactgatttc agacctcttg atgagagaaa gcacagaaaa tgttcccaga actcggcttg | 360 |
| aagaccctgc aatgtggtga tgggaaatga gacttgctct ctggccttt cctattttca | 420 |
| gcccatattt catcgtgtaa aacgagaatc cacccatccc accaatgcat gcagccactg | 480 |
| tgctgaattc tgcaatgttt tcctttgtca tcattgtata tatgtgtgtt taaataaagt | 540 |
| atcatgcatt c | 551 |

<210> SEQ ID NO 95
<211> LENGTH: 4382
<212> TYPE: DNA
<213> ORGANISM: Homo sapiens
<220> FEATURE:
<221> NAME/KEY: misc_feature

<223> OTHER INFORMATION: SEG_AB00161S

<400> SEQUENCE: 95

```
aagcttgctg aatcacctct taattcttgt agttgctttg tgcattcctt tgggtattcc      60
tcatagatac tcatgtctgc aaatggagaa tgtttacttt ttcatttta tgccttatat     120
ttcttttttg tgttttgct tgttgcatt tgttttttct atttgtatga ccaaaatctt      180
tagcagtaca ggtaggtaac aaccaaataa tgtagaaccc cataagccac gttacagagt     240
ttgaatttta ttttagcaca gtgggaatac attgaaggtc tttagttaag ctgttgctca     300
tgagcaacaa atgagcaatg acatatatgt atgtatatac acatatatat cattgatttt     360
atatatatat atatatatat atatatatat atatatatat atatatctat cttagtccac     420
ttgtgttgca ataacaaaat accacagact gggtcattta caaaaattaa atatatatat     480
acatatacac acatatatat atcatacata tacacataca tacatcattg ctcatttgtt     540
tgttataaat agcattaaca gcattttca agttatatcc tgggagtgtt tatgatttac      600
ttattcttca actaattcca taacaagatt tgaggtgctt agaacaattc atgccaagtt     660
aaaacaaaat aattgggcaa attgggataa agaataaaat ggagttgaaa acaagaggc      720
ccaggtaatg tcagttcaaa atatgcttac ctttaactac tttaaattta caggaggtat     780
agttacacat tttggctgaa tctcccagag actagaactg tttgagacac ttctgttccc     840
caatcccttg tgatatgttt ctcaggtaat aggccttcac agtaactccc aaactatcat     900
atataccaca cagacttgag attcactatt gagagaatct atgtactgtt tttctttttt     960
tttcttttt gttatagagc cggggtctt acactgtcac tgaggctgaa gtgcaatggc     1020
acgatcatgg ctcactgcag ccttgacctc ctgggctcaa tcctcttgcc tcagcctctc    1080
gaataactag gattacaggt gtgttccccc atgcctggct aatttttaaa aattttgtgt    1140
agagatgggg tcatgccatg tggcccaggc tggttcaaac tcctgagctc aagtatcctt    1200
ctacctctcc ctcccaaagt tctgagatta caggaatgag ccactgtgcc cagcctatag    1260
attgttttc ttgaagcaat ttttcagaaa ccttcctggt ttctgataat ttaaccttt      1320
caggttagga gagaaaaatg aacattttga tattacccac tgtcttagtc catttgtgtt    1380
gctgtaataa aatatcacag actgggatat ttataaacaa tagaaattaa tttctctcag    1440
ttctggaggc tggaaactcc aaaatcaaag tgccagcaga tttggcaact ggtgagggct    1500
gctctttgct tacaaaatgg caccttgttg ctgcatcctc agcaagggtc agtgctgtgt    1560
cttcacatag tggaaagaat agaagggggcc aactgtctcc tttgggcctt tttttaaaaa   1620
ggcactaatg cattcacaaa ggcagagccc taatggtcta atcaccactt aaaggcacct    1680
cctcttaata ctgttgaatt agggattaag tttcaacatg aattttggag ggaatacaaa    1740
cattgaaatg attatacgtg tttatttaat caagtatcca acaaaagcaa ataattcaag    1800
ccccaaattc actgcatctt tagtagataa gcagagtttt aaattacgat tgatctcctg    1860
ttaggaggaa tgcatggatt tccacaagaa aaaactgtac tgaggagaaa ctttccacag    1920
taatgtgcca cttttcagtc aacgacagac cacatatatg agtcccataa gataatacta    1980
tatttttact gtacctttc tatgtttaga tatgtttaga cacacaaata tcattgcatt    2040
acaattgcct acagtattca gtacagtaat atgctgtata gatttgtggt ctaggagcaa    2100
tagcctaagt gtgtagtagg ctgagccatc tattttgtgt tagtacactg tgatgttcag    2160
agaaggatga aattgcctaa ggatacattt ctcagaatgt atcctgttgt tcggtgacgc    2220
atgactgtat tccatgagca ctataatcac tatcatagta acacattagg agagaattct    2280
```

```
catttctaaa tccaatataa tttatcaccc attagttcat actctactgc tttgattgct    2340
tttctttggt tgtggctacc tgcatacagc agtaaagttt cagaaaaact gaagtcgcaa    2400
aaggtcaatt actcaatgaa ggaaagataa accattgcat tgggggacta aaagatactt    2460
ttaaaagttc tcagattatc aatttaatga tgtgtttcta tgtagtgaat aatgccttaa    2520
attcttgcca agagtattta gaaggaagtt gtcagaagta tatcagctaa ctcattttt    2580 tttatatcac tgctaatggt gtcattcaca cattgtgcaa cccataattc cagatttaat    2640
tctaccaaaa aatataggtc attgcaaaat gccatattaa aactgccaat gcatgacagg    2700
aagatgggga tgcagacaaa gcaaaggatg acaccaattc cttttttaaa gaagcaagat    2760
agggattgga caaaaaggct gagccatttt taatggatac ttttgaggga gtgttaattc    2820
caatttaatt aaaatgatgc attaatttaa aattgggata actggttgcc ctcgactgca    2880
cctgggttgc gccagtgctc tcggattaac ctaattgtac agaggtgccc ttgtttctca    2940
acttcatgca caaagcattg gaaattattt gtttgctttt tcttttccaa gtaaatcttt    3000
ttccagttat gcaaaaggga agtttgaggc aatggttaaa ggcacttaag ttataattat    3060
tgctgttatc attaacatta agcacgggta tggctttgtt gcaagttacc cacctacacc    3120
tgcaaatctc tcttgctagc acacgcccca gctctctcca cccgcagtgg tccgtggctg    3180
gaccgcttta agtcactgag cgggctgggc tctgaaggag gtcggtcccg ctcctcccag    3240
acccaagcgt agggctaggg aaaagctagg cgggaaggtc attgcactcc caggccccag    3300
gaaaagggcc cagggtctca tcatctctta ctttcgggca aaacttccca catcgcgacc    3360
ttccctccct ggggcactct gagaacacac ccagtcacct agcgcgctcc ccagaagtcg    3420
gcttggcaca cagcgcaccc cagcggccgc gcggcctcct tccagccgcc gccacttggc    3480
ttccggagag ctcgccgggc gctgccgccg ccgccgccgc cgccgccgcc tcctgggaac    3540
caggggactg aagagcctgc gagagcggaa cactgccgga ccccgggtgg ggggcgcag     3600 cagctgcgcc tggccccgcc caccacacct gggcgcccgt agaaccgcgc ggggcgggc     3660 ggggcaggag gctggcctgg cgctccggcc gctttgtcga aagccggccc gactggagca    3720
ggacgaaggg ggagggtctc gaggccgagt cctgttcttc tgagggacgg accccagctg    3780
gggtggaaaa gcagtaccag agagcctccg aggcgcgcgg tgccaaccat ggagcgggcc    3840
ggccccagct tcgggcagca gcgacagcag cagcagcccc agcagcagaa gcagcagcag    3900
agggatcagg actcggtcga agcatggctg gacgatcact gggactttac cttctcatac    3960
tttgttagaa aagccaccag gtaagaagag gaccacgga agacccgggg ctgatttctc     4020 tccctgttg  aattgtgccc ttcgttcacc cctgttccca ggccctttgc ttttgaagta    4080
ggtcctcggt cctgttacga ggtagaaacc tcaactctaa gcgagcacag tcgaaaaact    4140
caagtgtcgg atttgataca acttgctcac aaagttcaaa tacaaaatg tacttggttc     4200 aaatacaaaa atgtacttgc cgacctccca ccctcacccc cgcccctctt ggtattcccc    4260
gggaacatga ttattttcat acatccgtgc tcacgggcct tccccctagc cctctctagc    4320
cctctggttc cccaaaatcc aatcagcaaa acccaaacag tttctgagcc ccttccctgc    4380
ag                                                                   4382

<210> SEQ ID NO 96
<211> LENGTH: 3979
<212> TYPE: DNA
<213> ORGANISM: Homo sapiens
<220> FEATURE:
```

<221> NAME/KEY: misc_feature
<223> OTHER INFORMATION: Pde7a1: Acc. No. L12052

<400> SEQUENCE: 96

```
ggcggccgcg gcagggcggg cgccgcgcgg aggcagggcg ggcgtattca atggaagtgt    60
gttaccagct gccggtactg cccctggaca ggccggtccc ccagcacgtc ctcagccgcc   120
gaggagccat cagcttcagc tccagctccg ctctcttcgg ctgccccaat ccccggcagc   180
tctctcagag gcgtggagct atttcctatg acagttctga tcagactgca ttatacattc   240
gtatgctagg agatgtacgt gtaaggagcc gagcaggatt tgaatcagaa agaagaggtt   300
ctcacccata tattgatttt cgtatttcc actctcaatc tgaaattgaa gtgtctgtct    360
ctgcaaggaa tatcagaagg ctactaagtt ccagcgata tcttagatct tcacgctttt    420
ttcgtggtac tgcggtttca aattccctaa acattttaga tgatgattat aatggacaag   480
ccaagtgtat gctggaaaaa gttggaaatt ggaattttga tatctttcta tttgatagac   540
taacaaatgg aaatagtcta gtaagcttaa cctttcattt atttagtctt catggattaa   600
ttgagtactt ccatttagat atgatgaaac ttcgtagatt tttagttatg attcaagaag   660
attaccacag tcaaaatcct taccataacg cagtccacgc tgcggatgtt actcaggcca   720
tgcactgtta cttaaaggaa cctaagcttg ccaattctgt aactccttgg gatatcttgc   780
tgagcttaat tgcagctgcc actcatgatc tggatcatcc aggtgttaat caacctttcc   840
ttattaaaac taaccattac ttggcaactt tatacaagaa tacctcagta ctggaaaatc   900
accactggag atctgcagtg gcttattga gagaatcagg cttattctca catctgccat    960
tagaaagcag gcaacaaatg gagacacaga taggtgctct gatactagcc acagacatca  1020
gtcgccagaa tgagtatctg tctttgttta ggtcccattt ggatagaggt gatttatgcc  1080
tagaagacac cagacacaga catttggttt tacagatggc tttgaaatgt gctgatattt  1140
gtaacccatg tcggacgtgg gaattaagca agcagtggag tgaaaaagta acggaggaat  1200
tcttccatca aggagatata gaaaaaaaat atcatttggg tgtgagtcca ctttgcgatc  1260
gtcacactga atctattgcc aacatccaga ttggttttat gacttaccta gtggagcctt  1320
tatttacaga atgggccagg ttttccaata caaggctatc ccagacaatg cttggacacg  1380
tggggctgaa taaagccagc tggaagggac tgcagagaga acagtcgagc agtgaggaca  1440
ctgatgctgc atttgagttg aactcacagt tattacctca ggaaaatcgg ttatcataac  1500
ccccagaacc agtgggacaa actgcctcct ggaggttttt agaaatgtga atggggtct    1560
tgaggtgaga gaacttaact cttgactgcc aaggtttcca agtgagtgat gccagccagc  1620
attatttatt tccaagattt cctctgttgg atcatttgaa cccacttgtt aattgcaaga  1680
cccgaacata cagcaatatg aatttggctt tcatgtgaaa ccttgaatat aaagcccagc  1740
aggagagaat ccgaaggag taacaaagga agttttgata tgtgccacga cttttcaaa    1800
gcatctaatc ttcaaaacgt caaacttgaa ttgttcagca acaatctctt ggaatttaac  1860
cagtctgatg caacaatgtg tatcttgtac cttccactaa gttctctctg agaaaatgga  1920
aatgtgaagt gcccagcctc tgctgcctct ggcaagacaa tgtttacaaa tcaactctga  1980
aaatattggt tctaaattgc cttggagcat gattgtgaag gaaccactca aacaaattta  2040
aagatcaaac tttagactgc agctcttttcc ccctggtttg cctttttctt ctttggatgc  2100
caccaaagcc tcccatttgc tatagtttta tttcatgcac tggaaactga gcatttatcg  2160
tagagtaccg ccaagctttc actccagtgc cgtttggcaa tgcaattttt tttagcaatt  2220
```

-continued

```
agtttttaat ttggggtggg aggggaagaa caccaatgtc ctagctgtat tatgattctg    2280
cactcaagac attgcatgtt gttttcacta ctgtacactt gacctgcaca tgcgagaaaa    2340
aggtggaatg tttaaaacac cataatcagc tcaggtattt gccaatctga aataaaagtg    2400
ggatgggaga gcgtgtcctt cagatcaagg gtactaaagt ccctttcgct gcagtgagtg    2460
agaggtatgt tgtgtgtgaa tgtacggatg tgtgtttggt gatgtttgtg catgtgtgac    2520
gtgcatgtta tgtttctcca tgtgggcaaa gatttgaaag taagctttta tttattattt    2580
tagaatgtga cataatgagc agccacactc gggggagggg aaggttggta ggtaagctgt    2640
aacagattgc tccagttgcc ttaaactatg cacatagcta agtgaccaaa cttcttgttt    2700
tgatttgaaa aaagtgcatt gttttcttgt ccctcccttt gatgaaacgt tacccttttga   2760 cgggcctttt gatgtgaaca gatgttttct aggacaaact ataaggacta attttaaact    2820
tcaaacattc cacttttgta atttgtttta aattgtttta tgtatagtaa gcacaactgt    2880
aatctagttt taagagaaac cggtgctttc ttttagttca tttgtatttc ccttgttact    2940
gtaaaagact gtttattaat tgtttacagt ttgttgcaac agccattttc ttgggagaaa    3000
gcttgagtgt aaagccattt gtaaaaggct ttgccatact cattttaata tgtgcctgtt    3060
gctgttaact tttgatgaat aaaaacctat cttttcatga aacttctctc tatacaaatt    3120
gaaatacata atgctttctg gttcttcttc aaaccaaaac ttgtcaaatt catagacaag    3180
ataacagtaa aactgatgaa agtgttccat tgttggtata ccaggaacaa ggttatagag    3240
atgaaacttc aaagcttcac tcttcagtaa gctataagcc atctctgtaa gattgattcc    3300
aactattgca taagaatacc ctaattttgg atgatttgaa cgggaaagaa tctgatgagc    3360
ttcactagtg taattttcac tgaaatacac aagattgatt aacccaagta tgcccatgcc    3420
tctgaagtct gtcttgggat catcaccctg aaaaccaatt tcagcccact gcttggagat    3480
tctagcgttt aacttcttcg tgggcattag aagattccaa agcttcatga gtagctcttc    3540
atgctgtagg ttatcagaat catatggcct tttcctcaca ctttctacat ccaaatacag    3600
ctgtttataa ccagttatct gcagtaagca catcttcatg catattttaa aactggcatc    3660
cttctcaggg ttaatattct tttccttcat aatatcatct acatatttgt ccacttcact    3720
ctgaacaaca tgtgtcgcct tctgtaaaac cttattcttg gagtatgtca aggaattttc    3780
tatcctgtgt gtcctttgtg cacctacata ggtatcaaat attcgctgca attcacactt    3840
cccagtcatc tgtcgtaata gccatttcat ccaaaatcga aaaagtgcc catagaagaa    3900 ctcccacaaa gaaataaaca ttttttttc ctcacaggag cggaagaact aggggagca    3960 ggagctgcaa tgcggccgc                                                3979
```

<210> SEQ ID NO 97
<211> LENGTH: 2904
<212> TYPE: DNA
<213> ORGANISM: Homo sapiens
<220> FEATURE:
<221> NAME/KEY: misc_feature
<223> OTHER INFORMATION: Per-1:  Acc. No. AB005293

<400> SEQUENCE: 97

```
ggcacgagct ctgtgagact gaggtggcgg tcagccggag tgagtgttgg ggtcctgggg      60
cacctgcctt acatggcttg tttatgaaca ttaaagggaa gaagttgaag cttgaggagc     120
gaggatggca gtcaacaaag gcctcacctt gctggatgga gacctccctg agcaggagaa     180
tgtgctgcag cgggtcctgc agctgccggt ggtgagtggc acctgcgaat gcttccagaa    240
```

```
gacctacacc agcactaagg aagcccaccc cctggtggcc tctgtgtgca atgcctatga    300
gaagggcgtg cagagcgcca gtagcttggc tgcctggagc atggagccgg tggtccgcag    360
gctgtccacc cagttcacag ctgccaatga gctggcctgc cgaggcttgg accacctgga    420
ggaaaagatc cccgccctcc agtaccccc  tgaaaagatt gcttctgagc tgaaggacac    480
catctccacc cgcctccgca gtgccagaaa cagcatcagc gttcccatcg cgagcacttc    540
agacaaggtc ctgggggccg ctttggccgg gtgcgagctt gcctgggggg tggcagagtc    600
cactgcggaa tttgctgcca acactcgagc tggccgactg gcttctggag gggccgactt    660
ggccttgggc agcattgaga aggtggtgga gtacctcctc cctgcagaca aggaagagtc    720
agcccctgct cctggacacc agcaagccca gaagtctccc aaggccaagc caagcctctt    780
gagcagggtt ggggctctga ccaacaccct ctctcgatac accgtgcaga ccatggcccg    840
ggccctggag cagggccaca ccgtggccat gtggatccca ggcgtggtgc ccctgagcag    900
cctggcccag tggggtgcct cagtggccat gcaggcggtg tcccggcgga ggagcgaagt    960
gcgggtaccc tggctgcaca gcctcgcagc cgcccaggag gaggatcatg aggaccagac   1020
agacacggag ggagaggaca cggaggagga ggaagaattg gagactgagg agaacaagtt   1080
cagtgaggta gcagccctgc caggccctcg aggcctcctg ggtggtgtgg cacatacct    1140 gcagaagacc ctccagacca ccatctcggc tgtgacatgg gcacctgcag ctgtgctggg   1200
catggcaggg agggtgctgc acctcacacc agccccgct  gtctcctcaa ccaaggggag   1260
ggccatgtcc ctatcagatg ccctgaaggg cgttactgac aacgtggtgg acacagtggt   1320
gcattacgtg ccgctcccca ggctgtcgct gatggagccc gagagcgaat tccgggacat   1380
cgacaaccca ccagccgagg tcgagcgccg ggaggcggag cgcagagcgt ctggggcgcc   1440
gtccgccggc ccggagcccg ccccgcgtct cgcacagccc cgccgcagcc tgcgcagcgc   1500
gcagagcccc ggcgcgcccc ccggcccggg cctggaggac gaagtcgcca cgcccgcagc   1560
gccgcgcccg ggcttcccgg ccgtgccccg cgagaagcca aagcgcaggg tcagcgacag   1620
cttcttccgg cccagcgtca tggagcccat cgtgggccgc acgcattaca gccagctgcg   1680
caagaagagc tgagtcgccg caccagccgc gcgccccgg gccggcgggt ttctctaaca    1740
aataaacaga accgcactg  cccaggcgag cgttgccact ttcaaagtgg tccctgggg    1800 agctcagcct catcctgatg atgctgccaa ggcgcacttt ttattttat  tttattttta   1860 tttttttttt agcatccttt tggggcttca ctctcagagc cagttttaa  gggacaccag   1920 agccgcagcc tgctctgatt ctatggcttg gttgttacta taagagtaat tgcctaactt   1980
gatttttcat ctctttaacc aaacttgtgg ccaaaagata tttgaccgtt tccaaaattc   2040
agattctgcc tctgcggata aatatttgcc acgaatgagt aactcctgtc accactctga   2100
aggtccagac agaaggtttt gacacattct tagcactgaa ctcctctgtg atctaggatg   2160
atctgttccc cctctgatga acatcctctg atgatcaagg ctcccagcag gctactttga   2220
agggaacaat cagatgcaaa agctcttggg tgtttattta aaatactagt gtcactttct   2280
gagtacccgc cgcttcacag gctgagtcca ggcctgtgtg cttgtagag  ccagctgctt   2340 gctcacagca acatttccat ttgcatcatt actgccttca cctgcatagt cactcttttg   2400
atgctgggga accaaaatgg tgatgatata tagactttat gtatagccac agttcatccc   2460
caaccctagt cttcgaaatg ttaatatttg ataaatctag aaaatgcatt catacaatta   2520
cagaattcaa atattgcaaa aggatgtgtg tcttctcccc cgagctcccc tgttcccctt   2580
cattgaaaac caccacggtg ccatctcttg tgtatgcagg gctatgcacc tgcaggcacg   2640
```

| | | | |
|---|---|---|---|
| tgtgtatgca | ctccccgctt | gtgtttacac aagctgtggg gtgttacgca tgcctgcttt | 2700 |
| tttcacttaa | taatacagct | tggagagatt tttgtatcac attataaatc ccactcgctc | 2760 |
| tttttgatgg | ccacataata | actactgcat aatatggata cgccttattt gatttaacta | 2820 |
| gttccctaat | gatggacttt | taagttgttt ccttttttttt tctttttttgc tactgcaaac | 2880 |
| gatgctataa | taaatgtcct | tatc | 2904 |

<210> SEQ ID NO 98
<211> LENGTH: 4626
<212> TYPE: DNA
<213> ORGANISM: Homo sapiens
<220> FEATURE:
<221> NAME/KEY: misc_feature
<223> OTHER INFORMATION: TPP II: Acc. No. M73047

<400> SEQUENCE: 98

| | | | |
|---|---|---|---|
| gaattcccct | ccatcctgcg | tccatggcca ccgctgcgac tgaggagccc ttcccttttc | 60 |
| acggtctcct | gccgaagaag | gagaccggag ccgcctcctt cctctgccgc tacccggagt | 120 |
| atgatgggcg | gggggtgctc | atcgcagtcc tggacacggg ggtcgacccg ggggctccgg | 180 |
| gcatgcaggt | tacaactgat | ggaaaaccaa aaatcgttga tatcattgat acaacaggaa | 240 |
| gtggcgatgt | gaatactgct | acagaagtag agccaaagga tggtgagatt gttggccttt | 300 |
| caggaagagt | gcttaagatt | cctgcaagct ggacaaatcc ctcaggcaaa tatcatattg | 360 |
| gcataaaaaa | tggctatgac | ttctatccta aggcactcaa ggaaaggata cagaaagaac | 420 |
| ggaaggaaaa | atctgggac | cctgttcaca gagtggccct tgcagaagcc tgtagaaaac | 480 |
| aggaagaatt | tgatgttgcc | aacaacggct cttctcaagc aaataaacta atcaaggagg | 540 |
| aacttcaaag | tcaagtggaa | ttgctaaatt cttttgagaa gaaatacagc gatcctggcc | 600 |
| ctgtatatga | ctgcttggta | tggcatgatg gcgaagtctg gagagcctgc attgattcta | 660 |
| atgaagatgg | ggacttgagt | aaatctaccg tgttgagaaa ctacaaagaa gcccaagaat | 720 |
| atggctcttt | tggcacagct | gagatgttga attactccgt taatatatac gatgatagaa | 780 |
| acctgctctc | cattgtgacc | agtggaggag ctcatgggac acatgtagct agtatagctg | 840 |
| ctggacactt | tccagaagaa | cctgaacgga tgggggtagc tcctggtgct caaattcttt | 900 |
| ccatcaagat | tggtgataca | agactaagca caatggaaac aggcacaggc ctcataagag | 960 |
| ctatgataga | agttataaat | cataagtgtg atcttgtcaa ctacagttac ggagaagcaa | 1020 |
| ctcactggcc | aaattctggg | agaatttgtg aagtaattaa tgaagcagta tggaagcata | 1080 |
| atataattta | tgtttcaagt | gctggaaata tggtccatg cctgtctaca gttggttgtc | 1140 |
| caggtggaac | tacatcaagt | gtgataggtg ttggtgctta tgtttctcct gatatgatgg | 1200 |
| ttgctgagta | ttcactgaga | gagaaattac ctgcaaatca atatacttgg tcttctagag | 1260 |
| gacctagtgc | tgacgggcc | cttggtgtga gtatcagtgc gccaggagga gccattgctt | 1320 |
| ctgttcctaa | ctggacactg | agaggacgc agctgatgaa tggaacatct atgtcttccc | 1380 |
| ccaatgcatg | tggaggcatt | gccctgatcc tttcaggtct gaaagctaat aacattgact | 1440 |
| acacagttca | ttcagtcaga | agagctctag aaaacactgc agtgaaggct gacaatatag | 1500 |
| aagtatttgc | tcaaggacat | ggtattattc aggttgataa agcctatgac tacctcgttc | 1560 |
| agaatacatc | atttgctaat | aaattaggtt ttactgttac tgttggaaat aaccgtggca | 1620 |
| tctacctccg | agatcctgtt | caggtggctg caccttcaga tcatggcgtt ggcattgaac | 1680 |
| ctgtatttcc | ggagaacaca | gaaaactctg aaaaaatatc ccttcagctt catttagctc | 1740 |

-continued

| | |
|---|---|
| tgacttcaaa ttcatcttgg gttcagtgtc ccagccattt ggaactcatg aatcaatgta | 1800 |
| gacacataaa catacgtgtg gatcccaggg gcttaagaga aggattgcat tatacagagg | 1860 |
| tatgtggcta tgatatagca tccnctaacg caggtccgct cttcagagtt ccgatcactg | 1920 |
| cagttatagc agcaaaagta aatgaatcat cacattatga tctagccttt acagatgtac | 1980 |
| actttaaacc tggtcaaatt cgaaggcatt ttattgaggt tcctgagggt gcaacatggg | 2040 |
| ctgaagtgac agtgtgttcg tgttcttctg aggtgtcagc aaagtttgtt ctacatgcag | 2100 |
| tccagcttgt gaagcaaaga gcatatcgaa gccatgaatt ctataagttt tgttctcttc | 2160 |
| cagagaaagg aacactgact gaagcttttc ctgtcctagg tggaaaagca attgaatttt | 2220 |
| gcattgctcg ttggtgggca agtctcagtg atgtcaacat tgattatacc atttctttcc | 2280 |
| atgggatagt gtgtactgct cctcagttaa acattcatgc atcggaagga atcaaccgct | 2340 |
| ttgatgttca gtcctccttg aaatacgaag atctggctcc ctgcataact ttgaagaact | 2400 |
| gggtccaaac actgcgccca gtgagtgcaa aaacaaaacc tttaggatca agagatgttt | 2460 |
| tgccaaataa ccgtcaactt tatgagatgg tcctgacata taactttcat caacccaaga | 2520 |
| gtggggaagt aactccaagc tgcccactac tttgtgaact attatatgaa tctgaatttg | 2580 |
| acagccaact gtggattatt tttgaccaga acaaaagaca gatgggttca ggcgatgcct | 2640 |
| atccacatca gtattctttg aaactggaga aaggagatta tacaattcga ctacagattc | 2700 |
| gccatgagca aatcagtgat ttggaacgcc ttaaagacct tccatttatt gtttctcata | 2760 |
| gattgtctaa taccttgagc ttagatattc atgaaaatca tagttttgca cttctaggga | 2820 |
| agaagaaatc aagcaatttg acattaccac ccaaatataa ccagccattc tttgttactt | 2880 |
| ccttacctga tgataaaata cctaaggggc aggacctgg atgctatctt gcaggatcct | 2940 |
| taacattgtc aaagactgaa ctaggaaaga aagctgatgt aatccctgtt cattactact | 3000 |
| taatacctcc accaacaaag actaagaatg cagcaaaga taaggaaaaa gattcagaaa | 3060 |
| aagagaaaga tttaaaagaa gagtttactg aagcattacg agatcttaaa attcagtgga | 3120 |
| tgacaaagct ggattctagt gacatttata acgaattgaa agaaacatat cctaattatc | 3180 |
| ttcctctgta cgttgcacga cttcatcaat tggatgctga aaaggaacga atgaaaagac | 3240 |
| ttaatgaaat tgttgatgcg gcaaatgctg ttatttctca tatagatcaa acagccctag | 3300 |
| cagtttatat tgcaatgaag actgatccca ggcctgatgc agctactata aaaaatgaca | 3360 |
| tggacaaaca aaaatccacc ctcgtagatg ccctttgtag gaaaggttgt gccctggcag | 3420 |
| accatcttct tcacacccag gctcaagacg gagccatttc cactgatgca gaaggaaagg | 3480 |
| aggaggaagg agaaagtcct ttggattctc tggcagaaac attttgggaa actactaaat | 3540 |
| ggactgatct ctttgacaat aaggttttga catttgcata taaacatgca ttagtaaata | 3600 |
| aaatgtatgg gagaggcctt aaatttgcaa ctaaacttgt ggaagaaaaa ccaacaaaag | 3660 |
| aaaactggaa aaattgtatt caactgatga agttacttgg atggacccat tgtgcatctt | 3720 |
| ttactgaaaa ctggctcccc atcatgtatc ctcccgatta ttgcgtattc taaaatagga | 3780 |
| aacaagactt taaattttaa aaaggaagt tttatagtga atgggtataa aaacaaattt | 3840 |
| gtggcatttt tagtctaatg catgtttca tccactatcc agtactgatt attaaaatga | 3900 |
| catgtattta tcagagaatt cactgacgtg tggcttaata catgtaaatc tagacctctg | 3960 |
| acatcatggt gttttcttaa tgcctcacat tgctggcacg gggatgtgcc ctgcctgcca | 4020 |
| gcacctagga cttcgagttg ggttgcagct tatgacatgc atgataggtt ttggaaggta | 4080 |

-continued

| | |
|---|---|
| acttttaact gcaaacctat aaagtactat ttttattttt ataaatgaac agggttttaa | 4140 |
| cgtgctcaac tttaattttt ttcaattgta tgaaggcctt aaaaaagcta cattaagcgt | 4200 |
| agctaaaatt atttattgga ctaaaaacta acagaacttc atttccagaa tttttttttt | 4260 |
| ttttttttttt ttggcaaatg tttacattca attaagggga aaaagtagaa ccagcacaaa | 4320 |
| tgagtggcag ttgctggagc ataactgctt caataaatct tcatcttggg gtaattacag | 4380 |
| gcaagtcatt ttcacatcct cttgaggttc agagcatcag aatgaactct atgaatacat | 4440 |
| gtgtaagtgc cagacagctg aatctttatc aggtattgta aagatacaca tatgatatgt | 4500 |
| ttattaaaat tgaaataatg taaaacacat gaataaattt gcaaaaccaa gatcacagta | 4560 |
| caccatatgc actctggtac cttaattttt ttttataaat aataaaagtg aatattgaag | 4620 |
| cttctt | 4626 |

<210> SEQ ID NO 99
<211> LENGTH: 3224
<212> TYPE: DNA
<213> ORGANISM: Homo sapiens
<220> FEATURE:
<221> NAME/KEY: misc_feature
<223> OTHER INFORMATION: MTP: Acc. No. X59657

<400> SEQUENCE: 99

| | |
|---|---|
| actccctcac tggctgccat tgaaagagtc cacttctcag tgactcctag ctgggcactg | 60 |
| gatgcagttg aggattgctg gtcaatatga ttcttcttgc tgtgcttttt ctctgcttca | 120 |
| tttcctcata ttcagcttct gttaaaggtc acacaactgg tctctcatta ataatgacc | 180 |
| ggctgtacaa gctcacgtac tccactgaag ttcttcttga tcggggcaaa ggaaaactgc | 240 |
| aagacagcgt gggctaccgc atttcctcca acgtggatgt ggccttacta tggaggaatc | 300 |
| ctgatggtga tgatgaccag ttgatccaaa taacgatgaa ggatgtaaat gttgaaaatg | 360 |
| tgaatcagca gagaggagag aagagcatct tcaaaggaaa aagcccatct aaaataatgg | 420 |
| gaaaggaaaa cttggaagct ctgcaaagac ctacgctcct tcatctaatc catggaaagg | 480 |
| tcaaagagtt ctactcatat caaaatgagg cagtggccat agaaaatatc aagagaggtc | 540 |
| tggctagcct atttcagaca cagttaagct ctggaaccac caatgaggta gatatctctg | 600 |
| gaaattgtaa agtgacctac caggctcatc aagacaaagt gatcaaaatt aaggccttgg | 660 |
| attcatgcaa aatagcgagg tctggattta cgacccaaa tcaggtcttg ggtgtcagtt | 720 |
| caaaagctac atctgtcacc acctataaga tagaagacag cttttgttata gctgtgcttg | 780 |
| ctgaagaaac acacaatttt ggactgaatt tcctacaaac cattaagggg aaaatagtat | 840 |
| cgaagcagaa attagagctg aagacaaccg aagcaggccc aagattgatg tctggaaagc | 900 |
| aggctgcagc cataatcaaa gcagttgatt caaagtacac ggccattccc attgtggggc | 960 |
| aggtcttcca gagccactgt aaaggatgtc cttctctctc ggagctctgg cggtccacca | 1020 |
| ggaaatacct gcagcctgac aacctttcca aggctgaggc tgtcagaaac ttcctggcct | 1080 |
| tcattcagca cctcaggact gcgaagaaag aagagatcct tcaaatacta agatggaaa | 1140 |
| ataaggaagt attacctcag ctggtggatg ctgtcacctc tgctcagacc tcagactcat | 1200 |
| tagaagccat tttggactttt tggatttca aaagtgacag cagcattatc ctccaggaga | 1260 |
| ggtttctcta tgcctgtgga tttgcttctc atcccaatga agaactcctg agagccctca | 1320 |
| ttagtaagtt caaggttct attggtagca gtgacatcag agaaactgtt atgatcatca | 1380 |
| ctgggacact tgtcagaaag ttgtgtcaga atgaaggctg caaactcaaa gcagtagtgg | 1440 |

```
aagctaagaa gttaatcctg ggaggacttg aaaaagcaga gaaaaagag gacaccagga    1500 tgtatctgct ggctttgaag aatgccctgc ttccagaagg catcccaagt cttctgaagt   1560
atgcagaagc aggagaaggg cccatcagcc acctggctac cactgctctc cagagatatg   1620
atctcccttt cataactgat gaggtgaaga agaccttaaa cagaatatac caccaaaacc   1680
gtaaagttca tgaaaagact gtgcgcactg ctgcagctgc tatcatttta aataacaatc   1740
catcctacat ggacgtcaag aacatcctgc tgtctattgg ggagcttccc caagaaatga   1800
ataaatacat gctcgccatt gttcaagaca tcctacgttt ggaaatgcct gcaagcaaaa   1860
ttgtccgtcg agttctgaag gaaatggtcg ctcacaatta tgaccgtttc tccaggagtg   1920
gatcttcttc tgcctacact ggctacatag aacgtagtcc ccgttcggca tctacttaca   1980
gcctagacat tctctactcg ggttctggca ttctaaggag aagtaacctg aacatctttc   2040
agtacattgg gaaggctggt cttcacggta gccaggtggt tattgaagcc caaggactgg   2100 aagcctttaat cgcagccacc cctgacgagg gggaggagaa ccttgactcc tatgctggta   2160
tgtcagccat cctctttgat gttcagctca gacctgtcac cttttcaac ggatacagtg    2220 atttgatgtc caaaatgctg tcagcatctg gcgaccctat cagtgtggtg aaaggactta   2280
ttctgctaat agatcattct caggaacttc agttacaatc tggactaaaa gccaatatag   2340
aggtccaggg tggtctagct attgatattt caggtgcaat ggagtttagc ttgtggtatc   2400
gtgagtctaa aacccgagtg aaaaatagg tgactgtggt aataaccact gacatcacag    2460
tggactcctc ttttgtgaaa gctggcctgg aaaccagtac agaaacagaa gcaggcttgg   2520
agtttatctc cacagtgcag ttttctcagt acccattctt agtttgcatg cagatggaca   2580
aggatgaagc tccattcagg caatttgaga aaaagtacga aaggctgtcc acaggcagag   2640
gttatgtctc tcagaaaaga aaagaaagcg tattagcagg atgtgaattc ccgctccatc   2700
aagagaactc agagatgtgc aaagtggtgt ttgcccctca gccggatagt acttccagcg   2760
gatggttttg aaactgacct gtgatatttt acttgaattt gtctccccga aagggacaca   2820
atgtggcatg actaagtact tgctctctga gagcacagcg tttacatatt tacctgtatt   2880
taagattttt gtaaaaagct acaaaaaact gcagtttgat caaatttggg tatatgcagt   2940
atgctaccca cagcgtcatt ttgaatcatc atgtgacgct ttcaacaacg ttcttagttt   3000
acttatacct ctctcaaatc tcatttggta cagtcagaat agttattctc taagaggaaa   3060
ctagtgtttg ttaaaaacaa aaataaaaac aaaaccacac aaggagaacc caattttgtt   3120
tcaacaattt ttgatcaatg tatatgaagc tcttgatagg acttccttaa gcatgacggg   3180
aaaaccaaac acgttcccta atcaggaaaa aaaaaaaaaa aaaa                    3224
```

```
<210> SEQ ID NO 100
<211> LENGTH: 5856
<212> TYPE: DNA
<213> ORGANISM: Homo sapiens
<220> FEATURE:
<221> NAME/KEY: misc_feature
<223> OTHER INFORMATION: HisR: Acc. No. D14436

<400> SEQUENCE: 100
```

```
gagctcatca tttttatgg ctgcatagta ttccatggtg tatatgtgcc acattttctt     60
aatccagtct atcattgttg gacagttggg ttggttccaa gtctttgcta ctgtgaatag   120
tgcctcaata aacatatgtg tgcatgtgtc tttatagcag caagatttat agtcctttgg   180
gtatataccc agtaatggga tggctgggtc aaatggtatt tctagttcta catccctgag   240
```

```
gaatcgccac accgacttcc acaatggttg aactagttta cagtcccacc aaaagtgtaa    300
aaatgttcct atttctccac ttcctctcca gcatctgttg tttcctgact ttttaatgat    360
tgctattcta actggtgtga gatggtatct cattgtggtt ttgatttgca tttctctgat    420
ggccagtgat ggtgagcatt ttttcatgtg ttttttggat gcataaatgt cttcttttga    480
gaagtgtctg ttcatgtcct tcgcccactt tttgatgggg atgttttttt cttgtaaatt    540
tgtttgagtt cattgtagat tctggatatt agccctttgt cagatgagta ggttgtgaaa    600
attttctccc attttgtagg ttgcctgttc actctgatgg tagtttcttt tgctgtgcag    660
aaaatcttta gttaattag atcccatttg tcaattttgg cttttgttgc cattgttttt      720
ggtgttttag acatgaagtc cttgcccatg cctatgtcct gaatggtaat gcctaggatt    780
tcttctgggg gttttatggt tttaggtcta atgtttaagt cttaatcca tcttgaatta     840 attttttgtat aaggtgtaag aagggatcc agtttcagct ttctacatat ggctagccag    900
ttttcccagc acttttatt aaatagagaa tcctttcccc attgcttttc tcaggtttgt      960
caaagatcag atagttgtag atatgcaatg ctatttctga gggctctgtt ctgttccatt    1020
gatctatatc tctgttttgg taccagtacc atgctgtttt ggttactgtg gccttgtagt    1080
atagtttgaa gtcaggtagc atgatgcctc cagcttgtt cttttggctt aggattgact      1140
tggcgatgtg ggctcttttt ggttccatat gaactttaaa gtagttttttt ccaattctgt    1200 gaagaaagtc attggtagct tgatggggat ggcattgaat ctatcaatta ccttgggcag    1260
tatggccatt ttcaagatat tgattcttcc tacccatgag catggaatgt tcttccattt    1320
gtttgtatcc tcttttatt ccttgagcag tggtttgtag ttctcctcga agaggtcctt     1380 cacatcccctt gtaagttgga ttcctaggta ttttattctc tttgaagcaa ttgtgaatgg    1440
gagttcactc atgatttggc tctctgtttg tctgttattg gtgtattaga atgcttgtga    1500
tttttgtaca ttgattttgt atcctgagac tttgctgaag ttgcttatca gcttaaggag    1560
attttgggct gagacaatgg ggttttctag atatacaatc atgtcatctg caaacaggga    1620
caatttgact tcctctttttc ctaattgagt accctttatt tccttctcct gcctaattgc    1680
cctggccaga acttccaaca ctatgttgaa taggagtggt gagagagggc atccctgtct    1740
tgtgccagtt ttcaaaggga atgcttgcag ttttttgccca ttcagtatga tactggctgt    1800
gggtttgtca tagatagctc ttattatttt gagatacgtc ccatgaatac ctaatttatt    1860
gagagttttt agcatgaagg gttgttgaat tttgtcaaag gccttttctg catctattga    1920
gataatcatg tggttttgt ctttggttct gtttacatgc tggattacat ttattgattt      1980
gcatatattg aaccagcctt gcatcccagg gatgaagtcc acttgatcac ccccaacagc    2040
atacaactcc agtctgatga acatcatgct actaagtggc cactcatcac ccaagtctct    2100
gaccttactt tttctctctt ttctcccagg gagtgagcca taactggcgg ctgctcttgc    2160
gccaatgagc ctccccaatt cctcctgcct cttagaagac aagatgtgtg agggcaacaa    2220
gaccactatg gccagccccc agctgatgcc cctggtggtg gtcctgagca ctatctgctt    2280
ggtcacagta gggctcaacc tgctggtgct gtatgccgta cggagtgagc ggaagctcca    2340
cactgtgggg aacctgtaca tcgtcagcct ctcggtggcg gacttgatcg tgggtgccgt    2400
cgtcatgcct atgaacatcc tctacctgct catgtccaag tggtcactgg gccgtcctct    2460
ctgcctcttt tggctttcca tggactatgt ggccagcaca gcgtccattt tcagtgtctt    2520
catcctgtgc attgatcgct accgctctgt ccagcagccc tcaggtacc ttaagtatcg      2580 taccaagacc cgagcctcgg ccaccattct gggggcctgg tttctctctt ttctgtgggt    2640
```

```
tattcccatt ctaggctgga atcacttcat gcagcagacc tcggtgcgcc gagaggacaa    2700
gtgtgagaca gacttctatg atgtcacctg gttcaaggtc atgactgcca tcatcaactt    2760
ctacctgccc accttgctca tgctctggtt ctatgccaag atctacaagg ccgtacgaca    2820
acactgccag caccgggagc tcatcaatag gtccctccct tccttctcag aaattaagct    2880
gaggccagag aaccccaagg gggatgccaa gaaaccaggg aaggagtctc cctgggaggt    2940
tctgaaaagg aagccaaaag atgctggtgg tggatctgtc ttgaagtcac catcccaaac    3000
ccccaaggag atgaaatccc cagttgtctt cagccaagag gatgatagag aagtagacaa    3060
actctactgc tttccacttg atattgtgca catgcaggct gcggcagagg ggagtagcag    3120
ggactatgta gccgtcaacc ggagccatgg ccagctcaag acagatgagc agggcctgaa    3180
cacacatggg gccagcgaga tatcagagga tcagatgtta ggtgatagcc aatccttctc    3240
tcgaacggac tcagatacca ccacagagac agcaccaggc aaaggcaaat gaggagtgg    3300 gtctaacaca ggcctggatt acatcaagtt tacttggaag aggctccgct cgcattcaag    3360
acagtatgta tctgggttgc acatgaaccg cgaaaggaag gccgccaaac agttgggttt    3420
tatcatggca gccttcatcc tctgctggat cccttatttc atcttcttca tggtcattgc    3480
cttctgcaag aactgttgca atgaacattt gcacatgttc accatctggc tgggctacat    3540
caactccaca ctgaaccccc tcatctaccc cttgtgcaat gagaacttca agaagacatt    3600
caagagaatt ctgcatattc gctcctaagg gaggctctga ggggatgcaa caaaatgatc    3660
cttatgatgt ccaacaagga aatagaggac gaaggcctgt gtgttgccag gcaggcacct    3720
gggctttctg gaatccaaac cacagtctta ggggcttggt agtttggaaa gttcttaggc    3780
accatagaag aacagcagat ggcggtgatc agcagagaga ttgaactttg aggaggaagc    3840
agaatctttg caagaaagtc agacctgttt cttgtaactg ggttcaaaaa gaaaaaaata    3900
ataaaaataa aagagagaga gaatcagacc tgggtggaac tctcctgctc ctcaggaact    3960
atgggagcct cagactcatt gtaattcaag cttttccgagt caagtgattg acaactgaag    4020
agacacgtgg ctagggttcc actggagaat tgaaaaggac tcttgagccc tcctggaatg    4080
gagctgtata actgtgcaga gactttatcc atgccaatag ttgctgtccc cttccagggg    4140
tcaccttgag aggcatgaca gctgttccac aggggctatc ccttctcaga aaacttctct    4200
tctgagcctc tttaacagct ttctccagaa ccagtgtctg aaccaccctg gaaattctgc    4260
cttattattt cttactcaaa catgtttaga gtggatagaa aattatgcag cttgcacacc    4320
catcatcttt aaccccaaat ttcctttggc tattaaaaaa gtggtggcaa aaggcatcct    4380
caaaagaaag agaaatgaaa tatttttgaa tggttgcacg ttaaaaatta aagaaggaa    4440 tgggggcaga atgccatatt tttgagggct gtactaggtt tatctcattt aagccccaca    4500
acaccccaca ggagggtaat tttctaactc tagtttgcag aggagcaaat tgaggttcag    4560
caaggtgaga gaggtaccca aggtcacata gctagttatg tgagaaagtt agagtacaga    4620
tcctctgggg tttcagctta ttgtagcata ttttctccga aaggcaaaaa tgtgccottt    4680 tggccgggca tggtagctca gcctataat cccagcatgt tgagaggctg aggtgggcag    4740
atcatttgag gccaggagtt caagaccagt ctggccaata tggagaaacc ttgtctctac    4800
taaaaacaca aaaattatct gggcatggtg gggcatgcct gtagtcccac ttacttggga    4860
ggccgaggca cgagaatcgc ttgaacccgg gaggtgagg ttgccgtgag ccaagatcac    4920
gccactgcac tccagcctgg gcaacagagc aagactctgt ctcaaaaaaa aaaatacaat    4980
```

-continued

| | | | | |
|---|---|---|---|---|
| attttaacaa | tgtgccctct | taagtgtgca | cagatacaca | tacacggtat tcccaagagt | 5040 |
| ggtggcagct | caaaatgata | tgtttgagta | gacgaacagc | tgacatggag ttcccgtgca | 5100 |
| cctacggaag | gggacgcttt | gaaggaacca | agtgcatttt | tatctgtgag ttctgttgtg | 5160 |
| tttgtcaaaa | agtcattgta | atctttcata | gccatacctg | gtaagcaaaa actagtaaag | 5220 |
| acataggaac | atgtagtttt | acttggtgtt | tatgttgcaa | tctggttgtg atttatattt | 5280 |
| taaagcttgg | tgctaaacca | caatatgtat | agcacatgga | gtgcctgtac aagctgatgt | 5340 |
| tttgtatttt | gtgttcctct | ttgcatgatc | tgtcaaagtg | agatattttt acctgcctaa | 5400 |
| aatatgatgt | ttaaaagcat | actctatgtg | atttatttat | ttctaccttt ctgagtctct | 5460 |
| tggactaaga | agatgttttg | aaatgtacca | tcaaatgtta | acagagtttg atatgggctt | 5520 |
| tctctttggt | ttctcatcac | atttgtaaat | gtcttttcaa | aaggatttac tttttgtaaa | 5580 |
| aagcttcatt | ctcactctgc | tttgcatccc | ccaaacttct | tgttcaaaac gggggagtt | 5640 |
| taggagactt | taatcccggt | ttcagaagct | gcagctggtc | tgtttccagg tcagaaacca | 5700 |
| ttgttcagaa | gacctcccctg | tgagagagtt | gctcctcagg | gtccctcagg accaaagaac | 5760 |
| actcgaaaag | agcacttcac | acagacaagt | ggctaagtgt | ccattattta ccttgaacaa | 5820 |
| tcaaggcaac | tagtggagag | aactgattgt | gagctc | | 5856 |

<210> SEQ ID NO 101
<211> LENGTH: 2438
<212> TYPE: DNA
<213> ORGANISM: Homo sapiens
<220> FEATURE:
<221> NAME/KEY: misc_feature
<223> OTHER INFORMATION: CRP: Acc. No. M11880

<400> SEQUENCE: 101

| | | | | |
|---|---|---|---|---|
| aataaataac | tcacattgat | ttctctggtc | tgaaataatt | ttgcttcccc tcttcccgaa | 60 |
| gctctgacac | ctgccccaac | aagcaatgtt | ggaaaattat | ttacatagtg gcgcaaactc | 120 |
| ccttactgct | ttggatataa | atccaggcag | gaggaggtag | ctctaaggca agagatctag | 180 |
| gacttctagc | ccctgaactt | tcagccgaat | acatcttttc | caaggagtg aattcaggcc | 240 |
| cttgtatcac | tggcagcagg | acgtgaccat | ggagaagctg | ttgtgtttct tggtcttgac | 300 |
| cagcctctct | catgcttttg | gccagacagg | taagggccac | cccaggctat gggagagttt | 360 |
| tgatctgagg | tatgggggtg | gggtctaaga | ctgcatgaac | agtctcaaaa aaaaaaaaaa | 420 |
| aagactgtat | gaacagaaca | gtggagcatc | cttcatggtg | tgtgtgtgtg tgtgtgtgtg | 480 |
| tgtgtgtggt | gtgtaactgg | agaagggtc | agtctgtttc | tcaatcttaa attctatacg | 540 |
| taagtgaggg | gatagatctg | tgtgatctga | gaaacctctc | acatttgctt gttttctgg | 600 |
| ctcacagaca | tgtcgaggaa | ggcttttgtg | tttcccaaag | agtcggatac ttcctatgta | 660 |
| tccctcaaag | caccgttaac | gaagcctctc | aaagccttca | ctgtgtgcct ccacttctac | 720 |
| acggaactgt | cctcgacccg | tgggtacagt | attttctcgt | atgccaccaa gagacaagac | 780 |
| aatgagattc | tcatattttg | gtctaaggat | ataggataca | gttttacagt gggtgggtct | 840 |
| gaaatattat | tcgaggttcc | tgaagtcaca | gtagctccag | tacacatttg tacaagctgg | 900 |
| gagtccgcct | cagggatcgt | ggagttctgg | gtagatggga | agcccagggt gaggaagagt | 960 |
| ctgaagaagg | gatacactgt | gggggcagaa | gcaagcatca | tcttggggca ggagcaggat | 1020 |
| tccttcggtg | ggaactttga | aggaagccag | tccctagtgg | gagacattgg aaatgtgaac | 1080 |
| atgtgggact | ttgtgctgtc | accagatgag | attaacacca | tctatcttgg cgggcccttc | 1140 |

| | | | |
|---|---|---|---|
| agtcctaatg | tcctgaactg | gcgggcactg | aagtatgaag tgcaaggcga agtgttcacc | 1200 |
| aaacccagc | tgtggccctg | aggcccagct | gtgggtcctg aaggtacctc ccggttttt | 1260 |
| acaccgcatg | ggccccacgt | ctctgtctct | ggtacctccc gcttttttac actgcatggt | 1320 |
| tcccacgtct | ctgtctctgg | gcctttgttc | ccctatatgc attgaggcct gctccaccct | 1380 |
| cctcagcgcc | tgagaatgga | ggtaaagtgt | ctggtctggg agctcgttaa ctatgctggg | 1440 |
| aaatggtcca | aaagaatcag | aatttgaggt | gttttgtttt cattttatt tcaagttgga | 1500 |
| cagatcttgg | agataatttc | ttacctcaca | tagatgagaa aactaacacc cagaaaggag | 1560 |
| aaatgatgtt | ataaaaaact | cataaggcaa | gagctgagaa ggaagcgctg atcttctatt | 1620 |
| taattcccca | cccatgaccc | ccagaaagca | ggagcattgc ccacattcac agggctcttc | 1680 |
| agtatcagaa | tcaggacact | ggccaggtgt | ctggtttggg tccagagtgc tcatcatcat | 1740 |
| gtcatagaac | tgctgggccc | aggtctcctg | aaatgggaag cccagcaata ccacgcagtc | 1800 |
| cctccacttt | ctcaaagcac | actggaaagg | ccattagaat tgccccagca gagcagatct | 1860 |
| gcttttttc | cagagcaaaa | tgaagcacta | ggtataaata tgttgttact gccaagaact | 1920 |
| taaatgactg | gttttgttt | gcttgcagtg | ctttcttaat tttatggctc ttctgggaaa | 1980 |
| ctcctcccct | tttccacacg | aaccttgtgg | ggctgtgaat tctttcttca tccccgcatt | 2040 |
| cccaatatac | ccaggccaca | agagtggacg | tgaaccacag ggtgtcctgt cagaggagcc | 2100 |
| catctcccat | ctccccagct | ccctatctgg | aggatagttg gataggtacg tgttcctagc | 2160 |
| aggaccaact | acagtcttcc | caaggattga | gttatggact ttgggagtga gacatcttct | 2220 |
| tgctgctgga | tttccaagct | gagaggacgt | gaacctggga ccaccagtag ccatcttgtt | 2280 |
| tgccacatgg | agagagactg | tgaggacaga | agccaaactg gaagtggagg agccaaggga | 2340 |
| ttgacaaaca | acagagcctt | gaccacgtgg | agtctctgaa tcagccttgt ctggaaccag | 2400 |
| atctacacct | ggactgccca | ggtctataag | ccaataaa | 2438 |

<210> SEQ ID NO 102
<211> LENGTH: 1457
<212> TYPE: DNA
<213> ORGANISM: Homo sapiens
<220> FEATURE:
<221> NAME/KEY: misc_feature
<223> OTHER INFORMATION: CETP:  Acc. No. XM_008050

<400> SEQUENCE: 102

| | | | |
|---|---|---|---|
| cctggccctg | ctgggcaatg | cccatgcctg | ctccaaaggc acctcgcacg aggcaggcat | 60 |
| cgtgtgccgc | atcaccaagc | tgccctcct | ggtgttgaac cacgagactg ccaaggtgat | 120 |
| ccagaccgcc | ttccagcgag | ccagctaccc | agatatcacg ggcgagaagg ccatgatgct | 180 |
| ccttggccaa | gtcaagtatg | ggttgcacaa | catccagatc agccacttgt ccatcgccag | 240 |
| cagccaggtg | gagctggtgg | aagccaagtc | cattgatgtc tccattcaga acgtgtctgt | 300 |
| ggtcttcaag | gggaccctga | gtatggcta | ccactgcc tggtggctgg gtattgatca | 360 |
| gtccattgac | ttcgagatcg | actctgccat | tgacctccag atcaacacac agctgacctg | 420 |
| tgactctggt | agagtgcgga | ccgatgcccc | tgactgctac ctgtctcttcc ataagctgct | 480 |
| cctgcatctc | caaggggagc | gagagcctgg | gtggatcaag cagctgttca caaatttcat | 540 |
| ctccttcacc | ctgaagctgg | tcctgaaggg | acagatctgc aaagagatca acgtcatctc | 600 |
| taacatcatg | gccgattttg | tccagacaag | ggctgccagc atcctttcag atggagacat | 660 |
| tgggggtggac | atttccctga | caggtgatcc | cgtcatcaca gcctcctacc tggagtccca | 720 |

```
tcacaaggca gtgctggaga cctggggctt caacaccaac caggaaatct tccaagaggt    780
tgtcggcggc ttccccagcc aggcccaagt caccgtccac tgcctcaaga tgcccaagat    840
ctcctgccaa acaagggag tcgtggtcaa ttcttcagtg atggtgaaat tcctctttcc     900
acgcccagac cagcaacatt ctgtagctta cacatttgaa gaggatatcg tgactaccgt    960
ccaggcctcc tattctaaga aaagctctt cttaagcctc ttggatttcc agattacacc    1020
aaagactgtt tccaacttga ctgagagcag ctccgagtcc gtccagagct tcctgcagtc    1080
aatgatcacc gctgtgggca tccctgaggt catgtctcgg ctcgaggtag tgtttacagc    1140
cctcatgaac agcaaaggcg tgagcctctt cgacatcatc aaccctgaga ttatcactcg    1200
agatggcttc ctgctgctgc agatggactt tggcttccct gagcacctgc tggtggattt    1260
cctccagagc ttgagctaga agtctccaag gaggtcggga tggggcttgt agcagaaggc    1320
aagcaccagg ctcacagctg gaaccctggt gtctcctcca gcgtggtgga agttgggtta    1380
ggagtacgga gatggagatt ggctcccaac tcctccctat cctaaaggcc cactggcatt    1440
aaagtgctgt atccaag                                                   1457

<210> SEQ ID NO 103
<211> LENGTH: 2986
<212> TYPE: DNA
<213> ORGANISM: Homo sapiens
<220> FEATURE:
<221> NAME/KEY: misc_feature
<223> OTHER INFORMATION: ICAM:  Acc. No. J03132

<400> SEQUENCE: 103
gcgccccagt cgacgctgag ctcctctgct actcagagtt gcaacctcag cctcgctatg     60
gctcccagca gccccggcc cgcgctgccc gcactcctgg tcctgctcgg ggctctgttc    120
ccaggacctg gcaatgccca gacatctgtg tccccctcaa aagtcatcct gccccgggga    180
ggctccgtgc tggtgacatg cagcaccctc tgtgaccagc ccaagttgtt gggcatagag    240
accccgttgc ctaaaaagga gttgctcctg cctgggaaca ccggaaggt gtatgaactg    300 agcaatgtgc aagaagatag ccaaccaatg tgctattcaa actgccctga tgggcagtca    360
acagctaaaa ccttcctcac cgtgtactgg actccagaac gggtggaact ggcacccctc    420
ccctcttggc agccagtggg caagaacctt accctacgct gccaggtgga gggtggggca    480
ccccgggcca acctcaccgt ggtgctgctc cgtggggaga aggagctgaa acggagccaa    540
gctgtggggg agcccgctga ggtcacgacc acggtgctgg tgaggagaga tcaccatgga    600
gccaatttct cgtgccgcac tgaactggac ctgcggcccc aagggctgga gctgtttgag    660
aacacctcgg ccccctacca gctccagacc tttgtcctgc cagcgactcc cccacaactt    720
gtcagccccc gggtcctaga ggtggacacg caggggaccg tggtctgttc cctgacggg    780 ctgttcccag tctcggaggc ccaggtccac ctggcactgg ggaccagag gttgaacccc    840 acagtcacct atggcaacga ctccttctcg gccaaggcct cagtcagtgt gaccgcagag    900
gacgagggca cccagcggct gacgtgtgca gtaatactgg ggaaccagag ccaggagaca    960
ctgcagacag tgaccatcta cagctttccg gcgcccaacg tgattctgac gaagccagag   1020
gtctcagaag gaccgaggt gacagtgaag tgtgaggccc accctagagc caaggtgacg   1080
ctgaatgggg ttccagccca gccactgggc ccgagggccc agctcctgct gaaggccacc   1140
ccagaggaca acgggcgcag cttctcctgc tctgcaaccc tggaggtggc cggccagctt   1200
atacacaaga accagacccg ggagcttcgt gtcctgtatg gccccgact ggacgagagg   1260
```

-continued

```
gattgtccgg gaaactggac gtggccagaa aattcccagc agactccaat gtgccaggct    1320
tgggggaacc cattgcccga gctcaagtgt ctaaaggatg gcactttccc actgcccatc    1380
ggggaatcag tgactgtcac tcgagatctt gagggcacct acctctgtcg ggccaggagc    1440
actcaagggg aggtcacccg cgaggtgacc gtgaatgtgc tctcccccg gtatgagatt     1500 gtcatcatca ctgtggtagc agccgcagtc ataatgggca ctgcaggcct cagcacgtac    1560
ctctataacc gccagcggaa gatcaagaaa tacagactac aacaggccca aaaagggacc    1620
cccatgaaac cgaacacaca agccacgcct ccctgaacct atcccgggac agggcctctt    1680
cctcggcctt cccatattgg tggcagtggt gccacactga acagagtgga agacatatgc    1740
catgcagcta cacctaccgg ccctgggacg ccggaggaca gggcattgtc ctcagtcaga    1800
tacaacagca tttggggcca tggtacctgc acacctaaaa cactaggcca cgcatctgat    1860
ctgtagtcac atgactaagc caagaggaag gagcaagact caagacatga ttgatggatg    1920
ttaaagtcta gcctgatgag aggggaagtg gtggggagaa catagcccca ccatgaggac    1980
atacaactgg gaaatactga aacttgctgc ctattgggta tgctgaggcc cacagactta    2040
cagaagaagt ggccctccat agacatgtgt agcatcaaaa cacaaaggcc cacacttcct    2100
gacggatgcc agcttgggca ctgctgtcta ctgaccccaa cccttgatga tatgtattta    2160
ttcatttgtt attttaccag ctatttattg agtgtctttt atgtaggcta aatgaacata    2220
ggtctctggc ctcacggagc tcccagtcca tgtcacattc aaggtcacca ggtacagttg    2280
tacaggttgt acactgcagg agagtgcctg gcaaaaagat caaatggggc tgggacttct    2340
cattggccaa cctgcctttc cccagaagga gtgattttc tatcggcaca aaagcactat    2400
atggactggt aatggttcac aggttcagag attacccagt gaggccttat tcctcccttc    2460
cccccaaaac tgacaccttt gttagccacc tccccaccca catacatttc tgccagtgtt    2520
cacaatgaca ctcagcggtc atgtctggac atgagtgccc agggaatatg cccaagctat    2580
gccttgtcct cttgtcctgt ttgcatttca ctggagctt gcactattgc agctccagtt     2640
tcctgcagtg atcagggtcc tgcaagcagt ggggaagggg gccaaggtat ggaggactc     2700 cctcccagct ttggaagggt catccgcgtg tgtgtgtgtg tgtatgtgta gacaagctct    2760
cgctctgtca cccaggctgg agtgcagtgg tgcaatcatg gttcactgca gtcttgacct    2820
tttgggctca agtgatcctc ccacctcagc ctcctgagta gctgggacca taggctcaca    2880
acaccacacc tggcaaattt gattttttt ttttttttca gagacggggt ctcgcaacat      2940
tgcccagact tcctttgtgt tagttaataa agctttctca actgcc                   2986
```

<210> SEQ ID NO 104
<211> LENGTH: 3634
<212> TYPE: DNA
<213> ORGANISM: Homo sapiens
<220> FEATURE:
<221> NAME/KEY: misc_feature
<223> OTHER INFORMATION: X02910

<400> SEQUENCE: 104

```
gaattccggg tgatttcact cccggctgtc caggcttgtc ctgctacccc acccagcctt      60
tcctgaggcc tcaagcctgc caccaagccc ccagctcctt ctccccgcag gacccaaaca    120
caggcctcag gactcaacac agcttttccc tccaacccgt tttctctccc tcaacggact    180
cagctttctg aagcccctcc cagttctagt tctatctttt tcctgcatcc tgtctggaag    240
ttagaaggaa acagaccaca gacctggtcc ccaaaagaaa tggaggcaat aggttttgag    300
```

```
gggcatgggg acggggttca gcctccaggg tcctacacac aaatcagtca gtggcccaga    360
agacccccct cggaatcgga gcagggagga tggggagtgt gaggggtatc cttgatgctt    420
gtgtgtcccc aactttccaa atccccgccc ccgcgatgga gaagaaaccg agacagaagg    480
tgcagggccc actaccgctt cctccagatg agctcatggg tttctccacc aaggaagttt    540
tccgctggtt gaatgattct ttccccgccc tcctctcgcc cagggacat ataaaggcag     600
ttgttggcac acccagccag cagacgctcc ctcagcaagg acagcagagg accagctaag    660
agggagagaa gcaactacag accccccctg aaaacaaccc tcagacgcca catcccctga    720
caagctgcca ggcaggttct cttcctctca catactgacc cacggcttca ccctctctcc    780
cctggaaagg acaccatgag cactgaaagc atgatccggg acgtggagct ggccgaggag    840
gcgctcccca agaagacagg ggggcccag ggctccaggc ggtgcttgtt cctcagcctc     900
ttctccttcc tgatcgtggc aggcgccacc acgctcttct gcctgctgca ctttggagtg    960
atcggccccc agagggaaga ggtgagtgcc tggccagcct tcatccactc tcccacccaa   1020
ggggaaatga gagacgcaag agaggagag agatgggatg ggtgaaagat gtgcgctgat    1080
agggagggat gagagagaaa aaacatggaa gaaagacggg gatgcagaaa gagatgtggc   1140
aagagatggg gaagagagag agagaaagat ggagagacag gatgtctggc acatggaagg   1200
tgctcactaa gtgtgtatgg agtgaatgaa tgaatgaatg aatgaacaag cagatatata   1260
aataagatat ggagacagat gtggggtgtg agaagagaga tggggaaga aacaagtgat    1320
atgaataaag atggtgagac agaaagagcg ggaaatatga cagctaagga gagagatggg   1380
ggagataagg agagaagaag atagggtgtc tggcacacag aagacactca gggaaagagc   1440
tgttgaatgc tggaaggtga atacacagat gaatggagag agaaaaccag acacctcagg   1500
gctaagagcg caggccagac aggcagccag ctgttcctcc tttaagggtg actccctcga   1560
tgttaaccat tctccttctc cccaacagtt ccccagggac ctctctctaa tcagccctct   1620
ggcccaggca gtcagtaagt gtctccaaac ctctttccta attctgggtt tgggtttggg   1680
ggtagggtta gtaccggtat ggaagcagtg ggggaaattt aaagttttgg tcttggggga   1740
ggatggatga aggtgaaagt aggggggtat tttctaggaa gtttaagggt ctcagctttt   1800
tctttttctct ctcctcttca ggatcatctt ctcgaacccc gagtgacaag cctgtagccc   1860
atgttgtagg taagagctct gaggatgtgt cttggaactt ggagggctag gatttgggga   1920
ttgaagcccg gctgatggta ggcagaactt ggagacaatg tgagaaggac tcgctgagct   1980
caagggaagg gtggaggaac agcacaggcc ttagtgggat actcagaacg tcatggccag   2040
gtgggatgtg ggatgacaga cagagaggac aggaaccgga tgtggggtgg gcagagctcg   2100
agggccagga tgtggagagt gaaccgacat ggccacactg actctcctct ccctctctcc   2160
ctccctccag caaaccctca agctgagggg cagctccagt ggctgaaccg ccgggccaat   2220
gccctcctgg ccaatggcgt ggagctgaga gataaccagc tggtggtgcc atcagagggc   2280
ctgtacctca tctactccca ggtcctcttc aagggccaag gctgcccctc cacccatgtg   2340
ctcctcaccc acaccatcag ccgcatcgcc gtctcctacc agaccaaggt caacctcctc   2400
tctgccatca gagcccctg ccagaggag accccagagg gggctgaggc caagccctgg   2460
tatgagccca tctatctggg aggggtcttc cagctggaga agggtgaccg actcagcgct   2520
gagatcaatc ggcccgacta tctcgacttt gccgagtctg gcaggtcta ctttgggatc    2580
attgccctgt gaggaggacg aacatccaac cttcccaaac gctcccctg ccccaatccc    2640
tttattaccc cctccttcag acaccctcaa cctcttctgg ctcaaaaaga gaattggggg   2700
```

-continued

```
cttagggtcg gaacccaagc ttagaacttt aagcaacaag accaccactt cgaaacctgg   2760
gattcaggaa tgtgtggcct gcacagtgaa gtgctggcaa ccactaagaa ttcaaactgg   2820
ggcctccaga actcactggg gcctacagct ttgatccctg acatctggaa tctggagacc   2880
agggagcctt tggttctggc cagaatgctg caggacttga aagacctca cctagaaatt    2940 gacacaagtg gaccttaggc cttcctctct ccagatgttt ccagacttcc ttgagacacg   3000
gagcccagcc ctccccatgg agccagctcc ctctatttat gtttgcactt gtgattattt   3060
attatttatt tattatttat ttatttacag atgaatgtat ttatttggga gaccggggta   3120
tcctggggga cccaatgtag gagctgcctt ggctcagaca tgttttccgt gaaaacggag   3180
ctgaacaata ggctgttccc atgtagcccc ctggcctctg tgccttcttt tgattatgtt   3240
ttttaaaata tttatctgat taagttgtct aaacaatgct gatttggtga ccaactgtca   3300
ctcattgctg agcctctgct ccccagggga gttgtgtctg taatcgccct actattcagt   3360
ggcgagaaat aaagtttgct tagaaaagaa acatggtctc cttcttggaa ttaattctgc   3420
atctgcctct tcttgtgggt gggaagaagc tccctaagtc ctctctccac aggctttaag   3480
atccctcgga cccagtccca tccttagact cctagggccc tggagaccct acataaacaa   3540
agcccaacag aatattcccc atcccccagg aaacaagagc ctgaacctaa ttacctctcc   3600
ctcagggcat gggaatttcc aactctggga attc                              3634
```

<210> SEQ ID NO 105
<211> LENGTH: 11233
<212> TYPE: DNA
<213> ORGANISM: Homo sapiens

<400> SEQUENCE: 105

```
gaattccttc cgtagcttca ccagacacct aattggccaa gaaggtttga agacctgatg     60
tggttcttaa ttggggatgg ggaattaagg gctactgtat ctataggatt atcttttcac    120
ttgcatagac ctatttggtg tgttcagggc atagtgatac tataattgcc atatttaaca    180
gtttataaag ttcaagccca gcatattctt tgcctgttta atgatgtctt ggtatcagcc    240
ttttaatggt acttatcagc atagaaaatg gaaacaaaat aacttttaaa acagtagctc    300
tcaagcttta gtgtgctcag aatgaccaga gaaccttgtg aaatatacag atttctgggt    360
ccagatctgg ggcaggacca ggaagtctgc atttcatctg caccccccacc ctactctgag   420 gcttatagtc ctgagaacat gctttgaaaa aggctgtccc aagggctcgc agacaggcta    480
ttgaccagct actctttctt gatgttctcc aggaaaaacc caacaaagga atgcctttca    540
ttgagtagta gcagcatagg agcaatagtt gctcctgaat tatggtgggt ttcccctctt    600
catcaatgtg ctttaagggt acagtttcat ttggtctatc taccatgttc tataaaaaca    660
tgaaaattca caggtaagtt tgagatacag aaaataacta aactgattct tctcacgaac    720
tctgatcact aggctgtggt tgatttagct ctctaaccaa caagtaattt gttcttttggc   780 atgagtaagg ggggaaaagg aggagtgggt aaaagcagct gataacagat ggcttgcgcc    840
catctaaaat gtggggagag aaataaagct gtcccaagag aactaaagct gagttctctc    900
gtcatatatc tgaagattca tatcagggggt ctaaacatgg tatgtcgggt agcttaattg    960
gaaactcctg gactgtgagt gtcacagact catggatggg ccaatcagtg gccactttag   1020
tgtctgggct gcagcaaaat gagacaatag ctgtcattca caaaccttttg gaattaaaaa   1080 aaccccgaaa tgacattggt gctttaaagt aaaataaagt cctgccttta agtccagcat   1140
```

```
atcactgttg tttctgagtt taaatattaa gaaccacatt tcgttaatga ttaaaacaac   1200
agtgattgat ttaggggctc agtgagcatt taatctgtcc tgacttcagg taccatgcta   1260
aaggagcaca atgcctgatg ctgcaggaga acattaggt aactatttaa tggagtttta    1320
attttctgtt attattttta ataattaatt gtgattttga ctatttggaa gctacaggta   1380
tattttgtcc tccttttggg gtggtgttat tgccctgccc tgttttaatc agtggttctt   1440
agagaaagtg aactcaggag tgacttaaaa tgaaggaaga cggactttgg ctaaaattac   1500
aattaaataa tcaaatcatt ttcaaatata aagggagcat gcagatgatc tggcccaatc   1560
ctttcattct gcagatgaga aaactgagac tcataggaat gaaaagactt gcccaaagcc   1620
atacagcttg tttctgttgt ttggtgcatt aggccaaaag acctaggcct aatagatgga   1680
aaagatggca ggatgtcttg gccttgctct gacagttgct tctctgatct cagatatttc   1740 ccacccttg taatctgtgt tccacacagg aagtagttct tgttttttaa atatcgaagg    1800
tgtataaacg taaagttttt atagatgagc acccagggc caatatcgt ttaagtaaag     1860 acctaaatgc tttgcagaga cagtaaagtg tcatgtctgt cccagggaaa gaaatccagg   1920
acaggaaatg ctcagtcttc cagcactcct ctggctacct ggagctcagg ctatgagcct   1980
caacccctcc ctgaagcatt agctctggag cagaggctg gatttacttc agagatctgg    2040
gcaagtccct ttaacctggt agtccttcct ttccttgttt gtaaaacaga gagatgaggc   2100
tgatagctcc ctcacagctc catcagaggc agtgtgtgaa attagttcct gtttgggaag   2160
gtttaaaagc caccacattc cacctccctg ctaatatgat tactaaaatg ttttatatg    2220 aaagggccaa ttcctcatct cccctcttcc tttaaaaaca gaccaagggg catcttttct   2280
tgtctccctg tggcctaaaa ggttactgct tctgtggtta tctccttgga aagacagagt   2340
gtcaggactc ttaggtacac caaaaatgaa caaaaaaatc aacaacaacc ataacaccaa   2400
caaaaataac tgctgtgtcg gttcttaaga cggcttctga gctagaaaca gattttcta    2460 actgtaaaaa acgtggcccc agcctgtctg caggccacct ctgtctttag gccttggggg   2520
gaggagggaa gtgagctcat ttactggggt ctacctcagg gtcatcacca aggtgttcta   2580
caaaacgcac tttaagaatg ttttggaagg aaattcacct tttaacagcc caagaggtat   2640
ctctctctgg cacacagttc tgcacacagc ctgtttctca acgtttggaa atcttttaac   2700
agtttatgga aggccacctt ttaaaccgat ccaacagctc ctttctccat aacctgattt   2760
tagaggtgtt tcattatctc taattactca gggtaaatgg tgattactca gtgttttaat   2820
catcagtttg ggcagcagtt acactaaact cagggaagcc cagactccca tgggtatttt   2880
tggaaggtac ggcgactagt cggtgcatgc tttctagtac ctccgcacgt ggtccccagg   2940
tgagccccag ccgcttccca gagctggagg cagcggcgtc ccagctccga cggcagctgc   3000
ggactcgggc gctgcctggg cttccgggac ccgggcctgc taggcgaggt cgggcggctg   3060
gaggggagga tgtgggcggg gctcccatcc ccagaaaggg aggcgagcga gggaggaggg   3120
aaggagggag gggccgccgg ggaagaggag gaggaaggaa agaaagaaag cgagggaggg   3180
aaagaggagg aaggaagatg cgagaaggca gaggaggagg gagggaggga aggagcgcgg   3240
agcccggccc ggaagctagg tgagtgtggc atccgagctg agggacgcga gcctgagacg   3300
ccgctgctgc tccggctgag tatctagctt gtctccccga tgggattccc gtccaagcta   3360
tctcgagcct gcagcgccac agtccccggc cctcgcccag gttcactgca accgttcaga   3420
ggtccccagg agctgctgct ggcgagcccg ctactgcagg gacctatggt gagcaaggct   3480
acctggtgag gggagacagg cagaggggt ctaggagcct ccttgggggg aagaagctgg    3540
```

```
tcacaggctg tgaccgaggc aaaaggtggc ctaattattt tccaatagtg gtgctggagg    3600
tggggatgct ggcgctgaaa gacctttaaa tatcggctac tgcccctgcc caggccttct    3660
ctgtccagca gtccctggga gattctcacc tttgggaagt gcggggcagg agagcagaaa    3720
caagagaagc ccttggtagg ggggtcgttg ggaaaaactg tggggtcttg ggctgaacgc    3780
gttgcccacg ggctggaggt tgcgatcccc ggacggaaag cgcgggagga ggaaggagag    3840
aaccggctct gaggtccaga gagagtgagg gggcagagcg acggcgagat ggggagagaa    3900
cacctagctg gagcaggttc tgcggtagag agcgcagtcc tgctggcctc tggagagtgc    3960
gcgccgctac ggaggctgcg tcgaggggag tgtcacccaa tctggccccc agctggcggg    4020
gcgccctgag agcttgcgaa ctgcagttgc aggacgcgcc ttctccacga gctattttcg    4080
tcgacttgcg gaacccaagg aacctcgcct ctatcatttc acggtgtagg gtccctagag    4140
acgacagcca agatcccagg ggctcccagg acgcttgttc ctgcggtgtc gtgtcctatg    4200
gggagttcct ggcgggacga aaggcggacg cgcggctctt cctggccctc caggcccgga    4260
accgacggga aaggttcccg tgattcccga gtccctgcag gcttcttcca gcgggagttg    4320
gtccgggggc cttagaggcc tccaagcact gctttggagg atggtttcca aggatcgcgg    4380
tttgtgagtt gaaggctttg tgagaggtta accccccaaa agatacatac ttggtaaact    4440
gaggctacct gtaaacacat ttcggcatta ggagaagatt cgagtaggga agtgaaggac    4500
aaccaccccg agttacattc ctttccccca ataaaaagct ctggggatga aagttctttt    4560
ggcttttatc ttttcgattt aaaaatttga gaagaaaaat gtgactagag atgaatcctg    4620
gtgaatccga aattgaaaca caactccccc ttccccttcc tatcctctcg gttttagaac    4680
cgcgctctcc cgcccagga gattccttgg ggccgagggt tttccgggga acccgggcgc    4740
ccgcccttc tactgtccct ttgccccgcg ggcacagctt gcctccgtct gctttctcta    4800
cttctggacc tctcctcgcc gggcttttta aagggcttct gcgtctcaaa acaaaacaaa    4860
aaaacccttt gctcttccca acccttttcgc agcccgcccc agcggtggcg cgggaccagc    4920
aaaggcgaaa gccgcgcggc tcttgccggg cgcggacggt cgcgcagggg cgcccgcggc    4980
ctccgcaccc ggacctgagg tgttggtcga ctccgggcat ccacggtcgg gagggagggc    5040
tgagctgttc gatcctttac ttttcttcct caaagtctac ctgccaatgc ccctaagaag    5100
aaaaccaagt atgtgcgtgg agagtggggc ggcaggcaac ccgagttctt gagctccgga    5160
gcgacccaaa gcagcaactg gaacagcct caggaaaggg aggtcgggtg gagtgggctt    5220
tggggcagga gtcatggggc ccgggccccg ggacgacct ggcgctcccg gcctgctga    5280
acgctgagtt gcgcctagtc gggttttcga agaggccctt gcgcagagcg acccacgcgc    5340
gcggcagcat cttcgattag tcaggacatc ccagtaactg cttgaactgt aggtaggtaa    5400
aattcttgaa ggagtatttg ctgcgtgcga ctctgctgct ggtgcaacgg aggaaggggg    5460
tgggggaagg aagtggcggg ggaaggagtg tggtggtggt ttaaaaaata agggaagccg    5520
aggcgagaga gacgcagacg cagaggtcga gcgcaggccg aaagctgttc accgttttct    5580
cgactccggg gaacatggtg ggatttcctt tctgcgccgg gtcgggagtt gtaaaacctc    5640
ggccacatta agatctgaaa actgtgatgc gtcctttctg cagagacgcc tctttctgaa    5700
tctgcccgga gcttcgagcc ccggcgtctg tccctcagcc tggcatggct tcttcggggg    5760
tctgctttgc atggggagag gggccacgca gcggcggact aggtttgggg attctcggta    5820
atggacccgg agcaatgact aacagccgct ccctctcact ttcccacagc gatcaccctc    5880
```

| | |
|---|---|
| taacaccctc cctcccattc ccggccccgc gcgtgacaag gtcggctgct ttcagccggg | 5940 |
| agctagatcg gtggcccggc tcttcggagc cttagcaggc gttcgccaag gggtgactgg | 6000 |
| ctgtcattgg gagcaatatt tggccttgag gagaccctgg ggaggaagtg gcggggagct | 6060 |
| cgtgtttgct tgtgtgtgtg tgggggggg ggtgtgtgta cacgcgcgtg ggcagggtcc | 6120 |
| ctctgcgctt tcctttttaa gtgcctctcg gtggtgaggc tttgggcggg tgagactttc | 6180 |
| ccgacctcgc tcccggcccc acttaagccg ggttcgagct gggagacgca gtcccttcag | 6240 |
| tgcgcccaa atcctctggc ttcaggtggc ccggcgcggg ggcccagcac gacgcaccgc | 6300 |
| gccgagaacc gggttctccg tgcgctcgcg cagtagccct gggagcgcgg cggccgcggg | 6360 |
| gcaccggccg agggctctgc cgagcgccgc cgggagctcc tcccggaccg ctgaggctcg | 6420 |
| ggcggcgggc gcggaggttg gcctcgcctg gaggggcggg cccgcgaggg gcgggggct | 6480 |
| gtggaggagg ggagggcgcg caggcccttt cgccgcctgc cgcgggaggg gcctcggcgc | 6540 |
| tcacgtgact ccgaggggct ggaagaaaaa cagagcctgt ctgcggtgga gtctcattat | 6600 |
| attcaaatat tccttttagg agccattccg tagtgccatc ccgagcaacg cactgctgca | 6660 |
| gcttccctga gcctttccag caagtttgtt caagattggc tgtcaagaat catggactgt | 6720 |
| tattatatgc cttgttttct gtcagtgagt agacacctct tccttccccc tctccggaat | 6780 |
| tcactctgcc ctcaccaccc ctgctcgccg gctgtccctt ccgtcggacc tcctttacaa | 6840 |
| tatccacact ctgctccctg gcagcactgt cgctcccttc ttggcccggc agccggggcg | 6900 |
| ctggaagcgt acgggttcct tttaaagtgc tgctagcgcg cactcgccct ctcagcgttg | 6960 |
| caagaaaggg gagcgcgagg gagctaaaga gatgaaagcc cggggttgta ccttgagggc | 7020 |
| taaccactcc cttcccctat ccaacttgtc tgggagagcc cccagtgtct ccgtggcgcg | 7080 |
| ttcccactct cttgtcaaaa ctcacagagg tctctccgga atcgtctctc accccttccc | 7140 |
| tggggatgag cgggcacgat caggcacttt tggctgaata tttcaaactc atcggccaca | 7200 |
| ataaaataag ccctcaagcc acccggttag ctcccagacc accttctcgg cttctggacc | 7260 |
| ctgtcgccct ctgtcttcgc ccagcccctg cctctcactt tccctccctc tggctctgaa | 7320 |
| ccaactggaa gttgtgaaag ttgggctctg agggtggagg aaaagggaga gaagctgaag | 7380 |
| gtctaaagtg gagagcaatg ccattttaat tctccctccc ccacccctt tcacccctc | 7440 |
| aatgttaact gtttatcctt caagaagcca cgctgagatc atggcccaga tagcagttag | 7500 |
| gacaaaaaaa gattaacagg atggaggcta tctgatttgg ggttatttga ctgtaaacaa | 7560 |
| gttagaccaa gtaattacag ggcaattctt actttcaggc cgtgcatggc tgcagctggt | 7620 |
| gggtgggcgg gtggtgtgag ggagaagaca caaacttgat cttctgacc tgctttccat | 7680 |
| cttgcccctc catttctagc cctaaatgca tatgcagaca catctctatt tctccctatt | 7740 |
| tattggtgtt tgtttattct ttaaccttcc actcccctcc ccctcccag agacaccatg | 7800 |
| attcctggta accgaatgct gatggtcgtt ttattatgcc aagtcctgct aggaggcgcg | 7860 |
| agccatgcta gtttgatacc tgagacgggg aagaaaaaag tcgccgagat tcagggccac | 7920 |
| gcgggaggac gccgctcagg gcagagccat gagctcctgc gggacttcga ggcgacactt | 7980 |
| ctgcagatgt ttgggctgcg ccgccgcccg cagcctagca agagtgccgt cattccggac | 8040 |
| tacatgcggg atctttaccg gcttcagtct ggggaggagg aggaagagca gatccacagc | 8100 |
| actggtcttg agtatcctga gcgcccggcc agccgggcca acaccgtgag gagcttccac | 8160 |
| cacgaaggtc agtctcttcc cccagtctgc gtgggggagg gctggtggga ctggctagag | 8220 |
| gggcagtgaa agccctgggg aagaagagtt cgggttacat caaaccccag tccaggaggc | 8280 |

```
tgaggaacag agctgcttac ctccaagaat ttgcagagct gccgccgaac ttattttttg    8340
gagacagagg gggaggtgtt caggggaagg ggaatgacag cactcagacg tgggctagcc    8400
ccagcggtgt gttttgcta tatcaaagcc ttttctgcta ggttttctgc ccgttttttt    8460
caaagcacct actgaattta atattacagc tgtgtgtttg tcgggtttat tcaataggg    8520 ccttgtaatc cgatctgaat gtttcctagc ggatgtttct tttccaaagt aaatctgagt    8580
tattaatcca ccagcatcat tactgtgttg gaatttattt tcccctctgt aacatgatca    8640
acaaggcatg ctctgtgttt ccaagatcgc tggggaaatg tttagtaaca tactcaatag    8700
tggaagaggg agagggtggt tgtctccatg tttcctcctg cctgtgctct gttggcccct    8760
cttttctttt acaaccactt gtaaagaaaa ctgtggacac aaagccaagg tgggggttt    8820 aaaagaggag tctgattgtg gtgccataga ggagttgaca catagaaatt attagacata    8880
tcaaggaggc tggatatagt ttctgtcttt ggtgcttgag aaatgctagc tacattttgc    8940
tggtttgtta gctgccccac ttatctgctc cttcaaatta aggggtatgc ttattttccc    9000
ccagtaggtt tcccctgcat aagcagaatt caccattcat tgcccaaccc tgagctatct    9060
cttgactctt ccatctttga aaaagttca tatgcttttt cttttcccct tccttcctaa    9120
ctgtgcctag aacatctgga gaacatccca gggaccagtg aaaactctgc ttttcgtttc    9180
ctctttaacc tcagcagcat ccctgagaac gaggcgatct cctctgcaga gcttcggctc    9240
ttccgggagc aggtggacca gggccctgat tgggaaggg gcttccaccg tataaacatt    9300
tatgaggtta tgaagccccc agcagaagtg gtgcctgggc acctcatcac acgactactg    9360
gacacgagac tggtccacca caatgtgaca cggtgggaaa cttttgatgt gagccctgcg    9420
gtccttcgct ggacccggga gaagcagcca aactatgggc tagccattga ggtgactcac    9480
ctccatcaga ctcggaccca ccagggccag catgtcagga ttagccgatc gttacctcaa    9540
gggagtggga attgggccca gctccggccc ctcctggtca cctttggcca tgatggccgg    9600
ggccatgcct tgacccgacg ccggagggcc aagcgtagcc ctaagcatca ctcacagcgg    9660
gccaggaaga agaataagaa ctgccggcgc cactcgctct atgtggactt cagcgatgtg    9720
ggctggaatg actggattgt ggccccacca ggctaccagg ccttctactg ccatgggggac   9780 tgcccctttc cactggctga ccacctcaac tcaaccaacc atgccattgt gcagaccctg    9840
gtcaattctg tcaattccag tatccccaaa gcctgttgtg tgcccactga actgagtgcc    9900
atctccatgc tgtacctgga tgagtatgat aaggtggtac tgaaaaatta tcaggagatg    9960
gtagtagagg gatgtgggtg ccgctgagat caggcagtcc ttgaggatag acagatatac   10020
acaccacaca cacacaccac atacaccaca cacacacgtt cccatccact cacccacaca   10080
ctacacagac tgcttcctta tagctggact tttatttaaa aaaaaaaaa aaaaaatgga    10140 aaaaatccct aaacattcac cttgacctta tttatgactt tacgtgcaaa tgttttgacc   10200
atattgatca tatattttga caaaatatat ttataactac gtattaaaag aaaaaaataa   10260
aatgagtcat tattttaaag gtaaatcatg atttttttt ctccttaatc ctttctcttt    10320
tccttcgggc tcatctcttt tgaatgaggc ttttttctgt tcaggtgagt tggaggctgg   10380
atggaagtca aaaggtggta cctggaggtg gttaagttgt agggacagga agtaaactgt   10440
tggcagagag agatggtaat tgccagcatg aattgttttc tatttctatt taatgttaac   10500
aaggatgcag tatcctctcc catctggatg acacatgcct tggagaaaca ctgggatgaa   10560
aggagtgtag gtcagattaa agacttcatt tcaggcccct tgtacatctt ctgtttcact   10620
```

| | |
|---|---|
| cacctgttga ggtgtatcac agctgagcgt gatgaggtct caaccctaga aaaatgatac | 10680 |
| ccacctctgc tttcatgata cctcagggta tctccagtta ttacaggtac caatgtgata | 10740 |
| tttccaaatc aaaactaatt tgtacactaa catcataatg tgtgtgtgaa ggcatgtttt | 10800 |
| taaacttatt ttttttttct ccaggtagga ctcttttgtt ttttcttttg tcttttttttt | 10860 |
| tttgaaacaa gttctctctt tgttgcccca ggctggtctt gaactcctgg gctcaagcaa | 10920 |
| tcttctcatt tcggcctctt tgggattaca ggcatgcact gctattttgt ctttttttttt | 10980 |
| tttttgtaac aaataatgta ccctaccttc aaaaagtttg atgactactg ttttaatatg | 11040 |
| ccacttgata gaatttccca ttgtttcttg acttttttccc ttgtcctctt ttcccaatgt | 11100 |
| gaaggccttc atcaagttta ggatcccaac agattgggct gggtgggggt tgacaatggg | 11160 |
| gtcagatact aaagggtcag aatttctaag caggcactgt gaaggtgtcc cactattata | 11220 |
| cagaaatctc gag | 11233 |

<210> SEQ ID NO 106
<211> LENGTH: 1723
<212> TYPE: DNA
<213> ORGANISM: Homo sapiens
<220> FEATURE:
<221> NAME/KEY: misc_feature
<223> OTHER INFORMATION: BB1=BAR1 Acc. No. NM_000684

<400> SEQUENCE: 106

| | |
|---|---|
| tgctacccgc gcccgggctt ctggggtgtt ccccaaccac ggcccagccc tgccacaccc | 60 |
| cccgccccccg gcctccgcag ctcggcatgg gcgcgggggt gctcgtcctg ggcgcctccg | 120 |
| agcccggtaa cctgtcgtcg gccgcaccgc tccccgacgg cgcggccacc gcggcgcggc | 180 |
| tgctggtgcc cgcgtcgccg cccgcctcgt tgctgcctcc cgccagcgaa agccccgagc | 240 |
| cgctgtctca gcagtggaca gcgggcatgg gtctgctgat ggcgctcatc gtgctgctca | 300 |
| tcgtggcggg caatgtgctg gtgatcgtgg ccatcgccaa gacgccgcgg ctgcagacgc | 360 |
| tcaccaacct cttcatcatg tccctggcca gcgccgacct ggtcatgggg ctgctggtgg | 420 |
| tgccgttcgg ggccaccatc gtggtgtggg gccgctggga gtacggctcc ttcttctgcg | 480 |
| agctgtggac ctcagtggac gtgctgtgcg tgacggccag catcgagacc ctgtgtgtca | 540 |
| ttgccctgga ccgctacctc gccatcacct cgcccttccg ctaccagagc ctgctgacgc | 600 |
| gcgcgcgggc gcggggcctc gtgtgcaccg tgtgggccat ctcggccctg gtgtccttcc | 660 |
| tgcccatcct catgcactgg tggcgggcgg agagcgacga ggcgcgccgc tgctacaacg | 720 |
| accccaagtg ctgcgacttc gtcaccaacc gggcctacgc catcgcctcg tccgtagtct | 780 |
| ccttctacgt gcccctgtgc atcatggcct tcgtgtacct gcgggtgttc cgcgaggccc | 840 |
| agaagcaggt gaagaagatc gacagctgcg agcgccgttt cctcggcggc cagcgcggc | 900 |
| cgccctcgcc ctcgccctcg cccgtccccg cgcccgcgcc gccgcccgga ccccgcgcc | 960 |
| ccgccgccgc cgccgccacc gccccgctgg ccaacgggcg tgcgggtaag cggcggccct | 1020 |
| cgcgcctcgt ggccctacgc gagcagaagg cgctcaagac gctgggcatc atcatgggcg | 1080 |
| tcttcacgct ctgctggctg cccttcttcc tggccaacgt ggtgaaggcc ttccaccgcg | 1140 |
| agctggtgcc cgaccgcctc ttcgtcttct tcaactggct gggctacgcc aactcggcct | 1200 |
| tcaaccccat catctactgc cgcagccccg acttccgcaa ggccttccag ggactgctct | 1260 |
| gctgcgcgcg cagggctgcc cgccggcgcc acgcgaccca cggagaccgg ccgcgcgcct | 1320 |
| cgggctgtct ggcccggccc ggaccccgc catcgcccgg ggccgcctcg gacgacgacg | 1380 |

```
acgacgatgt cgtcggggcc acgccgcccg cgcgcctgct ggagccctgg gccggctgca    1440
acggcggggc ggcggcggac agcgactcga gcctggacga gccgtgccgc cccggcttcg    1500
cctcggaatc caaggtgtag ggcccggcgc ggggcgcgga ctccgggcac ggcttcccag    1560
gggaacgagg agatctgtgt ttacttaaga ccgatagcag gtgaactcga agcccacaat    1620
cctcgtctga atcatccgag gcaaagagaa aagccacgga ccgttgcaca aaaaggaaag    1680
tttgggaagg gatgggagag tggcttgctg atgttccttg ttg                      1723

<210> SEQ ID NO 107
<211> LENGTH: 1145
<212> TYPE: DNA
<213> ORGANISM: Homo sapiens
<220> FEATURE:
<221> NAME/KEY: misc_feature
<223> OTHER INFORMATION: IL-6: Acc. No. X04430

<400> SEQUENCE: 107
aggactggag atgtctgagg ctcattctgc cctcgagccc accggaacg aaagagaagc       60 tctatctccc ctccaggagc ccagctatga actccttctc cacaagcgcc ttcggtccag     120
ttgccttctc cctggggctg ctcctggtgt tgcctgctgc cttccctgcc ccagtacccc     180
caggagaaga ttccaaagat gtagccgccc cacacagaca gccactcacc tcttcagaac     240
gaattgacaa acaaattcgg tacatcctcg acggcatctc agccctgaga aaggagacat     300
gtaacaagag taacatgtgt gaaagcagca agaggcact ggcagaaaac aacctgaacc      360
ttccaaagat ggctgaaaaa gatggatgct tccaatctgg attcaatgag gagacttgcc      420
tggtgaaaat catcactggt cttttggagt ttgaggtata cctagagtac ctccagaaca      480
gatttgagag tagtgaggaa caagccgag ctgtccagat gagtacaaaa gtcctgatcc       540
agttcctgca gaaaaaggca agaatctag atgcaataac caccctgac ccaaccacaa       600 atgccagcct gctgacgaag ctgcaggcac agaaccagtg gctgcaggac atgcaactc       660 atctcattct gcgcagcttt aaggagttcc tgcagtccag cctgaggct cttcggcaaa       720 tgtagcatgg gcacctcaga ttgttgttgt taatgggcat tccttcttct ggtcagaaac      780
ctgtccactg ggcacagaac ttatgttgtt ctctatggag aactaaaagt atgagcgtta      840
ggacactatt ttaattattt taatttatt aatatttaaa tatgtgaagc tgagttaatt       900
tatgtaagtc atatttata ttttaagaa gtaccacttg aaacatttta tgtattagtt        960
ttgaaataat aatggaaagt ggctatgcag tttgaatatc ctttgtttca gagccagatc    1020
atttcttgga aagtgtaggc ttacctcaaa taaatgcta actttataca tatttttaaa     1080
gaaatattta tattgtattt atataatgta taaatggttt ttataccaat aaatggcatt    1140
ttaaa                                                                1145

<210> SEQ ID NO 108
<211> LENGTH: 2063
<212> TYPE: DNA
<213> ORGANISM: Homo sapiens
<220> FEATURE:
<221> NAME/KEY: misc_feature
<223> OTHER INFORMATION: U82535

<400> SEQUENCE: 108
tgccgggcgg taggcagcag caggctgaag ggatcatggt gcagtacgag ctgtgggccg       60
cgctgcctgg cgcctccggg gtcgccctgg cctgctgctt cgtggcggcg gccgtggccc     120
tgcgctggtc cggcgccgg acggcgcggg gcgcggtggt ccgggcgcga cagaagcagc      180
```

```
gagcgggcct ggagaacatg gacagggcgg cgcagcgctt ccggctccag aacccagacc      240
tggactcaga ggcgctgcta gccctgcccc tgcctcagct ggtgcagaag ttacacagta      300
gagagctggc ccctgaggcc gtgctcttca cctatgtggg aaaggcctgg gaagtgaaca      360
aagggaccaa ctgtgtgacc tcctatctgg ctgactgtga gactcagctg tctcaggccc      420
caaggcaggg cctgctctat ggcgtccctg tgagcctcaa ggagtgcttc acctacaagg      480
gccaggactc cacgctgggc ttgagcctga atgaaggggt gccggcggag tgcgacagcg      540
tagtggtgca tgtgctgaag ctgcaggdtg ccgtgccctt cgtgcacacc aatgttccac      600
agtccatgtt cagctatgac tgcagtaacc ccctctttgg ccagaccgtg aacccatgga      660
agtcctccaa agcccaggg ggctcctcag ggggtgaagg ggccctcatc gggtctggag       720 gctccccct gggcttaggc actgatatcg gaggcagcat ccgcttcccc tcctccttct       780
gcggcatctg cggcctcaag cccacaggga accgcctcag caagagtggc ctgaagggct      840
gtgtctatgg acaggaggca gtgcgtctct ccgtgggccc catggcccgg gacgtggaga      900
gcctggcact gtgcctgcga gccctgctgt gcgaggacat gttccgcttg gaccccactg      960
tgcctccctt gcccttcaga gaagaggtct acaccagctc tcagcccctg cgtgtggggt     1020
actatgagac tgacaactat accatgccct cccggccat gaggcgggcc gtgctggaga      1080
ccaaacagag ccttgaggct gcggggcaca cgctggttcc cttcttgcca agcaacatac     1140
cccatgctct ggagaccctg tcaacaggtg ggctcttcag tgatggtggc cacaccttcc     1200
tacagaactt caaaggtgat ttcgtggacc cctgcctggg ggacctggtc tcaattctga     1260
agcttcccca atggcttaaa ggactgctgg ccttcctggt gaagcctctg ctgccaaggc     1320
tgtcagcttt cctcagcaac atgaagtctc gttcggctgg aaaactctgg gaactgcagc     1380
acgagatcga ggtgtaccgc aaaaccgtga ttgcccagtg gagggcgctg gacctggatg     1440
tggtgctgac ccccatgctg gcccctgctc tggacttgaa tgcccaggc agggccacag      1500 gggccgtcag ctacactatg ctgtacaact gcctggactt ccctgcaggg gtggtgcctg     1560
tcaccacggt gactgctgag gacgaggccc agatggaaca ttacaggggc tactttgggg     1620
atatctggga caagatgctg cagaagggca tgaagaagag tgtggggctg ccggtggccg     1680
tgcagtgtgt ggctctgccc tggcaagaag agttgtgtct gcggttcatg cgggaggtgg     1740
agcgactgat gacccctgaa aagcagtcat cctgatggct ctggctccag aggacctgag     1800
actcacactc tctgcagccc agcctagtca gggcacagct gccctgctgc cacagcaagg     1860
aaatgtcctg catggggcag aggcttccgt gtcctctccc caaccccct gcaagaagcg      1920 ccgactccct gagtctggac ctccatccct gctctggtcc cctctcttcg tcctgatccc     1980
tccaccccca tgtggcagcc catgggtatg acataggcca aggcccaact aacagtcaag     2040
aaacaaaaaa aaaaaaaaaa aaa                                             2063

<210> SEQ ID NO 109
<211> LENGTH: 2729
<212> TYPE: DNA
<213> ORGANISM: Homo sapiens
<220> FEATURE:
<221> NAME/KEY: misc_feature
<223> OTHER INFORMATION: ACAT-1: Acc. No. XM_031119

<400> SEQUENCE: 109
agcttagcag gcgacgttgc gggccctggg cgccaggaga gcttcccgga gtcgaccttc       60
ctgctggctg ctctgtgacc gcttcccggc tctgccctct tggccgaagt gccgctgcc      120
```

```
gggcgcgggc ctcagacaat acaatggtgg gtgaagagaa gatgtctcta agaaaccggc    180
tgtcaaagtc cagggaaaat cctgaggaag atgaagacca gagaacccct gcaaaggagt    240
ccctagagac acctagtaat ggtcgaattg acataaaaca gttgatagca aagaagataa    300
agttgacagc agaggcagag gaattgaagc cattttttat gaaggaagtt ggcagtcact    360
ttgatgattt tgtgaccaat ctcattgaaa agtcagcatc attagataat ggtgggtgcg    420
ctctcacaac cttttctgtt cttgaaggag agaaaaacaa ccatagagcg aaggatttga    480
gagcacctcc agaacaagga aagattttta ttgcaaggcg ctctctctta gatgaactgc    540
ttgaagtgga ccacatcaga acaatatatc acatgtttat tgccctcctc attctcttta    600
tcctcagcac acttgtagta gattacattg atgaaggaag gctggtgctt gagttcagcc    660
tcctgtctta tgcttttggc aaatttccta ccgttgtttg gacctggtgg atcatgttcc    720
tgtctacatt ttcagttccc tattttctgt ttcaacattg ggccactggc tatagcaaga    780
gttctcatcc gctgatccgt tctctcttcc atggctttct tttcatgatc ttccagattg    840
gagttctagg ttttggacca acatatgttg tgttagcata tacactgcca ccagcttccc    900
ggttcatcat tatattcgag cagattcgtt ttgtaatgaa ggcccactca tttgtcagag    960
agaacgtgcc tcgggtacta aattcagcta aggagaaatc aagcactgtt ccaataccta   1020
cagtcaacca gtatttgtac ttcttatttg ctcctaccct tatctaccgt gacagctatc   1080
ccaggaatcc cactgtaaga tggggttatg tcgctatgaa gtttgcacag gtctttggtt   1140
gcttttctca tgtgtactac atctttgaaa ggctttgtgc cccttgtttt cggaatatca   1200
aacaggagcc cttcagcgct cgtgttctgg tcctatgtgt atttaactcc atcttgccag   1260
gtgtgctgat tctcttcctt acttttttg ccttttgca ctgctggctc aatgcctttg   1320
ctgagatgtt acgctttggt gacaggatgt tctataagga ttggtggaac tccacgtcat   1380
actccaacta ttatagaacc tggaatgtgg tggtccatga ctggctatat tactatgctt   1440
acaaggactt tctctggttt ttctccaaga gattcaaatc tgctgccatg ttagctgtct   1500
ttgctgtatc tgctgtagta cacgaatatg ccttggctgt ttgcttgagc ttttctatc   1560 ccgtgctctt cgtgctcttc atgttctttg gaatggcttt caacttcatt gtcaatgata   1620
gtcggaaaaa gccgatttgg aatgttctga tgtggacttc tctttcttg ggcaatggag   1680 tcttactctg cttttattct caagaatggt atgcacgtca gcactgtcct ctgaaaaatc   1740
ccacattttt ggattatgtc cggccacgtt cctggacttg tcgttacgtg ttttagaagc   1800
ttggactttg tttcctcctt gtcactgaag attgggtagc ccctgatttt ggagccagct   1860
gtttccagtt gttactgaag ttatctgtgt tatttggacc actccaggct ttacagatga   1920
ctcactccat tcctaggtca cttgaagcca aactgttgga agttcactgg agtcttgtac   1980
acttaagcag agcagaactt tttttgtggg gctgggtggg gggagaagac cgactaacag   2040
ctgaagtaat gacagattgt tgctgggtca tatcagcttt atcccttggt aattatatct   2100
gttttgtttc ttgactctgt ccaatcagag aataaacatc atagtttctt ggccactgaa   2160
ttagccaaaa cacttaggaa gaaatcactt aaatacctct ggcttagaaa ttttttcatg   2220
cacactgttg gaatgtatgc taattgaaca tgcaattggg gaagaaaaaa tgtagaatga   2280 ttttgctat ttctagtaga aagaaaatgt ctgttttcca aagataatgt tatacatcct   2340 atttgtaat tttttgaaa aaagttcaat gttcagtttt ccttagttt taccttgttt   2400 tctctatagg tcatgatttc tgtgaagcaa aaagatgcct tttaccatga attcttgagt   2460
```

```
ttacatcaat aatattgtat attaaggggga tcagaagtag gaaggaaaaa ataagagata    2520
gcagaggaaa aagaaaaaca tttcctctta taacttctga agtaatttgt aaaaaagatt    2580
tgtagagtca atcatgtgtt taaattattt tatcacaaac ttaacatgga agatattcct    2640 tttaacttt gtggtaactt ctttgaagtt atttagaaat atcctttgga acaattattt    2700
tattgtctaa taaatattga cttctcttg                                      2729
```

<210> SEQ ID NO 110
<211> LENGTH: 3779
<212> TYPE: DNA
<213> ORGANISM: Homo sapiens
<220> FEATURE:
<221> NAME/KEY: misc_feature
<223> OTHER INFORMATION: IBAT:  Acc. No. NM_000452

<400> SEQUENCE: 110

```
ttctattgaa agggaaatgg gagaacaata tgtgttccta tggctcagtc cctataagat      60
tctgtactat tcagagttga ttttaagtgt cacttaactg aaattatcca acaaaccttc     120
atggcatgaa acattaacac agctcttttt atatggcatg gttcctatgg ctcaatccct     180
ataagattct gtactagttc agagttgatt ttaaaagtca cttaactgaa attatccaac     240
aaaccctcga ggacattaaa cattaacgtg gctctttta tatggcatgg ttcattatca     300
tgccaataaa tgattaatcg taactctctg tcttgaccaa taattttgct ggacttttgt     360
gattcacaac gtgctctgtg ttgtaatgct acctcttgaa actgacatcc tagctttatt     420
gttttttatt acttccctaa ggtggctttc aaaagagaca ccaagtgaca tattttagg     480 aggggtttaa aagtttgatg gggtagaagt aaacgttgct taactcaacc agcagcagag     540
ccagggccca gggaccagcg cttctgtgga cttggccttt ccagcagcag acccagcaat     600
gaatgatccg aacagctgtg tggacaatgc aacagtttgc tctggtgcat cctgtgtggt     660
acctgagagc aatttcaata acatcctaag tgtggtccta agtacggtgc tgaccatcct     720
gttggccttg gtgatgttct ccatgggatg caacgtggaa atcaagaaat ttctagggca     780
cataaagcgg ccgtggggca tttgtgttgg cttcctctgt cagtttggaa tcatgcccct     840
cacaggattc atcctgtcgg tggcctttga catcctcccg ctccaggccg tagtggtgct     900
cattatagga tgctgccctg gaggaactgc ctccaatatc ttggcctatt gggtcgatgg     960
cgacatggac ctgagcgtca gcatgaccac atgctccaca ctgcttgccc tcggaatgat    1020
gccgctgtgc ctccttatct ataccaaaat gtgggtcgac tctgggagca tcgtaattcc    1080
ctatgataac ataggtacat ctctggttgc tctcgttgtt cctgtttcca ttggaatgtt    1140
tgttaatcac aaatggcccc aaaaagcaaa gatcatactt aaaattgggt ccatcgcggg    1200
cgccatcctc attgtgctca tagctgtggt tgaggaata ttgtaccaaa gcgcctggat    1260
cattgctccc aaactgtgga ttataggaac aatatttcct gtggcgggtt actccctggg    1320
gtttcttctg gctagaattg ctggtctacc ctggtacagg tgccgaacgg ttgcttttga    1380
aacggggatg cagaacacgc agctatgttc caccatcgtt cagctctcct tcactcctga    1440
ggagctcaat gtcgtattca ccttcccgct catctacagc attttccagc tcgcctttgc    1500
cgcaatattc ttaggatttt atgtggcata caagaaatgt catggaaaaa acaaggcaga    1560
aattccagag agcaaagaaa atggaacgga gccagagtca tcgttttata aggcaaatgg    1620
aggatttcaa cctgacgaaa agtagacatc aagtggacaa aacagacgag ttccaaatta    1680
cgttcttaaa ccgtaactat atttaattat ttgttttggt aggacagttg gcagaaaaga    1740
```

```
gttaaagtga aaattggaat tcattggaa ttcatgtatt ggtttcagta ccaagtgact    1800
ggtggcccaa ttctttaatg ggacaaatat tgtttcctat atatatgtat atgttttata    1860
tatgtatgta tactcatata gatatattgt cattgaaata ttcccccaaa atattctcag    1920
actaaacctg acatagggaa caccgagaat gaaaacatcg ttaacaccaa aactgaattc    1980
ttatgcagaa tttcctagcc catagatgac aacctgagtt tctgtatgtt aaagtagatg    2040
taatgaatta ttattattac agtggtcacg attttcttca gtgtttatga ttataaaaat    2100
tgacatgaac atctttcact gacattttaa tcattatttt aaaagctttg caacctatat    2160
atttatataa ctttgtaata taacatgggc aaatatctga cttcagtatt tttaaaaagt    2220
tgccttctcc agtggcagtc caaaagcaga aatgagagga aattattaca aaatagaatt    2280
caataaccat attggatgca ggctcttaac tcagcaggga tatcgtacat ctattgctct    2340
acctcagggg tccagtgata cccactagat cttccaagga aaaacataat tctttcaaac    2400
ggtgtgtatt tggcaaagag ctcttcaaat ctgggagagg gacttcctca aggttttcct    2460
gtgtgcagtg gatccacata gctaatatga cagctagtca gttgacaggg accacccaca    2520
gtaagcacca tggtcaggga ggtggcagga ggtgcaaaga cagaagtatt gagagaaaca    2580
ccaagactct agtggaggaa ttaattcaat gggagatagt ataaaataca tagaaaaacac   2640 aagtaacaga aacctggttg aaatgcttaa ctagagtcaa ttagatgtgc aggagtaagt    2700
agtataagaa gaatcaagtc cgagagtgat caggaaatga gtattaaaca gtatttgaaa    2760
cagagaacgt gtcccagggc ccaaaagtca gaagggcccc accagccagg aaagttgttt    2820
caatgctgta gtaggtgta gccaaggaa gccaggacta tctgatatac ggtagcaggg     2880
gtttacggct gccaggggaa aataactcat caagtgttgg actttcaatt ataagatcga    2940
atttaatttc ctttccctca ttctgcagca atcagaatac acaatcttaa ccactcggtc    3000
cttagtggtt ttgttccatt ttgcattggg tattttcact gcctcataga gtctatttca    3060
agtgtttggc tgaaagggct tttttgcattt gcatgttctg agttcagatt ctgctggtgc    3120
acccaagcat tatgggaaca ggaactcaac ttagctcttc cagtagaggg gtgagggatt    3180
ctgcttttca aattcataac attgatcttt ttatgcaaga tttccatta cagttgaata     3240 agtacttcat attttttccat cattagacaa atacaaaatg gactaaataa ttttaagaga    3300
tagtggaggc agcaggggt acagacttcc ttcttagaga gtgtcagaga atatgctccc     3360
aatggtggaa aggaagattt acagtctagc ggctaagtac ctcctacaca tttcccatca    3420
atcagaaaat agacaggtac actaaaggga cctgagaact cctcttgtaa tttcaacaca    3480
cccaaaatca agggcctgga tgccagcagc tgcagcaagc aggttttcc tccctgttga     3540 gcaagacagg tgaggcaaga taggacttgg ctttcttaca tgatgcggta acttgtgact    3600
tgagtctttt tccctaattt gctagtggga agaaaaatag ctgagctttc taaaatgata    3660
gctctctatt tttaaatgaa tttgaaaagt cgattaaatt atgtatttta ttgcctctga    3720
gtatcatatt aaatgaatat tttattttaa aggcttaaat aaatgaaaat gattttgt     3779
```

<210> SEQ ID NO 111
<211> LENGTH: 4067
<212> TYPE: DNA
<213> ORGANISM: Homo sapiens
<220> FEATURE:
<221> NAME/KEY: misc_feature
<223> OTHER INFORMATION: U28749

<400> SEQUENCE: 111

```
cttgaatctt ggggcaggaa ctcagaaaac ttccagcccg ggcagcgcgc gcttggtgca    60
agactcagga gctagcagcc cgtcccctc cgactctccg gtgccgccgc tgcctgctcc    120
cgccacccta ggaggcgcgg tgccacccac tactctgtcc tctgcctgtg ctccgtgccc    180
gaccctatcc cggcggagtc tccccatcct ccttttgcttt ccgactgccc aaggcacttt    240
caatctcaat ctcttctctc tctctctctc tctctctgtc tctctctctc tctctctctc    300
tctctctctc gcagggtggg gggaagagga ggaggaattc tttccccgcc taacatttca    360
agggacacaa ttcactccaa gtctcttccc tttccaagcc gcttccgaag tgctcccggt    420
gcccgcaact cctgatccca acccgcgaga ggagcctctg cgacctcaaa gcctctcttc    480 cttctcccctc gcttccctcc tcctcttgct acctccacct ccaccgccac ctccacctcc    540
ggcacccacc caccgccgcc gccgccaccg gcagcgcctc ctcctctcct cctcctcctc    600
ccctcttctc ttttttggcag ccgctggacg tccggtgttg atggtggcag cggcggcagc    660
ctaagcaaca gcagccctcg cagcccgcca gctcgcgctc gccccgccgg cgtcccccagc    720 cctatcacct catctcccga aaggtgctgg gcagctccgg ggcggtcgag gcgaagcggc    780
tgcagcggcg gtagcggcgg cgggaggcag gatgagcgca cgcggtgagg gcgcggggca    840
gccgtccact tcagcccagg gacaacctgc cgccccagcg cctcagaaga gaggacgcgg    900
ccgccccagg aagcagcagc aagaaccaac cggtgagccc tctcctaaga gacccagggg    960
aagacccaaa ggcagcaaaa acaagagtcc ctctaaagca gctcaaaaga aagcagaagc    1020
cactggagaa aaacggccaa gaggcagacc taggaaatgg ccacaacaag ttgttcagaa    1080
gaagcctgct caggaggaaa ctgaagagac atcctcacaa gagtctgccg aagaggacta    1140
gggggcgcaa cgttcgattt ctacctcagc agcagttgga tcttttgaag ggagaagaca    1200
ctgcagtgac cacttattct gtattgccat ggtctttcca ctttcatctg gggtggggtg    1260
gggtggggtg gggagggggg gggtggggtg gggagaaatc acataacctt aaaaaggact    1320
atattaatca ccttctttgt aatcccttca cagtcccagg tttagtgaaa aactgctgta    1380
aacacagggg acacagctta acaatgcaac ttttaattac tgttttcttt tttcttaacc    1440
tactaatagt ttgttgatct gataagcaag agtgggcggg tgagaaaaac cgaattgggt    1500
ttagtcaatc actgcactgc atgcaaacaa gaaacgtgtc acacttgtga cgtcgggcat    1560
tcatatagga agaacgcggt gtgtaacact gtgtacacct caaataccac cccaacccac    1620
tccctgtagt gaatcctctg tttagaacac caaagataag gactagatac tactttctct    1680
ttttcgtata atcttgtaga cacttacttg atgatttta actttttatt tctaaatgag    1740
acgaaatgct gatgtatcct ttcattcagc taacaaacta gaaaaggtta tgttcatttt    1800
tcaaaaaggg aagtaagcaa acaaatattg ccaactcttc tatttatgga tatcacacat    1860
atcagcagga gtaataaatt tactcacagc acttgttttc aggacaacac ttcattttca    1920
ggaaatctac ttcctacaga gccaaaatgc catttagcaa taaataacac ttgtcagcct    1980
cagagcattt aaggaaacta gacaagtaaa attatcctct ttgtaattta atgaaaaggt    2040
acaacagaat aatgcatgat gaactcacct aattatgagg tgggaggagc gaaatctaaa    2100
tttcttttgc tatagttata catcaattta aaaagcaaaa aaaaaagggg gggggcaatc    2160
tctctctgtg tctttctctc tctctctccc tctccctctc tcttttcatg tgtatcagtt    2220
tccatgaaag acctgaatac cacttacctc aaattaagca tatgtgttac ttcaagtaat    2280
acgttttgac ataagatggt tgaccaaggt gcttttcttc ggcttgagtt caccatctct    2340
tcattcaaac tgcacttttta gccagagatg caatatatcc ccactactca atactacctc    2400
```

```
tgaatgttac aacgaattta cagtctagta cttattacat gctgctatac acaagcaatg    2460
caagaaaaaa acttactggg taggtgattc taatcatctg cagttctttt tgtacactta    2520
attacagtta aagaagcaat ctccttactg tgtttcagca tgactatgta tttttctatg    2580
tttttttaat taaaaatttt taaaatactt gtttcagctt ctctgctaga tttctacatt    2640
aacttgaaaa tttttttaacc aagtcgctcc taggttctta aggataattt tcctcaatca   2700
cactacacat cacacaagat tgactgtaa tatttaaata ttaccctcca agtctgtacc     2760
tcaaatgaat tctttaagga gatggactaa ttgacttgca aagacctacc tccagacttc    2820
aaaaggaatg aacttgttac ttgcagcatt catttgtttt ttcaatgttt gaaatagttc    2880
aaactgcagc taaccctagt caaaactatt tttgtaaaag acatttgata gaaaggaaca    2940
cgtttttaca tacttttgca aaataagtaa ataataaata aaataaagcc aaccttcaaa    3000
gaacttgaag ctttgtaggt gagatgcaac aagccctgct tttgcataat gcaatcaaaa    3060
atatgtgttt ttaagattag ttgaatataa gaaaatgctt gacaaatatt ttcatgtatt    3120
ttacacaaat gtgattttg taatatgtct caaccagatt tattttaaac gcttcttatg     3180
tagagttttt atgcctttct ctcctagtga gtgtgctgac tttttaacat ggtattatca    3240
actgggccag gaggtagttt ctcatgacgg cttttgtcag tatggctttt agtactgaag    3300
ccaaatgaaa ctcaaaacca tctctcttcc agctgcttca gggaggtagt ttcaaaggcc    3360
acatacctct ctgagactgg cagatcgctc actgttgtga atcaccaaag gagctatgga    3420
gagaattaaa actcaacatt actgttaact gtgcgttaaa taagcaaata aacagtggct    3480
cataaaaata aaagtcgcat tccatatctt tggatgggcc ttttagaaac ctcattggcc    3540
agctcataaa atggaagcaa ttgctcatgt tggccaaaca tggtgcaccg agtgatttcc    3600
atctctggta aagttacact tttatttcct gtatgttgta caatcaaaac acactactac    3660
ctcttaagtc ccagtatacc tcattttca tactgaaaaa aaaagcttgt ggccaatgga    3720
acagtaagaa catcataaaa ttttatata tatagtttat ttttgtggga gataaatttt    3780
ataggactgt tctttgctgt tgttggtcgc agctacataa gactggacat ttaacttttc    3840
taccatttct gcaagttagg tatgtttgca ggagaaaagt atcaagacgt ttaactgcag    3900
ttgactttct ccctgttcct ttgagtgtct tctaacttta ttctttgttc tttatgtaga    3960
attgctgtct atgattgtac tttgaatcgc ttgcttgttg aaaatatttc tctagtgtat    4020
tatcactgtc tgttctgcac aataaacata acagcctctg tgatccc                 4067
```

<210> SEQ ID NO 112
<211> LENGTH: 511
<212> TYPE: DNA
<213> ORGANISM: Homo sapiens
<220> FEATURE:
<221> NAME/KEY: misc_feature
<223> OTHER INFORMATION: NM_016362

<400> SEQUENCE: 112

```
gcaggcccac ctgtctgcaa cccagctgag gccatgccct ccccagggac cgtctgcagc      60
ctcctgctcc tcggcatgct ctggctggac ttggccatgg caggctccag cttcctgagc     120
cctgaacacc agagagtcca gcagagaaag gagtcgaaga agccaccagc caagctgcag     180
ccccgagctc tagcaggctg gctccgcccg gaagatggag gtcaagcaga gggggcagag     240
gatgaactga agtccggtt caacgccccc tttgatgttg aatcaagct gtcagggtt       300 cagtaccagc agcacagcca ggccctgggg aagtttcttc aggacatcct ctgggaagag    360
```

```
gccaaagagg ccccagccga caagtgatcg cccacaagcc ttactcacct ctctctaagt      420
ttagaagcgc tcatctggct tttcgcttgc ttctgcagca actcccacga ctgttgtaca      480
agctcaggag gcgaataaat gttcaaactg t                                    511
```

<210> SEQ ID NO 113
<211> LENGTH: 2268
<212> TYPE: DNA
<213> ORGANISM: Homo sapiens
<220> FEATURE:
<221> NAME/KEY: misc_feature
<223> OTHER INFORMATION: S77410

<400> SEQUENCE: 113

```
accccaggca gcagcgagtg acaggacgtc tggaccggcg cgccgctagc agctctgccg       60
ggccgcggcg gtgatcgatg gggagcggct ggagcggacc cagcgagtga gggcgcacag      120
ccgggacgcc gaggcggcgg gcgggagacc cgcaccagcg cagccggccc tcggcgggac      180
gtgacgcagc gcccggggcg cgggtttgat atttgacaaa ttgatctaaa atggctgggt      240
ttttatctga ataactcact gatgccatcc cagaaagtcg gcaccaggtg tatttgatat      300
agtgtttgca acaaattcga cccaggtgat caaaatgatt ctcaactctt ctactgaaga      360
tggtattaaa agaatccaag atgattgtcc caaagctgga aggcataatt acatatttgt      420
catgattcct actttataca gtatcatctt tgtggtggga atatttggaa acagcttggt      480
ggtgatagtc atttacttt atatgaagct gaagactgtg ccagtgttt tcttttgaa      540 tttagcactg gctgacttat gcttttact gactttgcca ctatgggctg tctacacagc      600
tatggaatac cgctggcccct ttggcaatta cctatgtaag attgcttcag ccagcgtcag      660
tttcaacctg tacgctagtg tgtttctact cacgtgtctc agcattgatc gatacctggc      720
tattgttcac ccaatgaagt cccgccttcg acgcacaatg cttgtagcca agtcacctg      780 catcatcatt tggctgctgg caggcttggc cagtttgcca gctataatcc atcgaaatgt      840
atttttcatt gagaacacca atattacagt ttgtgctttc cattatgagt cccaaaattc      900 aaccccttccg atagggctgg gcctgaccaa aaatatactg ggtttcctgt ttccttttct      960
gatcattctt acaagttata ctcttatttg gaaggccta aagaaggctt atgaaattca     1020
gaagaacaaa ccaagaaatg atgatatttt taagataatt atggcaattg tgcttttctt     1080
tttcttttcc tggattcccc accaaatatt cacttttctg gatgtattga ttcaactagg     1140
catcatacgt gactgtagaa ttgcagatat tgtggacacg gccatgccta tcaccatttg     1200
tatagcttat tttaacaatt gcctgaatcc tctttttat ggctttctgg ggaaaaatt     1260 taaaagatat tttctccagc ttctaaaata tattccccca aaagccaaat cccactcaaa     1320
cctttcaaca aaaatgagca cgcttttccta ccgccctca gataatgtaa gctcatccac     1380
caagaagcct gcaccatgtt ttgaggttga gtgacatgtt cgaaacctgt ccataaagta     1440
attttgtgaa agaaggagca agagaacatt cctctgcagc acttcactac caaatgagca     1500
ttagctactt ttcagaattg aaggagaaaa tgcattatgt ggactgaacc gacttttcta     1560
aagctctgaa caaaagcttt tctttccttt tgcaacaaga caaagcaaag ccacattttg     1620
cattagacag atgacggctg ctcgaagaac aatgtcagaa actcgatgaa tgtgttgatt     1680
tgagaaattt tactgacaga aatgcaatct ccctagcctg cttttgtcct gttatttttt     1740
atttccacat aaaaggtattt agaatatatt aaatcgttag aggagcaaca ggagatgaga     1800
gttccagatt gttctgtcca gtttccaaag ggcagtaaag ttttcgtgcc ggttttcagc     1860
```

| | |
|---|---|
| tattagcaac tgtgctacac ttgcacctgg tactgcacat tttgtacaaa gatatgctaa | 1920 |
| gcagtagtcg tcaagttgca gatcttttg tgaaattcaa cctgtgtctt ataggtttac | 1980 |
| actgccaaaa caatgcccgt aagatggctt atttgtataa tggtgttact aaagtcacat | 2040 |
| ataaaagtta aactacttgt aaaggtgctg cactggtccc aagtagtagt gtcctcctag | 2100 |
| tatattagtt tgatttaata tctgagaagt gtatatagtt tgtggtaaaa agattatata | 2160 |
| tcataaagta tgccttcctg tttaaaaaaa gtatatattc tacacatata tatatatgta | 2220 |
| tatctatatc tctaaactgc tgttaattga ttaaaatctg gcaaagtt | 2268 |

```
<210> SEQ ID NO 114
<211> LENGTH: 785
<212> TYPE: DNA
<213> ORGANISM: Homo sapiens
<220> FEATURE:
<221> NAME/KEY: misc_feature
<223> OTHER INFORMATION: XM_166457

<400> SEQUENCE: 114
```

| | |
|---|---|
| gcgcgagccg cgccggcccc ggtcgggcct ccgaaaccat gaactttctg ctgtcttggg | 60 |
| tgcattggag ccttgccttg ctgctctacc tccaccatgc caagtggtcc caggctgcac | 120 |
| ccatggcaga aggaggaggg cagaatcatc acgaagtggt gaagttcatg gatgtctatc | 180 |
| agcgcagcta ctgccatcca atcgagaccc tggtggacat cttccaggag taccctgatg | 240 |
| agatcgagta catcttcaag ccatcctgtg tgcccctgat gcgatgcggg ggctgctgca | 300 |
| atgacgaggg cctggagtgt gtgcccactg aggagtccaa catcaccatg cagattatgc | 360 |
| ggatcaaacc tcaccaaggc cagcacatag gagagatgag cttcctacag cacaacaaat | 420 |
| gtgaatgcag accaaagaaa gatagagcaa gacaagaaaa aaaatcagtt cgaggaaagg | 480 |
| gaaaggggca aaaacgaaag cgcaagaaat cccggtataa gtcctggagc gtgtacgttg | 540 |
| gtgcccgctg ctgtctaatg ccctggagcc tccctggccc ccatccctgt gggccttgct | 600 |
| cagagcggag aaagcatttg tttgtacaag atccgcagac gtgtaaatgt tcctgcaaaa | 660 |
| acacagactc gcgttgcaag gcgaggcagc ttgagttaaa cgaacgtact tgcagatgtg | 720 |
| acaagccgag gcggtgagcc gggcaggagg aaggagcctc cctcagggtt tcgggaacca | 780 |
| gatct | 785 |

```
<210> SEQ ID NO 115
<211> LENGTH: 8460
<212> TYPE: DNA
<213> ORGANISM: Homo sapiens
<220> FEATURE:
<221> NAME/KEY: misc_feature
<223> OTHER INFORMATION: U29344
<220> FEATURE:
<221> NAME/KEY: misc_feature
<222> LOCATION: (1)..(8460)
<223> OTHER INFORMATION: n can be a or c or g or t

<400> SEQUENCE: 115
```

| | |
|---|---|
| cggccgtcga cacggcagcg gccccggcct ccctctccgc cgcgcttcag cctcccgctc | 60 |
| cgccgcgctc cagcctcgct ctccgccgcc cgcaccgccg cccgcgccct caccagagca | 120 |
| gccatggagg aggtggtgat tgccggcatg tccgggaagc tgccagagtc ggagaacttg | 180 |
| caggagttct gggacaacct catcggcggt gtggacatgg tcacggacga tgaccgtcgc | 240 |
| tggaaggcgg ggctctacgg cctgccccgg cggtccggca agctgaagga cctgtctagg | 300 |

-continued

```
tttgatgcct ccttcttcgg agtccacccc aagcaggcac acacgatgga ccctcagctg    360
cggctgctgc tggaagtcac ctatgaagcc atcgtggacg gaggcatcaa cccagattca    420
ctccgaggaa cacacactgg cgtctgggtg ggcgtgagcg gctctgagac ctcggaggcc    480
ctgagccgag accccgagac actcgtgggc tacagcatgg tgggctgcca gcgagcgatg    540
atggccaacc ggctctcctt cttcttcgac ttcagagggc ccagcatcgc actggacaca    600
gcctgctcct ccagcctgat ggccctgcag aacgcctacc aggccatcca cagcgggcag    660
tgccctgccg ccatcgtggg gggcatcaat gtcctgctga agcccaacac ctccgtgcag    720
ttcttgaggc tggggatgct cagccccgag ggcacctgca aggccttcga cacagcgggg    780
aatgggtact gccgctcgga gggtgtggtg gccgtcctgc tgaccaagaa gtccctggcc    840
cggcgggtgt acgccaccat cctgaacgcc ggcaccaata cagatggctt caaggagcaa    900
ggcgtgacct tcccctcagg ggatatccag gagcagctca tccgctcgtt gtaccagtcg    960
gccggagtgg cccctgagtc atttgaatac atcgaagccc acggcacagg caccaaggtg   1020
ggcgacccca aggagctgaa tgcatcacc cgagccctgt cgccacccg ccaggagccg    1080
ctgctcatcg gctccaccaa gtccaacatg gggcacccgg agccagcctc ggggctggca   1140
gccctggcca aggtgctgct gtccctggag cacgggctct gggcccccaa cctgcacttc   1200
catagcccca accctgagat ccagcgctg ttggatgggc ggctgcaggt ggtggaccag   1260
ccctgcccg tccgtggcgg caacgtgggc atcaactcct ttggcttcgg gggctccaac   1320
gtgcacatca tcctgaggcc caacacgcag ccgcccccg cacccgcccc acatgccacc   1380
ctgccccgtc tgctgcgggc cagcggacg accctgagg ccgtgcagaa gctgctggag   1440
cagggcctcc ggcacagcca ggacctggct ttcctgagca tgctgaacga catcgcgctg   1500
tccccgacca ccgccatgcc cttccgtggc tacgctgtgc tgggtggtga gcgcggtggc   1560
ccagaggtgc agcaggtgcc cgctggcgag cgcccgctct ggttcatctg ctctgggatg   1620
ggcacacagt ggcgcgggat ggggctgagc ctcatgcgcc tggaccgctt ccagagattcc   1680
atcctacgct ccgatgaggc tgtgaaccga ttcggcctga aggtgtcaca gctgctgctg   1740
agcacagacg agagcacctt tgatgacatc gtccattcgt ttgtgagcct gactgccatc   1800
cagataggcc tcatagacct gctgagctgc atggggctga ggccagatgg catcgtcggc   1860
cactccctgg gggaggtggc ctgtggctac gccgacggct gcctgtccca ggaggaggcc   1920
gtcctcgctg cctactggag gggacagtgc atcaaagaag cccatctccc gccgggcgcc   1980
atggcagccg tgggcttgtc ctgggaggag tgtaaacagc gctgccccc ggcggtggtg   2040
cccgcctgcc acaactccaa ggacacagtc accatctcgg gacctcaggc cccggtgttt   2100
gagttcgtgg agcagctgag gaaggagggt gtgtttgcca aggaggtgcg gaccggcggt   2160
atggccttcc actcctactt catggaggcc atcgcacccc cactgctgca ggagctcaag   2220
aaggtgatcc gggagccgaa gccacgttca gcccgctggc tcagcacctc tatccccgag   2280
gcccagtggc acagcagcct ggcacgcacg tcctccgccg agtacaatgt caacaacctg   2340
gtgagccctg tgctgttcca ggaggccctg tggcacgtgc ctgagcacgc ggtggtgctg   2400
gagatcgcgc ccacgccct gctgcaggct gtcctgaagc gtggcctgaa gccgagctgc   2460
accatcatcc ccctgatgaa gaaggatcac agggacaacc tggagttctt cctggccggc   2520
atccggagcc tgcacctctc aggcatcgac gccaaccca atgccttgtt cccacctgtg   2580
gagttcccag ctccccgagg aactcccctc atctccccac tcatcaagtg ggaccacagc   2640
ctggcctggg acgtgccggc cgccgaggac ttccccaacg gttcaggttc ccctcagcc   2700
```

-continued

```
gccatctaca acatcgacac cagctccgag tctcctgacc actacctggt ggaccacacc    2760
ctcgacggtc gcgtcctctt ccccgccact ggctacctga gcatagtgtg gaagacgctg    2820
gcccgacccc tgggcctggg cgtcgagcag ctgcctgtgg tgtttgagga tgtggtgctg    2880
caccaggcca ccatcctgcc caagactggg acagtgtccc tggaggtacg gctcctggag    2940
gcctcccgtg ccttcgaggt gtcagagaac ggcaacctgg tagtgagtgg aaggtgtac    3000
cagtgggatg accctgaccc caggctcttc gaccacccgg aaagcccac ccccaacccc    3060
acggagcccc tcttcctggc ccaggctgaa gtttacaagg agctgcgtct gcgtggctac    3120
gactacggcc ctcatttcca gggcatcctg gaggccagcc tggaaggtga ctcggggagg    3180
ctgctgtgga aggataactg ggtgagcttc atggacacca tgctgcagat gtccatcctg    3240
ggctcggcca agcacggcct gtacctgccc accgtgtca ccgccatcca catcgaccct    3300
gccacccaca ggcagaagct gtacacactg caggacaagg cccagtggc tgacgtggtg    3360
gtgagcaggt ggctgagggt cacagtggcc ggaggcgtcc acatctccgg gctccacact    3420
gagtcggccc cgcggcggca gcaggagcag caggtgccca tcctggagaa gttttgcttc    3480
acttcccaca cggaggaggg gtgcctgtct gagcgcgctg ccctgcagga ggagctgcaa    3540
ctgtgcaagg ggctggtgca ggcactgcag accaaggtga cccagcaggg gctgaagatg    3600
gtggtgcccg gactggatgg ggcccagatc ccccgggacc cctcacagca ggaactgccc    3660
cggctgttgt cggctgcctg caggcttcag ctcaacggga acctgcagct ggagctggcg    3720
caggtgctgg cccaggagag gcccaagctg ccagaggacc ctctgctcag cggcctcctg    3780
gactccccgg cactcaaggc ctgcctggac actgccgtgg agaacatgcc cagcctgaag    3840
atgaaggtgg tggaggtgct ggccggccac ggtcacctgt attccgcat cccaggcctg    3900
ctcagccccc atcccctgct gcagctgagc tacacggcca ccgaccgcca cccccaggcc    3960
ctggaggctg cccaggccga gctgcagcag cacgacgttg cccagggcca gtgggatccc    4020
gcagaccctg cccccagcgc cctgggcagc gccgacctcc tggtgtgcaa ctgtgctgtg    4080
gctgccctcg ggacccggc ctcagctctc agcaacatgg tggctgccct gagagaaggg    4140
ggctttctgc tcctgcacac actgctccgg gggcaccct cgggacatgt ggccttcctc    4200
acctccactg agccgcagta tggccagggc atcctgagcc aggacgcgtg ggagagcctc    4260
ttctccaggg tgtccgtgcg cctggtgggc ctgaagaagt ccttctacgg ctccacgctc    4320
ttcctgtgcc gccggcccac cccgcaggac agcccatct tcctgccggt ggacgatacc    4380
agcttccgct gggtggagtc tctgaagggc atcctggctg acgaagactc ttcccggcct    4440
gtgtggctga aggccatcaa ctgtgccacc tcgggcgtgg tgggcttggt gaactgtctc    4500
cgccgagagc ccgcggaac gctccggtgt gtgctgctct ccaacctcag cagcacctcc    4560
cacgtcccgg aggtggaccc gggctccgca gaactgcaga aggtgttgca gggagacctg    4620
gtgatgaacg tctaccgcga cggggcctgg ggggcttttcc gccacttcct gctggaggag    4680
gacaagcctg aggagccgac ggcacatgcc tttgtgagca ccctcacccg ggggacctg    4740
tcctccatcc gctgggtctg ctcctcgctg cgccatgccc agcccacctg ccctggcgcc    4800
cagctctgca cggtctacta cgcctcctc aacttccgcg acatcatgct ggccactggc    4860
aagctgtccc ctgatgccat cccagggaag tggacctccc aggacagcct gctaggtatg    4920
gagttctcgg gccgagacgc cagcggcaag cgtgtgatgg gactggtgcc tgccaagggc    4980
ctggccacct ctgtcctgct gtcaccggac ttcctctggg atgtgccttc caactggacg    5040
```

```
ctggaggagg cggcctcggt gcctgtcgtc tacagcacgg cctactacgc gctggtggtg    5100
cgtgggcggg tgcgcccgg ggagacgctg ctcatccact cgggctcggg cggcgtgggc      5160
caggccgcca tcgccatcgc cctcagtctg gctgccgcg tcttcaccac cgtggggtcg      5220
gctgagaagc gggcgtacct ccaggccagg ttcccccagc tcgacagcac cagcttcgcc    5280
aactcccggg acacatcctt cgagcagcat gtgctgtggc acacgggcgg gaagggcgtt    5340
gacctggtct tgaactcctt ggcggaagag aagctgcagg ccagcgtgag gtgcttggct    5400
acgcacggtc gcttcctgga aattggcaaa ttcgaccttt ctcagaacca cccgctcggc    5460
atggctatct tcctgaagaa cgtgacattc cacggggtcc tactggatgc gttcttcaac    5520
gagagcagtg ctgactggcg ggaggtgtgg gcgcttgtgc aggccggcat ccgggatggg    5580
gtggtacggc ccctcaagtg cacggtgttc catgggccc aggtggagga cgccttccgc      5640
tacatggccc aagggaagca cattggcaaa gtcgtcgtgc aggtgcttgc ggaggagccg    5700
gaggcagtgc tgaaggggc caaacccaag ctgatgtcgg ccatctccaa gaccttctgc      5760
ccggcccaca agagctacat catcgctggt ggtctgggtg gcttcggcct ggagttggcg    5820
cagtggctga tacagcgtgg ggtgcagaag ctcgtgttga cttctcgctc cgggatccgg    5880
acaggctacc aggccaagca ggtccgccgg tggagggccc agggcgtaca ggtgcaggtg    5940
tccaccagca acatcagctc actggagggg gcccgggggcc tcattgccga ggcggcgcag    6000
cttgggcccg tgggcggcgt cttcaacctg gccgtggtct tgagagatgg cttgctggag    6060
aaccagaccc cagagttctt ccaggacgtc tgcaagccca agtacagcgg caccctgaac    6120
ctggacaggg tgacccgaga ggcgtgccct gagctggact actttgtggt cttctcctct    6180
gtgagctgcg ggcgtggcaa tgcgggacag agcaactacg gctttgccaa ttccgccatg    6240
gagcgtatct gtgagaaacg ccggcacgaa ggcctcccag gcctggccgt gcagtggggc    6300
gccatcggcg acgtgggcat tttggtggag acgatgagca ccaacgacac gatcgtcagt    6360
ggcacgctgc cccaggccat ggcgtcctgc ctggaggtgc tggacctctt cctgaaccag    6420
ccccacatgg tcctgagcag ctttgtgctg gctgagaagg ctgcggccta tgggacagg    6480
gacagccagc gggacctggt ggaggccgtg gcacacatcc tgggcatccg cgacttggct    6540
gctgtcaacc tggacagctc actggcggac ctgggcctgg actcgctcat gagcgtggag    6600
gtgcgccaga cgctggagcg tgagctcaac ctggtgctgt ccgtgcgcga ggtgcggcaa    6660
ctcacgctcc ggaaaactgca ggagctgtcc tcaaaggcgg atgaggccag cgagctggca    6720
tgccccacgc ccaaggagga tggtctggcc cagcagcaga ctcagctgaa cctgcgctcc    6780
ctgctggtga acccggaggg ccccacccctg atgcggctca actccgtgca gagctcggag    6840
cggcccctgt tcctggtgca cccaatcgag ggctccacca ccgtgttcca cagcctggcc    6900
tcccggctca gcatccccac ctatggcctg cagtgcaccc gagctgcgcc ccttgacagc    6960
atccacagcc tggctgccta ctacatcgac tgcatcaggc aggtgcagcc cgagggcccc    7020
taccgcgtgg ccggctactc ctacgggcc tgcgtggcct ttgaaatgtg ctcccagctg    7080
caggcccagc agagcccagc ccccacccac aacagcctct tcctgttcga cggctcgccc    7140
acctacgtac tggcctacac ccagagctac cgggcaaagc tgaccccagg ctgtgaggct    7200
gaggctgaga cggaggccat atgcttcttc gtgcagcagt tcacggacat ggagcacaac    7260
agggtgctgg aggcgctgct gccgctgaag ggcctagagg agcgtgtggc agccgccgtg    7320
gacctgatca tcaagagcca ccaggggctg gaccgccagg agctgagctt tgcggcccgg    7380
tccttctact acaagctcgg tgccgctgag cagtacacac ccaaggccaa gtaccatggc    7440
```

| | |
|---|---|
| aacgtgatgc tactgcgcgc caagacgggt ggcgcctacg gcgaggacct gggcgcggat | 7500 |
| tacaacctct cccaggtatg cgacgggaaa gtatccgtcc acgtcatcga gggtgaccac | 7560 |
| cgcacgctgc tggagggcag cggcctggag tccatcatca gcatcatcca cagctccctg | 7620 |
| gctgagccac gcgtgagcgt gcgggagggc taggcccgtg cccccgcctg ccaccggagg | 7680 |
| tcactccacc atccccaccc caccccaccc caccccgcc atgcaacggg attgaagggt | 7740 |
| cctgccggtg ggaccctgtc cggcccagtg ccactgcccc cgaggctgc tagatgtagg | 7800 |
| tgttaggcat gtcccaccca cccgccgcct cccacggcac ctcggggaca ccagagctgc | 7860 |
| cgacttggag actcctggtc tgtgaagagc cggtggtgcc cgttcccgca ggaactgggc | 7920 |
| tgggcctcgt gcgcccgtgg ggtctgcgct tggtctttct gtgcttggat ttgcatattt | 7980 |
| attgcattgc tggtagagac ccccaggcct gtccaccctg ccaagactcc tcaggcagcg | 8040 |
| tgtgggtccc gcactctgcc cccatttccc cgatgtcccc tgcgggcgcg ggcagccacc | 8100 |
| caagcctgct ggctgcggcc ccctctcggc caggcattgg ctcagccngc tgagtggggg | 8160 |
| gtcgtgggcc agtccccgag gagctgggcc cctgcacagg cacacagggc ccggccacac | 8220 |
| ccagcggccc cccgcacagc cacccgtggg gtgctgccct tatcgcccgg cgccgggcac | 8280 |
| caactccatg tttggtgttt gtctgtgttt gttttcaag aaatgattca aattgctgct | 8340 |
| tggattttga aatttactgt aactgtcagt gtacacgtct ggaccccgtt tcatttttac | 8400 |
| accaatttgg taaaaatgct gctctcagcc tcccacaatt aaaccgcatg tgatctcccc | 8460 |

<210> SEQ ID NO 116
<211> LENGTH: 959
<212> TYPE: DNA
<213> ORGANISM: Homo sapiens
<220> FEATURE:
<221> NAME/KEY: misc_feature
<223> OTHER INFORMATION: NM_001639

<400> SEQUENCE: 116

| | |
|---|---|
| gggcatgaat atcagacgct aggggggacag ccactgtgtt gtctgctacc ctcatcctgg | 60 |
| tcactgcttc tgctataaca gccctaggcc aggaatatga acaagccgct gctttggatc | 120 |
| tctgtcctca ccagcctcct ggaagccttt gctcacacag acctcagtgg gaaggtgttt | 180 |
| gtatttccta gagaatctgt tactgatcat gtaaacttga tcacaccgct ggagaagcct | 240 |
| ctacagaact ttaccttgtg ttttcgagcc tatagtgatc tctctcgtgc ctacagcctc | 300 |
| ttctcctaca atacccaagg cagggataat gagctactag tttataaaga aagagttgga | 360 |
| gagtatagtc tatacattgg aagacacaaa gttacatcca aagttatcga aaagttcccg | 420 |
| gctccagtgc acatctgtgt gagctgggag tcctcatcag gtattgctga attttggatc | 480 |
| aatgggacac ctttggtgaa aaagggtctg cgacagggtt actttgtgga agctcagccc | 540 |
| aagattgtcc tggggcagga acaggattcc tatgggggca gtttgatag gagccagtcc | 600 |
| tttgtgggag agattgggga tttgtacatg tgggactctg tgctgccccc agaaaatatc | 660 |
| ctgtctgcct atcagggtac ccctctcccct gccaatatcc tggactggca ggctctgaac | 720 |
| tatgaaatca gaggatatgt catcatcaaa cccttggtgt gggtctgagg tcttgactca | 780 |
| acgagagcac ttgaaaatga aatgactgtc taagagatct ggtcaaagca actggatact | 840 |
| agatcttaca tctgcagtct ttcttctttg aatttcctat ctgtatgtct gcctaattaa | 900 |
| aaaaatatat attgtattat gctacctgca aaaaaaaaa aaaaaaaaa aaaaaaaa | 959 |

-continued

```
<210> SEQ ID NO 117
<211> LENGTH: 1471
<212> TYPE: DNA
<213> ORGANISM: Homo sapiens
<220> FEATURE:
<221> NAME/KEY: misc_feature
<223> OTHER INFORMATION: NM_000936

<400> SEQUENCE: 117
ggaactgcca cgatgctgcc actttggact ctttcactgc tgctgggagc agtagcagga      60
aaagaagttt gctacgaaag actcggctgc ttcagtgatg actccccatg gtcaggaatt     120
acggaaagac ccctccatat attgccttgg tctccaaaag atgtcaacac ccgcttcctc     180
ctatatacta atgagaaccc aaacaacttt caagaagttg ccgcagattc atcaagcatc     240
agtggctcca atttcaaaac aaatagaaaa actcgcttta ttattcatgg attcatagac     300
aagggagaag aaaactggct ggccaatgtg tgcaagaatc tgttcaaggt ggaaagtgtg     360
aactgtatct gtgtggactg gaaggtggc tcccgaactg gatacacaca agcctcgcag      420
aacatcagga tcgtgggagc agaagtggca tattttgttg aatttcttca gtcggcgttc     480
ggttactcac cttccaacgt gcatgtcatt ggccacagcc tgggtgccca cgctgctggg     540
gaggctggaa ggagaaccaa tgggaccatt ggacgcatca cagggttgga cccagcagaa     600
ccttgctttc agggcacacc tgaattagtc cgattggacc ccagcgatgc caaatttgtg     660
gatgtaattc acacggatgg tgcccccata gtccccaatt tggggtttgg aatgagccaa     720
gtcgtgggcc acctagattt ctttccaaat ggaggagtgg aaatgcctgg atgtaaaaag     780
aacattctct ctcagattgt ggacatagac ggaatctggg aagggactcg agactttgcg     840
gcctgtaatc acttaagaag ctacaaatat acactgata gcatcgtcaa ccctgatggc     900
tttgctggat tcccctgtgc ctcttacaac gtcttcactg caaacaagtg tttcccttgt     960
ccaagtggag gctgcccaca gatgggtcac tatgctgata gatatcctgg gaaaacaaat    1020
gatgtgggcc agaaattta tctagacact ggtgatgcca gtaattttgc acgttggagg     1080
tataaggtat ctgtcacact gtctggaaaa aaggttacag gacacatact agtttctttg    1140
ttcggaaata aggaaactc taagcagtat gaaattttca agggcactct caaaccagat    1200
agtactcatt ccaatgaatt tgactcagat gtggatgttg gggacttgca gatggttaaa    1260
tttatttggt ataacaatgt gatcaaccca acttacccta gagtgggagc atccaagatt    1320
atagtggaga caaatgttgg aaaacagttc aacttctgta gtccagaaac cgtcagggag    1380
gaagttctgc tcaccctcac accgtgttag gagactactg ttatttgacc aatgaattga    1440
cttctaataa aatctagtgg tgatgcaaaa a                                   1471

<210> SEQ ID NO 118
<211> LENGTH: 7452
<212> TYPE: DNA
<213> ORGANISM: Homo sapiens
<220> FEATURE:
<221> NAME/KEY: misc_feature
<223> OTHER INFORMATION: U89344

<400> SEQUENCE: 118
atggtcttgc ttctttgtct atcttgtctg attttctcct gtctgacctt ttcctggtta      60
aaaatctggg agaaaatgac ggactccaag ccgatcacca agagtaaatc agaagcaaac     120
ctcatcccga gccaggagcc ctttccagcc tctgataact caggggagac accgcagaga     180
aatggggagg gccacactct gcacaaagac acccagccag gccgagccca gcctcccaca     240
```

```
aaggcccaaa gatccggtcg gcggagaaac tccctaccac cctcccgcca gaagccccca    300
agaaaccccc tttcttccag tgacgcagca ccctccccag agcttcaagc caacgggact    360
gggacacaag gtctggaggc cacagatacc aatggcctgt cctcctcagc caggccccag    420
ggcagcaagc tggtcccctc caagaagac aagaagcagg caaacatcaa gaggcagctg    480
atgaccaact tcatcctggg ctcttttgat gactactcct ccgacgagga ctctgttgct    540
ggctcatctc gtgagtctac ccggaagggc agccgggcca gcttggggc cctgtccctg     600 gaggcttatc tgaccacagg tgaagctgag acccgcgtcc ccactatgag gccgagcatg    660
tcgggactcc acctggtgaa gaggggacgg gaacacaaga agctggacct gcacagagac    720
tttaccgtgg cttctcccgc tgagtttgtc acacgctttg gggggatcg ggtcatcgag      780 aaggtgctta ttgccaacaa cgggattgcc gctgtgaagt gcatgcgctc catccgcagg    840
tgggcctatg agatgttccg caacgagcgg gccatccggt tgttcgcat ggtgaccccc      900 gaggacctta aggccaacgc agagtacatc aagatggcgg atcattacgg gcccgcccca    960
ggagggccca ataacaacaa ctatgccaac gtggagctga ttgtggacat tgccaagaga   1020
atcccgttgc aggcggtgtg ggctggctgg ggccatgctt tagaaaaccc taaacttccg   1080
gagctgctgt gcaagaatgg agttgctttc ttaggccctc ccaggttgag gccaatggtg   1140
ggtctaggag ataagatcgc ctccaccgtt gtcgcccaga cgctacaggt cccaaccctg   1200
cccaggagtg gaagcgccct gacagtggag tggacagaag atgatctgca gcagggaaaa   1260
agaatcagtg tcccagaaga tgtttatgac aagggttgcg tgaaagacgt agatgagggc   1320
ttggaggcag cagaaagaat tggttttcca ttgatgatca aagcttctga aggtggcgga   1380
gggaagggaa tccgggaaac tgagagtgcg gaggacttcc cgatccttt cagacaagta    1440 cagagtgaga tcccaggctc gcccatcttt ctcatgaagc tggcccagca cgcccgtcac   1500
ctggaagttc agatcctcgc tgaccagtat gggaatgctg tgtctctgtt tggtcgcgac   1560
tgctccatcc agcggcggca tcagaagatc gttgaggaag caccggccac catcgcgccg   1620
ctggccatat tcgagttcat ggagcagtgt gccattcgcc tggccaagac cgtgggctat   1680
gtgagtgcag ggacagtgga ataccctat agtcaggatg gtagcttcca cttcttggag    1740
ctgaatcctc gcttgcaggt ggaacatccc tgcacagaaa tgattgctga cgttaatctg   1800
ccggccgccc agctacagat cgccatgggt gccccactgc accggctgaa agatatccgg   1860
cttctgtatg gagagtcacc ctggggagac tccccaattt ctttgaaaa ctcagctcat    1920 ctcccctgcc cccgaggcca cgtcattgcc accagaatca ccagcgaaaa cccagacgag   1980
ggttttaagc cgagctccgg gactgtccag gaactgaatt tccggagcag caagaacgtc   2040
tggggttact tcacggtggc cgctactgga ggcctgcacg agtttgcgat tcccagtttt   2100
gggcactgct tctcctgggg agagaaccgg aaagaggcca tttcgaacat ggtggtggct   2160
ttgaaggaac tgtccctccg aggcgacttt aggactaccg tggaatacct cattaacctc   2220
ctggagaccg agagcttcca gaacaactac atcgacaccg gtggttgga ctacctcatt     2280 gctgagaaag tgcaaaagaa accgaatatc atgcttgggg tggtatgcgg ggcccttgaa   2340
cgtggagatg cgatgttcag aacgtgcatg acagatttct tacactccct ggaaaggggc   2400
caggtcctcc cagcggattc actactgaac ctcgtagatg tggaattaat ttacgagggt   2460
gtaaagtaca ttctaaaggt gacccggcag tctctgacca tgttcgttct catcatgaat   2520
ggctgccaca tcgagattga tgccaccgg ctgaatgatg ggggctcct gctctcctac     2580 aatgggaaca gctacaccac ctacatgaag gaagaggttg acagttaccg taccatcggc   2640
```

```
aataagacgt gtgtttttga aaggagaac gatcctacag tcctgagatc cccctcggct    2700
gggaagctga cacagatcac agtggaggat gggggccacg ttgaggctgg gagacgctac    2760
gctgagatgg aggtgatgaa gatgatcatg accctgaacg ttcaggaaag aggccgggtg    2820
aagtacatca agcgtccagg tgcggtgctg gaagcaggct gcgtggtggc caggctggag    2880
ctcgatgacc cttctaaagt ccacccggct gaaccgttca caggagaact ccctgcccag    2940
cagaacactg ccgacctcgg aaagaaactg cacagggtct tccacagcgt cctgggaagc    3000
ctcaccaacg tcatgagtgg cttttgtctg ccagagccgt ttttagcat aaagctgaag     3060
gagtgggtgc agaagctcat gatgaccctc cggcacccgt cactgctgct ggacgtgcag    3120
gagatcatga ccagtcgtgc aggccgcatc ccccccctg ttgagaagtc tgtccgcaag      3180
gtgatggccc agtatgccag caacatcacc tcggtgctgt gccagttccc cagccagcag    3240
atagccacca tcctggactg ccatgcagcc accctgcagc ggaaggctga tcgagaggtc    3300
ttcttcatca cacccagag catggtgcag ttggtccaga ggtaccgaag tggaatccgc     3360
ggtcatatga aaacagtggt gatcgatctc ttgagaagat acttgcgtgt tgagaccatt    3420
ttcggcaagg caagagatgc tgatgccaac tccagtggga tggtgggggg cgtgaggagc    3480
ctgagctta cctctgtgtg ggtggttttg tctcccccag cccactacga caagtgtgtg     3540
ataaacctca gggaacagtt caagccagac atgtcccagg tgctgactg catcttctcc     3600
cacgcacagg tgaccaagaa gaaccagctg gtgatcatgt tgatcgatga gctgtgtggc    3660
ccagacccttt ccctgtcgga cgagctgatc tccatcctca acgagctcac tcagctgagc    3720
aaaagcgagc actgcaaagt ggccctcaga gcccggcaga tcctgatcgc ctccccctcc    3780
tacgagctgc ggcataacca ggtggagtcc attttcctgt ctgccattga catgtacggc    3840
caccagttct gccccgagaa cctccagaaa ttaatacttt cggaaacaac catcttcgac    3900
gtcctgaata ctttcttcta tcacgcaaac aaagtcgtgt gcatggcgtc cttggaggtt    3960
tacgtggggg gggcttacat cgcctatgtg ttaaacagcc tgcagcaccg gcagctcccg    4020
gacggcacct gcgtggtaga attccagttc atgctgccgt cctcccaccc aaaccggatg    4080
accgtgccca tcagcatcac caaccctgac ctgctgagc acgacaga gctcttcatg       4140
gacagcggct tctcccccact gtgccagcgc atgggagcca tggtagcctt caggagattc    4200
gaggacttca ccagaaattt tgatgaagtc atctcttgct tcgccaacgt gccgaaagac    4260
cccccccctct tcagcgaggc ccgcacctcc ctatactccg aggatgactg caagagcctc    4320
agagaagagc ccatccacat tctgaatgtg tccatccagt gtgcggacca cctggaggat    4380
gaggcactgg tgccgatttt acgtacattc gtacagtcca agaaaaatat ccttgtggat    4440
tatgactcc gacgaatccc attcttgatt gcccaagaga aagaatttcc caagttttc     4500
acattcagag caagagatga gtttgcagaa gatcgcattt accgtcactt ggaacctgcc    4560
ctggctttcc agctggaact caaccggatg cgtaacttcg atctgaccgc cgtgccctgt    4620
gccaaccaca agatgcacct ttacctgggt gctgccaagg tggaaggaag gtatgaagtg    4680
acggaccata ggttcttcat ccgtgccatc atcaggcact ctgacctgat cacaaaggaa    4740
gcctccttcg aatacctgca gaacgagggt gagcggctgc tcctggaggc catggacgag    4800
ctggaggtgg cgttcaataa caccaacgtg cgcaccgact gcaaccacat cttcctcaac    4860
ttcgtgccca ctgtcatcat ggaccccaac aagatcgagg agtccgtgcg ctacatggtt    4920
atgcgctacg gcagccggct gtggaaactc cgtgtgctac aggctgaggt caagatcaac    4980
```

```
atccgccaga ccaccaccgg cagtgccgtt cccatccgcc tgttcatcac caatgagtcg    5040
ggctactacc tggacatcag cctctacaaa gaagtgactg actccagatc tggaaatatc    5100
atgtttcact ccttcggcaa caagcaaggg ccccagcacg ggatgctgat caatactccc    5160
tacgtcacca aggatctgct ccaggccaag cgattccagg cccagaccct gggaaccacc    5220
tacatctatg acttcccgga aatgttcagg caggctctct ttaaactgtg gggctcccca    5280
gacaagtatc ccaaagacat cctgacatac actgaattag tgttggactc tcagggccag    5340
ctggtggaga tgaaccgact tcctggtgga aatgaggtgg gcatggtggc cttcaaaatg    5400
aggtttaaga cccaggagta cccggaagga cgggatgtga tcgtcatcgg caatgacatc    5460
accttttcgca ttggatcctt tggccctgga gaggaccttc tgtacctgcg ggcatccgag    5520
atggcccggg cagaggcgat tcccaaaatt tacgtggcag ccaacagtgg cgcccgtatt    5580
ggcatggcag aggagatcaa acacatgttc cacgtggctt gggtggaccc agaagacccc    5640
cacaaaggat ttaaatacct gtacctgact ccccaagact acaccagaat cagctccctg    5700
aactccgtcc actgtaaaca catcgaggaa ggaggagagt ccagatacat gatcacggat    5760
atcatcggga aggatgatgg cttgggcgtg gagaatctga ggggctcagg catgattgct    5820
ggggagtcct ctctggctta cgaagagatc gtcaccatta gcttggtgac ctgccgagcc    5880
attgggattg gggcctactt ggtgaggctg ggccagcgag tgatccaggt ggagaattcc    5940
cacatcatcc tcacaggagc aagtgctctc aacaaggtcc tggaagagag ggtctacaca    6000
tccaacaacc agctgggtgg cgttcagatc atgcattaca atggtgtctc ccacatcacc    6060
gtgccagatg actttgaggg ggtttatacc atcctggagt ggctgtccta tgccaaag    6120
gataatcaca gccctgtccc tatcatcaca cccactgacc ccattgacag agaaattgaa    6180
ttcctcccat ccagagctcc ctacgacccc cggtggatgc ttgcaggaag gcctcaccca    6240
actctgaagg gaacgtggca gagcggattc tttgaccacg gcagtttcaa ggaaatcatg    6300
gcaccctggg cgcagaccgt ggtgacagga cgagcaaggc ttgggggggat tcccgtggga    6360
gtgattgctg tggagacacg gactgtggag gtggcagtcc ctgcagaccc tgccaacctg    6420
gattctgagg ccaagataat tcagcaggca ggacaggtgt ggttcccaga ctcagcctac    6480
aaaaccgccc aggccatcaa ggacttcaac cgggagaagt tgcccctgat gatctttgcc    6540
aactggaggg ggttctccgg tggcatgaaa gacatgtatg accaggtgct gaagtttgga    6600
gcctacatcg tggacggcct tagacaatac aaacagccca tcctgatcta tatccgccct    6660
atgcgggagc tccggggagg ctcctgggtg gtcatagatg ccaccatcaa cccgctgtgc    6720
atagaaatgt atgcagacaa agagagcagg ggtggtgttc tggaaccaga ggggacagtg    6780
gagattaagt tccgaaagga agatctgata aagtccatga aaggatcga tccagcttac    6840
aagaagctca tggaacagct aggggaacct gatctctccg acaaggaccg aaaggacctg    6900
gagggccggc taaaggctcg cgaggacctg ctgctcccca tctaccacca ggtggcggtg    6960
cagttcgccg acttccatga cacacccggc cggatgctgg agaagggcgt catatctgac    7020
atcctggagt ggaagaccgc acgcaccttc ctgtattggc gtctgcgccg cctcctcctg    7080
gaggaccagg tcaagcagga gatcctgcag gccagcgggg agctgagtca cgtgcatatc    7140
cagtccatgc tgcgtcgctg gttcgtggag acggagggg ctgtcaaggc ctacttgtgg    7200
gacaacaacc aggtggttgt gcagtggctg aacagcact ggcaggcagg ggatggcccg    7260
cgctccacca tccgtgagaa catcacgtac ctgaagcacg actctgtcct caagaccatc    7320
cgaggcctgg ttgaagaaaa ccccgaggtg gccgtggact gtgtgatata cctgagccag    7380
```

-continued

```
cacatcagcc cagctgagcg ggcgcaggtc gttcacctgc tgtctaccat ggacagcccg      7440
gcctccacct ga                                                         7452

<210> SEQ ID NO 119
<211> LENGTH: 3259
<212> TYPE: DNA
<213> ORGANISM: Homo sapiens
<220> FEATURE:
<221> NAME/KEY: misc_feature
<223> OTHER INFORMATION: M31158

<400> SEQUENCE: 119
gacgcgcgcc gggagccggc ggccgggcca gccggcgccg gggcccagtg cgccgcgctc        60
gcagccggta gcgcgccagc cgtaggcgtc gctcggcagc cgcggggccc taggcgtgcc       120
ggggaggggg cgagggcggc caggcgcctg ccgccccgga ggcaggatga gcatcgagat       180
cccggcggga ctgacggagc tgctgcaggg cttcacggtg gaggtgctga ggcaccagcc       240
cgcggacctg ctggagttcg cgctgcagca cttcacccgc ctgcagcagg agaacgagcg       300
caaaggcacc gcgcgcttcg gccatgaggg caggacctgg ggggacctgg gcgccgctgc       360
cggggggcgg accccccagca agggggtcaa cttcgccgag gagcccatgc agtccgactc       420
cgaggacggg gaggaggagg aggcggcgcc cgcggacgca ggggcgttca atgctccagt       480
aataaaccga ttcacaaggc gtgcctcagt atgtgcagaa gcttataatc ctgatgaaga       540
agaagatgat gcagagtcca ggattataca tccaaaaact gatgatcaaa gaaataggtt       600
gcaagaggct tgcaaagaca tcctgctgtt taagaatctg gatccggagc agatgtctca       660
agtattagat gccatgtttg aaaaattggt caaagatggg gagcatgtaa ttgatcaagg       720
tgacgatggt gacaactttt atgtaattga tagaggcaca tttgatattt atgtgaaatg       780
tgatggtgtt ggaagatgtg ttggtaacta tgataatcgt gggagtttcg gcgaactggc       840
cttaatgtac aatacaccca gagcagctac aatcactgct acctctcctg tgctctgtg        900 gggtttggac agggtaacct tcaggagaat aattgtgaaa acaatgccaa aaagagaaa        960 aatgtatgaa agctttattg agtcactgcc attccttaaa tctttggagt tttctgaacg      1020
cctgaaagta gtagatgtga taggcaccaa agtatacaac gatggagaac aaatcattgc      1080
tcagggagat tcggctgatt cttttttcat tgtagaatct ggagaagtga aaattactat      1140
gaaaagaaag ggtaaatcag aagtggaaga gaatggtgca gtagaaatgc ctcgatgctc      1200
gcggggacag tactttggag agcttgccct ggtaactaac aaacctcgag cagcttctgc      1260
ccacgccatt gggactgtca aatgtttagc aatggatgtg caagcatttg aaaggcttct      1320
gggaccttgc atggaaatta tgaaaaggaa catcgctacc tatgaagaac agttagttgc      1380
cctgtttgga acgaacatgg atattgttga acccactgca tgaagcaaaa gtatggagca      1440
agacctgtag tgacaaaatt acacagtagt ggttagtcca ctgagaatgt gtttgtgtag      1500
atgccaagca ttttctgtga tttcaggttt ttttcctttt tacatttac aacgtatcaa       1560 taaacagtag tgatttaata gtcaataggc tttaacatca ctttctaaag agtagttcat      1620
aaaaaaatca acatactgat aaaatgactt tgtactccac aaaattatga ctgaaaggtt      1680
tattaaaatg attgtaatat atagaaagta tctgtgttta agaagataat taaggatgt       1740 tatcataggc tatatgtgtt ttacttattc agactgataa tcatattagt gactatcccc      1800
atgtaagagg gcacttggca attaaacatg ctacacagca tggcatcact tttttttata      1860
actcattaaa cacagtaaaa ttttaatcat ttttgtttta aagttttcta gcttgataag      1920
```

```
ttatgtgctg ccttggccta ttggtgaaat ggtataaaat atcatatgca gttttaaaac    1980
tttttatatt tttgcaataa agtacatttt gactttgttg gcataatgtc agtaacatac    2040
atattccagt ggttttatgg acaggcaatt tagtcattat gataataagg aaaacagtgt    2100
tttagatgag agatcattaa tgcatttttc cctcatcaag catatatctg ctttttttta    2160
ttttgcaatt ctctgtattc tatgtcttta aaaatttgat cttgacattt aatgtcacaa    2220
agttttgttt tttaaaaag tgatttaaac ttaagatccg acatttttg tattctttaa    2280 gattttacac ctaaaaaatc tctcctatcc caaaataat gtgggatcct tatcagcatg    2340
cccacagttt atttctttgt tcttcactag gcctgcataa tacagtccta tgtagacatc    2400
tgttcccttg ggtttccgtt cttcttagg atggttgcca acccacaatc tcattgatca    2460
gcagccaata tgggtttgtt tggttttttt aattcttaaa aacatcctct agaggaatag    2520
aaacaaattt ttatgagcat aaccctatat aaagacaaaa tgaatttctg accttaccat    2580
atataccatt aggccttgcc attgctttaa tgtagactca tagttgaaat tagtgcagaa    2640
agaactcaga tgtactagat tttcattgtt cattgatatg ctcagtatgc tgccacataa    2700
gatgaattta attatattca accaaagcaa tatactctta catgatttct aggccccatg    2760
acccagtgtc tagagacatt aattctaacc agttgtttgc ttttaaatga gtgatttcat    2820
tttgggaaac aggtttcaaa tgaatatata tacatgggta aaattactct gtgctagtgt    2880
agtcttacta gagaatgttt atggtcccac ttgtatatga aaatgtggtt agaatgttaa    2940
ttggataatg tatatataag aagttaaagt atgtaaagta aacttcagc cacattttta    3000 gaacactgtt taacattttt gcaaaacctt cttgtaggaa aagagagctc tctacatgaa    3060
gatgacttgt tttatatttc agattttatt ttaaaagcca tgtctgttaa acaagaaaaa    3120
acacaaaaga actccagatt cctggttcat cattctgtat tcttactcac tttttcaagt    3180
tatctatttt gttgcataaa ctaattgtta actattcatg gaacagcaaa cgcctgttta    3240
ataaagaact ttgaccaag                                                 3259
```

<210> SEQ ID NO 120
<211> LENGTH: 3261
<212> TYPE: DNA
<213> ORGANISM: Homo sapiens
<220> FEATURE:
<221> NAME/KEY: misc_feature
<223> OTHER INFORMATION: XM_008512

<400> SEQUENCE: 120

```
gcccgggacc ccacggaggc ggggagacca ctcttctccc acacgagccc agctctccct     60
tcgagtagca accgccttca agctcacaag cacccgtggg cctggggtgt gcctgcgtct    120
agctggttgc acactgggcc acagaggatc cagcaaggat gaagaaatgg agcagcacag    180 acttggggc agctgcggac ccactccaaa aggacacctg cccagacccc ctggatggag    240
accctaactc caggccacct ccagccaagc cccagctctc cacggccaag agccgcaccc    300
ggctctttgg gaagggtgac tcggaggagg ctttcccggt ggattgccct cacgaggaag    360
gtgagctgga ctcctgcccg accatcacag tcagccctgt tatcaccatc cagaggccag    420 agacggctc caccggtgcc aggctgctgt cccaggactc tgtcgccgcc agcaccgaga    480
agaccctcag gctctatgat cgcaggagta tctttgaagc cgttgctcag aataactgcc    540
aggatctgga gagcctgctg ctcttcctgc agaagagcaa gaagcacctc acagacaacg    600
agttcaaaga ccctgagaca gggaagacct gtctgctgaa agccatgctc aacctgcatg    660
```

```
acggacagaa caccaccatc ccctgctcc tggagatcgc gcggcaaacg gacagcctga    720
aggagcttgt caacgccagc tacacggaca gctactacaa gggccagaca gcactgcaca    780
tcgccatcga gagacgcaac atggccctgg tgaccctcct ggtggagaac ggagcagacg    840
tccaggctgc ggcccatggg gacttcttta agaaaaccaa agggcggcct ggattctact    900
tcggtgaact gcccctgtcc ctggccgcgt gcaccaacca gctgggcatc gtgaagttcc    960
tgctgcagaa ctcctggcag acggccgaca tcagcgccag ggactcggtg gcaacacgg    1020
tgctgcacgc cctggtggag gtggccgaca cacggccga caacacgaag tttgtgacga    1080
gcatgtacaa tgagattctg atcctggggg ccaaactgca cccgacgctg aagctggagg    1140
agctcaccaa caagaaggga atgacgccgc tggctctggc agctgggacc gggaagatcg    1200
gggtcttggc ctatattctc cagcgggaga tccaggagcc cgagtgcagg cacctgtcca    1260
ggaagttcac cgagtgggcc tacgggcccg tgcactcctc gctgtacgac ctgtcctgca    1320
tcgacacctg cgagaagaac tcggtgctgg aggtgatcgc ctacagcagc agcgagaccc    1380
ctaatcgcca cgacatgctc ttggtggagc cgctgaaccg actcctgcag acaagtggg    1440
acagattcgt caagcgcatc ttctacttca acttcctggt ctactgcctg tacatgatca    1500
tcttcaccat ggctgcctac tacaggcccg tggatggctt gcctcccttt aagatggaaa    1560
aaattggaga ctatttccga gttactggag agatcctgtc tgtgttagga ggagtctact    1620
tcttttttccg agggattcag tatttcctgc agaggcggcc gtcgatgaag accctgtttg    1680
tggacagcta cagtgagatg ctttctttc tgcagtcact gttcatgctg gccaccgtgg    1740
tgctgtactt cagccacctc aaggagtatg tggcttccat ggtattctcc ctggccttgg    1800
gctggaccaa catgctctac tacacccgcg gtttccagca gatgggcatc tatgccgtca    1860
tgatagagaa gatgatcctg agagacctgt gccgtttcat gtttgtctac atcgtcttct    1920
tgttcgggtt ttccacagcg gtggtgacgc tgattgaaga cgggaagaat gactccctgc    1980
cgtctgagtc cacgtcgcac aggtggcggg ggcctgcctg caggcccccc gatagctcct    2040
acaacagcct gtactccacc tgcctggagc tgttcaagtt caccatcggc atgggcgacc    2100
tggagttcac tgagaactat gacttcaagg ctgtcttcat catcctgctg ctggcctatg    2160
taattctcac ctacatcctc ctgctcaaca tgctcatcgc cctcatgggt gagactgtca    2220
acaagatcgc acaggagagc aagaacatct ggaagctgca gagagccatc accatcctgg    2280
acacggagaa gagcttcctt aagtgcatga ggaaggcctt ccgctcaggc aagctgctgc    2340
aggtggggta cacacctgat ggcaaggacg actaccggtg gtgcttcagg gtggacgagg    2400
tgaactggac cacctggaac accaacgtgg gcatcatcaa cgaagacccg gcaactgtg    2460
agggcgtcaa gcgcacccctg agcttctccc tgcggtcaag cagagtttca ggcagacact    2520
ggaagaactt tgccctggtc cccttttaa gagaggcaag tgctcgagat aggcagtctg    2580
ctcagcccga ggaagtttat ctgcgacagt tttcagggtc tctgaagcca gaggacgctg    2640
aggtcttcaa gagtcctgcc gcttccgggg agaagtgagg acgtcacgca gacagcactg    2700
tcaacactgg gccttaggag accccgttgc cacgggggc tgctgaggga acaccagtgc    2760
tctgtcagca gcctggcctg gtctgtgcct gcccagcatg ttcccaaatc tgtgctggac    2820
aagctgtggg aagcgttctt ggaagcatgg ggagtgatgt acatccaacc gtcactgtcc    2880
ccaagtgaat ctcctaacag actttcaggt ttttactcac tttactaaac agtttggatg    2940
gtcagtctct actgggacat gttaggccct tgttttcttt gatttttattc ttttttttga    3000
```

```
gacagaattt cactcttctc acccaggctg gaatgcagtg gcacaatttt ggctccctgc    3060
aacctccgcc tcctggattc cagcaattct cctgcctcgg cttcccaagt agctgggatt    3120
acaggcacgt gccaccatgt ctggctaatt ttttgtattt ttttaataga tatggggttt    3180
cgccatgttg gccaggctgg tctcgaactc ctgacctcag gtgatccgcc cacctcggcc    3240
tcccaaagtg ctgggattac a                                              3261

<210> SEQ ID NO 121
<211> LENGTH: 4307
<212> TYPE: DNA
<213> ORGANISM: Homo sapiens
<220> FEATURE:
<221> NAME/KEY: misc_feature
<223> OTHER INFORMATION: NM_005099

<400> SEQUENCE: 121
cacagacaca tatgcacgag agagacagag gaggaaagag acagagacaa aggcacagcg      60
gaagaaggca gagacagggc aggcacagaa gcggcccaga cagagtccta cagagggaga    120
ggccagagaa gctgcagaag acacaggcag ggagagacaa agatccagga aaggagggct    180
caggaggaga gtttggagaa gccagacccc tgggcacctc tcccaagccc aaggactaag    240
ttttctccat ttcctttaac ggtcctcagc ccttctgaaa actttgcctc tgaccttggc    300
aggagtccaa gccccaggc tacagagagg agctttccaa agctagggtg tggaggactt    360
ggtgccctag acggcctcag tccctcccag ctgcagtacc agtgccatgt cccagacagg    420
ctcgcatccc gggaggggct tggcaggcg ctggctgtgg ggagcccaac cctgcctcct    480
gctccccatt gtgccgctct cctggctggt gtggctgctt ctgctactgc tggcctctct    540
cctgccctca gccggctgg ccagccccct ccccgggag gaggagatcg tgtttccaga    600
gaagctcaac ggcagcgtcc tgcctggctc gggcaccccct gccaggctgt tgtgccgctt    660
gcaggccttt ggggagacgc tgctactaga gctggcagag gactccggtg tgcaggtcga    720
ggggctgaca gtgcagtacc tgggccaggc gcctgagctg ctgggtggag cagagcctgg    780
cacctacctg actggcacca tcaatgagga tccggagtcg gtggcatctc tgcactggga    840
tgggggagcc ctgttaggcg tgttacaata tcgggggggc gaactccacc tccagccct    900 ggagggaggc accctaact ctgctggggg acctggggct cacatcctac gccggaagag    960
tcctgccagc ggtcaaggtc ccatgtgcaa cgtcaaggct cctcttggaa gccccagccc   1020
cagaccccga gagccaagc gctttgcttc actgagtaga tttgtggaga cactggtggt   1080
ggcagatgac aagatggccg cattccacgg tgcggggcta aagcgctacc tgctaacagt   1140
gatggcagca gcagccaagg ccttcaagca cccaagcatc cgcaatcctg tcagcttggt   1200
ggtgactcgg ctagtgatcc tggggtcagg cgaggagggg cccaagtgg ggcccagtgc   1260 tgcccagacc ctgcgcagct tctgtgcctg gcagcgggc ctcaacaccc ctgaggactc   1320
ggaccctgac cactttgaca cagccattct gtttacccgt caggacctgt gtggagtctc   1380
cacttgcgac acgctgggta tggctgatgt gggcaccgtc tgtgacccgg ctcggagctg   1440
tgccattgtg gaggatgatg gctccagtc agccttcact gctgctcatg aactgggtca   1500
tgtcttcaac atgctccatg acaactccaa gccatgcatc agtttgaatg gcctttgag   1560 cacctctcgc catgtcatgg ccctgtgat ggctcatgtg gatcctgagg agccctggtc   1620
cccctgcagt gcccgcttca tcactgactt cctggacaat ggctatggc actgtctctt   1680 agacaaaacca gaggctccat tgcatctgcc tgtgactttc cctggcaagg actatgatgc   1740
```

```
tgaccgccag tgccagctga ccttcgggcc cgactcacgc cattgtccac agctgccgcc   1800
gccctgtgct gccctctggt gctctggcca cctcaatggc catgccatgt gccagaccaa   1860
acactcgccc tgggccgatg cacaccctg cgggcccgca caggcctgca tgggtggtcg    1920
ctgcctccac atggaccagc tccaggactt caatattcca caggctggtg ctgggtcc    1980 ttggggacca tggggtgact gctctcggac ctgtgggggt ggtgtccagt tctcctcccg   2040
agactgcacg aggcctgtcc cccggaatgg tggcaagtac tgtgagggcc gccgtacccg   2100
cttccgctcc tgcaacactg aggactgccc aactggctca gccctgacct tccgcgagga   2160
gcagtgtgct gcctacaacc accgcaccga cctcttcaag agcttcccag ggcccatgga   2220
ctgggttcct cgctacacag gcgtggcccc ccaggaccag tgcaaactca cctgccaggc   2280
ccgggcactg ggctactact atgtgctgga gccacgggtg gtagatggga ccccctgttc   2340
cccggacagc tcctcggtct gtgtccaggg ccgatgcatc catgctggct gtgatcgcat   2400
cattggctcc aagaagaagt tgacaagtg catggtgtgc ggaggggacg gttctggttg    2460
cagcaagcag tcaggctcct tcaggaaatt caggtacgga tacaacaatg tggtcactat   2520
ccccgcgggg gccacccaca ttcttgtccg gcagcaggga aaccctggcc accggagcat   2580
ctacttggcc ctgaagctgc cagatggctc ctatgccctc aatggtgaat acacgctgat   2640
gccctccccc acagatgtgg tactgcctgg ggcagtcagc ttgcgctaca gcggggccac   2700
tgcagcctca gagacactgt caggccatgg ccactggcc cagcctttga cactgcaagt    2760
cctagtggct ggcaaccccc aggacacacg cctccgatac agcttcttcg tgccccggcc   2820
gaccccttca cgccacgcc ccactcccca ggactggctg caccgaagag cacagattct    2880
ggagatcctt cggcggcgcc cctgggcggg caggaaataa cctcactatc ccggctgccc   2940
tttctgggca ccggggcctc ggacttagct gggagaaaga gagagcttct gttgctgcct   3000
catgctaaga ctcagtgggg aggggctgtg ggcgtgagac ctgccctcc tctctgccct    3060 aatgcgcagg ctgccctgc cctggtttcc tgccctggga ggcagtgatg ggttagtgga    3120 tggaagggc tgacagacag ccctccatct aaactgcccc ctctgccctg cgggtcacag    3180
gagggagggg gaaggcaggg agggcctggg ccccagttgt atttatttag tatttattca   3240 cttttatta gcaccaggga aggggacaag gactagggtc ctggggaacc tgaccctga    3300 cccctcatag ccctcaccct ggggctagga atccagggt ggtggtgata ggtataagtg    3360
gtgtgtgtat gcgtgtgtgt gtgtgtgtga aaatgtgtgt gtgcttatgt atgaggtaca   3420
acctgttctg ctttcctctt cctgaatttt atttttgggg aaaagaaaag tcaagggtag   3480
ggtgggcctt cagggagtga gggattatct ttttttttt tctttctttt ctttctttt    3540 tttttttgag acagaatctc gctctgtcgc ccaggctgga gtgcaatggc acaatctcgg   3600
ctcactgcat cctccgcctc ccgggttcaa gtgattctca tgcctcagcc tcctgagtag   3660
ctgggattac aggctcctgc caccacgccc agctaatttt tgttttgttt tgtttggaga   3720
cagagtctcg ctattgtcac cagggctgga atgatttcag ctcactgcaa ccttcgccac   3780
ctgggttcca gcaattctcc tgcctcagcc tcccgagtag ctgagattat aggcacctac   3840
caccacgccc ggctaatttt tgtatttta gtagagacgg ggtttcacca tgttggccag   3900
gctggtctcg aactcctgac cttaggtgat ccactcgcct tcatctccca aagtgctggg   3960
attacaggcg tgagccaccg tgcctggcca cgcccaacta ttttttgtat tttagtagaa   4020
gacagggttt caccatgttg gccaggctgc tcttgaactc ctgacctcag gtaatcgacc   4080
tgcctcggcc tcccaaagtg ctgggattac aggtgtgagc caccacgccc ggtacatatt   4140
```

```
tttaaattg aattctacta tttatgtgat cctttggag tcagacagat gtggttgcat    4200
cctaactcca tgtctctgag cattagattt ctcatttgcc aataataata cctcccttag    4260
aagtttgttg tgaggattaa ataatgtaaa taaagaacta gcataac                  4307
```

<210> SEQ ID NO 122
<211> LENGTH: 1423
<212> TYPE: DNA
<213> ORGANISM: Homo sapiens
<220> FEATURE:
<221> NAME/KEY: misc_feature
<223> OTHER INFORMATION: U94320

<400> SEQUENCE: 122

```
gaaaggctat cggtaacaac tgacctgcca caaagttaga agaaaggatt gattcaagaa     60
agactataat atggatttag agctcgacga gtattataac aagacacttg ccacagagaa    120
taatactgct gccactcgga attctgattt cccagtctgg gatgactata aaagcagtgt    180
agatgactta cagtatttc tgattgggct ctatacattt gtaagtcttc ttggctttat    240
ggggaatcta cttatttaa tggctctcat gaaaaagcgt aatcagaaga ctacggtaaa    300
cttcctcata ggcaatctgg ccttttctga tatcttggtt gtgctgtttt gctcacctt    360 cacactgacg tctgtcttgc tggatcagtg gatgtttggc aaagtcatgt gccatattat    420 gcctttctt caatgtgtgt cagttttggt ttcaactta attttaatat caattgccat    480
tgtcaggtat catatgataa acatcccat atctaataat ttaacagcaa accatggcta    540
ctttctgata gctactgtct ggacactagg ttttgccatc tgttctcccc ttccagtgtt    600
tcacagtctt gtggaacttc aagaaacatt tggttcagca ttgctgagca gcaggtattt    660
atgtgttgag tcatggccat ctgattcata cagaattgcc tttactatct ctttattgct    720
agttcagtat attctgcccc tagtttgtct tactgtaagt catacaagtg tctgcagaag    780
tataagctgt ggattgtcca acaaagaaaa cagacttgaa gaaaatgaga tgatcaactt    840
aactcttcat ccatccaaaa agagtgggcc tcaggtgaaa ctctctggca gccataaatg    900
gagttattca ttcatcaaaa aacacagaag aagatatagc aagaagacag catgtgtgtt    960
acctgctcca gaaagaccct ctcaagagaa ccactccaga atacttccag aaaactttgg   1020
ctctgtaaga agtcagctct cttcatccag taagttcata ccaggggtcc ccacttgctt   1080
tgagataaaa cctgaagaaa attcagatgt tcatgaattg agagtaaaac gttctgttac   1140
aagaataaaa aagagatctc gaagtgtttt ctacagactg accatactga tattagtatt   1200
tgctgttagt tggatgccac tacaccttt ccatgtggta actgatttta atgacaatct   1260
tatttcaaat aggcattttca agttggtgta ttgcatttgt catttgttgg gcatgatgtc   1320
ctgttgtctt aatccaattc tatatgggtt tcttaataat gggattaaag ctgatttagt   1380
gtcccttata cactgtcttc atatgtaata attctcactg ttt                     1423
```

<210> SEQ ID NO 123
<211> LENGTH: 5078
<212> TYPE: DNA
<213> ORGANISM: Homo sapiens
<220> FEATURE:
<221> NAME/KEY: misc_feature
<223> OTHER INFORMATION: NM_002410

<400> SEQUENCE: 123

```
taatactcct ttattccctg ttttaaaaat tttttaaat ttgatacaat aattatacat      60
```

-continued

| | | | | | |
|---|---|---|---|---|---|
| aataatggag | taccatgtga | gattcaatcc | acatatacat | tgtgaaatga | tcaaattagg | 120 |
| atagttagca | tgcacatcac | ccccaaataa | ttattacttt | tgtggtgaga | acacttaaaa | 180 |
| ttgtctcttt | tagaaatata | cgttattatt | aaccatagtc | acctcgctgt | gcaatagaac | 240 |
| accagaactt | attcctccta | aatgtaactt | tttacccatt | gaccactccc | tcctcacccc | 300 |
| cctctctcct | ccccaccccT | ggtaaccact | gttctgttat | ctcctatgat | agcaactttt | 360 |
| tagcttctgc | atgtgagatt | gtacggtagt | tgcctttctg | tgcctggatt | atttcattta | 420 |
| gcataatgtc | cttcgggtat | atccctgttg | ctgcaaaaga | caggatttct | ctctcttttt | 480 |
| ctggttgaat | agtattccat | tgtcagagaa | tgttgtaaga | ctaggaaagg | aacactgcag | 540 |
| gctggagccc | tggggaaatg | gtctgaggca | ggtggtggga | ctagagctgg | ggtctggcaa | 600 |
| acaggctggg | tttgattgtc | agcataatag | agagcactca | tgtgccagct | gggtgggagg | 660 |
| agcagccgag | tgaagaaggg | gaagcctctc | aggaagcatg | tgcagggttt | atggtaatga | 720 |
| gcagaccagc | aggtacgtag | tgggagaggg | gtgtgatggg | gcagaggaac | ttacgttatg | 780 |
| atagtacaag | acagaggttg | agcctcattt | taataggcat | tgtggtgggt | gttgaatagt | 840 |
| gatggaatgt | atgggtctgg | aatcaggctg | cctggtcaag | ggctctgaaa | catgagtgtg | 900 |
| catcagaatc | acctcgaggc | ttgttaaagg | ataggctgtg | gaccacatct | cctcagttgc | 960 |
| tgattcagtg | ggtgtgggtg | gggcctgaga | attcacattt | cccactggtg | atgctgctgt | 1020 |
| tactgattgg | gaccacattt | ggggaacact | ggtctagaat | tgagaggttg | gcaaaccttc | 1080 |
| tctgttaaga | ggtagatagt | aaatatttta | ggccttctgg | gctacaaaga | gtatctgtta | 1140 |
| catatttttt | attgcttttc | atgacccatt | aagcatatat | atatcattct | ctgccatata | 1200 |
| caaacaggct | gttggggag | tgaggatgat | gtagggaagg | tggggcatgg | tttaataacc | 1260 |
| cctgggccat | gcctagatga | tcagtcctct | gccacatagc | tggctgacct | ttgccaagtt | 1320 |
| aatcacctTt | tacctttatt | ttctcatgtt | tctaataaaa | cagagacgat | aatattcata | 1380 |
| cttcttacca | tatagaactt | ctgaggattc | agtgagcaaa | gccacaaaag | atggtatgtc | 1440 |
| acaatatctg | ggatatagct | agaatttata | atttattttt | actctgttga | taggcaatgg | 1500 |
| gaaaacagta | agaggcagac | caacagtgat | ccagggctct | gaaagctaat | tgcttcaaga | 1560 |
| tcctgctacc | attttctttt | gggccgcttg | caaagaagaa | tcctttgact | gaagcatgta | 1620 |
| tgtacactct | gaagtacagc | ctgggttagt | ctcttataag | ggatcggatc | attgctcagc | 1680 |
| tctcccttga | gtggcactta | gaaaatggcg | ctattcgtaa | gctgactggt | attgggccca | 1740 |
| ggactctggc | tgaaggggtg | ggcatgctgg | taaccatttg | caacctatgc | tcaggtccta | 1800 |
| cttgttggga | agccctgatt | gagaagagtg | gcctggtctg | tgctggcatt | agataggatc | 1860 |
| tggctgcatt | aatattgaaa | ctactctgcc | ttttaatgtc | tcattttgcc | tcatggtggg | 1920 |
| agtgaaagtg | agaaccacag | aaaatctgcc | tgccaggtgt | tccacatttc | ttgtgctaca | 1980 |
| gcatgcaagt | gagcagtgag | gtgtacccttt | tcctcatgta | gctgggaaag | caatacccct | 2040 |
| gcttgtacct | ctggcatatc | ttctctgtgc | tggtgcacct | agagaggttg | cctggtggcc | 2100 |
| ctgagagagc | catctcatca | ctaaacactg | atggtgaaaa | gctggccatg | ctcaaataag | 2160 |
| atgtagcaat | ctacctcttc | tttgtctagt | taccccaag | ggggcatcca | ctttcttgct | 2220 |
| cacctcacca | gttgcatgtt | ctagtccttg | ccagaagcac | ataataatga | ctttgtaagc | 2280 |
| ttaagttaca | ggcacacaaa | agggcctgat | ggtgatatga | ctccaccctc | ccgttttg | 2340 |
| ctgacattcc | gccaaatatc | cttctgtctc | ctccccacct | tgcaaaacaa | acttcctgtt | 2400 |
| ttgaatttgg | tccaggctgg | aacagcccca | ccacacctgt | taacacacgc | agacgcacac | 2460 |

```
ttcccccttc ataattgctt agcttcttgt tgcctagcca gatttcccct cagcttacag    2520
ttcctgaatc ataagatatt gaaccagcaa atttaagagt tgacatttta cttagaggta    2580
ttcaagtgaa aacatggctt ctggtttatt ttgctgtatt gtgccatgac cacttggcta    2640
attcttctcc tccttcacat cagaatgaaa gtgaggaaag caaccagct gacacaggag     2700 ccagagtgag accagcagac tctcacactc aacctacacc atgaatttgt gtctatcttc    2760
tacgcgttaa gagccaagga caggtgaagt tgccagagag caatggctct cttcactccg    2820
tggaagttgt cctctcagaa gctgggcttt tcctggtga cttttggctt catttggggt      2880
atgatgcttc tgcactttac catccagcag cgaactcagc ctgaaagcag ctccatgctg    2940
cgcgagcaga tcctggacct cagcaaaagg tacatcaagg cactggcaga agaaaacagg    3000
aatgtggtgg atgggccata cgctggagtc atgacagctt atgatctgaa gaaaacccctt   3060 gctgtgttat tagataacat tttgcagcgc attggcaagt tggagtcgaa ggtggacaat    3120
cttgttgtca atggcaccgg aacaaactca accaactcca ctacagctgt tcccagcttg    3180
gttgcacttg agaaaattaa tgtggcagat atcattaacg gagctcaaga aaaatgtgta    3240
ttgcctccta tggacggcta ccctcactgt gagggaaaga tcaagtggat gaaagacatg    3300
tggcgttcag atccctgcta cgcagactat ggagtggatg gatccacctg ctcttttttt    3360
atttacctca gtgaggttga aaattggtgt cctcatttac cttggagagc aaaaaatccc    3420
tacgaagaag ctgatcataa ttcattggcg gaaattcgta cagattttaa tattctctac    3480
agtatgatga aaaagcatga agaattccgg tggatgagac tacggatccg gcgaatggct    3540
gacgcatgga tccaagcaat caagtccctg gcagaaaagc agaaccttga aaagagaaag    3600
cggaagaaag tcctcgttca cctgggactc ctgaccaagg aatctggatt taagattgca    3660
gagacagctt tcagtggtgg ccctcttggt gaattagttc aatggagtga tttaattaca    3720
tctctgtact tactgggcca tgacattagg atttcagctt cactggctga gctcaaggaa    3780
atcatgaaga aggttgtagg aaaccgatct ggctgcccaa ctgtaggaga cagaattgtt    3840
gagctcattt acattgatat tgtaggactt gctcaattca agaaaactct tggaccatcc    3900
tgggttcatt accagtgcat gctccgagtc cttgattcat ttggtactga acccgaattt    3960
aatcatgcaa attatgccca atcgaaaggc cacaagaccc cttggggaaa atggaatctg    4020
aaccctcagc agttttatac catgttccct catacccagc acaacagctt tctgggttt     4080 gtggttgagc agcacctgaa ctccagtgat atccaccaca ttaatgaaat caaaaggcag    4140
aaccagtccc ttgtgtatgg caaagtggat agcttctgga gaataagaa gatctacttg     4200 gacattattc acacatacat ggaagtgcat gcaactgttt atggctccag cacaaagaat    4260
attcccagtt acgtgaaaaa ccatggtatc ctcagtggac gggacctgca gttccttctt    4320
cgagaaacca gttgtttgt tggacttggg ttcccttacg agggcccagc tccctggaa      4380 gctatcgcaa atgatgtgc ttttctgaat cccaagttca acccacccaa agcagcaaa      4440 aacacagact tttcattgg caagccaact ctgagagagc tgacatccca gcatccttac      4500
gctgaagttt tcatcgggcg gccacatgtg tggactgttg acctcaacaa tcaggaggaa    4560
gtagaggatg cagtgaaagc aatttttaaat cagaagatta gccatacat gccatatgaa    4620 tttacgtgcg aggggatgct acagagaatc aatgctttca ttgaaaaaca ggacttctgc    4680
catgggcaag tgatgtggcc acccctcagc gccctacagg tcaagcttgc tgagcccggg    4740
cagtcctgca agcaggtgtg ccaggagagc cagctcatct gcgagccttc tttcttccag    4800
```

| | |
|---|---|
| cacctcaaca aggacaagga catgctgaag tacaaggtga cctgccaaag ctcagagctg | 4860 |
| gccaaggaca tcctggtgcc ctcctttgac cctaagaata agcactgtgt gtttcaaggt | 4920 |
| gacctcctgc tcttcagctg tgcaggcgcc caccccaggc accagagggt ctgcccctgc | 4980 |
| cgggacttca tcaagggcca ggtggctctc tgcaaagact gcctatagca gctacctgct | 5040 |
| cagccctgca ccatgctgct ggggaagaca gtggcccc | 5078 |

```
<210> SEQ ID NO 124
<211> LENGTH: 887
<212> TYPE: DNA
<213> ORGANISM: Homo sapiens
<220> FEATURE:
<221> NAME/KEY: misc_feature
<223> OTHER INFORMATION: X16863

<400> SEQUENCE: 124
```

| | |
|---|---|
| tctttggtga cttgtccact ccagtgtggc atcatgtggc agctgctcct cccaactgct | 60 |
| ctgctacttc tagtttcagc tggcatgcgg actgaagatc tcccaaaggc tgtggtgttc | 120 |
| ctggagcctc aatggtacag cgtgcttgag aaggacagtg tgactctgaa gtgccaggga | 180 |
| gcctactccc ctgaggacaa ttccacacag tggtttcaca atgagagcct catctcaagc | 240 |
| caggcctcga gctacttcat tgacgctgcc acagtcaacg acagtggaga gtacaggtgc | 300 |
| cagacaaacc tctccaccct cagtgacccg gtgcagctag aagtccatat cggctggctg | 360 |
| ttgctccagg cccctcggtg ggtgttcaag gaggaagacc ctattcacct gaggtgtcac | 420 |
| agctggaaga acactgctct gcataaggtc acatatttac agaatggcaa agacaggaag | 480 |
| tattttcatc ataattctga cttccacatt ccaaaagcca cactcaaaga tagcggctcc | 540 |
| tacttctgca ggggcttgt tgggagtaaa aatgtgtctt cagagactgt gaacatcacc | 600 |
| atcactcaag gtttggcagt gtcaaccatc tcatcattct ctccacctgg gtaccaagtc | 660 |
| tctttctgct tggtgatggt actccttttt gcagtggaca caggactata tttctctgtg | 720 |
| aagacaaaca tttgaagctc aacaagagac tggaaggacc ataaacttaa atggagaaag | 780 |
| gaccctcaag acaaatgacc cccatcccat gggagtaata agagcagtgg cagcagcatc | 840 |
| tctgaacatt tctctggatt tgcaacccca tcatcctcag gcctctc | 887 |

```
<210> SEQ ID NO 125
<211> LENGTH: 1800
<212> TYPE: DNA
<213> ORGANISM: Homo sapiens
<220> FEATURE:
<221> NAME/KEY: misc_feature
<223> OTHER INFORMATION: XM_042961

<400> SEQUENCE: 125
```

| | |
|---|---|
| cttctctgcc agaagatacc atttcaactt taacacagca tgatcgaaac atacaaccaa | 60 |
| acttctcccc gatctgcggc cactggactg cccatcagca tgaaaatttt tatgtattta | 120 |
| cttactgttt ttcttatcac ccagatgatt gggtcagcac ttttgctgt gtatcttcat | 180 |
| agaaggttgg acaagataga agatgaaagg aatcttcatg aagattttgt attcatgaaa | 240 |
| acgatacaga gatgcaacac aggagaaaga tccttatcct tactgaactg tgaggagatt | 300 |
| aaaagccagt ttgaaggctt tgtgaaggat ataatgttaa acaaagagga gacgaagaaa | 360 |
| gaaaacagct ttgaaatgca aaaggtgat cagaatcctc aaattgcggc acatgtcata | 420 |
| agtgaggcca gcagtaaaac aacatctgtg ttacagtggg ctgaaaaagg atactacacc | 480 |
| atgagcaaca acttggtaac cctggaaaat gggaaacagc tgaccgttaa aagacaagga | 540 |

```
ctctattata tctatgccca agtcaccttc tgttccaatc gggaagcttc gagtcaagct    600
ccatttatag ccagcctctg cctaaagtcc cccggtagat tcgagagaat cttactcaga    660
gctgcaaata cccacagttc cgccaaacct tgcgggcaac aatccattca cttgggagga    720
gtatttgaat tgcaaccagg tgcttcggtg tttgtcaatg tgactgatcc aagccaagtg    780
agccatggca ctggcttcac gtcctttggc ttactcaaac tctgaacagt gtcaccttgc    840
aggctgtggt ggagctgacg ctgggagtct tcataataca gcacagcggt taagcccacc    900
ccctgttaac tgcctatttta taaccctagg atcctcctta tggagaacta tttattatac    960
actccaaggc atgtagaact gtaataagtg aattacaggt cacatgaaac caaaacgggc   1020
cctgctccat aagagcttat atatctgaag cagcaacccc actgatgcag acatccagag   1080
agtcctatga aaagacaagg ccattatgca caggttgaat tctgagtaaa cagcagataa   1140
cttgccaagt tcagttttgt ttctttgcgt gcagtgtctt tccatggata atgcatttga   1200
tttatcagtg aagatgcaga agggaaatgg ggagcctcag ctcacattca gttatggttg   1260
actctgggtt cctatggcct tgttggaggg ggccaggctc tagaacgtct aacacagtgg   1320
agaaccgaaa cccccccccc ccccccgcca ccctctcgga cagttattca ttctctttca   1380
atctctctct ctccatctct ctctttcagt ctctctctct caacctctttt cttccaatct   1440 ctctttctca atctctctgt ttccctttgt cagtctcttc cctcccccag tctctcttct   1500
caatccccct ttctaacaca cacacacaca cacacacaca cacacacaca cacacacaca   1560
cacacacaga gtcaggccgt tgctagtcag ttctcttctt tccaccctgt ccctatctct   1620
accactatag atgagggtga ggagtaggga gtgcagccct gagcctgccc actcctcatt   1680
acgaaatgac tgtatttaaa ggaaatctat tgtatctacc tgcagtctcc attgtttcca   1740
gagtgaactt gtaattatct tgttatttat tttttgaata ataaagacct cttaacatta   1800

<210> SEQ ID NO 126
<211> LENGTH: 1450
<212> TYPE: DNA
<213> ORGANISM: Homo sapiens
<220> FEATURE:
<221> NAME/KEY: misc_feature
<223> OTHER INFORMATION: J04101

<400> SEQUENCE: 126
ttgggaagaa agtcggattt cccccgtccc cttccccctg ttactaatcc tcattaaaaa      60
gaaaaacaac aataactgca aacttgctac catcccgtac gtcccccact cctggcacca    120
tgaaggcggc cgtcgatctc aagccgactc tcaccatcat caagacggaa aaagtcgatc    180
tggagctttt cccctccccg gatatggaat gtgcagatgt cccactatta actccaagca    240
gcaaagaaat gatgtctcaa gcattaaaag ctactttcag tggtttcact aaagaacagc    300
aacgactggg gatcccaaaa gaccccggc agtggacaga aacccatgtt cgggactggg    360
tgatgtgggc tgtgaatgaa ttcagcctga aggtgtagac cttccagaag ttctgtatga    420
atggagcagc cctctgcgcc ctgggtaaag actgctttct cgagctggcc ccagactttg    480
ttggggacat cttatgggaa catctagaga tcctgcagaa agaggatgtg aaaccatatc    540
aagttaatgg agtcaaccca gcctatccag aatcccgcta tacctcggat tacttcatta    600
gctatggtat tgagcatgcc cagtgtgttc caccatcgga gttctcagag cccagcttca    660
tcacagagtc ctatcagacg ctccatccca tcagctcgga gagctcctcc tccctcaagt    720
atgagaatga ctaccccctcg gtcattctcc gagaccctct ccagacagac accttgcaga    780
```

```
atgactactt tgctatcaaa caagaagtcg tcaccccaga caacatgtgc atggggagga      840
ccagtcgtgg taaactcggg ggccaggact cttttgaaag catagagagc tacgatagtt      900
gtgatcgcct cacccagtcc tggagcagcc agtcatcttt caacagcctg cagcgtgttc      960
cctcctatga cagcttcgac tcagaggact atccggctgc cctgcccaac cacaagccca     1020
agggcacctt caaggactat gtgcgggacc gtgctgacct caataaggac aagcctgtca     1080
ttcctgctgc tgccctagct ggctacacag gcagtggacc aatccagcta tggcagtttc     1140
ttctggaatt actcactgat aaatcctgtc agtctttat cagctggaca ggagatggct     1200
gggaattcaa actttctgac ccagatgagg tggccaggag atgggaaag aggaaaaaca     1260 aacctaagat gaattatgag aaactgagcc gtggcctacg ctactattac gacaaaaaca     1320
tcatccacaa gacagcgggg aaacgctacg tgtaccgctt tgtgtgtgac ctgcagagcc     1380 tgctgggta caccctgag gagctgcacg ccatgctgga cgtcaagcca gatgccgacg     1440
agtgatggca                                                            1450
```

<210> SEQ ID NO 127
<211> LENGTH: 6069
<212> TYPE: DNA
<213> ORGANISM: Homo sapiens
<220> FEATURE:
<221> NAME/KEY: misc_feature
<223> OTHER INFORMATION: XM_047802

<400> SEQUENCE: 127

```
gcagctgccg actggggatg acggcgggca ggaggagacc gcagccgaag ggacacagac       60
acgccgcttc accagctcgc ctcaggctgc cccctgcat ttttgtttta attttacgg        120 cttttttccc tctctttctt ccttcctcc tggtcccagc agagccaagg aaacccacaa       180
aataagaaag gaagtgggcc ccggagcttg gaacctccac agccggcttg tccagcgcag       240 cgcggggcg ggaggctgcg cgcaccagtt gccagcccgg tgcgcggtac ctttccttac       300
ttttcttgaa acagcgatcg tgcctgcatt tggtggtttt ttggttttg tttttttcct      360 ttccccgtat ttgctgaatc tccactatcc gactttttt ttttaatctt ttcttttcccc     420 ccccccccac cccacctctt tctggagcac gaatccaaac attttccaa gcaacaaaga       480 aaagttcgca cgctggcacc gcagcccgga caggctggcg ctgctgccgg gccccctcc      540 ctccgacact tgactcaatc ctgcaagcaa gtgtgtgtgt gtccccatcc cccgccccgt      600
taacttcata gcaaataaca aatacccata aagtcccagt cgcgcagccc ctccccgcgg     660
gcagcgcact atgctgctcg ggtgggcgtc cctgctgctg tgcgcgttcc gcctgcccct     720
ggccgcggtc ggccccgccg cgacacctgc ccaggataaa gccgggcagc ctccgactgc     780
tgcagcagcc gcccagcccc gccggcggca gggggaggag gtgcaggagc gagccgagcc     840
tcccggccac ccgcaccccc tggcgcagcg gcgcaggagc aagggctgg tgcagaacat     900 cgaccaactc tactccggcg gcggcaaggt gggctacctc gtctacgcgg gcggccggag     960
gttcctcttg gacctggagc gagatggttc ggtgggcatt gctggcttcg tgcccgcagg    1020
aggcgggacg agtgcgccct ggcgccaccg gagccactgc ttctatcggg gcacagtgga    1080
cggtagtccc cgctctctgg ctgtctttga cctctgtggg ggtctcgacg gcttcttcgc    1140
ggtcaagcac gcgcgctaca ccctaaagcc actgctgcgc ggaccctggg cggaggaaga    1200
aaaggggcgc gtgtacgggg atgggtccgc acggatcctg cacgtctaca cccgcgaggg    1260
cttcagcttc gaggccctgc cgccgcgcgc cagctgcgaa accccgcgt ccacaccgga    1320
```

```
ggcccacgag catgctccgg cgcacagcaa cccgagcgga cgcgcagcac tggcctcgca    1380
gctcttggac cagtccgctc tctcgcccgc tgggggctca ggaccgcaga cgtggtggcg    1440
gcggcggcgc cgctccatct cccgggcccg ccaggtggag ctgcttctgg tggctgacgc    1500
gtccatggcg cggttgtatg gccggggcct gcagcattac ctgctgaccc tggcctccat    1560
cgccaatagg ctgtacagcc atgctagcat cgagaaccac atccgcctgg ccgtggtgaa    1620
ggtggtggtg ctaggcgaca aggacaagag cctggaagtg agcaagaacg ctgccaccac    1680
actcaagaac ttttgcaagt ggcagcacca acacaaccag ctgggagatg accatgagga    1740
gcactacgat gcagctatcc tgtttactcg ggaggattta tgtgggcatc attcatgtga    1800
caccctggga atggcagacg ttgggaccat atgttctcca gagcgcagct gtgctgtgat    1860
tgaagacgat ggcctccacg cagccttcac tgtggctcac gaaatcggac atttacttgg    1920
cctctcccat gacgattcca aattctgtga agagaccttt ggttccacag aagataagcg    1980
cttaatgtct tccatcctta ccagcattga tgcatctaag ccctggtcca aatgcacttc    2040
agccaccatc acagaattcc tggatgatgg ccatggtaac tgtttgctgg acctaccacg    2100
aaagcagatc ctgggccccg aagaactccc aggacagacc tacgatgcca cccagcagtg    2160
caacctgaca ttcgggcctg agtactccgt gtgtcccggc atggatgtct gtgctcgcct    2220
gtggtgtgct gtggtacgcc agggccagat ggtctgtctg accaagaagc tgcctgcggt    2280
ggaagggacg ccttgtggaa aggggagaat ctgcctgcag ggcaaatgtg tggacaaaac    2340
caagaaaaaa tattattcaa cgtcaagcca tggcaactgg ggatcttggg gatcctgggg    2400
ccagtgttct cgctcatgtg gaggaggagt gcagtttgcc tatcgtcact gtaataaccc    2460
tgctcccaga acaacggac gctactgcac agggaagagg gccatctacc gctcctgcag    2520
tctcatgccc tgcccaccca atggtaaatc atttcgtcat gaacagtgtg aggccaaaaa    2580
tggctatcag tctgatgcaa aaggagtcaa aacttttgtg aatgggttc ccaaatatgc    2640 aggtgtcctg ccagcggatg tgtgcaagct gacctgcaga gccaagggca ctggctacta    2700
tgtggtattt tctccaaagg tgaccgatgg cactgaatgt aggctgtaca gtaattccgt    2760
ctgcgtccgg gggaagtgtg tgagaactgg ctgtgacggc atcattggct caaagctgca    2820
gtatgacaag tgcggagtat gtggaggaga caactccagc tgtacaaaga ttgttggaac    2880 cttaataag aaaagtaagg gttacactga cgtggtgagg attcctgaag ggcaaccca    2940 cataaaagtt cgacagttca aagccaaaga ccagactaga ttcactgcct atttagccct    3000
gaaaaagaaa aacggtgagt accttatcaa tggaaagtac atgatctcca cttcagagac    3060
tatcattgac atcaatggaa cagtcatgaa ctatagcggt tggagccaca gggatgactt    3120
cctgcatggc atgggctact ctgccacgaa ggaaattcta atagtgcaga ttcttgcaac    3180
agaccccact aaaccattag atgtccgtta tagcttttt gttcccaaga agtccactcc    3240
aaaagtaaac tctgtcacta gtcatggcag caataaagtg ggatcacaca cttcgcagcc    3300
gcagtgggtc acgggcccat ggctcgcctg ctctaggacc tgtgacacag gttggcacac    3360
cagaacggtg cagtgccagg atggaaaccg gaagttagca aaaggatgtc ctctctccca    3420
aaggccttct gcgtttaagc aatgcttgtt gaagaaatgt tagcctgtgg ttatgatctt    3480
atgcacaaag ataactggag gattcagcac tgatgcagtc gtggtgaaca ggaggtctac    3540
ctaacgcaca gaaagtcatg cttcagtgac attgtcaaca ggagtccaat tatgggcaga    3600
atctgctctc tgtgaccaaa agaggatgtg cactgcttca cgtgacagtg gtgaccttgc    3660
```

```
aatatagaaa aacttgggag ttattgaaca tccctgggc ttacaagaaa cactgatgaa    3720
tgtaaaatca ggggacattt gaagatggca gaactgtctc cccttgtca cctacctctg    3780 atagaatgtc tttaatggta tcataatcat tttcacccat aatacacagt agcttcttct    3840
tactgtttgt aaatacattc tcccttggta tgtcacttta tatccctgg ttctattaaa    3900 atatccatat atatttctat aaaaaagtg tttgaccaaa gtaggtctgc agctatttca    3960
acttccttcc gtttccagaa agagctgtgg atattttact ggaaattaag aacttgctgc    4020
tgttttaata agatgtagta tattttctga ctacaggaga taaaatttca gtcaaaaaac    4080
cattttgaca gcaagtatct tctgagaaat tttgaaaagt aaatagatct cagtgtatct    4140
agtcacttaa atacatacac gggttcattt acttaaacct ttgactgcct gtatttttt    4200 caggtagcta gccaaattaa tgcataattt cagatgtaga agtagggttt gcgtgtgtgt    4260
gtgtgatcat actcaagagt ctaaaaacta gtttccttgt gttggaaatt taaaaggaaa    4320
aaaatcgtat ttcactgtgt tttcaattta tattttcaca actactttct ctctccagag    4380 cttttcatctg atatctcaca atgtatgata tacgtacaaa acacacagca agttttctat    4440
catgtccaac acattcaaca ctggtatacc tcctaccagc aagcctttaa aatgcatttg    4500
tgtttgctta tttgttttgt tcaagggttc agtaagacct acaatgtttt gtatttcttg    4560
acttatttta ttagaaacat taaagatcac ttggtagtta gccacattga gaagtggtta    4620
tcattgttaa tgtggttaat gccaaaaagt ggttaatatt aataagactg tttccacacc    4680
ataggcaata atttcttaat ttaaaaaatc taagtatatt cctattgtac taaatatttt    4740
tcccaactgg aaagcacttg attgtacccg taagtgtttg agtgatgaca tgtgatgatt    4800
ttcagaaagt tgttgttttt gtttccatag cctgtttaag taggttgtaa gtttgaatag    4860
ttagacatgg aaattatttt ataagcacac acctaaagat atcttttag atgataaaat    4920 gtacacccc ccatcaccaa cctcacaact tagaaaatct aagttgtttg atttctttgg    4980
gatttctttt gttgtgaaac actgcaaagc caatttttct ttataaaaat tcatagtaat    5040
cctgccaaat gtgcctattg ttaaagattt gcatgtgaag atcttaggga accactgttt    5100
gagttctaca agctcatgag agttttattt tattataaga tgttttttaat ataaaagaat    5160 tatgtaactg atcactatat tacatcattt cagtgggcca ggaaaataga tgtcttgctg    5220
ttttcagtat tttcttaaga aattgcttt aaacaaata attgttttac aaaaccaata    5280
attatccttt gaattttcat agactgactt tgcttttgac gtagaaattt ttttttctcaa    5340 taaattatca ctttgagaaa tgaggcctgt acaaggctga taacctatat gtgatggaga    5400
tcacccaatg ccaagggcag aaagcaaacc tagttaaata ggtgagaaaa aaaataataa    5460
tcccagtgcc atttgtctgt gcaaagagaa ttaggagaga ggttaatgtt acttttttcc    5520
attttggaaa taatttaat caagtaactc aaatgtgaca aaatttattt ttatttttg    5580 tggttatatt cccaacaaca ttaaaaaata ctcgaggcat aaatgtagtt gtctcctact    5640
ctgcttctct tactatactc atacattttt aatatggttt atcaatgatt catgtttccc    5700
tcaaatagtg atggtttaca cctgtcatgg aaacaatcct agagagctca gagcaattaa    5760
accactattc catgctttta agtagttttc tccacctttt tcttatgagt ctcactagat    5820
tgactgagga atgtatgtct aaattcctgg agaagatgat atggattgga aactgaaatt    5880
cagagaaatg gagtgttcaa tagataccac gaattgtgaa caagggaaa attctataca    5940 actcaatcta agtcagtcca ctttgacttc gtactgtctt tcacctttcc attgttgcat    6000
cttgaatttt ttaaaatgtc tagaattcag gatgctaggg gctacttctt taaaaaaaaa    6060
```

```
aaaaaaaaa                                                              6069

<210> SEQ ID NO 128
<211> LENGTH: 3318
<212> TYPE: DNA
<213> ORGANISM: Homo sapiens
<220> FEATURE:
<221> NAME/KEY: misc_feature
<223> OTHER INFORMATION: NM_002827

<400> SEQUENCE: 128
gtgatgcgta gttccggctg ccggttgaca tgaagaagca gcagcggcta gggcggcggt      60
agctgcaggg gtcggggatt gcagcgggcc tcggggctaa gagcgcgacg cggcctagag     120
cggcagacgg cgcagtgggc cgagaaggag gcgcagcagc cgccctggcc cgtcatggag     180
atggaaaagg agttcgagca gatcgacaag tccgggagct gggcggccat ttaccaggat     240
atccgacatg aagccagtga cttcccatgt agagtggcca agcttcctaa gaacaaaaac     300
cgaaataggt acagagacgt cagtcccttt gaccatagtc ggattaaaac tacatcaagaa     360 gataatgact atatcaacgc tagtttgata aaaatggaag aagcccaaag gagttacatt     420
cttacccagg gcccttttgcc taacacatgc ggtcactttt gggagatggt gtgggagcag     480
aaaagcaggg gtgtcgtcat gctcaacaga gtgatggaga aggttcgtt aaaatgcgca     540 caatactggc cacaaaaaga agaaaaagag atgatctttg aagacacaaa tttgaaatta     600
acattgatct ctgaagatat caagtcatat tatacagtgc gacagctaga attggaaaac     660
cttacaaccc aagaaactcg agagatctta catttccact ataccacatg gcctgacttt     720
ggagtccctg aatcaccagc ctcattcttg aactttcttt tcaaagtccg agagtcaggg     780
tcactcagcc cggagcacgg gcccgttgtg gtgcactgca gtgcaggcat cggcaggtct     840
ggaaccttct gtctggctga tacctgcctc ttgctgatgg acaagaggaa agacccttct     900
tccgttgata tcaagaaagt gctgttagaa atgaggaagt ttcggatggg gctgatccag     960
acagccgacc agctgcgctt ctcctacctg gctgtgatcg aaggtgccaa attcatcatg    1020
ggggactctt ccgtgcagga tcagtggaag gagcttttcc cacgaggacct ggagccccca    1080 cccgagcata tccccccacc tccccggcca cccaaacgaa tcctggagcc acacaatggg    1140
aaatgcaggg agttcttccc aaatcaccag tgggtgaagg aagagaccca ggaggataaa    1200
gactgcccca tcaaggaaga aaaaggaagc cccttaaatg ccgcacccta cggcatcgaa    1260
agcatgagtc aagacactga agttagaagt cgggtcgtgg ggggaagtct tcgaggtgcc    1320
caggctgcct ccccagccaa aggggagccg tcactgcccg agaaggacga ggaccatgca    1380
ctgagttact ggaagccctt cctggtcaac atgtgcgtgg ctacggtcct cacggccggc    1440
gcttacctct gctacaggtt cctgttcaac agcaacacat agcctgaccc tcctccactc    1500
cacctccacc cactgtccgc ctctgcccgc agagcccacg cccgactagc aggcatgccg    1560
cggtaggtaa gggccgccgg accgcgtaga gagccgggcc ccggacggac gttggttctg    1620
cactaaaacc catcttcccc ggatgtgtgt ctcacccctc atccttttac tttttgcccc    1680
ttccactttg agtaccaaat ccacaagcca ttttttgagg agagtgaaag agagtaccat    1740
gctggcggcg cagagggaag gggcctacac ccgtcttggg gctcgcccca cccagggctc    1800
cctcctggag catccaggc gggcggcacg ccaacagccc cccccttgaa tctgcaggga    1860
gcaactctcc actccatatt tatttaaaca atttttttccc caaaggcatc catagtgcac    1920 tagcatttc ttgaaccaat aatgtattaa aattttttga tgtcagcctt gcatcaaggg    1980
```

```
cttatcaaa  aagtacaata  ataaatcctc  aggtagtact  gggaatggaa  ggctttgcca      2040
tgggcctgct  gcgtcagacc  agtactggga  aggaggacgg  ttgtaagcag  ttgttattta      2100
gtgatattgt  gggtaacgtg  agaagataga  acaatgctat  aatatataat  gaacacgtgg      2160
gtatttaata  agaaacatga  tgtgagatta  ctttgtcccg  cttattctcc  tccctgttat      2220
ctgctagatc  tagttctcaa  tcactgctcc  cccgtgtgta  ttagaatgca  tgtaaggtct      2280
tcttgtgtcc  tgatgaaaaa  tatgtgcttg  aaatgagaaa  ctttgatctc  tgcttactaa      2340
tgtgccccat  gtccaagtcc  aacctgcctg  tgcatgacct  gatcattaca  tggctgtggt      2400
tcctaagcct  gttgctgaag  tcattgtcgc  tcagcaatag  ggtgcagttt  tccaggaata      2460
ggcatttgcc  taattcctgg  catgacactc  tagtgacttc  ctggtgaggc  ccagcctgtc      2520
ctggtacagc  agggtcttgc  tgtaactcag  acattccaag  ggtatgggaa  gccatattca      2580
cacctcacgc  tctggacatg  atttagggaa  gcagggacac  ccccgcccc   ccacctttgg      2640 gatcagcctc  cgccattcca  agtcaacact  cttcttgagc  agaccgtgat  ttggaagaga      2700
ggcacctgct  ggaaaccaca  cttcttgaaa  cagcctgggt  gacggtcctt  taggcagcct      2760
gccgccgtct  ctgtcccggt  tcaccttgcc  gagagaggcg  cgtctgcccc  accctcaaac      2820
cctgtggggc  ctgatggtgc  tcacgactct  tcctgcaaag  ggaactgaag  acctccacat      2880
taagtggctt  tttaacatga  aaaacacggc  agctgtagct  cccgagctac  tctcttgcca      2940
gcattttcac  attttgcctt  tctcgtggta  gaagccagta  cagagaaatt  ctgtggtggg      3000
aacattcgag  gtgtcaccct  gcagagctat  ggtgaggtgt  ggataaggct  taggtgccag      3060
gctgtaagca  ttctgagctg  ggcttgttgt  ttttaagtcc  tgtatatgta  tgtagtagtt      3120
tgggtgtgta  tatatagtag  catttcaaaa  tggacgtact  ggtttaacct  cctatccttg      3180
gagagcagct  ggctctccac  cttgttacac  attatgttag  agaggtagcg  agctgctctg      3240
ctatatgcct  taagccaata  tttactcatc  aggtcattat  tttttacaat  ggccatggaa      3300
taaaccattt  ttacaaaa                                                        3318
```

<210> SEQ ID NO 129
<211> LENGTH: 1973
<212> TYPE: DNA
<213> ORGANISM: Homo sapiens
<220> FEATURE:
<221> NAME/KEY: misc_feature
<223> OTHER INFORMATION: NM_002421

<400> SEQUENCE: 129

```
gggatattgg  agtagcaaga  ggctgggaag  ccatcactta  ccttgcactg  agaaagaaga       60
caaaggccag  tatgcacagc  tttcctccac  tgctgctgct  gctgttctgg  ggtgtggtgt      120
ctcacagctt  cccagcgact  ctagaaacac  aagagcaaga  tgtggactta  gtccagaaat      180
acctggaaaa  atactacaac  ctgaagaatg  atgggaggca  agttgaaaag  cggagaaata      240
gtggcccagt  ggttgaaaaa  ttgaagcaaa  tgcaggaatt  ctttgggctg  aaagtgactg      300
ggaaaccaga  tgctgaaacc  ctgaaggtga  tgaagcagcc  agatgtggga  gtgcctgatg      360
tggctcagtt  tgtcctcact  gaggggaacc  ctcgctggga  gcaaacacat  ctgacctaca      420
ggattgaaaa  ttacacgcca  gatttgccaa  gagcagatgt  ggaccatgcc  attgagaaag      480
ccttccaact  ctggagtaat  gtcacacctc  tgacattcac  caaggtctct  gagggtcaag      540
cagacatcat  gatatctttt  gtcagggag   atcatcggga  caactctcct  tttgatggac      600
ctggaggaaa  tcttgctcat  gcttttcaac  caggcccagg  tattggaggg  gatgctcatt      660
```

```
ttgatgaaga tgaaaggtgg accaacaatt tcagagagta caacttacat cgtgttgcgg    720
ctcatgaact cggccattct cttggactct cccattctac tgatatcggg gctttgatgt    780
accctagcta caccttcagt ggtgatgttc agctagctca ggatgacatt gatggcatcc    840
aagccatata tggacgttcc caaaatcctg tccagcccat cggcccacaa accccaaaag    900
cgtgtgacag taagctaacc tttgatgcta taactacgat tcggggagaa gtgatgttct    960
ttaaagacag attctacatg cgcacaaatc ccttctaccc ggaagttgag ctcaatttca   1020
tttctgtttt ctggccacaa ctgccaaatg gcttgaagc tgcttacgaa tttgccgaca   1080
gagatgaagt ccggtttttc aaagggaata agtactgggc tgttcaggga cagaatgtgc   1140
tacacggata ccccaaggac atctacagct cctttggctt ccctagaact gtgaagcata   1200
tcgatgctgc tctttctgag gaaaacactg gaaaaaccta cttctttgtt gctaacaaat   1260
actggaggta tgatgaatat aaacgatcta tggatccagg ttatcccaaa atgatagcac   1320
atgactttcc tggaattggc cacaaagttg atgcagtttt catgaaagat ggattttctc   1380
atttctttca tggaacaaga caatacaaat ttgatcctaa aacgaagaga attttgactc   1440
tccagaaagc taatagctgg ttcaactgca ggaaaaattg aacattacta atttgaatgg   1500
aaaacacatg gtgtgagtcc aaagaaggtg ttttcctgaa gaactgtcta ttttctcagt   1560
catttttaac ctctagagtc actgatacac agaatataat cttatttata cctcagtttg   1620
catatttttt tactatttag aatgtagccc tttttgtact gatataattt agttccacaa   1680
atggtgggta caaaaagtca agtttgtggc ttatggattc ataggcca gagttgcaaa    1740 gatcttttcc agagtatgca actctgacgt tgatcccaga gagcagcttc agtgacaaac   1800
atatcctttc aagacagaaa gagacaggag acatgagtct tgccggagg aaaagcagct    1860 caagaacaca tgtgcagtca ctggtgtcac cctggatagg caagggataa ctcttctaac   1920
acaaaataag tgttttatgt ttggaataaa gtcaaccttg tttctactgt ttt          1973
```

<210> SEQ ID NO 130
<211> LENGTH: 2279
<212> TYPE: DNA
<213> ORGANISM: Homo sapiens
<220> FEATURE:
<221> NAME/KEY: misc_feature
<223> OTHER INFORMATION: NM_001752

<400> SEQUENCE: 130

```
tgcctgctga gggtggagac ccacgagccg aggcctcctg cagtgttctg cacagcaaac     60
cgcacgctat ggctgacagc cgggatcccg ccagcgacca gatgcagcac tggaaggagc    120
agcgggccgc gcagaaagct gatgtcctga ccactggagc tggtaaccca gtaggagaca    180
aacttaatgt tattacagta gggccccgtg ggcccccttct tgttcaggat gtggttttca    240
ctgatgaaat ggctcatttt gaccgagaga gaattcctga gagagttgtg catgctaaag    300
gagcaggggc ctttggctac tttgaggtca cacatgacat taccaaatac tccaaggcaa    360
aggtatttga gcatattgga aagaagactc ccatcgcagt tcggttctcc actgttgctg    420
gagaatcggg ttcagctgac acagttcggg accctcgtgg gtttgcagtg aaattttaca    480
cagaagatgg taactgggat ctcgttggaa ataacacccc catttttcttc atcagggatc    540 ccatattgtt tccatctttt atccacagcc aaaagagaaa tcctcagaca catctgaagg    600
atccggacat ggtctgggac ttctggagcc tacgtcctga gtctctgcat caggtttctt    660
tcttgttcag tgatcggggg attccagatg acatcgcca catgaatgga tatggatcac    720
```

| | |
|---|---|
| atactttcaa gctggttaat gcaaatgggg aggcagttta ttgcaaattc cattataaga | 780 |
| ctgaccaggg catcaaaaac ctttctgttg aagatgcggc gagactttcc caggaagatc | 840 |
| ctgactatgg catccgggat cttttaacg ccattgccac aggaaagtac ccctcctgga | 900 |
| cttttacat ccaggtcatg acatttaatc aggcagaaac ttttccattt aatccattcg | 960 |
| atctcaccaa ggtttggcct cacaaggact accctctcat cccagttggt aaactggtct | 1020 |
| taaaccggaa tccagttaat tactttgctg aggttgaaca gatagccttc gacccaagca | 1080 |
| acatgccacc tggcattgag gccagtcctg acaaaatgct tcagggccgc ctttttgcct | 1140 |
| atcctgacac tcaccgccat cgcctgggac ccaattatct tcatatacct gtgaactgtc | 1200 |
| cctaccgtgc tcgagtggcc aactaccagc gtgatggccc gatgtgcatg caggacaatc | 1260 |
| agggtggtgt tccaaattac taccccaaca gctttggtgc tccggaacaa cagccttctg | 1320 |
| ccctggagca cagcatccaa tattctggag aagtgcggag attcaacact gccaatgatg | 1380 |
| ataacgttac tcaggtgcgg gcattctatg tgaacgtgct gaatgaggaa cagaggaaac | 1440 |
| gtctgtgtga gaacattgcc ggccacctga aggatgcaca aattttcatc cagaagaaag | 1500 |
| cggtcaagaa cttcactgag gtccaccctg actacgggag ccacatccag gctcttctgg | 1560 |
| acaagtacaa tgctgagaag cctaagaatg cgattcacac ctttgtgcag tccggatctc | 1620 |
| acttggcggc aagggagaag gcaaatctgt gaggccgggg ccctgcacct gtgcagcgaa | 1680 |
| gcttagcgtt catccgtgta acccgctcat cactggatga agattctcct gtgctagatg | 1740 |
| tgcaaatgca agctagtggc ttcaaaatag agaatcccac tttctatagc agattgtgta | 1800 |
| acaattttaa tgctatttcc ccaggggaaa atgaaggtta ggatttaaca gtcatttaaa | 1860 |
| aaaaaaattt gttttgacgg atgattggat tattcattta aaatgattag aaggcaagtt | 1920 |
| tctagctaga aatatgattt tatttgacaa aatttgttga aattatgtat gtttacatat | 1980 |
| cacctcatgg cctattatat taaaatatgg ctataaatat ataaaagaa aagataaaga | 2040 |
| tgatctactc agaaattttt attttctaa ggttctcata ggaaaagtac atttaataca | 2100 |
| gcagtgtcat cagaagataa cttgagcacc gtcatggctt aatgttatt cctgataata | 2160 |
| attgatcaaa ttcattttt tcactggagt tacattaatg ttaattcagc actgatttca | 2220 |
| caacagatca atttgtaatt gcttacattt ttacaataaa taatctgtac gtaagaaca | 2279 |

<210> SEQ ID NO 131
<211> LENGTH: 2438
<212> TYPE: DNA
<213> ORGANISM: Homo sapiens
<220> FEATURE:
<221> NAME/KEY: misc_feature
<223> OTHER INFORMATION: NM_016155

<400> SEQUENCE: 131

| | |
|---|---|
| ccggcggggg cgccgcggag agcggagggc gccgggctgc ggaacgcgaa gcggagggcg | 60 |
| cgggaccctg cacgccgccc gcgggccat gtgagcgcca tgcggcgccg cgcagcccgg | 120 |
| ggacccggcc cgccgccccc agggcccgga ctctcgcggt tgccgctgct gccgctgccg | 180 |
| ctgctgctgc tgctggcgct ggggacccgc ggggctgcg ccgcgcccgc acccgcgccg | 240 |
| cgcgccgagg acctcagcct gggagtggag tggctaagca ggttcggtta cctgccccg | 300 |
| gctgacccca aacagggca gctgcagacg caagaggagc tgtctaaggc catcacagcc | 360 |
| atgcagcagt ttggtggcct ggaggccacc ggcatcctgg acgaggccac cctgccctg | 420 |
| atgaaaaccc cacgctgctc cctgccagac ctccctgtcc tgacccaggc tcgcaggaga | 480 |

```
cgccaggctc cagcccccac caagtggaac aagaggaacc tgtcgtggag ggtccggacg        540
ttcccacggg actcaccact ggggcacgac acggtgcgtg cactcatgta ctacgccctc        600
aaggtctgga gcgacattgc gccctgaac ttccacgagg tggcgggcag caccgccgac        660
atccagatcg acttctccaa ggccgaccat aacgacggct accccttcga cggccccggc        720
ggcaccgtgg cccacgcctt cttccccggc caccaccaca ccgccgggga cacccacttt        780
gacgatgacg aggcctggac cttccgctcc tcggatgccc acgggatgga cctgtttgca        840
gtggctgtcc acgagtttgg ccacgccatt gggttaagcc atgtggccgc tgcacactcc        900
atcatgcggc cgtactacca gggcccggtg ggtgacccgc tgcgctacgg gctcccctac        960
gaggacaagg tgcgcgtctg gcagctgtac ggtgtgcggg agtctgtgtc tcccacggcg       1020
cagcccgagg agcctcccct gctgccgagg ccccagaca accggtccag cgccccgccc       1080
aggaaggacg tgccccacag atgcagcact cactttgacg cggtggccca gatccgcggt       1140
gaagctttct tcttcaaagg caagtacttc tggcggctga cgcggaccg gcacctggtg       1200 tccctgcagc cggcacagat gcaccgcttc tggcggggcc tgccgctgca cctggacagc       1260
gtggacgccg tgtacgagcg caccagcgac cacaagatcg tcttctttaa aggagacagg       1320
tactgggtgt tcaaggacaa taacgtagag gaaggatacc cgcgccccgt ctccgacttc       1380
agcctcccgc ctggcggcat cgacgctgcc ttctcctggg cccacaatga caggacttat       1440
ttctttaagg accagctgta ctggcgctac gatgaccaca cgaggcacat ggaccccggc       1500
taccccgccc agagcccct gtggaggggt gtccccagca cgctggacga cgccatgcgc       1560
tggtccgacg gtgcctccta cttcttccgt ggccaggagt actggaaagt gctggatggc       1620
gagctggagg tggcacccgg gtacccacag tccacggccc gggactggct ggtgtgtgga       1680
gactcacagg ccgatggatc tgtggctgcg ggcgtggacg cggcagaggg gccccgcgcc       1740
cctccaggac aacatgacca gagccgctcg gaggacggtt acgaggtctg ctcatgcacc       1800
tctggggcat cctctccccc ggggccccca ggcccactgg tggctgccac catgctgctg       1860
ctgctgccgc cactgtcacc aggcgccctg tggacagcgg cccaggccct gacgctatga       1920
cacacagcgc gagcccatga aggacagag gcggtggac agcctggcca cagagggcaa       1980
ggactgtgcc ggagtccctg ggggaggtgc tggcgcggga tgaggacggg ccaccctggc       2040
accggaaggc cagcagaggg cacggcccgc cagggctggg caggctcagg tgcaaggac       2100 ggagctgtcc cctagtgagg gactgtgttg actgacgagc cgaggggtgg ccgctccaga       2160
agggtgccca gtcaggccgc accgccgcca gcctcctccg gccctggagg gagcatctcg       2220 ggctggggc caccctct ctgtgccggc gccaccaacc ccacccacac tgctgcctgg       2280
tgctcccgcc ggcccacagg gcctccgtcc ccaggtcccc agtggggcag ccctccccac       2340
agacgagccc cccacatggt gccgcggcac gtcccccctg tgacgcgttc cagaccaaca       2400
tgacctctcc ctgctttgta aaaaaaaaa aaaaaaa                                 2438
```

<210> SEQ ID NO 132
<211> LENGTH: 1356
<212> TYPE: DNA
<213> ORGANISM: Homo sapiens
<220> FEATURE:
<221> NAME/KEY: misc_feature
<223> OTHER INFORMATION: U94332

<400> SEQUENCE: 132

```
gtatatataa cgtgatgagc gtacgggtgc ggagacgcac cggagcgctc gcccagccgc         60
```

```
cgyctccaag cccctgaggt ttccggggac cacaatgaac aagttgctgt gctgcgcgct    120
cgtgtttctg gacatctcca ttaagtggac cacccaggaa acgtttcctc caaagtacct    180
tcattatgac gaagaaacct ctcatcagct gttgtgtgac aaatgtcctc ctggtaccta    240
cctaaaacaa cactgtacag caaagtggaa gaccgtgtgc gccccttgcc ctgaccacta    300
ctacacagac agctggcaca ccagtgacga gtgtctatac tgcagccccg tgtgcaagga    360
gctgcagtac gtcaagcagg agtgcaatcg cacccacaac cgcgtgtgcg aatgcaagga    420
agggcgctac cttgagatag agttctgctt gaaacatagg agctgccctc ctggatttgg    480
agtggtgcaa gctggaaccc cagagcgaaa tacagtttgc aaaagatgtc cagatgggtt    540
cttctcaaat gagacgtcat ctaaagcacc ctgtagaaaa cacacaaatt gcagtgtctt    600
tggtctcctg ctaactcaga aaggaaatgc aacacacgac aacatatgtt ccggaaacag    660
tgaatcaact caaaaatgtg gaatagatgt taccctgtgt gaggaggcat tcttcaggtt    720
tgctgttcct acaaagttta cgcctaactg gcttagtgtc ttggtagaca atttgcctgg    780
caccaaagta aacgcagaga gtgtagagag gataaaacgg caacacagct cacaagaaca    840
gactttccag ctgctgaagt tatggaaaca tcaaaacaaa gcccaagata tagtcaagaa    900
gatcatccaa gatattgacc tctgtgaaaa cagcgtgcag cggcacattg gacatgctaa    960
cctcaccttc gagcagcttc gtagcttgat ggaaagctta ccgggaaaga aagtgggagc   1020
agaagacatt gaaaaaacaa taaaggcatg caaacccagt gaccagatcc tgaagctgct   1080
cagtttgtgg cgaataaaaa atggcgacca agacaccttg aagggcctaa tgcacgcact   1140
aaagcactca aagacgtacc actttcccaa aactgtcact cagagtctaa agaagaccat   1200
caggttcctt cacagcttca caatgtacaa attgtatcag aagttatttt tagaaatgat   1260
aggtaaccag gtccaatcag taaaaataag ctgcttataa ctggaaatgg ccattgagct   1320
gtttcctcac aattggcgag atcccatgga tgataa                             1356
```